United States Patent
Bartkovitz et al.

(10) Patent No.: US 8,513,239 B2
(45) Date of Patent: *Aug. 20, 2013

(54) CHIRAL CIS-IMIDAZOLINES

(75) Inventors: David Joseph Bartkovitz, Nutley, NJ (US); Jianping Cai, West Caldwell, NJ (US); Xin-Jie Chu, Livingston, NJ (US); Hongju Li, Edison, NJ (US); Allen John Lovey, North Caldwell, NJ (US); Binh Thanh Vu, North Caldwell, NJ (US); Chunlin Zhao, Livingston, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 925 days.

This patent is subject to a terminal disclaimer.

(21) Appl. No.: 12/248,095

(22) Filed: Oct. 9, 2008

(65) Prior Publication Data

US 2009/0111789 A1 Apr. 30, 2009

Related U.S. Application Data

(60) Provisional application No. 60/978,506, filed on Oct. 9, 2007, provisional application No. 61/092,759, filed on Aug. 29, 2008.

(51) Int. Cl.
| | | |
|---|---|---|
| *A61K 31/55* | (2006.01) | |
| *A61K 31/03* | (2006.01) | |
| *A61K 31/44* | (2006.01) | |
| *A61K 31/535* | (2006.01) | |
| *A61K 31/505* | (2006.01) | |
| *C07D 243/06* | (2006.01) | |
| *C07D 243/14* | (2006.01) | |
| *C07D 279/10* | (2006.01) | |
| *C07D 413/08* | (2006.01) | |
| *C07D 403/08* | (2006.01) | |
| *C07D 239/02* | (2006.01) | |
| *C07D 215/02* | (2006.01) | |

(52) U.S. Cl.
USPC ...... 514/221; 514/210.18; 514/218; 514/235; 514/269; 514/278; 540/492; 540/573; 544/58.2; 544/121; 544/295; 544/319; 546/16; 546/194

(58) Field of Classification Search
USPC .............. 514/210.18, 221, 269, 252.19, 218, 514/278, 235.8, 341; 546/16, 194; 544/121, 544/295, 58.2, 319; 540/492, 573
See application file for complete search history.

(56) References Cited

U.S. PATENT DOCUMENTS

| | | | |
|---|---|---|---|
| 6,617,346 B1 | 9/2003 | Kong et al. | |
| 6,734,302 B2 | 5/2004 | Kong et al. | |
| 7,705,007 B2 * | 4/2010 | Fotouhi et al. | 514/269 |
| 2007/0167437 A1 | 7/2007 | Fotouhi et al. | |

FOREIGN PATENT DOCUMENTS

| | | |
|---|---|---|
| WO | WO 00/78725 | 12/2000 |
| WO | WO 2007/063013 | 6/2007 |

OTHER PUBLICATIONS (Translation of Taiwan Off. Act. For TW097138773 Jul. 15, 2011).
(Chilean Office Action in Corres Appl.02982-2008 Feb. 28, 2012.).
(Translation of Chinese Off Act in Corres Chinese Appl 200880110704.7 Oct. 9, 2012).

* cited by examiner

*Primary Examiner* — James O Wilson
*Assistant Examiner* — Ebenezer O Sackey

(57) ABSTRACT

There are provided compounds of the formula (I)

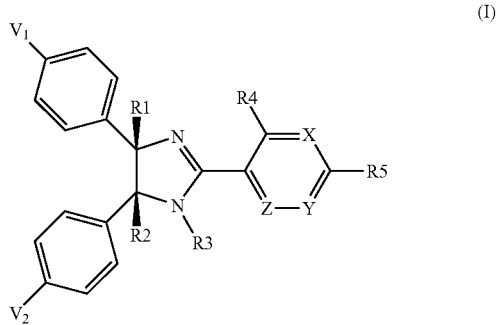

or the pharmaceutically acceptable salts thereof, wherein X, Y, Z, $V_1$, $V_2$, $R^1$, $R^2$, $R^3$, $R^4$ and $R^5$ are herein described. These compounds are useful as anticancer agents.

36 Claims, No Drawings

CHIRAL CIS-IMIDAZOLINES

PRIORITY OF RELATED APPLICATION(S)

This application claims the benefit of U.S. Provisional Application No. 60/978,506, filed Oct. 9, 2007, and U.S. Provisional Application No. 61/092759; filed Aug. 29, 2008. The entire contents of the above-identified applications are hereby incorporated by reference.

FIELD OF THE INVENTION

This invention is related to at least one compound selected from a compound of formula I

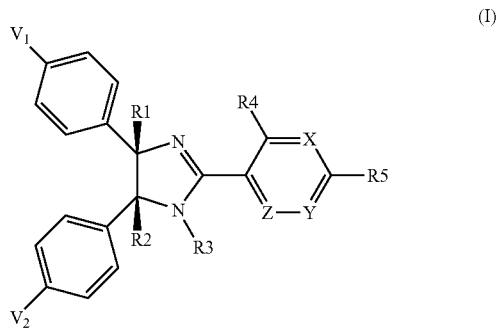

or the pharmaceutically acceptable salts thereof, wherein X, Y, Z, $V_1$, $V_2$, $R^1$, $R^2$, $R^3$, $R^4$ and $R^5$ are described in this application. These compounds are believed to inhibit the interaction of MDM2 protein with a p-53-like peptide and have antiproliferative activity.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

Wells et al. *J. Org. Chem.*, 1972, 37, 2158-2161, report synthesis of imidazolines. Hunter et al., *Can. J. Chem.*, 1972, Vol. 50, pgs. 669-77, report the preparation of amarine and isoamarine compounds which had previously been studied for chemiluminescence (McCapra et al. *Photochem. and Photobiol.* 1965, 4, 1111-1121). Zupanc et al. *Bull. Soc. Chem. & Tech.* (Yugoslavia) 1980-81, 27/28, 71-80, report the use of triaryl imidazolines as starting materials in the preparation of EDTA derivatives.

EP 363 061 to Matsumoto reports imidazoline derivatives useful as immunomodulators. The compounds were indicated to have low toxicity. Treatment and/or prevention of rheumatoid arthritis, multiple sclerosis, systemic lupus, erythemathodes, and rheumatic fever were implicated. WO 00/78725 to Choueiry et al. report a method for making substituted amidine compounds, and indicate that imidazoline-type compounds may be useful in the treatment of diabetes or related diseases involving impaired glucose disposal.

U.S. Pat. No. 6,617,346 B1 issued Sep. 9, 2003 and U.S. Pat. No. 6,734,302 B2 issued May 11, 2004 disclose related racemic cis-imidazolines.

SUMMARY OF THE INVENTION

The present invention provides at least one compound of formula I

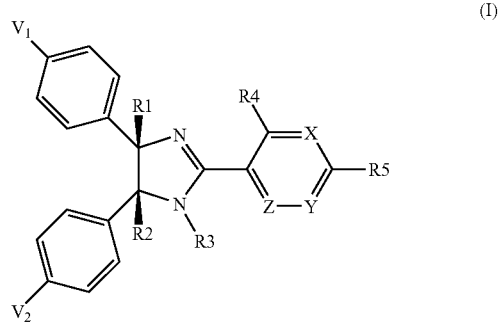

or the pharmaceutically acceptable salts thereof, wherein X, Y, Z, $V_1$, $V_2$, $R^1$, $R^2$, $R^3$, $R^4$ and $R^5$ are as described herein.

DETAILED DESCRIPTION OF THE INVENTION

The present invention provides cis-imidazolines which are small molecule inhibitors of the MDM2-p53 interaction. In cell-free and cell-based assays, compounds of the present invention are shown to inhibit the interaction of MDM2 protein with a p53-like peptide with a potency that is approximately 100 fold greater than a p53-derived peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations.

Therefore, the activity of MDM2 antagonists is likely linked to its mechanism of action. These compounds can be potent and selective anticancer agents.

The present invention provides at least one compound of formula (I) wherein

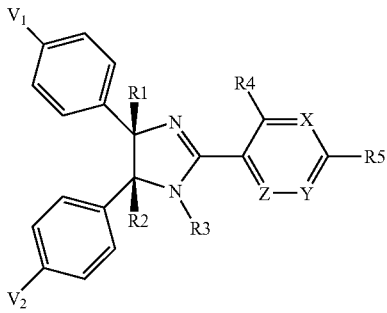

(I)

wherein X, Y and Z are carbon or nitrogen,
with the proviso that at least one of X, Y and Z is nitrogen;
$V_1$ and $V_2$ are selected from the group consisting of halogen, acetylene, cyano, trifluoromethyl and nitro;
$R^1$ and $R^2$ are H or $CH_3$,
with the proviso that $R^1$ and $R^2$ are not both H;
$R^3$ is H or —C(=O)—$R^6$;
$R^4$ is —$OCH_3$, —$OCH_2CH_3$, —$OCH_2CH_2F$, —$OCH_2CH_2OCH_3$, or —$OCH(CH_3)_2$;
$R^5$ is selected from the group consisting of:
i)—H
ii)—halogen,
iii)—$CH_3$,
iv)—$CF_3$,
v)—$OCH_3$ or —$COCH_2CH_3$,
vi)—$C(CH_3)_2$,
vii)—cyano,
viii)—$C(CH_3)_3$,
ix)—$C(CH_3)_2$ OR (where R is H, $CH_3$ or $CH_2CH_3$),
x)—$C(CH_3)_2$CH—OR (where R is H, $CH_3$, $CH_2CH_2OH$ or $CH_2CH_2OCH_3$),
xi)—$C(CH_3)_2$CN,
xii)—$C(CH_3)_2$COR (where R is $CH_3$),
xiii)—$C(CH_3)_2$COOR (where R is H, $CH_3$, or $CH_2CH_3$),
xiv)—$C(CH_3)_2$CONR$^a$R$^b$ (where R$^a$ is H or $CH_3$ and R$^b$ is H or $CH_3$),
xv)—$SCH_3$ or —$SO_2CH_3$,
xvi)—NR$^a$R$^b$ (where R$^a$ is H or $CH_3$ and R$^b$ is H or $CH_3$), and
xvii)—4-morpholinyl;
and $R^6$ is selected from the group consisting of:
i)—lower alkyl,
ii)—cyclopropyl or cyclobutyl,
iii)—phenyl or phenyl substituted by chloro, $OCH_3$ or cyano,
iv)—4-morpholinyl, 1-(3-oxopiperazinyl), 1-piperidinyl, 4-thiomorpholinyl, 4-thiomorpholinyl-1,1-dioxide or 1-(1,4-diazepinyl-5-oxo),
v)—NR$^c_2$ (wherein R$^c$ is hydrogen, —$CH_3$, —$CH_2CH_3$, —$CH_2CH_2OH$, —$CH_2CH_2OCH_3$ or —$CH_2CH(OH)CH_2OH$),
vi)—a substituted piperazine of the formula:

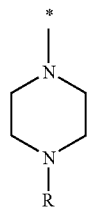

wherein R is selected from the group consisting of:
a) hydrogen,
b) lower alkyl,
c) —$CH_2CH(OH)CH_2OH$, —$CH_2CH_2CH(OH)CH_2OH$ or 4-tetrahydro-2H-thiopyranyl-1,1-dioxide,
d) —$CH_2CH_2R^d$ (wherein $R^d$ is —OH, —$OCH_3$, —$OCH_2CH_2OH$, —$OCH_2CH_2OCH_3$, —CN, —$CF_3$, —$SO_2CH_3$, —$SO_2NH_2$, —$SO_2N(CH_3)_2$, —$CONH_2$, —$CON(CH_3)_2$, —$NH_2$, —$NHCOCH_3$, —$NHSO_2CH_3$, —$N(CH_3)_2$, 1-pyrrolidinyl, 1-piperidinyl or 4-morpholinyl),
e)—$CH_2CH_2CH_2R^e$ (wherein $R^e$ is —OH, —$OCH_3$, —$SO_2CH_3$, —$SO_2CH_2CH_3$, —$SO_2N(CH_3)_2$, —CN, —$N(CH_3)_2$, 1-pyrrolidinyl, 1-piperidinyl, 4-morpholinyl, —$COOCH_3$, —$COOCH_2CH_3$, —$COOC(CH_3)_3$, —$CON(CH_3)_2$, —CO—$R^f$ (wherein $R^f$ is $CH_3$, $CH_2CH_3$, cyclopropyl, phenyl, 2-thienyl, 3-thienyl, 2-furanyl or 3-furanyl), —$COCH_2$—$R^g$ (wherein $R^g$ is H, —$NHCH_2CH_2OH$, —$NHCH_2CH_2OCH_3$, —$NHCH_2CH_2N(CH_3)_2$, 1-piperidinyl, 1-(piperidinyl-4-methanol), 4-morpholinyl or —$N(CH_3)$-(3-(1-methylpyrrolidinyl)),
f)—$CH_2$—CO—$R^h$ (wherein $R^h$ is substituted or unsubstituted lower alkyl, —OH, —$OCH_3$, —$OCH_2CH_3$, —$NH_2$, —$(CH_2)_n$ substituted or unsubstituted heteroaryl where n is 0 or 1, —NH cycloalkyl, —N (lower alkyl)n where n is 1 or 2, —$NHCH_2C(OH)CH_2OH$, —$NHCH_2CF_3$, —$NHCH_2CH_2OH$, —$N(CH_2CH_2OH)_2$, —$N(CH_2CH_2OCH_3)_2$, —$N(CH_3)CH_2CH_2OH$, —$NH(CH_2OH)(CH_3)$ $CH_2CH_2OH$, —$NH(CH_2OH)(CH_3)CH_3$, —$CH_2CH_2CH_2SO_2NH_2$, —$N(CH_2CH_3)$heteroaryl, —$N(CH_3)CH_2CH_2OCH_3$, —$NHCH_2CH_2OCH_3$, —$NH(CH_2)_n$ mono- or di- substituted heteroaryl where n is 0 or 1, —$NHCH_2CH_2$ substituted or unsubstituted heteroaryl, —NH mono- or di-substituted aryl, —$NH(CH_2)_n$ heterocycle where n is 0 or 1, —$NH(CH_2)_n$—OH where n is 2 or 3, —$(CH_2)_n$ substituted or unsubstituted heterocycle where n is 1 or 2 or —$N(CH_2CH_3)$mono- or di-substituted heteroaryl),
g) —$SO_2R^i$ (wherein $R^i$ is —$CH_3$, —$CH_2CH_3$, —CH$(CH_3)_2$, phenyl, 4-methylphenyl, 4-propylphenyl, $CF_3$, 2-thienyl, 3-thienyl, $NH_2$, $NHCH_3$, $N(CH_3)_2$, $NHCH_2CH_2OCH_3$, $N(CH_2CH_2OCH_3)_2$, 1-pyrrolidinyl, 1-piperidinyl, 4-morpholinyl,1-piperazyl-4-ethanol, 1-(4-acetylpiperazinyl) or 1-(3-oxopiperazinyl)),
h) —COR$^j$ (wherein R$^j$ is lower alkyl, cycloalkyl, 2-tetrahydrofuranyl, 2-thienyl, 3-thienyl, $NH_2$, $NHCH_3$, $N(CH_3)_2$, 1-pyrrolidinyl, 1-piperidinyl, 4-morpholinyl, 1-piperazinyl-4-ethanol, 1-(4-acetylpiperazinyl) or 1-(3-oxopiperazinyl)), and i) substituted or unsubstituted heteroaryl or heterocycle;
vii)—a substituted piperidine of the formula:

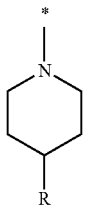

wherein R is hydrogen, lower alkyl, —CH$_2$CH(OH)CH$_2$OH, —CH$_2$CH$_2$CH(OH)CH$_2$OH or 4-tetrahydro-2H-thiopyranyl-1,1-dioxide, —CH$_2$CH$_2$R$^d$ (wherein R$^d$ is —OH, —OCH$_3$, —OCH$_2$CH$_2$OH, —OCH$_2$CH$_2$OCH$_3$, —CN, —CF$_3$, —SO$_2$CH$_3$, —SO$_2$NH$_2$, —SO$_2$N(CH$_3$)$_2$, —CONH$_2$, —CON(CH$_3$)$_2$, —NH$_2$, —NHCOCH$_3$, —NHSO$_2$CH$_3$, —N(CH$_3$)$_2$, 1-pyrrolidinyl, 1-piperidinyl or 4-morpholinyl), —CH$_2$CH$_2$CH$_2$R$^e$ (wherein R$^e$ is —OH, —OCH$_3$, —SO$_2$CH$_3$, —SO$_2$CH$_2$CH$_3$, —SO$_2$N(CH$_3$)$_2$, —CN, —N(CH$_3$)$_2$, 1-pyrrolidinyl, 1-piperidinyl, 4-morpholinyl, —COOCH$_3$, —COOCH$_2$CH$_3$, —COOC(CH$_3$)$_3$, —CON(CH$_3$)$_2$, —CO—R$^f$ (wherein R$^f$ is CH$_3$, CH$_2$CH$_3$, cyclopropyl, phenyl, 2-thienyl, 3-thienyl, 2-furanyl or 3-furanyl), —COCH$_2$—R$^g$ (wherein R$^g$ is H, —NHCH$_2$CH$_2$OH, —NHCH$_2$CH$_2$OCH$_3$, —NHCH$_2$CH$_2$N(CH$_3$)$_2$, 1-piperidinyl, 1-4-methanol), 4-morpholinyl or —N(CH$_3$)-(3-(1-methylpyrrolidinyl)), —CH$_2$—CO—R$^h$ (wherein R$^h$ is substituted or unsubstituted lower alkyl, —OH, —OCH$_3$, —OCH$_2$CH$_3$, —NH$_2$, —(CH$_2$)$_n$ heteroaryl where n is 0 or 1 —NH lower alkyl, —NH cycloalkyl, —N (lower alkyl)$_n$ where n is 1 or 2, —NHCH$_2$C(OH)CH$_2$OH, —NHCH$_2$CF$_3$, —NHCH$_2$CH$_2$CH$_2$OH, —N(CH$_2$CH$_2$OH)$_2$, —N(CH$_2$CH$_2$OCH$_3$)$_2$, —N(CH$_3$)CH$_2$CH$_2$OH, —NH(CH$_2$OH)(CH$_3$) CH$_2$CH$_2$OH, —NH(CH$_2$OH)(CH$_3$)CH$_3$, —CH$_2$CH$_2$CH$_2$SO$_2$NH$_2$, —N(CH$_2$CH$_3$)heteroaryl, —N(CH$_3$)CH$_2$CH$_2$OCH$_3$, —NHCH$_2$CH$_2$OCH$_3$, —NH(CH$_2$)$_n$ mono- or di-substituted heteroaryl where n is 0 or 1, —NHCH$_2$CH$_2$ substituted or unsubstituted heteroaryl, —NH mono- or di-substituted aryl, —NH(CH$_2$)$_n$ heterocycle where n is 0 or 1, —NH(CH$_2$)$_n$—OH where n is 2 or 3, substituted or unsubstituted heterocycle or —N(CH$_2$CH$_3$) mono- or di-substituted heteroaryl), —SO$_2$R$^i$ (wherein R$^i$ is —CH$_3$, —CH$_2$CH$_3$, —CH(CH$_3$)$_2$, phenyl, 4-methylphenyl, 4-propylphenyl, CF$_3$, 2-thienyl, 3-thienyl, NH$_2$, NHCH$_3$, N(CH$_3$)$_2$, NHCH$_2$CH$_2$OCH$_3$, N(CH$_2$CH$_2$OCH$_3$)$_2$, 1-pyrrolidinyl, 1-piperidinyl, 4-morpholinyl, 1-piperazyl-4-ethanol, 1-(4-acetylpiperazinyl) or 1-(3-oxopiperazinyl)), —COR$^j$ (wherein R$^j$ is lower alkyl, cycloalkyl, 2-tetrahydrofuranyl, 2-thienyl, 3-thienyl, NH$_2$, NHCH$_3$, N(CH$_3$)$_2$, 1-pyrrolidinyl, 1-piperidinyl, 4-morpholinyl, 1-piperazinyl-4-ethanol, 1-(4-acetylpiperazinyl) or 1-(3-oxopiperazinyl)), substituted or unsubstituted heteroaryl or heterocycle, NH$_2$, NHCOCH$_3$, NHCOCH$_2$NH$_2$, NHCOCH$_2$NHCH$_3$, NHCOCH$_2$N(CH$_3$)$_2$, NHCOCH$_2$N(CH$_2$CH$_2$OH)$_2$, NHCOCH$_2$N(CH$_2$CH$_2$OCH$_3$)$_2$, NHCOCH$_2$NHCH$_2$CH$_2$OH, NHCOCH$_2$-(1-(4-acetylpiperazinyl)), NHCOCH$_2$-(1-(3-oxopiperazinyl)), NHCOCH$_2$—NHCONHCH$_3$, NHCOO lower alkyl, NHCHCH$_3$, NHCO lower alkyl, NH(CH$_2$)$_n$ SO$_2$CH$_3$ where n is 0-2, NH(CH$_3$)SO$_2$CH$_3$, (1-piperidinecarboxamide), NHCOCH$_2$—(N,N-diethyl-1-piperidinylcarboxamide), NHCOCH$_2$-(1-(3-hydroxypiperidinyl)), NHCOCH$_2$-(1-(piperidinyl-4-methanol)), NHCON(CH$_3$)$_2$, NHCSNHCH$_3$, NHCSNHPh, NHCH$_2$CONH$_2$ or —NHCH$_2$CH$_2$SO$_2$CH$_3$ and viii)—a substituted piperidine of the formula:

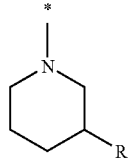

wherein R is —OH, CH$_2$OH, CH$_2$CH$_2$OH, or C(O)NH$_2$ and the pharmaceutically acceptable salts and esters thereof.

More preferred compounds are those wherein further V$_1$ and V$_2$ are chloro.

More preferred compounds are those wherein further R$^3$ is —C(=O)—R$^6$.

More preferred compounds are those wherein further R$^4$ is —OCH$_3$, —OCH$_2$CH$_3$, or —OCH(CH$_3$)$_2$ and R$^5$ is —C(CH$_3$)$_3$, —C(CH$_3$)$_2$ or (where R is H or CH$_3$), —C(CH$_3$)$_2$CH—OR (where R is H or CH$_3$), —C(CH$_3$)$_2$CN, or —C(CH$_3$)$_2$COR (where R is CH$_3$).

Also more preferred compounds are those wherein R$^6$ is a substituted piperazine of the formula:

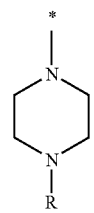

wherein R is —CH$_2$COR$^h$.

Yet more preferred compounds are those where R$^h$ is 4-morpholinyl, 1-pyrrolidinyl, 1-piperidinyl, NH$_2$, or N(CH$_3$)$_2$.

More preferred compounds are those wherein R$^6$ is a substituted piperazine of the formula:

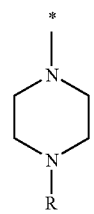

wherein R is —CH$_2$CH$_2$R$^d$.

Yet more preferred compounds are those wherein R$^d$ is —SO$_2$CH$_3$, —NHSO$_2$CH$_3$, —NHCOCH$_3$, or CF$_3$.

More preferred compounds are those wherein R$^6$ is a substituted piperazine of the formula:

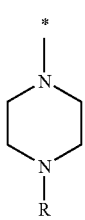

wherein R is —CH₂CH₂CH₂Rᵉ.

Yet more preferred compounds are those wherein Rᵉ is —SO₂CH₃ or —SO₂CH₂CH₃.

More preferred compounds are those wherein R⁶ is a substituted piperidine of the formula

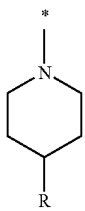

wherein R is —CH₂COR^h where R^h is as above, 4-tetrahydro-2H-thiopyranyl-1,1-dioxide or 1-(1,4-diazepinyl-5-oxo).

Further preferred are compounds where R^h is NH₂.

Also preferred compounds are those wherein R¹ and R² of the imidazoline ring are in a cis configuration to each other. The compounds may be in a racemic form and may be optically active. The preferred absolute stereochemistry at the 4 and 5 position of the imidazoline ring are S and R, respectively.

Especially preferred compounds are for example:

2-{4-[(4S,5R)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-acetamide,

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(1,1-dioxo-hexahydro-thiopyran-4-yl)-piperazin-1-yl]-methanone,

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(3-methanesulfonyl-propyl)-piperazin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3-methanesulfonyl-propyl)-piperazin-1-yl]-methanone, rac-[(4S*,5R*)-2-(6-tert-Butyl-2-ethoxy-pyridin-3-yl)-4,5-bis-(4-chloro-phenyl)-4,5-dimethyl-4,5-dihydro-imidazol-1-yl]-[4-(3-methanesulfonyl-propyl)-piperazin-1-yl]-methanone, rac-[(4S*,5R*)-4,5-Bis-(4-chloro-phenyl)-2-(2,4-dimethoxy-pyrimidin-5-yl)-4,5-dimethyl-4,5-dihydro-imidazol-1-yl]-[4-(3-methanesulfonyl-propyl)-piperazin-1-yl]-methanone, rac-[(4S*,5R*)-4,5-Bis-(4-chloro-phenyl)-2-(2-dimethylamino-4-ethoxy-pyrimidin-5-yl)-4,5-dimethyl-4,5-dihydro-imidazol-1-yl]-[4-(3-methanesulfonyl-propyl)-piperazin-1-yl]-methanone, rac-[(4S*,5R*)-4,5-Bis-(4-chloro-phenyl)-2-(4-ethoxy-2-pyridin-3-yl-pyrimidin-5-yl)-4,5-dimethyl-4,5-dihydro-imidazol-1-yl]-[4-(3-methanesulfonyl-propyl)-piperazin-1-yl]-methanone, rac-[(4S*,5R*)-4,5-Bis-(4-chloro-phenyl)-2-(2,6-dimethoxypyridin-3-yl)-4,5-dimethyl-4,5-dihydro-imidazol-1-yl]-[4-(3-methanesulfonylpropyl)-piperazin-1-yl]-methanone, 4-[(4S,5R)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-2-one, rac-[(4S*,5R*)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(2-hydroxy-ethyl)-piperazin-1-yl]-methanone, 2-(2-tert-Butyl-4-ethoxy-pyrimidin-5-yl)-4,5-bis-(4-chloro-phenyl)-4,5-dimethyl-4,5-dihydro-imidazol-1-yl]-piperazin-1-yl-methanone,

[2-(2-tert-Butyl-4-ethoxy-pyrimidin-5-yl)-4,5-bis-(4-chloro-phenyl)-4,5-dimethyl-4,5-dihydro-imidazol-1-yl]-[4-((R)-3,4-dihydroxy-butyl)-piperazin-1-yl]-methanone, 4-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazine-1-carboxylic acid dimethylamide, N-(2-{4-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-ethyl)-acetamide, 1-{4-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-ethanone,

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-{4-[2-(2-hydroxy-ethoxy)-ethyl]-piperazin-1-yl}-methanone,

[2-(2-tert-Butyl-4-ethoxy-pyrimidin-5-yl)-4,5-bis-(4-chloro-phenyl)-4,5-dimethyl-4,5-dihydro-imidazol-1-yl]-[4-(3-hydroxy-propyl)-piperazin-1-yl]-methanone, 2-{4-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-N,N-dimethyl-acetamide,

[1,4']Bipiperidinyl-1'-yl-[2-(2-tert-butyl-4-ethoxy-pyrimidin-5-yl)-4,5-bis-(4-chloro-phenyl)-4,5-dimethyl-4,5-dihydro-imidazol-1-yl]-methanone,

[2-(2-tert-Butyl-4-ethoxy-pyrimidin-5-yl)-4,5-bis-(4-chloro-phenyl)-4,5-dimethyl-4,5-dihydro-imidazol-1-yl]-(4-hydroxy-[1,4']bipiperidinyl-1'-yl)-methanon,

[2-(2-tert-Butyl-4-ethoxy-pyrimidin-5-yl)-4,5-bis-(4-chloro-phenyl)-4,5-dimethyl-4,5-dihydro-imidazol-1-yl]-(3-hydroxy-[1,4']bipiperidinyl-1'-yl)-methanone,

[2-(2-tert-Butyl-4-ethoxy-pyrimidin-5-yl)-4,5-bis-(4-chloro-phenyl)-4,5-dimethyl-4,5-dihydro-imidazol-1-yl]-(3-hydroxymethyl-[1,4']bipiperidinyl-1'-yl)-methanone,

[2-(2-tert-Butyl-4-ethoxy-pyrimidin-5-yl)-4,5-bis-(4-chloro-phenyl)-4,5-dimethyl-4,5-dihydro-imidazol-1-yl]-(4-pyrrolidin-1-yl-piperidin-1-yl)-methanone,

[2-(2-tert-Butyl-4-ethoxy-pyrimidin-5-yl)-4,5-bis-(4-chloro-phenyl)-4,5-dimethyl-4,5-dihydro-imidazol-1-yl]-(3-hydroxy-piperidin-1-yl)-methanone,

[2-(2-tert-Butyl-4-ethoxy-pyrimidin-5-yl)-4,5-bis-(4-chloro-phenyl)-4,5-dimethyl-4,5-dihydro-imidazol-1-yl]-(3-hydroxymethyl-piperidin-1-yl)-methanone, 1-{1-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperidin-4-yl}-[1,4]diazepan-5-one,

[2-(2-tert-Butyl-4-ethoxy-pyrimidin-5-yl)-4,5-bis-(4-chloro-phenyl)-4,5-dimethyl-4,5-dihydro-imidazol-1-yl]-(4-hydroxy-piperidin-1-yl)-methanone, 1-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperidine-4-carboxylic acid amide, 1-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperidine-3-carboxylic acid amide,

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-[4-((S)-2,3-dihydroxy-propyl)-piperazin-1-yl]-methanone, rac-[(4S*,5R*)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(2-methanesulfonyl-ethyl)-piperazin-1-yl]-methanone, rac-[(4S*,5R*)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(2-methoxy-ethyl)-piperazin-1-yl]-methanone, rac-N-tert-Butyl-2-{4-[(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl]-piperazin-1-yl}-acetamide, rac-2-{4-[(4S*,5R*)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-1-morpholin-4-yl-ethanone, rac-4-{4-[(4S*,5R*)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-butyronitrile, rac-[(4S*,5R*)-4,5-Bis-(4-chloro-phenyl)-2-(4-ethoxy-2-methylsulfanyl-pyrimidin-5-yl)-4,5-dimethyl-4,5-dihydro-imidazol-1-yl]-[4-(3-methanesulfonyl-propyl)-piperazin-1-yl]-methanone, rac-4-[(4S*,5R*)-4,5-Bis-(4-chloro-phenyl)-2-(4-ethoxy-2-methylsulfanyl-pyrimidin-5-yl)-4,5-dimethyl-4,5-dihydro-imidazole-1-carbonyl]-piperazin-2-one, rac-4-[(4S*,5R*)-4,5-Bis-(4-chloro-phenyl)-2-(4-ethoxy-2-morpholin-4-yl-pyrimidin-5-yl)-4,5-dimethyl-4,5-dihydro-imidazole-1-carbonyl]-piperazin-2-on, rac-[(4S*,5R*)-4,5-Bis-(4-chloro-phenyl)-2-(2,4-diethoxy-pyrimidin-5-yl)-4,5-dimethyl-4,5-dihydro-imidazol-1-yl]-[4-(3-methanesulfonyl-propyl)-piperazin-1-yl]-methanone, rac-[(4S*,5R*)-4,5-Bis-(4-chloro-phenyl)-2-(4-methoxy-2-methylsulfanyl-pyrimidin-5-yl)-4,5-dimethyl-4,5-dihydro-imidazol-1-yl]-[4-(3-methanesulfonyl-propyl)-piperazin-1-yl]-methanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetamide, rac-[(4S*,5R*)-2-(6-tert-Butyl-4-ethoxy-pyridin-3-yl)-4,5-bis-(4-chloro-phenyl)-4,5-dimethyl-4,5-dihydro-imidazol-1-yl]-[4-((S)-2,3-dihydroxy-propyl)-piperazin-1-yl]-methanone, 1-[(4S,5R)-2-(2-tert-Butyl-4-ethoxy-pyrimidin-5-yl)-4,5-bis-(4-chloro-phenyl)-4,5-dimethyl-4,5-dihydro-imidazole-1-carbonyl]-[1,4]diazepan-5-one, 1-{1-[(4S,5R)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperidin-4-yl}-[1,4]diazepan-5-one,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-methanesulfonylmethyl-piperidin-1-yl)-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methanesulfonyl-ethyl)-piperidin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(1,1-dioxo-hexahydro-1$\lambda^6$-thiopyran-4-yl)-piperazin-1-yl]-methanone, 3-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-propane-1-sulfonic acid amide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methanesulfonyl-ethyl)-piperazin-1-yl]-methanone, 4-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-butyronitrile,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3,3,3-trifluoro-propyl)-piperazin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3-ethanesulfonyl-propyl)-piperazin-1-yl]-methanone, -(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-ethyl)-acetamide, 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2-(thiazol-2-ylamino)-ethanone, 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2-methyl-propan-1-one, 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2,2-dimethyl-propan-1-one, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-methoxy-ethyl)-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-cyclopropyl-acetamide, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid dimethylamide, 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2-tetrazol-1-yl-ethanone, 3-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-propionamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(1-methyl-1H-pyrrole-2-carbonyl)-piperazin-1-yl]-methanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-cyclopropyl-propionamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(tetrahydro-furan-2-ylmethyl)-acetamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3-methanesulfonyl-propyl)-piperidin-1-yl]-methanone, 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2-(4-methyl-thiazol-2-yl)-ethanone, 9-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-3,9-diaza-spiro[5.5]undecane-3-carboxylic acid tert-butyl ester,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3,9-diaza-spiro[5.5]undec-3-yl)-methanone, 2-{9-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-3,9-diaza-spiro[5.5]undec-3-yl}-acetamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(1,1-dioxo-tetrahydro-1λ6-thiophen-3-yl)-piperazin-1-yl]-methanone, 3-{4-[(4S,5R)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-propane-1-sulfonic acid amide, rac-[(4S*,5R*)-2-(2-tert-Butyl-4-ethoxy-pyrimidin-5-yl)-4,5-bis-(4-chloro-phenyl)-4,5-dimethyl-4,5-dihydro-imidazol-1-yl]-piperidin-1-yl-methanone, 2-{1-[(4S,5R)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperidin-4-yl}-acetamide,

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(2-methanesulfonyl-ethyl)-piperidin-1-yl]-methanone, rac-[(4S*,5R*)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(1,2-dihydroxy-ethyl)-piperidin-1-yl]-methanone,

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-(4-methanesulfonylmethyl-piperidin-1-yl)-methanone,

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(3-methanesulfonyl-propyl)-piperidin-1-yl]-methanone, rac-[(4S*,5R*)-4,5-Bis-(4-chloro-phenyl)-2-(3,6-dimethoxy-pyridazin-4-yl)-4,5-dimethyl-4,5-dihydro-imidazol-1-yl]-[4-(3-methanesulfonyl-propyl)-piperazin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-ethanesulfonyl-piperazin-1-yl)-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-hydroxy-ethyl)-piperidin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methoxy-ethyl)-piperazin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-pyrrolidin-1-yl-piperidin-1-yl)-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-isopropyl-piperazin-1-yl)-methanone,

[1,4']Bipiperidinyl-1'-yl-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone, 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-ethanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-dimethylamino-piperidin-1-yl)-methanone, {4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(tetrahydro-furan-2-carbonyl)-piperazin-1-yl]-methanone, 4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazine-1-carboxylic acid dimethylamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3-methoxy-propyl)-piperazin-1-yl]-methanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-(1,1-dioxo-1λ6-thiomorpholin-4-yl)-ethanone, 4-(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetyl)-piperazin-2-one, 1-(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetyl)-[1,4]diazepan-5-one,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-hydroxy-piperidin-1-yl)-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3-hydroxy-piperidin-1-yl)-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-hydroxymethyl-piperidin-1-yl)-methanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-pyrrolidin-1-yl-ethanone, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-[1,4]diazepan-5-one,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-((R)-3-methyl-piperazin-1-yl)-methanone, -{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2,3-dihydroxy-propyl)-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-isopropyl-N-methyl-acetamide, N-tert-Butyl-2-{4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-methanesulfonyl-piperazin-1-yl)-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-{4-[2-(2-hydroxy-ethoxy)-ethyl]-piperazin-1-yl}-methanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-(4-methyl-piperazin-1-yl)-ethanone, 4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-cyclopropanecarbonyl-piperazin-1-yl)-methanone, 4-[4-(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetyl)-piperazin-1-yl]-benzonitrile, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-hydroxy-1,1-dimethyl-ethyl)-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-hydroxy-1-hydroxymethyl-1-methyl-ethyl)-acetamide, 4-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-piperazin-2-one, 4-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-methyl -piperazin-2-one,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3,4-dihydroxy-butyl)-piperazin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(1,1-dioxo-1$\lambda$6-thiomorpholin-4-yl)-methanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-piperidin-1-yl-ethanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-hydroxy-ethyl)-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-[1,4]dioxan-2-ylmethyl-acetamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3-hydroxy-pyrrolidin-1-yl)-methanone, {(S)-1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-pyrrolidin-3-yl}-carbamic acid tert-butyl ester, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-thiazol-5-yl-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-3-yl-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-phenyl-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-4-yl-acetamide, (3-Amino-pyrrolidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone, N-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-pyrrolidin-3-yl}-oxalamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(2,3,4,5-tetrahydro-benzo[b][1,4]diazepin-1-yl)-methanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-(3-hydroxy-azetidin-1-yl)-ethanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(tetrahydro-pyran-4-yl)-acetamide, (1S,5R)-3-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-3-aza-bicyclo[3.1.0]hexane-6-carboxylic acid ethyl ester 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N,N-bis-(2-methoxy-ethyl)-acetamide, 1-Azetidin-1-yl-2-{4-[(4S,5R)-2-(6-tert-butyl-4-ethoxy-pyridin-3-yl)-4,5-bis(4-chloro-phenyl)-4,5-dimethyl-4,5-dihydro-imidazole-1-carbonyl]-piperazin-1-yl}-ethanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N,N-bis-(2-hydroxy-ethyl)-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-[2-(4-methoxy-phenyl)-ethyl]-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-[2-(2-methoxy-phenyl)-ethyl]-acetamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(7,8-dimethoxy-1,2,3,5-tetrahydro-benzo[e][1,4]diazepin-4-yl)-methanone,

[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-(7,8-dimethoxy-2,3,4,5-tetrahydro-benzo[e][1,4]diazepin-1-yl)-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[(1S,5R)-6-(3-hydroxy-azetidine-1-carbonyl)-3-aza-bicyclo[3.1.0]hex-3-yl]-methanone, (1S,5R)-3-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-3-aza-bicyclo[3.1.0]hexane-6-carboxylic acid (2-hydroxy-ethyl)-amide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[(1S,5R)-6-(3-hydroxy-pyrrolidine-1-carbonyl)-3-aza-bicyclo[3.1.0]hex-3-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-methyl-[1,4]diazepan-1-yl)-methanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-[1,4]diazepan-1-yl}-acetamide, 4-(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-[1,4]diazepan-1-yl}-acetyl)-piperazin-2-one, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(6-methoxy-2-methyl-pyridin-3-yl)-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-methyl-pyridin-3-yl)-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-methoxy-pyridin-3-yl)-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-ethyl-N-pyridin-3-yl-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2,6-dimethyl-pyridin-3-yl)-acetamide, (S)-4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazine-2-carboxylic acid tert-butylamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(4-methyl-piperazin-1-yl)-piperidin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-morpholin-4-yl-piperidin-1-yl)-methanone, N-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-methyl-[1,4']bipiperidinyl-1'-yl)-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(4-ethyl-piperazin-1-yl)-piperidin-1-yl]-methanone, N-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-methanesulfonamide, N-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-methanesulfonamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methanesulfonyl-ethylamino)-piperidin-1-yl]-methanone, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid methyl ester, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-pyrrolidin-1-yl-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-dimethyl-acetamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-diethylamino-piperidin-1-yl)-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-{4-[(2-methanesulfonyl-ethyl)-methyl-amino]-piperidin-1-yl}-methanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-hydroxy-ethyl)-acetamide, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-methyl-urea,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(pyrrolidine-1-carbonyl)-piperidin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(piperazine-1-carbonyl)-piperidin-1-yl]-methanone, 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-3-methylsulfanyl-propan-1-one, 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-3-methanesulfonyl-propan-1-one, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid (2-methanesulfonyl-ethyl)-amide, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid (2-methanesulfonyl-ethyl)-methyl-amide, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid (2-hydroxy-ethyl)-amide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(1,1-dioxo-1λ6-thiomorpholine-4-carbonyl)-piperidin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methanesulfonyl-ethoxy)-piperidin-1-yl]-methanone, rac-4-[(4S*,5R*)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-2-one, rac-[(4S*,5R*)-2-(6-tert-Butyl-4-ethoxy-pyridin-3-yl)-4,5-bis-(4-chloro-phenyl)-4,5-dimethyl-4,5-dihydro-imidazol-1-yl]-[4-(morpholine-4-carbonyl)-piperazin-1-yl]-methanone, 4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-2-one, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide, rac-1-{1-[(4S*,5R*)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-[1,4]diazepan-5-one, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-[1,4]diazepan-5-one, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-2-yl-acetamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-piperazin-1-yl-methanone, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid ((S)-3,4-dihydroxy-butyl)-amide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3,6-dihydro-2H-pyridin-1-yl)-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3,4-dihydroxy-piperidin-1-yl)-methanone, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid methyl-((2S,3R,4R,5R)-2,3,4,5,6-pentahydroxy-hexyl)-amide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-2-ylmethyl-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-3-ylmethyl-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-4-ylmethyl-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-furan-2-ylmethyl-acetamide, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-pyridin-2-ylmethyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-pyridin-3-yl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-methyl-piperazin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-bis-(2-methoxy-ethyl)-acetamide, 4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazine-1-sulfonic acid dimethylamide, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid (2-hydroxy-ethyl)-amide, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid (2-hydroxy-ethyl)-methyl-amide, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid bis-(2-methoxy-ethyl)-amide, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-carbamic acid tert-butyl ester, (4-Amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone, 4-{[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-amino}-piperidine-1-carboxylic acid tert-butyl ester, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid (1-methanesulfonyl-piperidin-4-yl)-amide, 4-{[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-amino}-piperidine-1-carboxylic acid ethylamide, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid (1-carbamoylmethyl-piperidin-4-yl)-amide, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-one, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid methyl ester, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid, 3-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yloxy}-propionamide, 3-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yloxy}-propionitrile, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-isopropyl-urea, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-pyridin-3-yl-urea, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-((R)-3-methoxy-pyrrolidin-1-yl)-ethanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-((S)-3-methoxy-pyrrolidin-1-yl)-ethanone, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-ethyl-urea, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-phenyl-urea, (4-{[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-amino}-piperidin-1-yl)-acetic acid ethyl ester,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[(1S,5R)-6-((R)-3-methoxy-pyrrolidine-1-carbonyl)-3-aza-bicyclo[3.1.0]hex-3-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[(1S,5R)-6-((S)-3-methoxy-pyrrolidine-1-carbonyl)-3-aza-bicyclo[3.1.0]hex-3-yl]-methanone, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid [1-(2-methanesulfonyl-ethyl)-piperidin-4-yl]-amide, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-cyclopentyl-urea, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-acetic acid ethyl ester, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-pyridin-4-yl-urea, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-N-(2-hydroxy-ethyl)-acetamide, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-acetic acid, Pyrrolidine-1-carboxylic acid {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-amide, 3-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1,1-dimethyl-urea, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-bis-(3-methoxy-propyl)-acetamide, 3-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-propionic acid, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-bis-(2-ethoxy-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-bis-(2-isopropoxy-ethyl)-acetamide, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid [(2R,3R,4S)-3,4-dihydroxy-1-(2-hydroxy-ethyl)-pyrrolidin-2-ylmethyl]-amide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N,N-bis-(2-ethoxy-ethyl)-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N,N-bis-(2-isopropoxy-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-diethyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-methyl-[1,4]diazepan-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(2-methyl-pyrrolidin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-((R)-1-phenyl-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-diisopropyl-acetamide, N-Butyl-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cyclohexyl-N-isopropyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-chloro-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2,3-difluoro-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-fluoro-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-propyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-piperidin-1-yl-ethanone 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-isopropyl-N-(2-methoxy-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[2-(4-fluoro-phenyl)-ethyl]-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((S)-1-cyclohexyl-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-m-tolyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-isobutyl-piperazin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(1,3-dihydro-isoindol-2-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[(S)-1-(2-fluoro-phenyl)-ethyl]-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[2-(2,5-dimethyl-phenyl)-ethyl]-acetamide N-Butyl-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-N-isopropyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-((S)-1-phenyl-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methoxy-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-fluoro-benzyl)-N-methyl-acetamide, 4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazine-1-carboxylic acid amide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-N-(2,3-dihydroxy-propyl)-acetamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(4-methyl-piperazine-1-carbonyl)-piperidin-1-yl]-methanone, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-(1,1-dioxo-tetrahydro-1λ6-thiophen-3-yl)-urea, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid cyclopentylamide, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-(1,1-dioxo-tetrahydro-1λ6-thiophen-3-yl)-urea, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid cyclopentyl-methyl-amide, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid phenylamide, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid cyclobutylamide, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid ([1,4]dioxan-2-ylmethyl)-amide, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid methylamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-methoxy-phenyl)-N-methyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(2-trifluoromethyl-pyrrolidin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cycloheptylmethyl-acetamide, N-But-3-enyl-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-propyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-2-methyl-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-isopropyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((S)-1-cyclopropyl-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-acetamide 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-methyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-propyl-N-(tetrahydro-pyran-4-yl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-m-tolyl-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-dimethylamino-piperidin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-sec-butyl-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cyclohexyl-acetamide 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cyclohexylmethyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cycloheptyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(3,4-dihydro-1H-isoquinolin-2-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-fluoro-5-methyl-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-chloro-5-methyl-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2,5-dimethyl-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-2-methyl-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-4-methyl-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-chloro-2-methyl-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-fluoro-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-isopropyl-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-chloro-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-methyl-butyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-pentyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-hexyl-acetamide, N-Benzyl-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-acetamide 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-phenethyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-propyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-dipropyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-propyl-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2,4-difluoro-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2,5-difluoro-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(6-methyl-3,4-dihydro-2H-quinolin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-isopropyl-N-phenyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3,5-dimethyl-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-isopropyl-N-methyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-(3-methyl-butyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((R)-1-phenyl-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((S)-1-phenyl-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[2-(3-fluoro-phenyl)-ethyl]-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4aR,8aS)-octahydro-isoquinolin-2-yl-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-isopropyl-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-butyl-phenyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(5,6,7,8-tetrahydro-naphthalen-2-yl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((R)-1-p-tolyl-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-isopropyl-piperazin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(hexahydro-cyclopenta[c]pyrrol-2-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((R)-1,2-dimethyl-propyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-fluoro-3-methyl-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-methoxy-phenyl)-N-methyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(3,3-dimethyl-piperidin-1-yl)-ethanone 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(1-ethyl-propyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-diisobutyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-m-tolyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-isobutyl-N-methyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cyclopentyl-N-methyl-acetamide 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-p-tolyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-p-tolyl-acetamide, N-((R)-sec-Butyl)-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((S)-2-methyl-butyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((R)-1-phenyl-propyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((S)-1-methyl-pentyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((R)-1,2,2-trimethyl-propyl)-acetamide 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-o-tolyl-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-((S)-2-methyl-piperidin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[(R)-1-(4-fluoro-phenyl)-ethyl]-acetamide 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-fluoro-benzyl)-N-methyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-benzyl)-N-methyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-(3-methyl-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-fluoro-4-methyl-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-5-methyl-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-ethoxymethyl-piperidin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-ethoxy-piperidin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-methoxymethyl-piperidin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-(tetrahydro-pyran-4-yl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[(S)-1-(3-fluoro-phenyl)-ethyl]-acetamide and 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(3-pyrrolidin-1-yl-azetidin-1-yl)-ethanone.

In the specification, where indicated, the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, —$SO_2CH_3$, $SCH_3$, lower-alkylsufonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, carbamoyl-lower cycloalkyl, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl, aryl which can be optionally substituted by the above substituents and lower-alkyl which can optionally be substituted with halogen, hydroxy, $NH_2$, N(H, lower-alkyl) or N(lower-alkyl)$_2$. Preferred substituents for the alkyl, aryl, heteroaryl and heterocycle rings are halogen, lower alkoxy, lower alkyl and amino.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" or "heterocycloalkyl" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I as well as their salts that have at least one asymmetric carbon atom may be present as racemic mixtures or different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or sturctural isomeric form depicted in formula I above.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier/excipient material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"$IC_{50}$" refers to the concentration of a particular compound required to inhibit 50% of a specific measured activity. $IC_{50}$ can be measured, inter alia, as is described subsequently.

The compounds of the present invention can be prepared according to schemes 1-4. Briefly, the process involves the formation of imidazoline 5 either by condensation of a tetra-substituted 1,2-diamine 2 with an aromatic acid 3 to form a monoamide derivative 4 followed by cyclodehydration (scheme 1) or by reaction of a tetrasubstituted 1,2-diamine 2 with an aromatic ester 6 in the presence of trimethylaluminum (procedure described by Moormann, A. E. et al *J. Med. Chem.* 1990, 33, 614-626, scheme 2). Alternatively, the diamine 2 can react with the aldehyde 7 in the presence of iodine and potassium carbonate (procedure described by Ishihara, M. and Togo, H. *Synlett* 2006, 2, 227-230 and *ibid Tetrahedron* 2007, 63, 1474-1480, scheme 3) to give the imidazoline 5. The acids 3, esters 6, and aldehydes 7 are either commercially available or prepared using the procedures known in the art.

Scheme 1: Coupling of diamines with acids

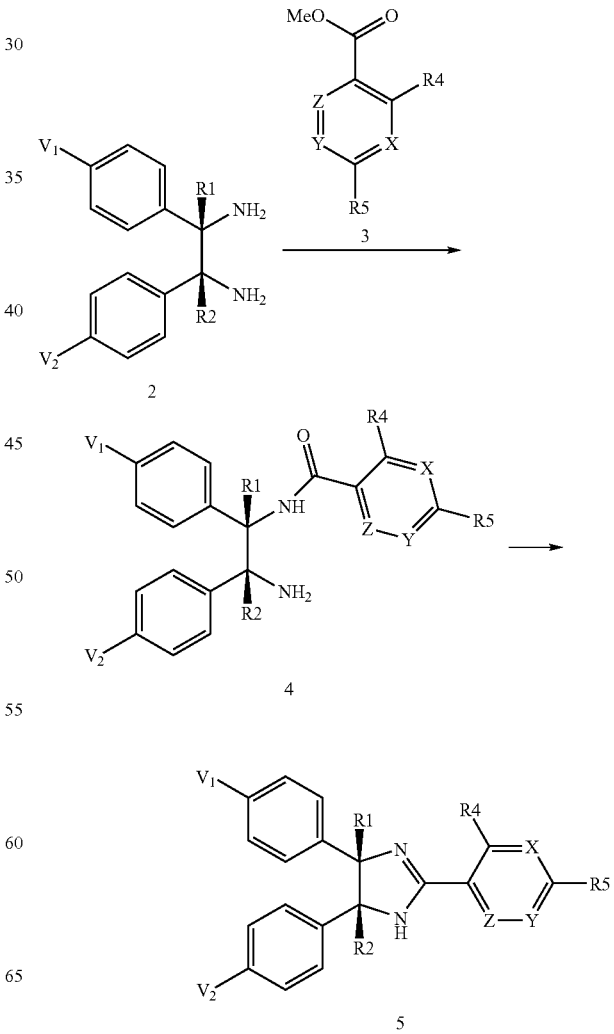

Scheme 2: Coupling of diamines with esters

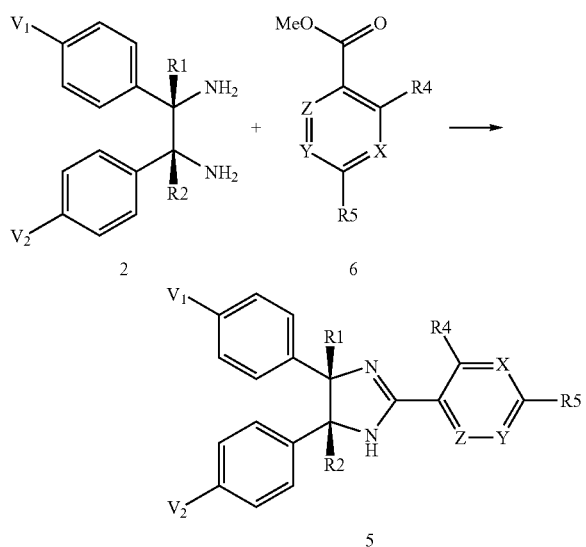

Scheme 3: Coupling of diamines with aldehydes

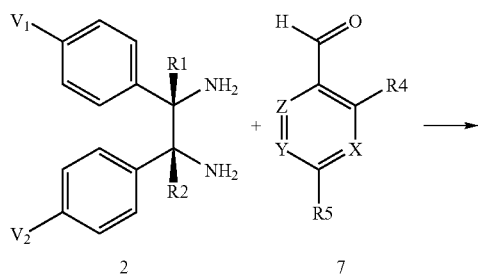

-continued

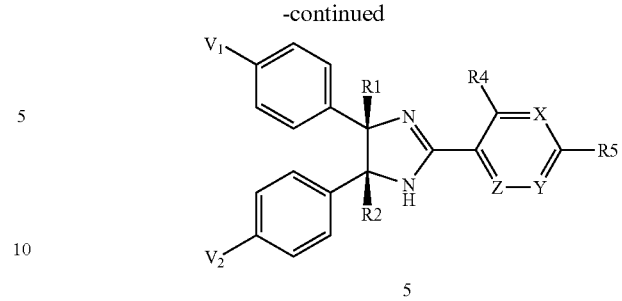

Treatment of the imidazoline 5 with phosgene in the presence of a base such as triethylamine gives the racemic carbamoyl chloride 8 (scheme 4). Coupling of the racemic carbamoyl chloride 8 with appropriate R amine groups provides the compounds of the formula 1 as racemic mixtures. Many R amine groups are commercially available. If it is desired, R amine groups can be prepared using synthetic methods known in the art. Suitable processes for making these R amine groups are provided in the examples. If it is desired to prepare the optically active compounds of formula 1, the enantiomers of the racemic carbamoyl chloride 8 can be separated using chiral chromatography. Coupling of the desired enantiomer 8A with appropriate R amine groups provides the optically active compounds of the formula 1. Also the optically active compounds of formula 1 can be obtained by chiral separation of the racemic mixtures of 1.

The absolute stereochemistry of the preferred enantiomer of 1 is determined based on the crystal structure of its complex with the human MDM2 (Vassilev et al. *Science,* 2004, 303, 844-848).

Scheme 4: Derivatization of the imidazolines

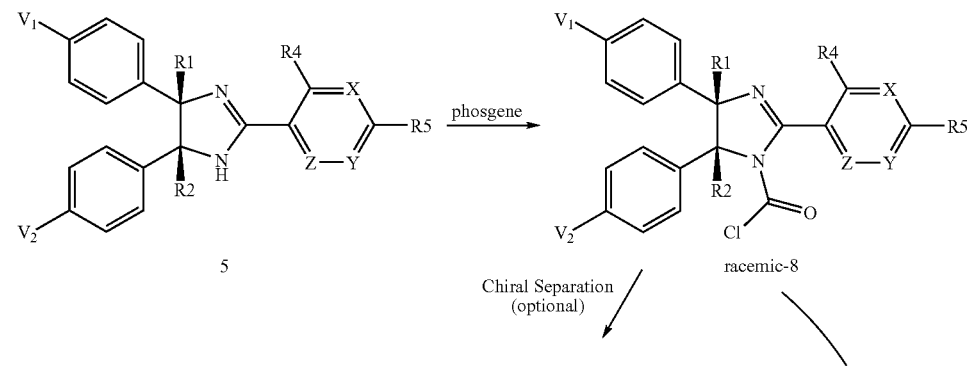

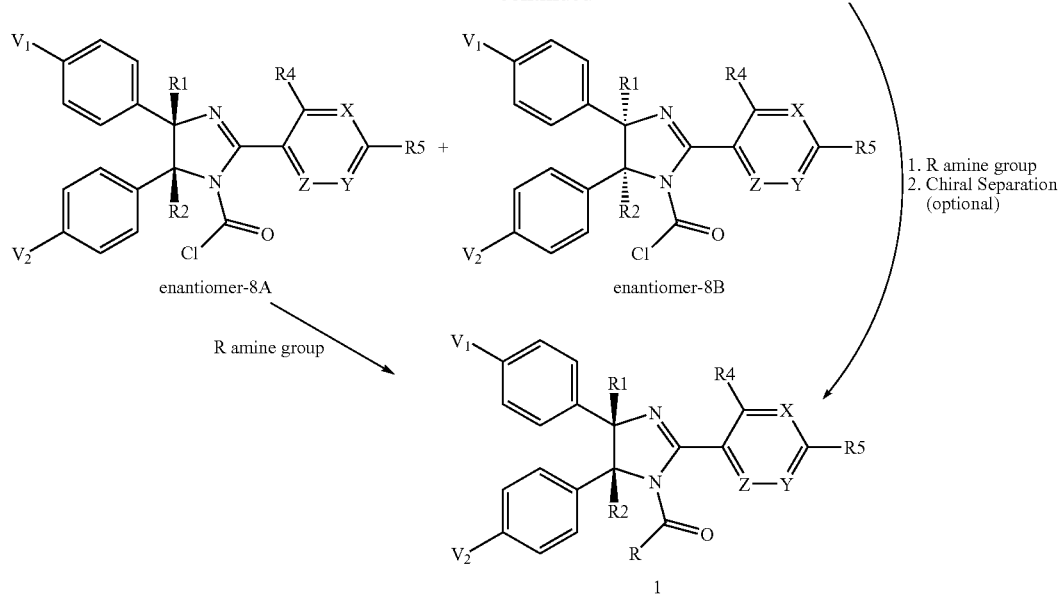

enantiomer-8A     enantiomer-8B

1. R amine group
2. Chiral Separation (optional)

R amine group

1

The following examples and references are provided to aid the understanding of the present invention, the true scope of which is set forth in the appended claims.

EXAMPLE 1

Rac-5-[(4S*,5R*)-4,5-Bis-(4-chloro-phenyl)-4,5-dimethyl-4,5-dihydro-1H-imidazol-2-yl]-2-tert-butyl-4-ethoxy-pyrimidine

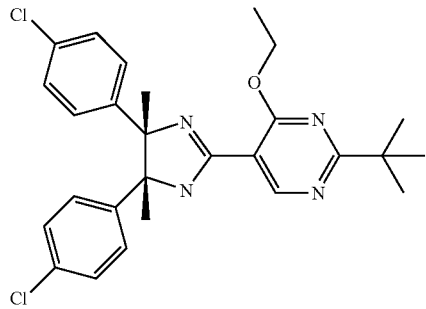 [SMILES: CCOc1nc(C(C)(C)C)ncc1C1=N[C@@](C)(c2ccc(Cl)cc2)[C@@](C)(c2ccc(Cl)cc2)N1]

A solution of 4-hydroxy-2-tert-butyl-pyrimidine-5-carboxylic acid ethyl ester (3 g, 13.377 mmol, prepared in an analogous manner as described for the preparation of 2-ethyl-4-hydroxy-pyrimidine-5-carboxylic acid ethyl ester, Dostert, P. et al. *Eur. J. Med. Chem.* 1982, 17, 437-444) in dimethylformamide (10 mL) was added slowly to the suspension of sodium hydride (800 mg, 60% in mineral oil, Aldrich) in dimethylformamide cooled to 0° C. After the addition, the ice-bath was removed and the reaction mixture was stirred at room temperature for 2 h. The reaction mixture was stirred at room temperature for 4 h then quenched with saturated solution of ammonium chloride. It was extracted with ethyl acetate (2×). The organic extracts were washed with brine (1×), dried over anhydrous sodium sulfate and concentrated. Purification of the crude residue by flash column chromatography (120 g of silica gel, eluting with a gradient of 5-60% ethyl acetate in hexane gave 4-ethoxy-2-tert-butyl-pyrimidine-5-carboxylic acid ethyl ester (1.12 g, 30%).

meso-2,3-Bis-(4-chlorophenyl)-2,3-butanediamine (1.838 g, 5.95 mmol, prepared as described in Ding, Q. et al. WO2007063013) was added in small portions to a solution of trimethylaluminum (3 mL, 2M solution in toluene, Aldrich) in 15 mL of toluene at 0° C. The mixture was stirred for 10 min at 0° C., 15 min at room temperature and heated at 90° C. for 30 min. After cooling down to 0° C., a solution of 4-ethoxy-2-tert-butyl-pyrimidine-5-carboxylic acid ethyl ester (1.5 g, 5.95 mmol) in 5 mL of toluene was added. The mixture was heated to reflux for 2 d then cooled to 0° C. and quenched by the dropwise addition of 1M solution of potassium sodium tartrate (50 mL). The mixture was stirred vigorously overnight and extracted with ethyl acetate. The organic layer was washed with 1M solution of potassium sodium tartrate, water and brine. It was then dried over anhydrous magnesium sulfate, filtered and concentrated under reduced pressure to give a light yellow solid. Purification by chromatography on silica gel, eluting with 10-30% of ethyl acetate in hexane provided 880 mg of rac-5-[(4S*,5R*)-4,5-bis-(4-chloro-phenyl)-4,5-dimethyl-4,5-dihydro-1H-imidazol-2-yl]-2-tert-butyl-4-ethoxy-pyrimidine.

EXAMPLE 2

(4S,5R)-2-(2-tert-Butyl-4-ethoxy-pyrimidin-5-yl)-4,
5-bis-(4-chloro-phenyl)-4,5-dimethyl-4,5-dihydro-
imidazole-1-carbonyl chloride

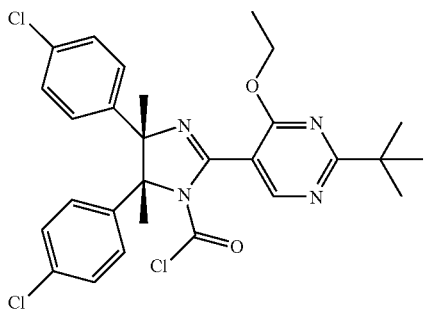 [SMILES: CCOc1nc(C(C)(C)C)ncc1C1=N[C@@](C)(c2ccc(Cl)cc2)[C@@](C)(c2ccc(Cl)cc2)N1C(=O)Cl]

To a solution of rac-5-[(4S*,5R*)-4,5-bis-(4-chloro-phenyl)-4,5-dimethyl-4,5-dihydro-1H-imidazol-2-yl]-2-tert-butyl-4-ethoxy-pyrimidine (850 mg, 1.71 mmol) and triethylamine (600 uL, 4.28 mmol) in 10 mL of dichloromethane at 0° C. was added 1.88 mL solution of 20% phosgene in toluene (Fluka). After stirring for 30 min the mixture was concentrated to dryness under reduced pressure. Purification by flash column chromatography on silica gel, eluting with 10-20% of ethyl acetate in hexane provided 861 mg of rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride as an off-white solid.

Chiral separation of rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride (449 mg) by supercritical fluid chromatography (Berger Instrument Multi-Gram II, Daicel ChiralPak OJ-H 3×25 cm, 35° C. at 100 bar, eluting with 15% acetonitrile in carbon dioxide) gave the title compound (pre peak, 200 mg).

EXAMPLE 3

2-{4-[(4S,5R)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-acetamide

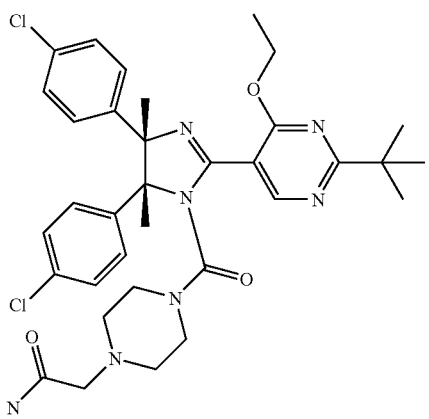 [SMILES: CCOc1nc(C(C)(C)C)ncc1C1=N[C@@](C)(c2ccc(Cl)cc2)[C@@](C)(c2ccc(Cl)cc2)N1C(=O)N1CCN(CC(N)=O)CC1]

rac-(4S*,5R*)-2-(2-tert-Butyl-4-ethoxy-pyrimidin-5-yl)-4,5-bis-(4-chloro-phenyl)-4,5-dimethyl-4,5-dihydro-imidazole-1-carbonyl chloride (110 mg, 0.2 mmol) was added to the mixture of triethylamine (140 uL, 1.0 mmol) and 2-piperazin-1-yl-acetamide dihydrochloride (52 mg, 0.24 mmol, Matrix Scientific) in 3 mL of dichloromethane at 0° C. The mixture was allowed to react for 16 h then concentrated to dryness under reduced pressure. Purification of the crude residue by flash column chromatography (40 g of silica gel, eluting with a gradient of 5 to 100% of 9:1 ethyl acetate-methanol and ethyl acetate) provided 105 mg of rac-2-{4-[(4S*,5R*)-2-(2-tert-butyl-4-ethoxy-pyrimidin-5yl)-4,5-bis-(4-chloro-phenyl)-4,5-dimethyl-4,5-dihydro-imidazole-1-carbonyl]-piperazin-1-yl}-acetamide as white solids.

Chiral separation of 95 mg of the enantiomers by supercritical fluid chromatography (Berger Instrument Multi-Gram II, Daicel ChiralPak OD-H 3×25 cm, 35° C. at 100 bar, eluting with 35% methanol in carbon dioxide) gave the title compound (post peak, 46 mg). HR-MS (ES, m/z) calculated for $C_{34}H_{42}N_7O_3Cl_2$ [(M+H)$^+$] 666.2721, observed 666.2723.

EXAMPLE 4

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(1,1-dioxo-hexahydro-thiopyran-4-yl)-piperazin-1-yl]-methanone

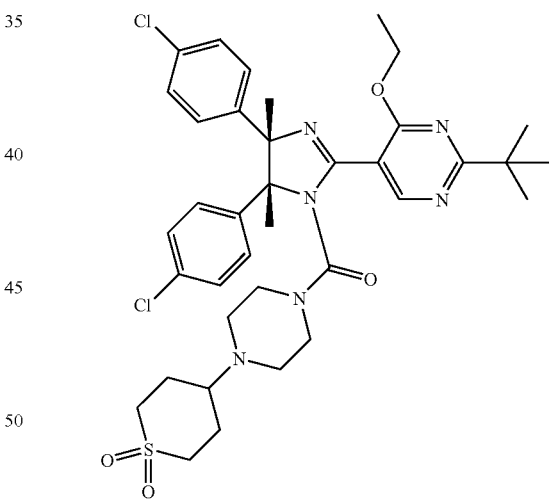

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 1-(1,1-dioxo-hexahydro-thiopyran-4-yl)-piperazine dihydrochloride (prepared as described in Ding, Q. et al. WO2007063013) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 40% methanol in carbon dioxide). HR-MS (ES, m/z) calculated for $C_{37}H_{47}Cl_2N_6O_4S$ [(M+H)$^+$] 741.2751, observed 741.2751.

EXAMPLE 5

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(3-methanesulfonyl-propyl)-piperazin-1-yl]-methanone

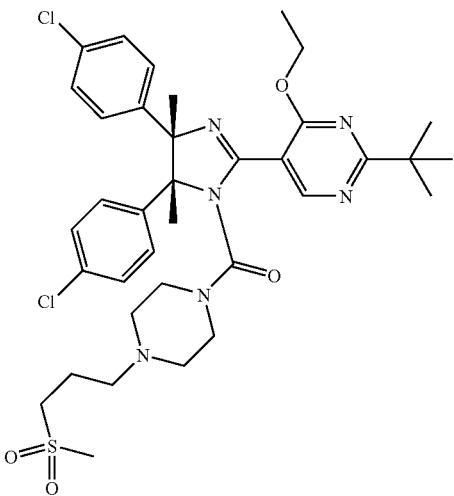 [SMILES: CCOc1nc(C(C)(C)C)ncc1C1=N[C@@](C)(c2ccc(Cl)cc2)[C@@](C)(c2ccc(Cl)cc2)N1C(=O)N1CCN(CCCS(C)(=O)=O)CC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 4-[3-(methylsulfonyl)propyl]-piperazine (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3'25 cm, 35° C. at 100 bar, eluting with 35% methanol in carbon dioxide). HR-MS (ES, m/z) calculated for $C_{36}H_{47}Cl_2N_6O_4S$ [(M+H)$^+$] 729.2751, observed 729.2749.

EXAMPLE 6

Rac-5-[(4S*,5R*)-4,5-Bis-(4-chloro-phenyl)-4,5-dimethyl-4,5-dihydro-1H-imidazol-2-yl]-2-tert-butyl-4-ethoxy-pyridine

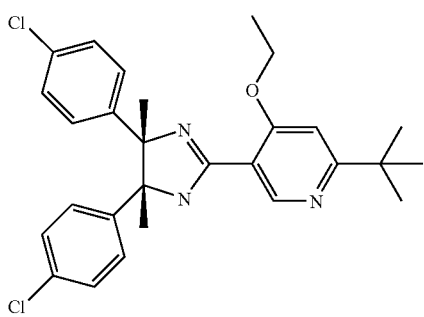 [SMILES: CCOc1cc(C(C)(C)C)ncc1C1=N[C@@](C)(c2ccc(Cl)cc2)[C@@](C)(c2ccc(Cl)cc2)N1]

6-tert-Butyl-4-oxo-4H-pyran-3-carboxylic acid ethyl ester (300 mg, 1.34 mmol, prepared according to the literature procedure by McCombie, S. W. et al. *J. Org. Chem.* 1991, 56, 4963-4967) and ammonium acetate (300 mg, 4.16 mmol) were combined in ethanol/water (8 mL/3 ml). Acetic acid was added and reaction mixture was heated at 95° C. for 30 min. It was concentrated and basified with aqueous sodium hydroxide and extracted with methylene chloride (2×20 mL). The combined organic layers were dried over magnesium sulfate, filtered and evaporated to give 6-tert-butyl-4-hydroxy-nicotinic acid ethyl ester as a white solid (230 mg, 76%). LR-MS: 224 [(M+H)$^+$]

6-tert-Butyl-4-hydroxy-nicotinic acid ethyl ester (110 mg, 0.5 mmol) was dissolved in dimethylformamide (6 mL). Potassium carbonate was added followed by dropwise addition of ethyl iodine (0.13 mL, 1.5 mmol). The reaction mixture was stirred at room temperature overnight. It was diluted with water and brine and extracted with diethyl ether (2×30 mL). Combined organics washed with brine/water, dried and concentrated to give 6-tert-butyl-4-ethoxy-nicotinic acid ethyl ester as viscous oil (100 mg, 80%). LR-MS: 251 [(M+H)$^+$]

6-tert-Butyl-4-ethoxy-nicotinic acid ethyl ester (100 mg, 0.4 mmol) was dissolved in ethanol. Potassium hydroxide (46 mg, 0.8 mmol) in 1 mL of water was added. It was stirred at 80° C. for 1 hr, checked by thin layer chromatography and LC-MS until the reaction was completed. The mixture was concentrated at high vacuum and dried overnight to give 6-tert-butyl-4-ethoxy-nicotinic acid as a white solid which was used in the next reaction without further purification. The 6-tert-butyl-4-ethoxy-nicotinic acid was heated at 70° C. in 3 mL of SOCl$_2$ for 2 hrs. The reaction mixture containing 6-tert-butyl-4-ethoxy-nicotinoyl chloride was concentrated to dryness then suspended in tetrahydrofuran (6 mL) with 0.1 mL of triethylamine and used for the next reaction immediately.

To a solution of meso-2,3-bis(4-chloro-phenyl)-butane-2,3-diamine (309 mg, 1 mmol, prepared as described in Ding, Q. et al. WO2007063013) in tetrahydrofuran (6 mL) at −10° C. (brine/ice), was added diisopropylethylamine (0.7 mL, 4 mmol) followed by drop wise addition of 6-tert-butyl-4-ethoxy-nicotinoyl chloride (280 mg, 1.2 mmol) in tetrahydrofuran (6 mL). It was stirred at −10° C. for 50 min then diluted with brine (8 mL) and water (10 mL). The reaction mixture was extracted with ethyl acetate (2×15 mL). The organic layer was separated, dried over magnesium sulfate, filtered and evaporated. Purification was by chromatography (methylene chloride to 50% ethyl acetate/methylene chloride) to give rac-N-[(1S*,2R*)-2-amino-1,2-bis-(4-chloro-phenyl)-1-methyl-propyl]-6-tert-butyl-4-ethoxy-nicotinamide as a semi solid (440 mg, 85%). LR-MS: 514 [(M+H)$^+$]

rac-N-[(1S*,2R*)-2-Amino-1,2-bis-(4-chloro-phenyl)-1-methyl-propyl]-6-tert-butyl-4-ethoxy-nicotinamide (200 mg, 0.4 mmol) was dissolved in toluene (8 mL) and phosphorus oxychloride (0.2 mL, 0.83 mmol) was added. The reaction mixture was refluxed under nitrogen overnight. It was allowed to cool to room temperature and poured into ice water, basified with saturated solution of sodium sulfate (10 mL). Reaction mixture was extracted with ethyl acetate (2×20 mL) and methylene chloride (2×10 mL). The combined organic layers were washed with brine and water, dried with magnesium sulfate, filtered and evaporated. Purification was by chromatography (silica gel, eluting with 0-30% ethyl acetate/methylene chloride, then 5% methanol/methylene chloride) to give rac-5-[(4S*,5R*)-4,5-bis-(4-chloro-phenyl)-4,5-dimethyl-4,5-dihydro-1H-imidazol-2-yl]-2-tert-butyl-4-ethoxy-pyridine as a solid. (20 mg). LR-MS: 496 [(M+H)$^+$]

EXAMPLE 7

Rac-(4S*,5R*)-2-(6-tert-Butyl-4-ethoxy-pyridin-3-yl)-4,5-bis-(4-chloro-phenyl)-4,5-dimethyl-4,5-dihydro-imidazole-1-carbonyl chloride

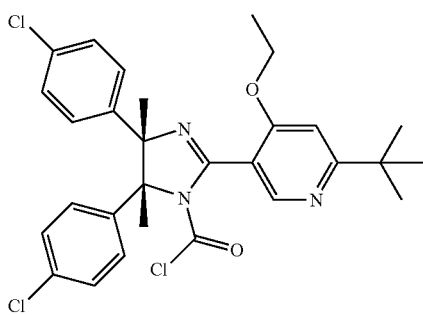 [SMILES: CCOc1cc(C(C)(C)C)ncc1C1=N[C@@](C)(c2ccc(Cl)cc2)[C@@](C)(c2ccc(Cl)cc2)N1C(=O)Cl]

To a solution of rac-5-[(4S*,5R*)-4,5-bis-(4-chloro-phenyl)-4,5-dimethyl-4,5-dihydro-1H-imidazol-2-yl]-2-tert-butyl-4-ethoxy-pyridine (20 mg) and triethylamine (200 uL, 1.43 mmol) in 5 mL of methylene chloride at 0° C. was added 0.3 mL of 1.9 M phosgene in toluene solution (Fluka). After stirring for 30 min the mixture was taken up in methylene chloride and washed with water, dried over anhydrous sodium sulfate, filtered and concentrated to give rac-(4S*,5R*)-2-(6-tert-butyl-4-ethoxy-pyridin-3-yl)-4,5-bis-(4-chloro-phenyl)-4,5-dimethyl-4,5-dihydro-imidazole-1-carbonyl chloride as a white solid (22 mg). It was used in the next reaction without purification

EXAMPLE 8

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3-methanesulfonyl-propyl)-piperazin-1-yl]-methanone

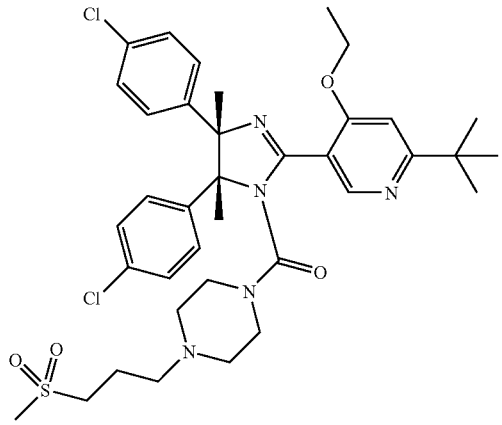 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CCCS(C)(=O)=O)CC1]

1-(3-Methanesulfonyl-propyl)-piperazine (30 mg, 0.11 mmol, prepared as described in Fotouhi, N. et al. WO 2005110996) was suspended in 5 mL of methylene chloride and cooled to 0° C. Triethylamine was added followed by drop wise addition of rac-(4S*,5R*)-2-(6-tert-butyl-4-ethoxy-pyridin-3-yl)-4,5-bis-(4-chloro-phenyl)-4,5-dimethyl-4,5-dihydro-imidazole-1-carbonyl chloride in 2 mL of methylene chloride. The mixture was stirred at room temperature for 30 min and then taken up in methylene chloride and washed successively with 10% sodium hydrogen carbonate and water. The methylene chloride phase was dried over anhydrous sodium sulfate, filtered and concentrated under reduced pressure. Purification by chromatography on silica gel eluting with methylene chloride/methanol (95:5) gave rac-[(4S*,5R*)-2-(6-tert-butyl-4-ethoxy-pyridin-3-yl)-4,5-bis-(4-chloro-phenyl)-4,5-dimethyl-4,5-dihydro-imidazol-1-yl]-[4-(3-methanesulfonyl-propyl)-piperazin-1-yl]-methanone as a white solid (16 mg). HR-MS (ES, m/z) calculated for $C_{37}H_{48}N_5O_4SCl_2$ [(M+H)$^+$] 728.2799, observed 728.2793.

The enantiomers were then separated by supercritical fluid chromatography (Berger Instrument Multi-Gram II, Daicel ChiralPak OD-H 3×25 cm, 35° C. at 100 bar, eluting with 20% ethanol/acetonitrile in carbon dioxide). HR-MS (ES, m/z) calculated for $C_{37}H_{48}N_5O_4SCl_2$ [(M+H)$^+$] 728.2799, observed 728.2798.

EXAMPLE 9

Rac-[(4S*,5R*)-2-(6-tert-Butyl-2-ethoxy-pyridin-3-yl)-4,5-bis-(4-chloro-phenyl)-4,5-dimethyl-4,5-dihydro-imidazol-1-yl]-[4-(3-methanesulfonyl-propyl)-piperazin-1-yl]-methanone

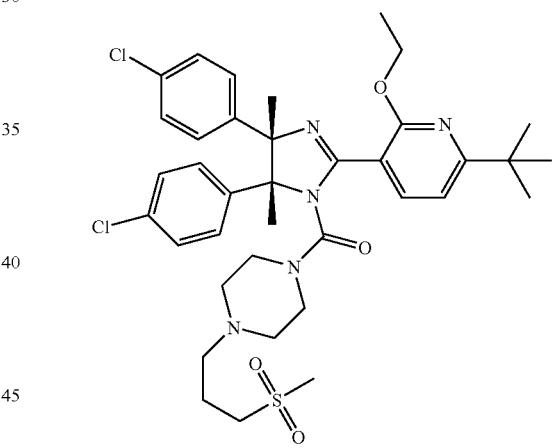

6-tert-Butyl-2-ethoxy-nicotinonitrile (1.10 g, 5.3 mmol, prepared according to the literature procedure by Youngdale, G. A. and T. F. Oglia J. Med. Chem. 1985, 28, 1791) and potassium hydroxide (1.80 g, 32.3 mmol) were combined in ethanol/water (30 ml/7 ml) and heated at 90° C. overnight. The reaction was concentrated, acidified with 2N hydrochloric acid solution (20 ml) and extracted with chloroform. The combined organic layers were washed with water, dried over anhydrous magnesium sulfate and concentrated to give 6-tert-butyl-2-ethoxy-nicotinic acid as a white solid (1.00 g, 95%) LR-MS: 222 [(M–H)$^+$]

Starting from 6-tert-butyl-2-ethoxy-nicotinic acid and following the scheme of examples 6-8, rac-[(4S*,5R*)-2-(6-tert-butyl-2-ethoxy-pyridin-3-yl)-4,5-bis-(4-chloro-phenyl)-4,5-dimethyl-4,5-dihydro-imidazol-1-yl]-[4-(3-methanesulfonyl-propyl)-piperazin-1-yl]-methanone was prepared in a similar manner. HR-MS (ES, m/z) calculated for $C_{37}H_{48}N_5O_4SCl_2$ [(M+H)$^+$] 728.2799, observed 728.2797.

EXAMPLE 10

Rac-5-[(4S*,5R*)-4,5-Bis-(4-chloro-phenyl)-4,5-dimethyl-4,5-dihydro-1H-imidazol-2-yl]-2,4-dimethoxy-pyrimidine

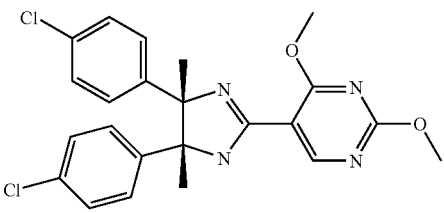 [SMILES: COc1ncc(C2=N[C@@](C)(c3ccc(Cl)cc3)[C@@](C)(c3ccc(Cl)cc3)N2)c(OC)n1]

The title compound was prepared using the procedure described by Ishihara, M. and Togo, H. *Synlett* 2006, 2, 227-230 and *ibid Tetrahedron* 2007, 63,1474-1480. Iodine (172 mg, 0.68 mg) was dissolved in tert-butanol (20 mL) and potassium carbonate (300 mg, 2.2 mmol) was added. 2,4-Dimethoxy-5-formylpyrimidine (100 mg, 0.6 mmol, Frontier) and (rac)-2,3-Bis(4-chloro-phenyl)-butane-2,3-diamine (200 mg, 0.65 mmol) was added to the mixture. This was warmed to 65° C. for 2 h. This was cooled, diluted with ethyl ether (50 mL) and filtered through Celite. After evaporating to dryness, the residue was purified by flash column chromatography (silica gel, eluting with 2-5% methanol/methylene chloride) to give rac-5-[(4S*,5R*)-4,5-bis-(4-chloro-phenyl)-4,5-dimethyl-4,5-dihydro-1H-imidazol-2-yl]-2,4-dimethoxy-pyrimidine.

EXAMPLE 11

Rac-[(4S*,5R*)-4,5-Bis-(4-chloro-phenyl)-2-(2,4-dimethoxy-pyrimidin-5-yl)-4,5-dimethyl-4,5-dihydro-imidazol-1-yl]-[4-(3-methanesulfonyl-propyl)-piperazin-1-yl]-methanone

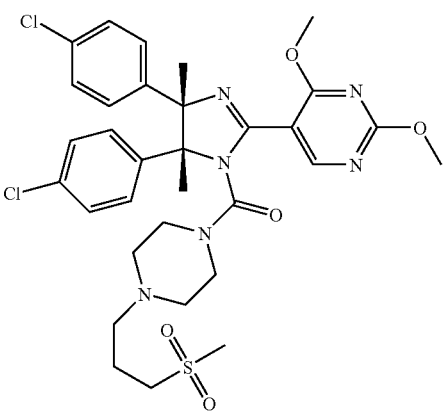 [SMILES: COc1ncc(C2=N[C@@](C)(c3ccc(Cl)cc3)[C@@](C)(c3ccc(Cl)cc3)N2C(=O)N2CCN(CCCS(C)(=O)=O)CC2)c(OC)n1]

rac-5-[(4S*,5R*)-4,5-bis-(4-chloro-phenyl)-4,5-dimethyl-4,5-dihydro-1H-imidazol-2-yl]-2,4-dimethoxy-pyrimidine was converted to the corresponding carbonyl chloride using phosgene and triethylamine in a manner similar to example 2. The carbonyl chloride was then reacted with 4-[3-(methylsulfonyl)propyl]-piperazine (prepared as described in Fotouhi, N. et al. WO 2005110996) following the synthetic procedure as described in example 3 to give the title compound. HR-MS (ES, m/z) calculated for $C_{32}H_{38}N_6O_5SCl_2$ [(M+H)$^+$] 689.2074, observed 689.2072.

EXAMPLE 12

Rac-[(4S*,5R*)-4,5-Bis-(4-chloro-phenyl)-2-(2-dimethylamino-4-ethoxy-pyrimidin-5-yl)-4,5-dimethyl-4,5-dihydro-imidazol-1-yl]-[4-(3-methanesulfonyl-propyl)-piperazin-1-yl]-methanone

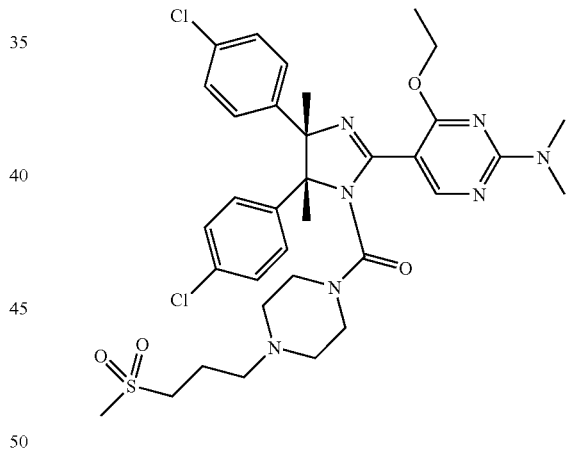

4-Ethoxy-2-methanesulfonyl-pyrimidine-5-carboxylic acid ethyl ester (60 mg, 0.22 mmol) was dissolved in acetonitrile. Dimethylamine (0.6 mL, 2.0 M in methanol) was added and reaction mixture was stirred in seal tube at 80° C. for 3 h. The reaction progress was checked by LC-MS. After the reaction was completed, it was concentrated to give 2-dimethylamino-4-ethoxy-pyrimidine-5-carboxylic acid ethyl ester as a white solid (50 mg). LR-MS: 239 [(M+H)$^+$]

Starting from 2-dimethylamino-4-ethoxy-pyrimidine-5-carboxylic acid ethyl ester and following the same scheme as examples 6-8, rac-[(4S*,5R*)-4,5-bis-(4-chloro-phenyl)-2-(2-dimethylamino-4-ethoxy-pyrimidin-5-yl)-4,5-dimethyl- 4,5-dihydro-imidazol-1-yl]-[4-(3-methanesulfonyl-propyl)-piperazin-1-yl]-methanone was prepared in a similar manner. LR-MS: 716 [(M+H)+]

EXAMPLE 13

Rac-[(4S*,5R*)-4,5-Bis-(4-chloro-phenyl)-2-(4-ethoxy-2-pyridin-3-yl-pyrimidin-5-yl)-4,5-dimethyl-4,5-dihydro-imidazol-1-yl]-[4-(3-methanesulfonyl-propyl)-piperazin-1-yl]-methanone

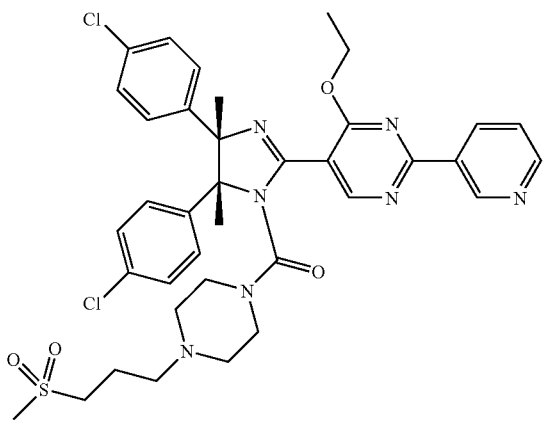 [SMILES: CCOc1nc(-c2cccnc2)ncc1C1=N[C@@](C)(c2ccc(Cl)cc2)[C@@](C)(c2ccc(Cl)cc2)N1C(=O)N1CCN(CCCS(C)(=O)=O)CC1]

4-Hydroxy-2-pyridin-3-yl-pyrimidine-5-carboxylic acid ethyl ester was synthesized according to the literature procedure (Yurugi, S. et al. *Chem. Pharm. Bull.* 1971, 19, 2354)

Starting from 4-hydroxy-2-pyridin-3-yl-pyrimidine-5-carboxylic acid ethyl ester and following the same scheme as examples 6-8, rac-[(4S*,5R*)-4,5-Bis-(4-chloro-phenyl)-2-(4-ethoxy-2-pyridin-3-yl-pyrimidin-5-yl)-4,5-dimethyl-4,5-dihydro-imidazol-1-yl]-[4-(3-methanesulfonyl-propyl)-piperazin-1-yl]-methanone was prepared in a similar manner. HR-MS (ES, m/z) calculated for $C_{37}H_{42}N_7O_4SCl_2$ [(M+H)+] 750.2391, observed 750.2389.

EXAMPLE 14

Rac-[(4S*,5R*)-4,5-Bis-(4-chloro-phenyl)-2-(2,6-dimethoxypyridin-3-yl)-4,5-dimethyl-4,5-dihydro-imidazol-1-yl]-[4-(3-methanesulfonylpropyl)-piperazin-1-yl]-methanone

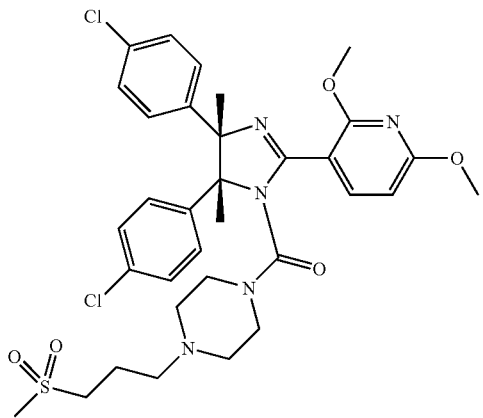

Starting with 2,6-dimethoxy-3-formylpiridine (Frontier), rac-[(4S*,5R*)-4,5-Bis-(4-chloro-phenyl)-2-(2,6-dimethoxypyridin-3-yl)-4,5-dimethyl-4,5-dihydro-imidazol-1-yl]-[4-(3-methanesulfonylpropyl)-piperazin-1-yl]-methanone was prepared using a scheme similar to that of examples 10-11. HR-MS (ES, m/z) calculated for $C_{33}H_{39}N_5O_5SCl_2$ [(M+H)+] 688.2122, observed 688.2116.

EXAMPLE 15

4-[(4S,5R)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-2-one

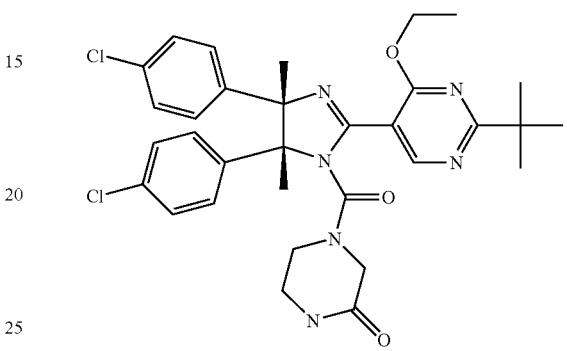

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 2-piperazinone (Avocado Organics) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). HR-MS (ES, m/z) calculated for $C_{32}H_{37}N_6O_3Cl_2$ [(M+H)+] 623.2299, observed 623.2298.

EXAMPLE 16

Rac-[(4S*,5R*)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(2-hydroxy-ethyl)-piperazin-1-yl]-methanone

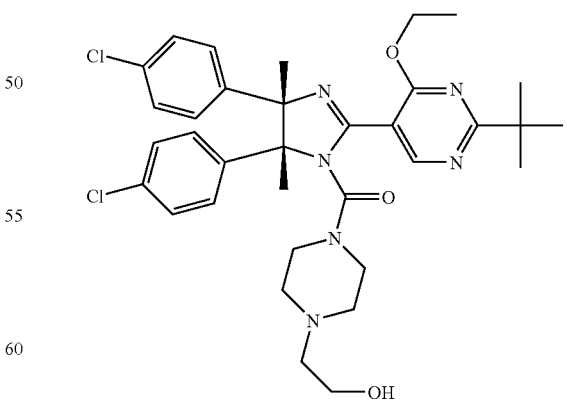

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 2-piperazin-1-ylethanol (Chemical Dynamics) to give the title compound. HR-MS (ES, m/z) calculated for $C_{34}H_{42}N_6O_3Cl_2$ $[(M+H)^+]$ 653.2768 observed 653.2766.

EXAMPLE 17

[2-(2-tert-Butyl-4-ethoxy-pyrimidin-5-yl)-4,5-bis-(4-chloro-phenyl)-4,5-dimethyl-4,5-dihydro-imidazol-1-yl]-piperazin-1-yl-methanone

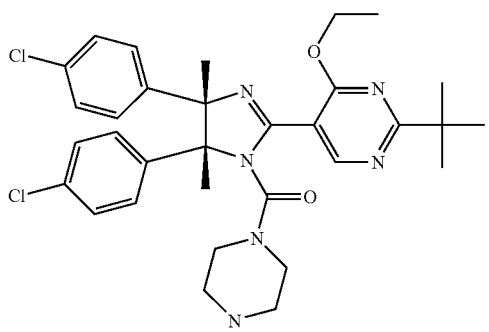 [SMILES: CCOc1nc(C(C)(C)C)ncc1C1=N[C@@](C)(c2ccc(Cl)cc2)[C@@](C)(c2ccc(Cl)cc2)N1C(=O)N1CCNCC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with piperazine (Aldrich) to give the title compound. HR-MS (ES, m/z) calculated for $C_{32}H_{39}N_6O_2Cl_2$ $[(M+H)^+]$ 609.2506 observed 609.2509.

EXAMPLE 18

[2-(2-tert-Butyl-4-ethoxy-pyrimidin-5-yl)-4,5-bis-(4-chloro-phenyl)-4,5-dimethyl-4,5-dihydro-imidazol-1-yl]-[4-((R)-3,4-dihydroxy-butyl)-piperazin-1-yl]-methanone

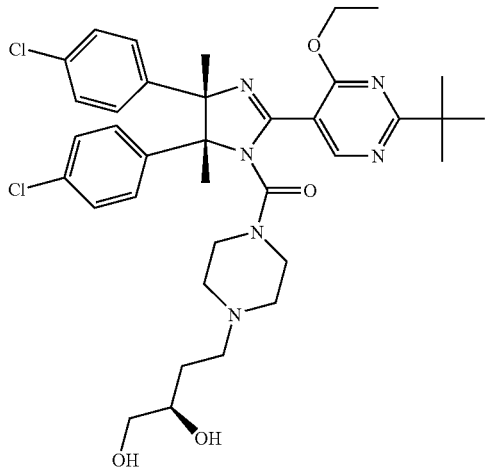 [SMILES: CCOc1nc(C(C)(C)C)ncc1C1=N[C@@](C)(c2ccc(Cl)cc2)[C@@](C)(c2ccc(Cl)cc2)N1C(=O)N1CCN(CC[C@@H](O)CO)CC1]

The mixture of [2-(2-tert-butyl-4-ethoxy-pyrimidin-5-yl)-4,5-bis-(4-chloro-phenyl)-4,5-dimethyl-4,5-dihydro-imidazol-1-yl]-piperazin-1-yl-methanone (80 mg, 0.13 mmol), methanesulfonic acid 2-((R)-2,2-dimethyl-[1,3]dioxolan-4-yl)-ethyl ester (437 mg, 1.95 mmol, prepared from 2-((R)-2,2-dimethyl-[1,3]dioxolan-4-yl)-ethanol and methanesulfonyl chloride in the present of triethylamine) and diisopropylethylamine (110 uL, 0.65 mmol) in dry dimethylformamide (3 mL) was heated in the microwave at 180° C. for 20 min. Upon cooling to room temperature, the reaction mixture was diluted with ethyl acetate and washed with water (5×) and brine. The organic layer was dried over anhydrous sodium sulfate and concentrated under reduced pressure. Purification of the crude residue by flash column chromatography (silica gel, eluting with ethyl acetate and hexane) gave rac-[(4S*,5R*)-2-(2-tert-butyl-4-ethoxy-pyrimidin-5-yl)-4,5-bis-(4-chloro-phenyl)-4,5-dimethyl-4,5-dihydro-imidazol-1-yl]-{4-[2-((R)-2,2-dimethyl-[1,3]dioxolan-4-yl)-ethyl]-piperazin-1-yl}-methanone (45 mg).

To a solution of rac-[(4S*,5R*)-2-(2-tert-butyl-4-ethoxy-pyrimidin-5-yl)-4,5-bis-(4-chloro-phenyl)-4,5-dimethyl-4,5-dihydro-imidazol-1-yl]-{4-[2-((R)-2,2-dimethyl-[1,3]dioxolan-4-yl)-ethyl]-piperazin-1-yl}-methanone (30 mg) in tetrahydrofuran (1 mL) was added 10 drops of trifluoroacetic acid. The mixture was stirred at room temperature for 2 d and concentrated. Purification of the crude residue by reversed phase HPLC (C18-silica gel, eluting with water and acetonitrile) gave the title compound as white solids (6.6 mg). HR-MS (ES, m/z) calculated for $C_{36}H_{47}N_6O_4Cl_2$ $[(M+H)^+]$ 697.3031, observed 697.3027.

EXAMPLE 19

4-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazine-1-carboxylic acid dimethylamide

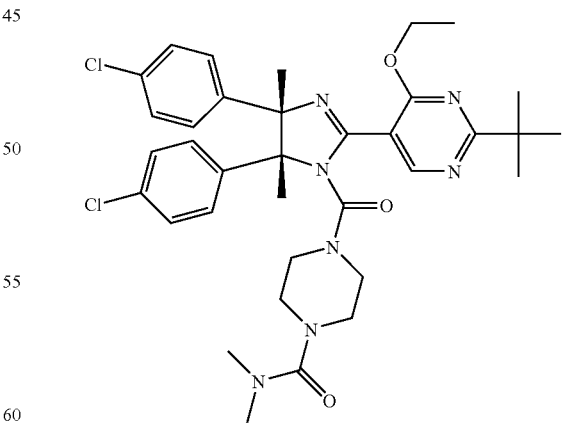

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with piperazine-1-carboxylic acid dimethylamide (Oakwood) to give the title compound. HR-MS (ES, m/z) calculated for $C_{35}H_{44}N_7O_3Cl_2$ [(M+H)⁺] 680.2877, observed 680.288.

EXAMPLE 20

N-(2-{4-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-ethyl)-acetamide

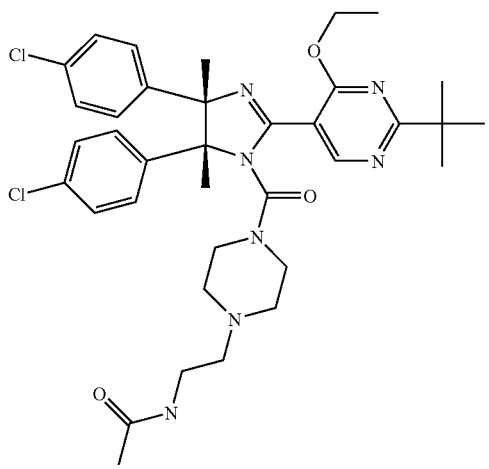 [SMILES: CCOc1nc(C(C)(C)C)ncc1C1=N[C@@](C)(c2ccc(Cl)cc2)[C@@](C)(c2ccc(Cl)cc2)N1C(=O)N1CCN(CCNC(C)=O)CC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with N-(2-piperazin-1-yl-ethyl)-acetamide dihydrochloride (prepared as described in Fotouhi, N. et al. WO 2005110996) to give the title compound. HR-MS (ES, m/z) calculated for $C_{36}H_{46}N_7O_3Cl_2$ [(M+H)⁺] 694.3034, observed 694.3035.

EXAMPLE 21

1-{4-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-ethanone

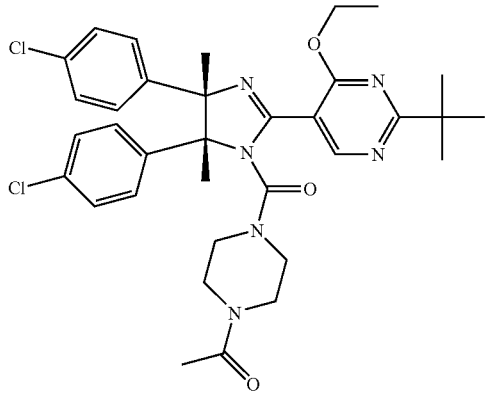 [SMILES: CCOc1nc(C(C)(C)C)ncc1C1=N[C@@](C)(c2ccc(Cl)cc2)[C@@](C)(c2ccc(Cl)cc2)N1C(=O)N1CCN(C(C)=O)CC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 1-acetyl-piperazine (Aldrich) to give the title compound. HR-MS (ES, m/z) calculated for $C_{34}H_{40}N_6O_3Cl_2$ [(M+H)⁺] 651.2612, observed 651.2615.

EXAMPLE 22

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-{4-[2-(2-hydroxy-ethoxy)-ethyl]-piperazin-1-yl}-methanone

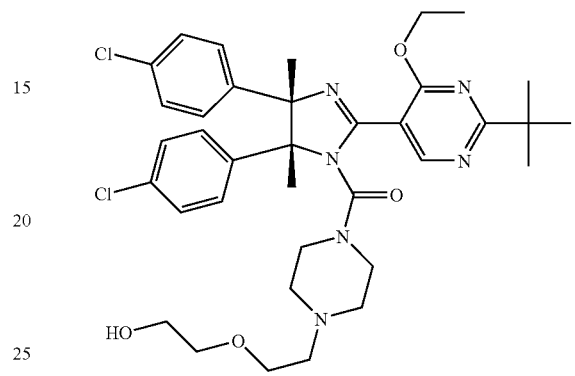

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 1-[2-(2-hydroxy-ethoxy)-ethyl]-piperazine (Aldrich) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). HR-MS (ES, m/z) calculated for $C_{36}H_{46}N_6O_4Cl_2$ [(M+H)⁺] 697.3031, observed 697.3026.

EXAMPLE 23

[2-(2-tert-Butyl-4-ethoxy-pyrimidin-5-yl)-4,5-bis-(4-chloro-phenyl)-4,5-dimethyl-4,5-dihydro-imidazol-1-yl]-[4-(3-hydroxy-propyl)-piperazin-1-yl]-methanone

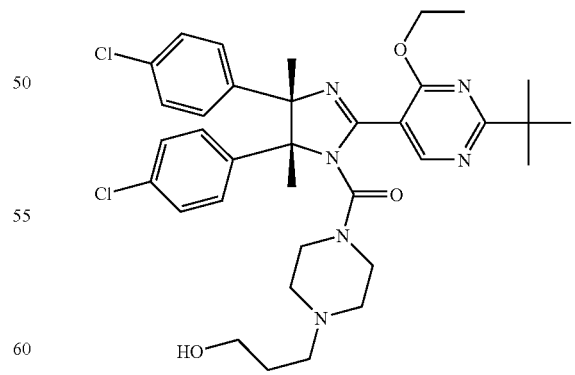

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 3-piperazin-1-yl-propan-1-ol (Acros) to give the title compound as a racemic mixture. HR-MS (ES, m/z) calculated for $C_{35}H_{45}N_6O_3Cl_2$ [(M+H)$^+$] 667.2925, observed 667.2923.

EXAMPLE 24

2-{4-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-N,N-dimethyl-acetamide

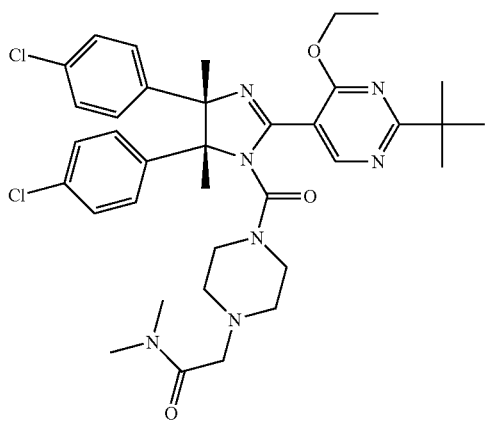 [SMILES: CCOc1nc(C(C)(C)C)ncc1C1=N[C@@](C)(c2ccc(Cl)cc2)[C@@](C)(c2ccc(Cl)cc2)N1C(=O)N1CCN(CC(=O)N(C)C)CC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with N,N-dimethyl-2-piperazin-1-yl-acetamide (Oakwood Products) to give the title compound as a racemic mixture. HR-MS (ES, m/z) calculated for $C_{36}H_{46}N_7O_3Cl_2$ [(M+H)$^+$] 694.3034, observed 694.3035.

EXAMPLE 25

[1,4']Bipiperidinyl-1'-yl-[2-(2-tert-butyl-4-ethoxy-pyrimidin-5-yl)-4,5-bis-(4-chloro-phenyl)-4,5-dimethyl-4,5-dihydro-imidazol-1-yl]-methanone

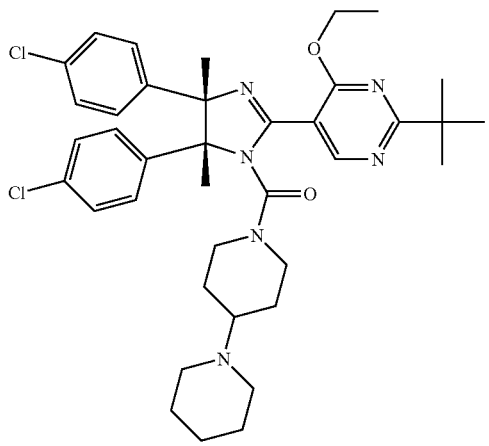 [SMILES: CCOc1nc(C(C)(C)C)ncc1C1=N[C@@](C)(c2ccc(Cl)cc2)[C@@](C)(c2ccc(Cl)cc2)N1C(=O)N1CCC(N2CCCCC2)CC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 4-piperidino-piperidine (Aldrich) to give the title compound as a racemic mixture. HR-MS (ES, m/z) calculated for $C_{38}H_{48}N_6O_2Cl_2$ [(M+H)$^+$] 691.3289, observed 691.3291.

EXAMPLE 26

[2-(2-tert-Butyl-4-ethoxy-pyrimidin-5-yl)-4,5-bis-(4-chloro-phenyl)-4,5-dimethyl-4,5-dihydro-imidazol-1-yl]-(4-hydroxy-[1,4']bipiperidinyl-1'-yl)-methanone

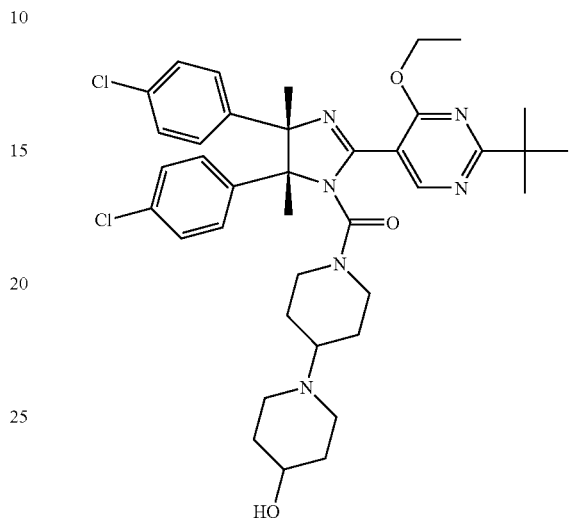

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 4-hydroxy-[1,4']bipiperidine (ChemBridge) to give the title compound as a racemic mixture. HR-MS (ES, m/z) calculated for $C_{38}H_{49}N_6O_3Cl_2$ [(M+H)$^+$] 707.3238, observed 707.3232.

EXAMPLE 27

[2-(2-tert-Butyl-4-ethoxy-pyrimidin-5-yl)-4,5-bis-(4-chloro-phenyl)-4,5-dimethyl-4,5-dihydro-imidazol-1-yl]-(3-hydroxy-[1,4']bipiperidinyl-1'-yl)-methanone

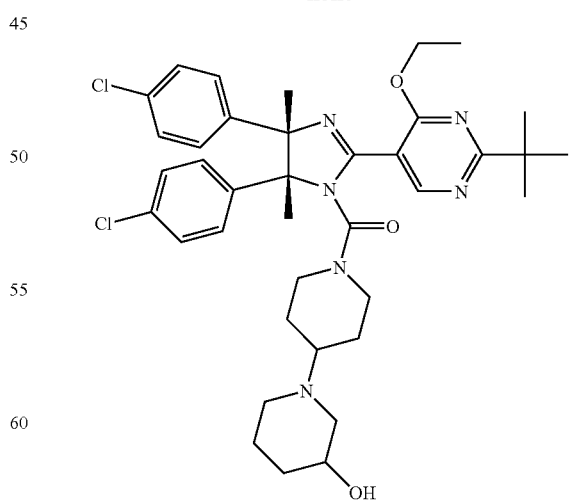

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 3-hydroxy-[1,4']bipiperidine (ChemBridge) to give the title compound as a racemic mixture. HR-MS (ES, m/z) calculated for $C_{38}H_{49}N_6O_3Cl_2$ [(M+H)$^+$] 707.3238, observed 707.3232.

EXAMPLE 28

[2-(2-tert-Butyl-4-ethoxy-pyrimidin-5-yl)-4,5-bis-(4-chloro-phenyl)-4,5-dimethyl-4,5-dihydro-imidazol-1-yl]-(3-hydroxymethyl-[1,4']bipiperidinyl-1'-yl)-methanone

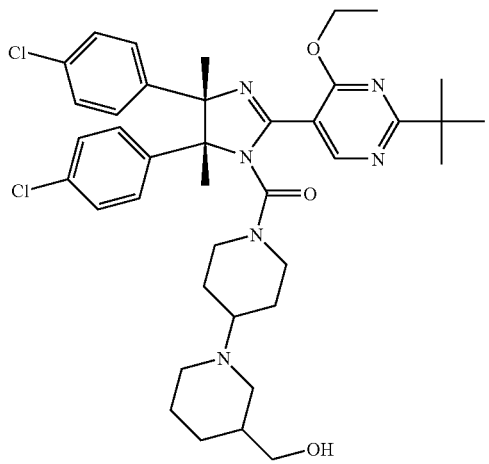 [SMILES: CCOc1nc(C(C)(C)C)ncc1C1=N[C@@](C)(c2ccc(Cl)cc2)[C@@](C)(c2ccc(Cl)cc2)N1C(=O)N1CCC(N2CCCC(CO)C2)CC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 3-hydroxymethyl-[1,4']bipiperidine (ChemBridge) to give the title compound as a racemic mixture. HR-MS (ES, m/z) calculated for $C_{39}H_{51}N_6O_3Cl_2$ [(M+H)$^+$] 721.3394, observed 721.3392.

EXAMPLE 29

[2-(2-tert-Butyl-4-ethoxy-pyrimidin-5-yl)-4,5-bis-(4-chloro-phenyl)-4,5-dimethyl-4,5-dihydro-imidazol-1-yl]-(4-pyrrolidin-1-yl-piperidin-1-yl)-methanone

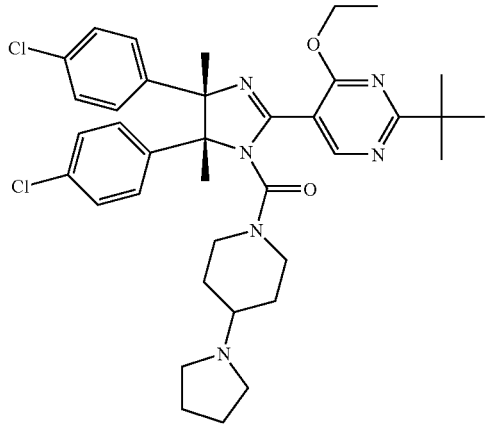 [SMILES: CCOc1nc(C(C)(C)C)ncc1C1=N[C@@](C)(c2ccc(Cl)cc2)[C@@](C)(c2ccc(Cl)cc2)N1C(=O)N1CCC(N2CCCC2)CC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 4-pyrrolidin-1-yl-piperidine (Aldrich) to give the title compound as a racemic mixture. HR-MS (ES, m/z) calculated for $C_{37}H_{47}N_6O_2Cl_2$ [(M+H)$^+$] 677.3132, observed 677.3132.

EXAMPLE 30

[2-(2-tert-Butyl-4-ethoxy-pyrimidin-5-yl)-4,5-bis-(4-chloro-phenyl)-4,5-dimethyl-4,5-dihydro-imidazol-1-yl]-(3-hydroxy-piperidin-1-yl)-methanone

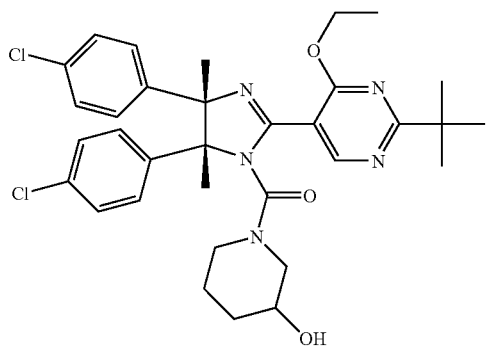 [SMILES: CCOc1nc(C(C)(C)C)ncc1C1=N[C@@](C)(c2ccc(Cl)cc2)[C@@](C)(c2ccc(Cl)cc2)N1C(=O)N1CCCC(O)C1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 3-hydroxy-piperidine (TCI America) to give the title compound as a racemic mixture. HR-MS (ES, m/z) calculated for $C_{33}H_{40}N_5O_3Cl_2$ [(M+H)$^+$] 624.2503, observed 624.2502.

EXAMPLE 31

[2-(2-tert-Butyl-4-ethoxy-pyrimidin-5-yl)-4,5-bis-(4-chloro-phenyl)-4,5-dimethyl-4,5-dihydro-imidazol-1-yl]-(3-hydroxymethyl-piperidin-1-yl)-methanone

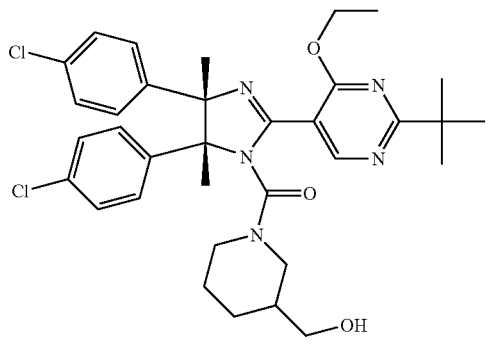 [SMILES: CCOc1nc(C(C)(C)C)ncc1C1=N[C@@](C)(c2ccc(Cl)cc2)[C@@](C)(c2ccc(Cl)cc2)N1C(=O)N1CCCC(CO)C1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 3-hydroxymethyl-piperidine (Aldrich) to give the title compound as a racemic mixture. HR-MS (ES, m/z) calculated for $C_{34}H_{42}N_5O_3Cl_2$ [(M+H)$^+$] 638.2659, observed 638.266.

EXAMPLE 32

1-{1-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperidin-4-yl}-[1,4]diazepan-5-one

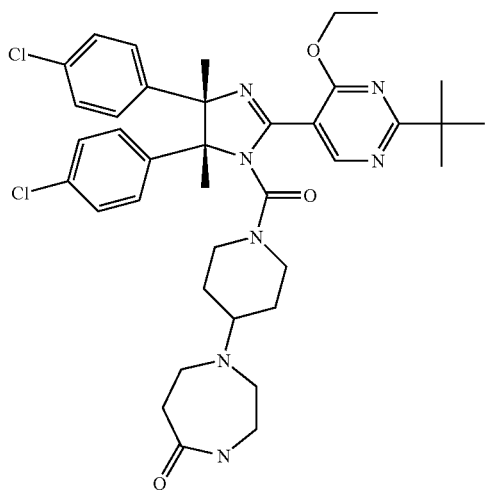 [SMILES: CCOc1nc(C(C)(C)C)ncc1C1=N[C@@](C)(c2ccc(Cl)cc2)[C@@](C)(c2ccc(Cl)cc2)N1C(=O)N1CCC(N2CCNC(=O)CC2)CC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 1-piperidin-4-yl-[1,4]diazepan-5-one (ChemBridge) to give the title compound as a racemic mixture. HR-MS (ES, m/z) calculated for $C_{38}H_{48}N_7O_3Cl_2$ [(M+H)$^+$] 720.319, observed 720.3196.

EXAMPLE 33

[2-(2-tert-Butyl-4-ethoxy-pyrimidin-5-yl)-4,5-bis-(4-chloro-phenyl)-4,5-dimethyl-4,5-dihydro-imidazol-1-yl]-(4-hydroxy-piperidin-1-yl)-methanone

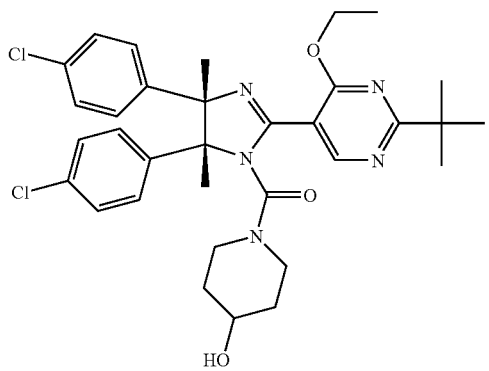 [SMILES: CCOc1nc(C(C)(C)C)ncc1C1=N[C@@](C)(c2ccc(Cl)cc2)[C@@](C)(c2ccc(Cl)cc2)N1C(=O)N1CCC(O)CC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 4-hydroxy-piperidine (Aldrich) to give the title compound as a racemic mixture. HR-MS (ES, m/z) calculated for $C_{33}H_{40}N_5O_3Cl_2$ [(M+H)$^+$] 624.2503, observed 624.2505.

EXAMPLE 34

1-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperidine-4-carboxylic acid amide

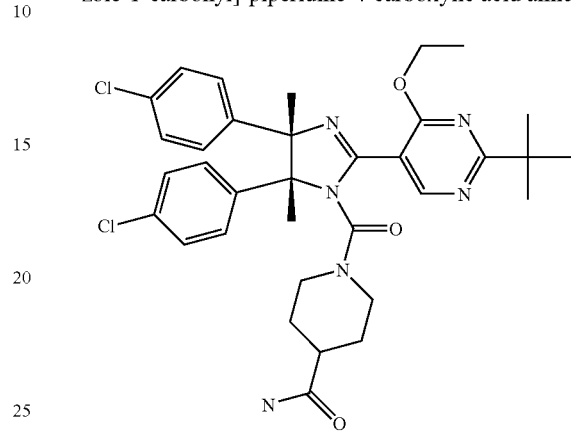

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with piperidine-4-carboxylic acid amide (isonipecotamide, Aldrich) to give the title compound as a racemic mixture. HR-MS (ES, m/z) calculated for $C_{34}H_{41}N_6O_3Cl_2$ [(M+H)$^+$] 651.2612, observed 651.2613.

EXAMPLE 35

1-[2-(2-tert-Butyl-4-ethoxy-pyrimidin-5-yl)-4,5-bis-(4-chloro-phenyl)-4,5-dimethyl-4,5-dihydro-imidazole-1-carbonyl]-piperidine-3-carboxylic acid amide

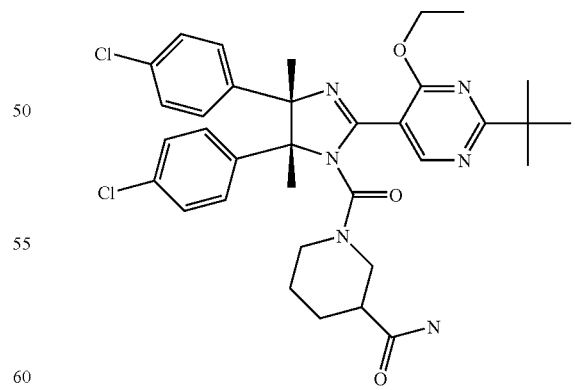

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with piperidine-3-carboxylic acid amide (nipecotamide, Aldrich) to give the title compound as a racemic mixture. HR-MS (ES, m/z) calculated for $C_{34}H_{41}N_6O_3Cl_2$ $[(M+H)^+]$ 651.2612, observed 651.2616.

EXAMPLE 36

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-[4-((S)-2,3-dihydroxy-propyl)-piperazin-1-yl]-methanone

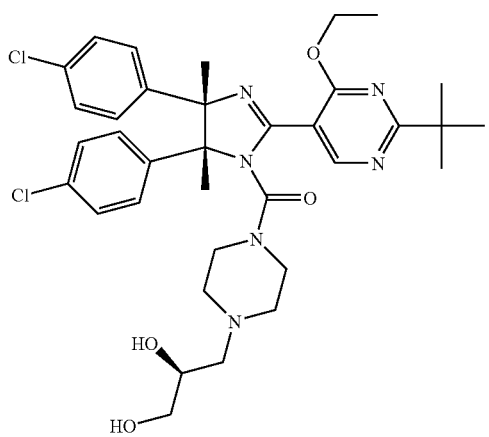 [SMILES: CCOc1nc(C(C)(C)C)ncc1C1=N[C@@](C)(c2ccc(Cl)cc2)[C@@](C)(c2ccc(Cl)cc2)N1C(=O)N1CCN(C[C@H](O)CO)CC1]

The mixture of [2-(2-tert-butyl-4-ethoxy-pyrimidin-5-yl)-4,5-bis-(4-chloro-phenyl)-4,5-dimethyl-4,5-dihydro-imidazol-1-yl]-piperazin-1-yl-methanone (170 mg, 0.28 mmol) and R-glycidol (63 mg, 0.84 mmol) in ethanol (1 mL) was heated in the microwave at 120° C. for 10 min. Upon cooling to room temperature, the reaction mixture was concentrated under reduced pressure. Purification of the crude residue by flash column chromatography (silica gel, eluting with 0-20% methanol in ethyl acetate) gave cis-2-(2-tert-butyl-4-ethoxy-pyrimidin-5-yl)-4,5-bis-(4-chloro-phenyl)-4,5-dimethyl-4,5-dihydro-imidazol-1-yl]-[4-((S)-2,3-dihydroxy-propyl)-piperazin-1-yl]-methanone (98 mg). The diastereomers were then separated by supercritical fluid chromatography (Berger Instrument Multi-Gram II, Daicel ChiralPak OD-H 3×25 cm, 35° C. at 100 bar, eluting with 25% ethanol in carbon dioxide) to give the title compound (post peak, 40 mg). HR-MS (ES, m/z) calculated for $C_{35}H_{45}N_6O_4Cl_2$ $[(M+H)^+]$ 683.2874, observed 683.2871.

EXAMPLE 37

Rac-[(4S*,5R*)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(2-methanesulfonyl-ethyl)-piperazin-1-yl]-methanone

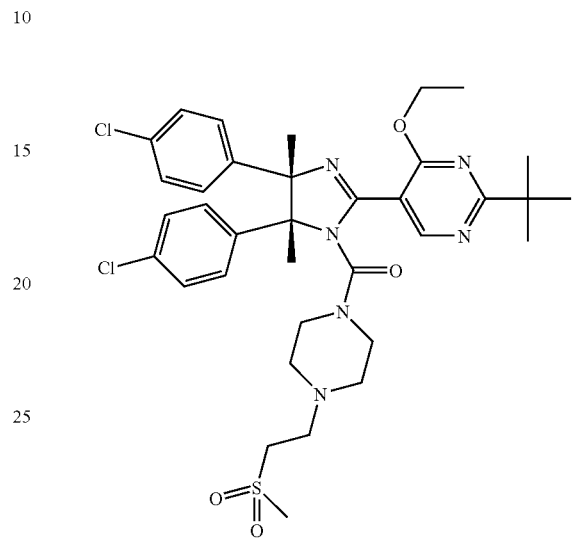

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 1-(2-methanesulfonyl-ethyl)-piperazine (prepared as described in Fotouhi, N. et al. WO 2005110996) to give the title compound. HR-MS (ES, m/z) calculated for $C_{35}H_{45}N_6O_4SCl_2$ $[(M+H)^+]$ 715.2595, observed 715.259.

EXAMPLE 38

Rac-[(4S*,5R*)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(2-methoxy-ethyl)-piperazin-1-yl]-methanone

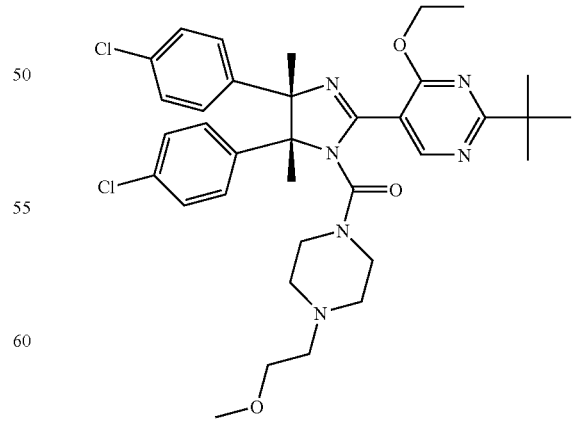

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 4-(2-methoxy-ethyl)-piperazine (Oakwood) to give the title compound. HR-MS (ES, m/z) calculated for $C_{35}H_{45}N_6O_3Cl_2$ [(M+H)$^+$] 667.2925, observed 667.2919.

EXAMPLE 39

Rac-N-tert-Butyl-2-{4-[(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl]-piperazin-1-yl}-acetamide

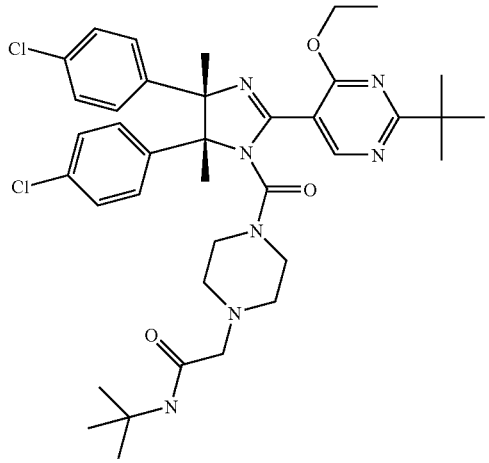 [SMILES: CCOc1nc(C(C)(C)C)ncc1C1=N[C@@](C)(c2ccc(Cl)cc2)[C@@](C)(c2ccc(Cl)cc2)N1C(=O)N1CCN(CC(=O)NC(C)(C)C)CC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with N-tert-butyl-2-piperazin-1-yl-acetamide (Enamine-BB) to give the title compound. HR-MS (ES, m/z) calculated for $C_{38}H_{50}N_7O_3Cl_2$ [(M+H)$^+$] 722.3347, observed 722.3341.

EXAMPLE 40

Rac-2-{4-[(4S*,5R*)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-1-morpholin-4-yl-ethanone

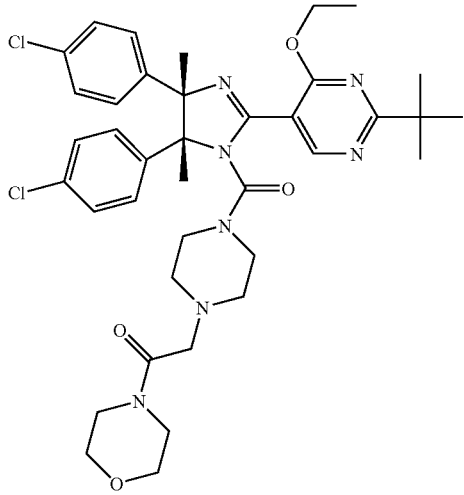 [SMILES: CCOc1nc(C(C)(C)C)ncc1C1=N[C@@](C)(c2ccc(Cl)cc2)[C@@](C)(c2ccc(Cl)cc2)N1C(=O)N1CCN(CC(=O)N2CCOCC2)CC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 4-(1-piperazinylacetyl)-morpholine (Oakwood Products) to give the title compound. HR-MS (ES, m/z) calculated for $C_{38}H_{47}N_7O_4Cl_2$ [(M+H)$^+$] 736.314, observed 736.3134.

EXAMPLE 41

Rac-4-{4-[(4S*,5R*)-2-(2-tert-Butyl-4-ethoxy-pyrimidin-5-yl)-4,5-bis-(4-chloro-phenyl-4,5-dimethyl-4,5-dihydro-imidazole-1-carbonyl]-piperazin-1-yl}-butyronitrile

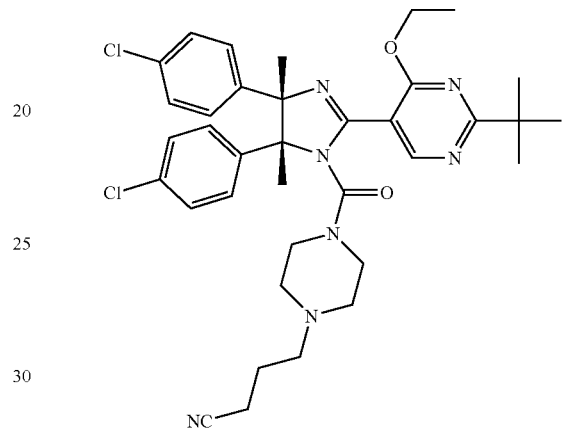

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 4-piperazin-1-yl-butyronitrile (Oakwood Products) to give the title compound. HR-MS (ES, m/z) calculated for $C_{36}H_{44}N_7O_2Cl_2$ [(M+H)$^+$] 676.2928, observed 676.2925.

EXAMPLE 42

Rac-[(4S*,5R*)-4,5-Bis-(4-chloro-phenyl)-2-(4-ethoxy-2-methylsulfanyl-pyrimidin-5-yl)-4,5-dimethyl-4,5-dihydro-imidazol-1-yl]-[4-(3-methanesulfonyl-propyl)-piperazin-1-yl]-methanone

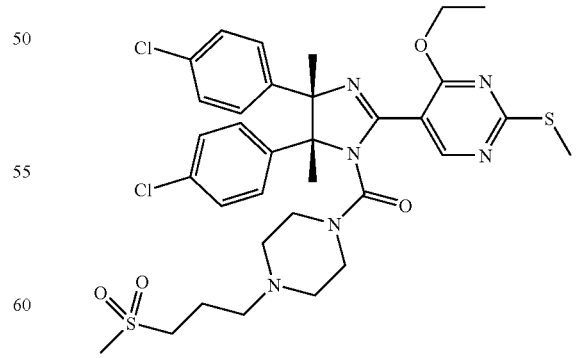

Ethoxy-2-methanesulfonyl-pyrimidine-5-carboxylic acid ethyl ester (1.880 g, 7.76 mmol) was reacted with meso-2,3-bis-(4-chlorophenyl)-2,3-butanediamine (2.0 g, 6.467 mmol, prepared as described in Ding, Q. et al. WO2007063013) in the presence of trimethylaluminum (2M solution in toluene, Aldrich) using the procedure to that described in example 1 to give rac-5-[(4S*,5R*)-4,5-bis-(4-chloro-phenyl)-4,5-dimethyl-4,5-dihydro-1H-imidazol-2-yl]-4-ethoxy-2-methylsulfanyl-pyrimidine as fellow foam (1.024 g, 32%)

In a manner analogous to the method described in examples 2-3, rac-5-[(4S*,5R*)-4,5-bis-(4-chloro-phenyl)-4,5-dimethyl-4,5-dihydro-1H-imidazol-2-yl]-4-ethoxy-2-methylsulfanyl-pyrimidine was coupled with 4-[3-(methylsulfonyl)propyl]-piperazine (prepared as described in Fotouhi, N. et al. WO 2005110996) to give the title compound. HR-MS (ES, m/z) calculated for $C_{33}H_{41}N_6O_4S_2Cl_2$ [(M+H)$^+$] 719.2003, observed 719.2005.

EXAMPLE 43

Rac-4-[(4S*,5R*)-4,5-Bis-(4-chloro-phenyl)-2-(4-ethoxy-2-methylsulfanyl-pyrimidin-5-yl)-4,5-dimethyl-4,5-dihydro-imidazole-1-carbonyl]-piperazin-2-one

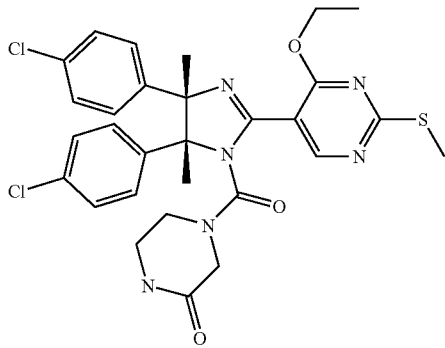 [SMILES: CCOc1nc(SC)ncc1C1=N[C@@](C)(c2ccc(Cl)cc2)[C@@](C)(c2ccc(Cl)cc2)N1C(=O)N1CCNC(=O)C1]

In a manner analogous to the method described in examples 2-3, rac-5-[(4S*,5R*)-4,5-bis-(4-chloro-phenyl)-4,5-dimethyl-4,5-dihydro-1H-imidazol-2-yl]-4-ethoxy-2-methylsulfanyl-pyrimidine was coupled with 2-piperazinone (Alfa) to give the title compound. HR-MS (ES, m/z) calculated for $C_{29}H_{31}N_6O_3SCl_2$ [(M+H)$^+$] 613.155, observed 613.1549.

EXAMPLE 44

Rac-4-[(4S*,5R*)-4,5-Bis-(4-chloro-phenyl)-2-(4-ethoxy-2-morpholin-4-yl-pyrimidin-5-yl)-4,5-dimethyl-4,5-dihydro-imidazole-1-carbonyl]-piperazin-2-one

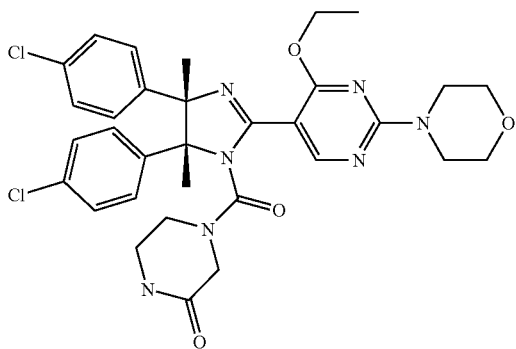 [SMILES: CCOc1nc(N2CCOCC2)ncc1C1=N[C@@](C)(c2ccc(Cl)cc2)[C@@](C)(c2ccc(Cl)cc2)N1C(=O)N1CCNC(=O)C1]

To a solution of rac-4-[(4S*,5R*)-4,5-bis-(4-chloro-phenyl)-2-(4-ethoxy-2-methylsulfanyl-pyrimidin-5-yl)-4,5-dimethyl-4,5-dihydro-imidazole-1-carbonyl]-piperazin-2-one (160 mg, 0.261 mmol) in methylene chloride cooled to 0° C. was added 100 mg of m-chloroperoxybenzoic acid (≦77%, Aldrich). After 10 min, sodium bisulfite solution was added to quench the reaction. The product was extracted with methylene chloride. The organic layer was washed with saturated solution of sodium bicarbonate, brine, dried over Na2SO4 and concentrated to give the crude sulphoxide as light yellow foam. The crude sulphoxide/sulphone was taken in 20 mL of tetrahydrofuran, and morpholine (200 uL, 3.34 mmol, Aldrich) was added. The mixture was heated at reflux overnight. Upon cooling to room temperature, the reaction mixture was concentrated under reduced pressure. Purification of the crude residue by flash column chromatography (silica gel, eluting with 50-100% ethyl acetate in hexanes, then with 0-5% methanol in ethyl acetate) gave the tittle compound (94 mg, 55%). HR-MS (ES, m/z) calculated for $C_{32}H_{36}N_7O_4Cl_2$ [(M+H)$^+$] 652.2201, observed 652.2202.

EXAMPLE 45

Rac-[(4S*,5R*)-4,5-Bis-(4-chloro-phenyl)-2-(2,4-diethoxy-pyrimidin-5-yl)-4,5-dimethyl-4,5-dihydro-imidazol-1-yl]-[4-(3-methanesulfonyl-propyl)-piperazin-1-yl]-methanone

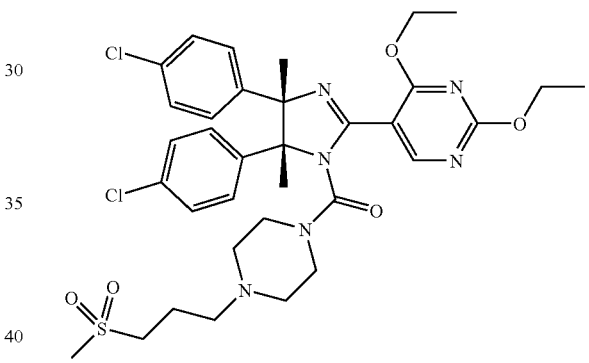

To a solution of rac-5-[(4S*,5R*)-4,5-bis-(4-chloro-phenyl)-4,5-dimethyl-4,5-dihydro-1H-imidazol-2-yl]-4-ethoxy-2-methylsulfanyl-pyrimidine (250 mg, 0.513 mmol) in methanol (10 mL) was added sodium methoxide (4.1 mL, 0.5M solution in methanol, Aldrich). The mixture was stirred at room temperature overnight then concentrated under reduced pressure. The crude residue was taken in ethyl acetate and washed with water and brine. The organic layer was dried over anhydrous sodium sulfate, filtered and concentrate under reduced pressure to give rac-5-[(4S*,5R*)-4,5-bis-(4-chloro-phenyl)-4,5-dimethyl-4,5-dihydro-1H-imidazol-2-yl]-2,4-dimethoxy-pyrimidine (~200 mg). It was then taken in ethanol (15 mL) and sodium ethoxide (58.1 mg, Fluka) was added. The reaction mixture was left in the fridge overnight then concentrated under reduced pressure. The crude residue was taken in ethyl acetate and washed with water and brine. The organic layer was dried over anhydrous sodium sulfate, filtered and concentrate under reduced pressure. Purification of the crude residue by flash column chromatography (12 g of silica gel, eluting with 20-100% ethyl acetate in hexanes then with 3% methanol in ethyl acetate) gave rac-5-[(4S*,5R*)-4,5-bis-(4-chloro-phenyl)-4,5-dimethyl-4,5-dihydro-1H-imidazol-2-yl]-2,4-diethoxy-pyrimidine as an off-white foam (132 mg, 62%). HR-MS (ES, m/z) calculated for $C_{25}H_{27}N_4O_2Cl_2$ [(M+H)$^+$] 485.1506, observed 485.1508.

In a manner analogous to the method described in examples 2-3, rac-5-[(4S*,5R*)-4,5-bis-(4-chloro-phenyl)-4,5-dimethyl-4,5-dihydro-1H-imidazol-2-yl]-2,4-diethoxy-pyrimidine (100 mg, 0.206 mmol) was coupled with 4-[3-(methylsulfonyl)propyl]-piperazine (86.3 mg, 0.309 mmol, prepared as described in Fotouhi, N. et al. WO 2005110996) to give the title compound as off-white solids (133.0 mg, 90%). HR-MS (ES, m/z) calculated for $C_{34}H_{43}N_6O_5SCl_2$ [(M+H)$^+$] 717.2387, observed 717.2387.

EXAMPLE 46

Rac-[(4S*,5R*)-4,5-Bis-(4-chloro-phenyl)-2-(4-methoxy-2-methylsulfanyl-pyrimidin-5-yl)-4,5-dimethyl-4,5-dihydro-imidazol-1-yl]-[4-(3-methanesulfonyl-propyl)-piperazin-1-yl]-methanone

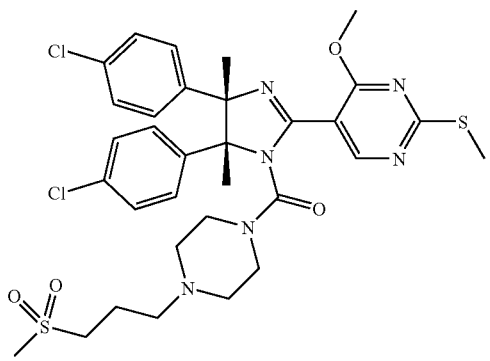

In a manner analogous to the method described in examples 46, rac-5-[(4S*,5R*)-4,5-bis-(4-chloro-phenyl)-4,5-dimethyl-4,5-dihydro-1H-imidazol-2-yl]-4-ethoxy-2-methylsulfanyl-pyrimidine was converted to rac-5-[(4S*,5R*)-4,5-bis-(4-chloro-phenyl)-4,5-dimethyl-4,5-dihydro-1H-imidazol-2-yl]-4-methoxy-2-methylsulfanyl-pyrimidine. HR-MS (ES, m/z) calculated for $C_{23}H_{23}N_4O_2Cl_2$ [(M+H)$^+$] 457.1193, observed 457.1192.

In a manner analogous to the method described in examples 2-3, rac-5-[(4S*,5R*)-4,5-bis-(4-chloro-phenyl)-4,5-dimethyl-4,5-dihydro-1H-imidazol-2-yl]-4-methoxy-2-methylsulfanyl-pyrimidine was coupled with 4-[3-(methylsulfonyl)propyl]-piperazine (prepared as described in Fotouhi, N. et al. WO 2005110996) to give the title compound. HR-MS (ES, m/z) calculated for $C_{32}H_{39}N_6O_4S_2Cl_2$ [(M+H)$^+$] 705.1846, observed 705.1847.

EXAMPLE 47

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetamide

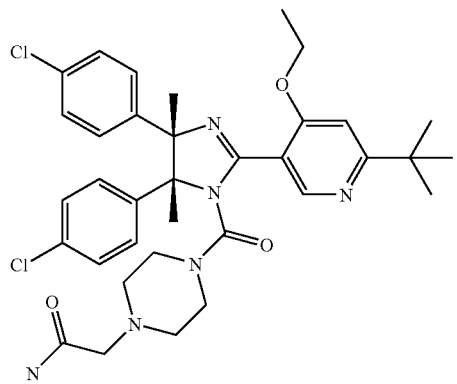 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(N)=O)CC1]

In a manner analogous to the method described in examples 8, rac-(4S*,5R*)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 7) was coupled with 2-piperazin-1-yl-acetamide dihydrochloride (Matrix Scientific) to give the title compound as a racemic mixture. HR-MS (ES, m/z) calculated for $C_{35}H_{43}N_6O_3Cl_2$ [(M+H)$^+$] 665.2768, observed 665.2767.

The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). HR-MS (ES, m/z) calculated for $C_{35}H_{43}N_6O_3Cl_2$ [(M+H)$^+$] 665.2768, observed 665.2765.

EXAMPLE 48

Rac-[(4S*,5R*)-2-(6-tert-Butyl-4-ethoxy-pyridin-3-yl)-4,5-bis-(4-chloro-phenyl)-4,5-dimethyl-4,5-dihydro-imidazol-1-yl]-[4-((S)-2,3-dihydroxy-propyl)-piperazin-1-yl]-methanone

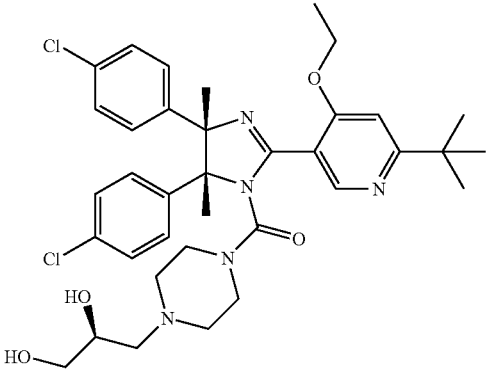 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C[C@H](O)CO)CC1]

(S)-(+)-2,2-Dimethyl-1,3-dioxolan-4-ylmethyl p-toluenesulfonate (286 mg, 1.0 mmol, Aldrich) and piperazine-1-carboxylic acid benzyl ester (235 mg, 1.1 mmol, Aldrich)

were combined with potassium carbonate (148 g, 1.1 mmol) in dry toluene (6 mL) in a 10 mL pressure vessel. This was well stirred and heated to 127° C. for 20 h. The reaction was cooled, diluted with ethyl ether (20 mL) and 20 mL of water. The organics were washed with water, brine, dried (MgSO4) and evaporated to give 4-(S)-(−)-(2,2-dimethyl-[1,3]dioxolan-4-ylmethyl)-piperazine-1-carboxylic acid benzyl ester as a heavy oil which was purified by flash column chromatography (silica gel, eluting with 3% triethylamine and 1:1 ethyl acetate:hexane to ethyl acetate). LR-MS: 334 [(M+H)$^+$]. 4-(S)-(−)-(2,2-dimethyl-[1,3]dioxolan-4-ylmethyl)-piperazine-1-carboxylic acid benzyl ester (220 mg, 0.65 mmol) was dissolved in 20 mL of ethanol and 10% palladium on carbon (50 mg, Aldrich). The mixture was hydrogenated in a Parr reactor at 40 psi for 18 h. The reaction mixture was filtered through Celite and evaporated to give an oil. The oil was mostly dissolved in hexane, treated with Norite, filtered and crystallized from cold hexane to give 1-(S)-(−)-(2,2-dimethyl-[1,3]dioxolan-4-ylmethyl)-piperazine. LR-MS: 200 [(M+H)$^+$].

In a manner analogous to the method described in examples 8, rac-(4S*,5R*)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 7) was coupled with 1-((S)-2,2-dimethyl-[1,3]dioxolan-4-ylmethyl)-piperazine to give the title compound after deprotection with 2N hydrochloric acid. HR-MS (ES, m/z) calculated for $C_{36}H_{46}N_5O_4Cl_2$ [(M+H)$^+$] 682.2926, observed 682.2922.

EXAMPLE 49

1-[(4S,5R)-2-(2-tert-Butyl-4-ethoxy-pyrimidin-5-yl)-4,5-bis-(4-chloro-phenyl)-4,5-dimethyl-4,5-dihydro-imidazole-1-carbonyl]-[1,4]diazepan-5-one

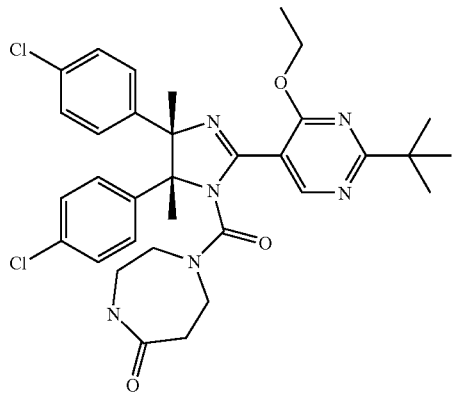 [SMILES: CCOc1nc(C(C)(C)C)ncc1C1=N[C@@](C)(c2ccc(Cl)cc2)[C@@](C)(c2ccc(Cl)cc2)N1C(=O)N1CCNC(=O)CC1]

In a manner analogous to the method described in example 3, (4S,5R)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with [1,4]-diazepan-5-one (Oakwood Products) to give the title compound. HR-MS (ES, m/z) calculated for $C_{33}H_{39}N_6O_3Cl_2$ [(M+H)$^+$] 637.2455, observed 637.2452.

EXAMPLE 50

1-{1-[(4S,5R)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperidin-4-yl}-[1,4]diazepan-5-one

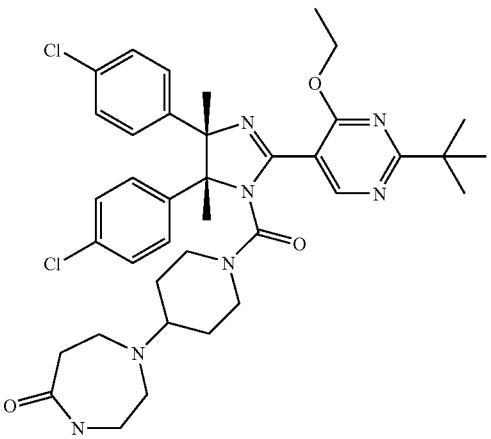 [SMILES: CCOc1nc(C(C)(C)C)ncc1C1=N[C@@](C)(c2ccc(Cl)cc2)[C@@](C)(c2ccc(Cl)cc2)N1C(=O)N1CCC(N2CCNC(=O)CC2)CC1]

In a manner analogous to the method described in example 3, (4S,5R)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 1-piperidin-4-yl-[1,4]diazepan-5-one (ChemBridge) to give the title compound. HR-MS (ES, m/z) calculated for $C_{38}H_{48}N_7O_3Cl_2$ [(M+H)$^+$] 720.3190, observed 720.3190.

EXAMPLE 51

(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl chloride

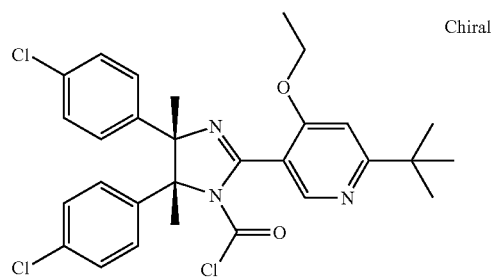 [SMILES: CCOc1cc(C(C)(C)C)ncc1C1=N[C@@](C)(c2ccc(Cl)cc2)[C@@](C)(c2ccc(Cl)cc2)N1C(=O)Cl]

The enantiomers of rac-(4S*,5R*)-2-(6-tert-Butyl-4-ethoxy-pyridin-3-yl)-4,5-bis-(4-chloro-phenyl)-4,5-dimethyl-4,5-dihydro-imidazole-1-carbonyl chloride (example 7) were separated by supercritical fluid chromatography (Berger Instrument Multi-Gram II, Daicel ChiralPak OD-H eluting with 15% acetonitrile in carbon dioxide) to give the title compound as white solids (pre peak).

EXAMPLE 52

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-methanesulfonylmethyl-piperidin-1-yl)-methanone

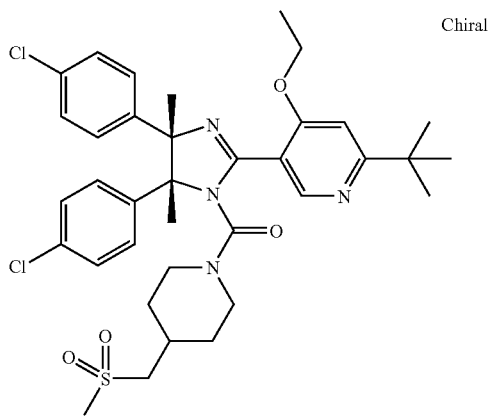 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CS(C)(=O)=O)CC1]

To a solution of N-Boc-4-piperidinemethanol (5.69 g, 26.43 mmol, Aldrich) in pyridine (50 mL) cooled to 0° C. was added tosyl chloride (10.077 g, 52.86 mmol). The reaction mixture was stirred for 3 h. The mixture was then poured into ice water and stirred vigorously. The product was extracted with ethyl acetate. The organic layer was washed with water and dried over anhydrous sodium sulfate. The solids were filtered off, and the filtrate was concentrated to give a light pink oil as crude product of 4-(toluene-4-sulfonyloxymethyl)-piperidine-1-carboxylic acid tert-butyl ester (10 g). It was used without further purification.

To a solution of 4-(toluene-4-sulfonyloxymethyl)-piperidine-1-carboxylic acid tert-butyl ester (9.765 g, 26.43 mmol) in methanol (100mL) at room temperature was added sodium thiomethoxide (5.557 g, 79.29 mmol, Aldrich). The reaction mixture was stirred at room temperature for 2 h then concentrated. The residue was taken in methylene chloride and washed with water (3×) and brine (1×). The organic layer was dried over anhydrous sodium sulfate and concentrated to give a clear oil as crude product of 4-methylsulfanylmethyl-piperidine-1-carboxylic acid tert-butyl ester (6.37 g).

To the solution of 4-methylsulfanylmethyl-piperidine-1-carboxylic acid tert-butyl ester (6.37 g) in methylene chloride (80 mL) cooled to 0° C. was added 3-chloroperoxybenzoic acid (11.636 g, 51.92 mmol). The ice bath was then removed, and the reaction mixture was stirred at room temperature overnight. It was then diluted with methylene chloride and washed with cold solution of sodium hydroxide (1N, 150 mL), water and brine. The organic layer was dried over anhydrous sodium sulfate and concentrated to give a white solid. It was purified by flash column chromatography (330 g of silica gel, eluting with a gradient of 0-10% of methanol in ethyl acetate) to give 4-methanesulfonylmethyl-piperidine-1-carboxylic acid tert-butyl ester as white solid (6 g).

4-Methanesulfonylmethyl-piperidine-1-carboxylic acid tert-butyl ester as white solid (6 g) was suspended in hydrochloric acid (4N solution in 1,4-dioxane) at 0° C. The ice bath was removed and the mixture was stirred at room temperature overnight. It was concentrated to give 4-methanesulfonylmethyl-piperidine hydrochloride as white solid (4.52 g).

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 4-methanesulfonylmethyl-piperidine hydrochloride to give the title compound. HR-MS (ES, m/z) calculated for $C_{36}H_{45}N_4O_4SCl_2$ [(M+H)$^+$] 699.2533, observed 699.2533.

EXAMPLE 53

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methanesulfonyl-ethyl)-piperidin-1-yl]-methanone

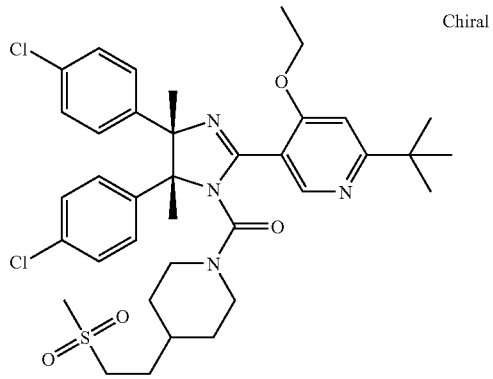 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CCS(C)(=O)=O)CC1]

Starting with N-Boc-4-piperidine-ethanol, 4-(2-methanesulfonyl-ethyl)-piperidine hydrochloride was prepared in an analogous manner as described for the preparation of 4-methanesulfonylmethyl-piperidine hydrochloride (example 52).

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 4-(2-methanesulfonyl-ethyl)-piperidine hydrochloride to give the title compound. HR-MS (ES, m/z) calculated for $C_{37}H_{47}N_4O_4SCl_2$ [(M+H)$^+$] 713.2690, observed 713.2689.

EXAMPLE 54

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(1,1-dioxo-hexahydro-1λ⁶-thiopyran-4-yl)-piperazin-1-yl]-methanone

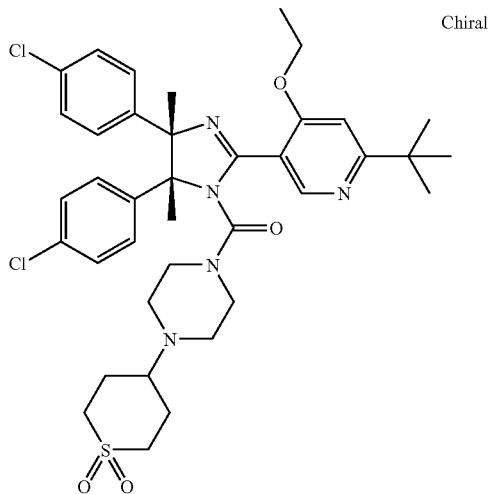 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C2CCS(=O)(=O)CC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-(1,1-dioxo-hexahydro-1λ6-thiopyran-4-yl)-piperazine dihydrochloride (prepared as described in Ding, Q. et al. WO2007063013) to give the title compound. HR-MS (ES, m/z) calculated for $C_{38}H_{48}N_5O_4SCl_2$ [(M+H)$^+$] 740.2799, observed 740.2802.

EXAMPLE 55

3-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-propane-1-sulfonic acid amide

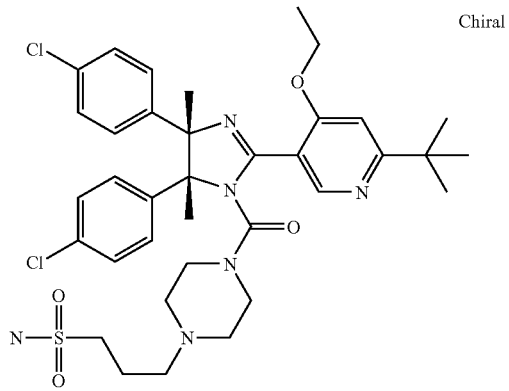 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CCCS(N)(=O)=O)CC1]

In a three-neck round bottom flask equipped with argon inlet was charged with anhydrous tetrahydrofuran and 3-chloropropane sulfonyl chloride (500 mg, 2.82 mmol, Aldrich). The flask was cooled down to 0° C., and aminodiphenylmethane (0.49 mL, 2.82 mmol, Fluka) was added, followed by triethylamine (0.59 mL, 4.23 mmol). The reaction mixture was stirred at 0° C. and monitored by the thin layer chromatography. Upon completion, water was added the reaction mixture. It was concentrated then diluted with ethyl acetate. The organic layer was washed with brine, dried over anhydrous sodium sulfate, and concentrated to give 3-chloro-propane-1-sulfonic acid benzhydryl-amide (1.083 g, light brown solid). The crude product was used without further purification.

In a three-neck round bottom flask equipped with argon inlet was charged with anhydrous dimethylformamide and 3-chloro-propane-1-sulfonic acid benzhydryl-amide (893 mg, 2.76 mmol). 1-Boc-piperazine (771 mg, 4.14 mmol, Aldrich) was added, followed by triethylamine (0.77 mL, 5.52 mmol). The mixture was stirred at 60° C. overnight. It was then heated at 120° C. for 10 min and at 180° C. for 15 min using the microwave synthesizer. Upon cooling, the reaction mixture was concentrated, and the residue was diluted with ethyl acetate. The organic layer was washed with water, brine, and concentrated. Purification of the crude residue by flash column chromatography gave 4-[3-(benzhydryl-sulfamoyl)-propyl]-piperazine-1-carboxylic acid tert-butyl ester as yellow oil (688 mg).

A suspension of 4-[3-(benzhydryl-sulfamoyl)-propyl]-piperazine-1-carboxylic acid tert-butyl ester (650 mg, 1.37 mmol) and palladium hydroxide (1.154 g, 1.64 mmol, 20% w from Aldrich) in methanol (10 mL) was hydrogenated at room temperature overnight using a Parr apparatus (50 psi). The reaction mixture was filtered through a Celite cake, and the filtrate was concentrated. Purification of the crude residue by flash column chromatography (40 g of silica gel, eluting with methanol and ethyl acetate) gave 4-(3-sulfamoyl-propyl)-piperazine-1-carboxylic acid tert-butyl ester as an off-white solid (334 mg).

4-(3-Sulfamoyl-propyl)-piperazine-1-carboxylic acid tert-butyl ester (310 mg) in methanol (5 mL) was deprotected with 4 N hydrochloric acid in dioxane (3 mL) to give 3-piperazin-1-yl-propane-1-sulfonic acid amide dihydrochloride (229 mg, white solids)

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 3-piperazin-1-yl-propane-1-sulfonic acid amide dihydrochloride to give the title compound. HR-MS (ES, m/z) calculated for $C_{36}H_{47}N_6O_4SCl_2$ [(M+H)$^+$] 729.2751, observed 729.2754.

EXAMPLE 56

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methanesulfonyl-ethyl)-piperazin-1-yl]-methanone

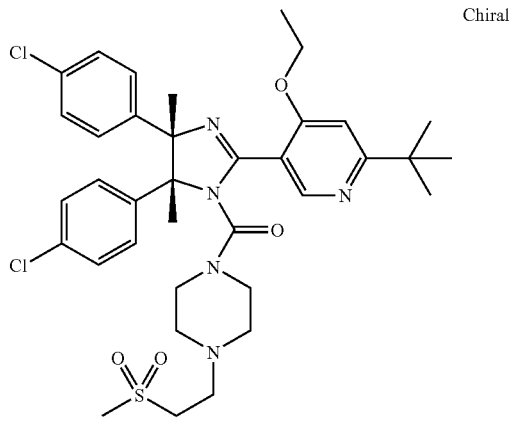 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CCS(C)(=O)=O)CC1]

In a manner analogous to the method described in examples 8, (4S,5R)-2-(6-tert-butyl-4-ethoxy-pyridin-3-yl)-

4,5-bis-(4-chloro-phenyl)-4,5-dimethyl-4,5-dihydro-imidazole-1-carbonyl chloride (example 51) was coupled with 1-(2-methanesulfonyl-ethyl)-piperazine (prepared as described in Fotouhi, N. et al. WO 2005110996) to give the title compound. HR-MS (ES, m/z) calculated for $C_{36}H_{46}Cl_2N_5O_4S$ [(M+H)$^+$] 714.2642, observed 714.2641.

EXAMPLE 57

4-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-butyronitrile

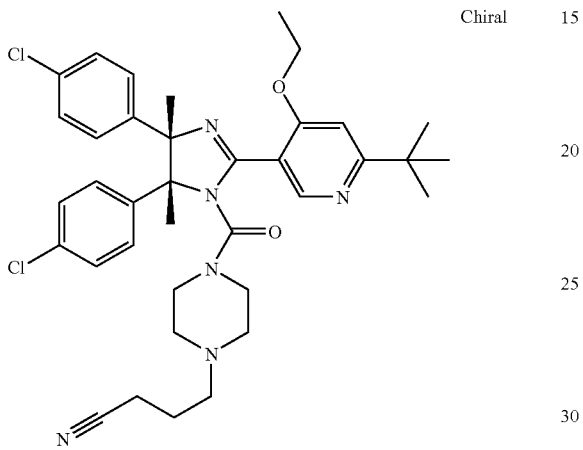

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 4-piperazin-1-yl-butyronitrile (Aldrich) to give the title compound. HR-MS (ES, m/z) calculated for $C_{37}H_{45}Cl_2N_6O_2$ [(M+H)$^+$] 675.2976, observed 675.2972.

EXAMPLE 58

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3,3,3-trifluoro-propyl)-piperazin-1-yl]-methanone

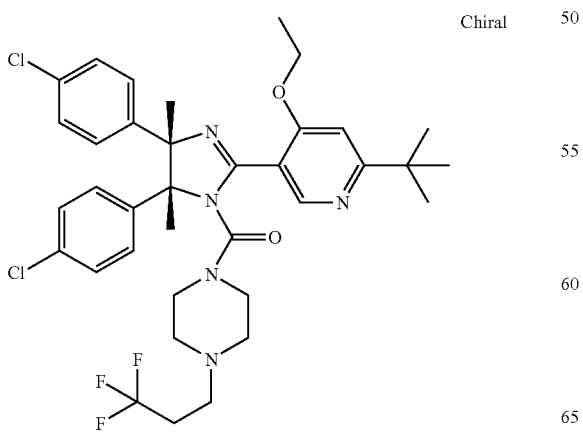

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-(3,3,3-trifluoro-propyl)-piperazine (prepared as described in Fotouhi, N. et al. WO 2005110996) to give the title compound. HR-MS (ES, m/z) calculated for $C_{36}H_{43}Cl_2F_3N_5O_2$ [(M+H)$^+$] 704.2741, observed 704.274.

EXAMPLE 59

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3-ethanesulfonyl-propyl)-piperazin-1-yl]-methanone

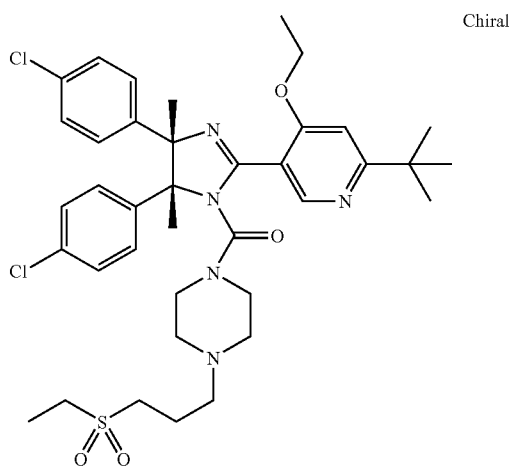 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CCCS(=O)(=O)CC)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-(3-ethanesulfonyl-propyl)-piperazine dihydrochloride (prepared from 3-ethylsulfanyl-propan-1-ol in an analogous manner as the method described for 1-(3-methanesulfonyl-propyl)-piperazine dihydrochloride, Ding, Q. et al.

WO2007063013) to give the title compound. HR-MS (ES, m/z) calculated for $C_{38}H_{50}Cl_2N_5O_4S$ [(M+H)$^+$] 742.2955, observed 742.2952.

EXAMPLE 60

N-(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-ethyl)-acetamide

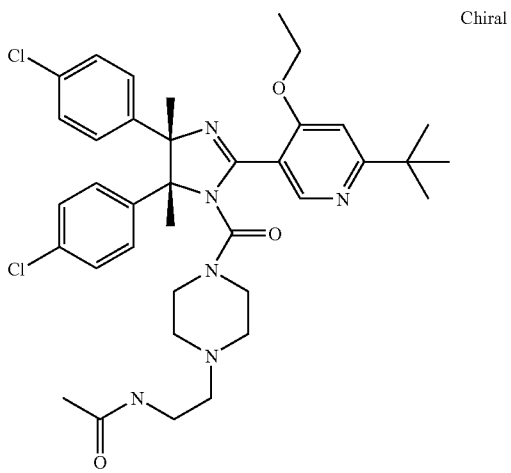 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CCNC(C)=O)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with N-(2-piperazin-1-yl-ethyl)-acetamide (prepared as described in Fotouhi, N. et al. WO 2005110996) to give the title compound. HR-MS (ES, m/z) calculated for $C_{37}H_{47}Cl_2N_6O_3$ [(M+H)$^+$] 693.3081, observed 693.3082.

EXAMPLE 61

1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2-(thiazol-2-ylamino)-ethanone

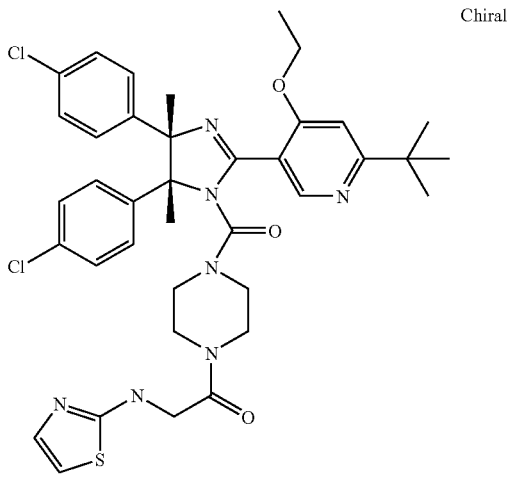 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C(=O)CNc2nccs2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-piperazin-1-yl-2-(thiazol-2-ylamino)-ethanone dihydrochloride (Oakwood) to give the title compound. HR-MS (ES, m/z) calculated for $C_{38}H_{44}Cl_2N_7O_3S$ [(M+H)$^+$] 748.2598, observed 748.2602.

EXAMPLE 62

1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2-methyl-propan-1-one

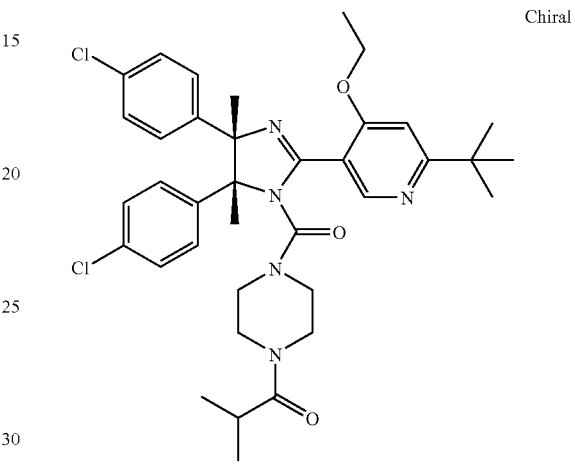

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 2-methyl-1-piperazin-1-yl-propan-1-one (Oakwood) to give the title compound. HR-MS (ES, m/z) calculated for $C_{37}H_{46}Cl_2N_5O_3$ [(M+H)$^+$] 678.2972, observed 678.2975.

EXAMPLE 63

1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2,2-dimethyl-propan-1-one

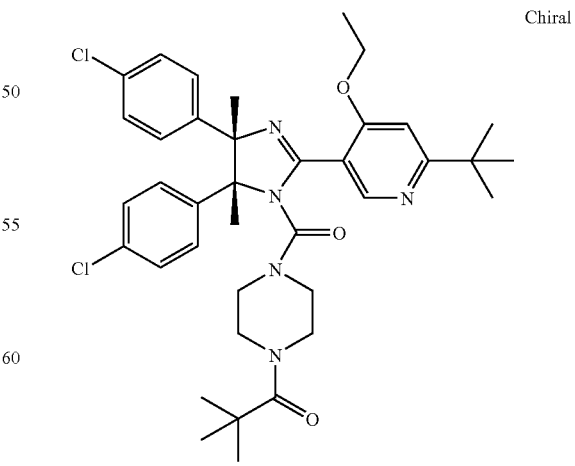

In a manner analogous to the method described in examples 8, (4S,5R)-2-(6-tert-butyl-4-ethoxy-pyridin-3-yl)-

4,5-bis-(4-chloro-phenyl)-4,5-dimethyl-4,5-dihydro-imidazole-1-carbonyl chloride (example 51) was coupled with 2,2-dimethyl-1-piperazin-1-yl-propan-1-one (Oakwood) to give the title compound. HR-MS (ES, m/z) calculated for $C_{38}H_{48}Cl_2N_5O_3$ [(M+H)$^+$] 692.3129, observed 692.3129.

EXAMPLE 64

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-methoxy-ethyl)-acetamide

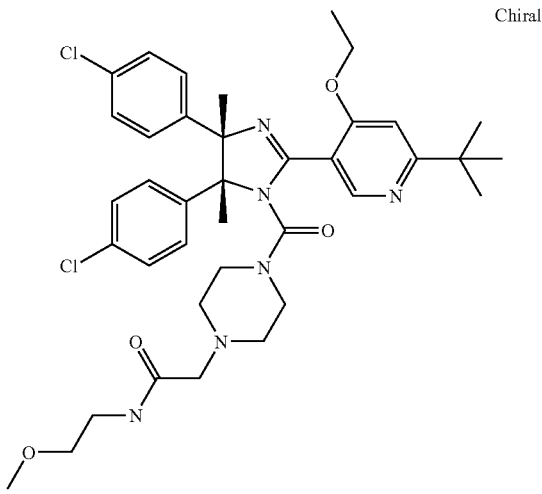 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)NCCOC)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with N-(2-methoxy-ethyl)-2-piperazin-1-yl-acetamide (Enamine) to give the title compound. HR-MS (ES, m/z) calculated for $C_{38}H_{49}Cl_2N_6O_4$ [(M+H)$^+$] 723.3187, observed 723.3191.

EXAMPLE 65

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-cyclopropyl-acetamide

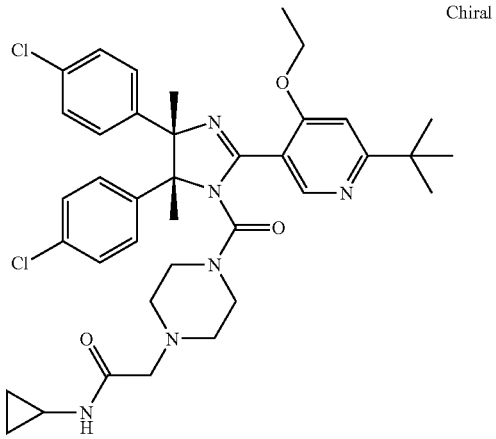 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)NC2CC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with N-cyclopropyl-2-piperazin-1-yl-acetamide (Enamine) to give the title compound. HR-MS (ES, m/z) calculated for $C_{38}H_{47}Cl_2N_6O_3$ [(M+H)$^+$] 705.3081, observed 705.308.

EXAMPLE 66

(4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid dimethylamide

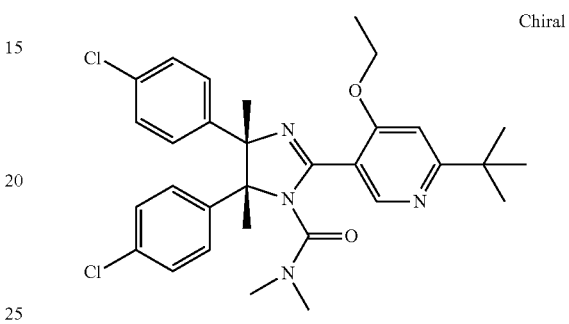

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with dimethylamine (Aldrich) to give the title compound. HR-MS (ES, m/z) calculated for $C_{31}H_{37}Cl_2N_4O_2$ [(M+H)$^+$] 567.2288, observed 567.2292.

EXAMPLE 67

1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2-tetrazol-1-yl-ethanone

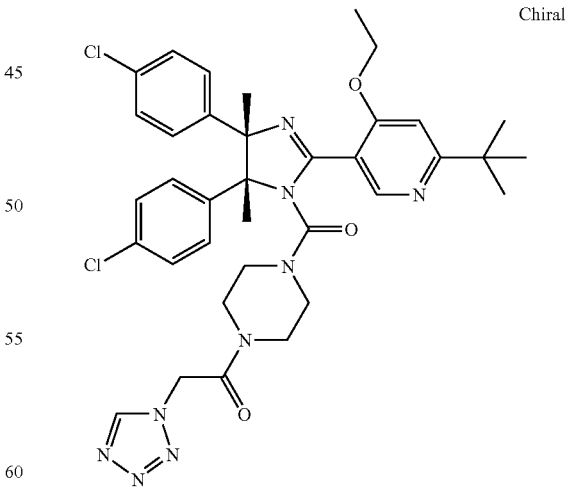

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-piperazin-1-yl-2-tetrazol-1-yl-ethanone (Enamine) to give the title compound. HR-MS (ES, m/z) calculated for $C_{36}H_{41}Cl_2N_9O_3$ [(M+H)$^+$] 718.2782, observed 718.2788.

EXAMPLE 68

3-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-propionamide

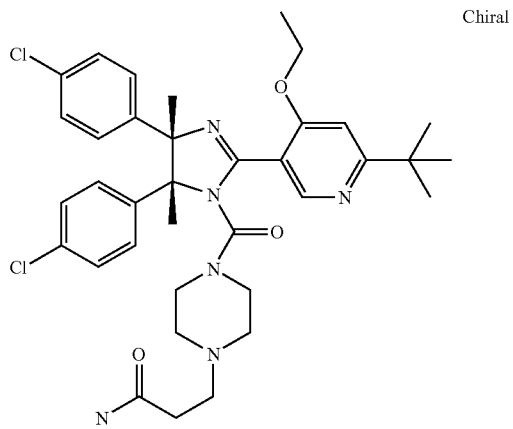 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CCC(N)=O)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 3-piperazin-1-yl-propionamide (Oakwood) to give the title compound. HR-MS (ES, m/z) calculated for $C_{36}H_{45}Cl_2N_6O_3$ [(M+H)$^+$] 679.2925, observed 679.2928.

EXAMPLE 69

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(1-methyl-1H-pyrrole-2-carbonyl)-piperazin-1-yl]-methanone

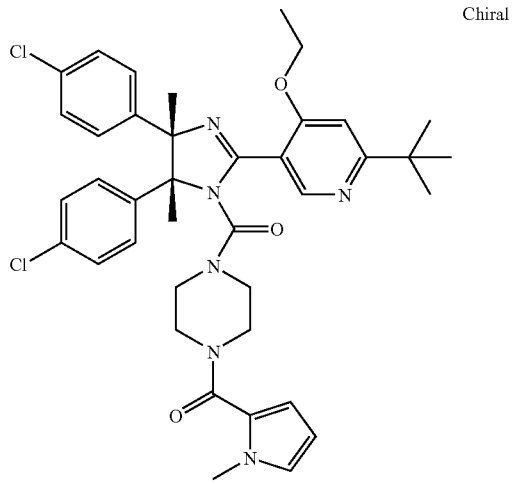 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C(=O)c2cccn2C)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with (1-methyl-1H-pyrrol-2-yl)-piperazin-1-yl-methanone (Enamine) to give the title compound. HR-MS (ES, m/z) calculated for $C_{39}H_{45}Cl_2N_6O_3$ [(M+H)$^+$] 715.2925, observed 715.2926.

EXAMPLE 70

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-cyclopropyl-propionamide

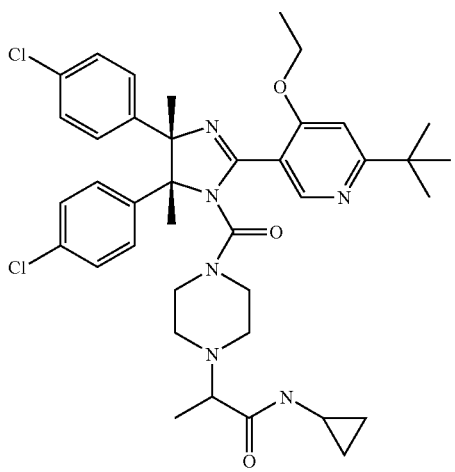 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C(C)C(=O)NC2CC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with N-cyclopropyl-2-piperazin-1-yl-propionamide (Enamine) to give the title compound as a mixture of diastereomers. HR-MS (ES, m/z) calculated for $C_{39}H_{49}Cl_2N_6O_3$ [(M+H)$^+$] 719.3238, observed 719.3244.

EXAMPLE 71

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(tetrahydro-furan-2-ylmethyl)-acetamide

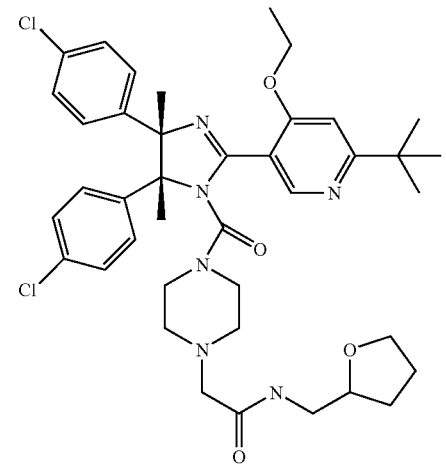 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)NCC2CCCO2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 2-piperazin-1-yl-N-(tetrahydro-furan-2-ylmethyl)-acetamide (Enamine) to give the title compound as a mixture of diastereomers. HR-MS (ES, m/z) calculated for $C_{40}H_{51}Cl_2N_6O_4$ [(M+H)⁺] 749.3344, observed 749.3341.

EXAMPLE 72

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3-methanesulfonyl-propyl)-piperidin-1-yl]-methanone

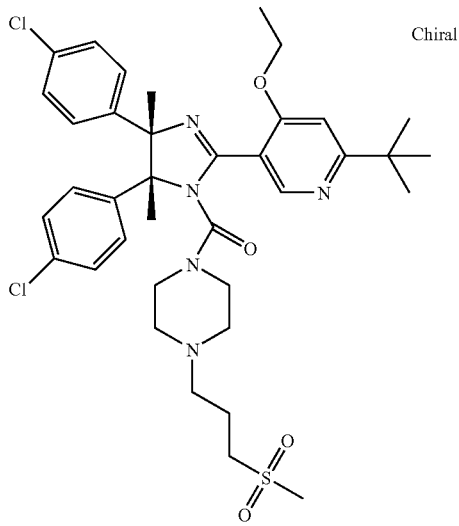 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CCCS(C)(=O)=O)CC1]

In a round bottom flask was charged with 4-pyridinepropanol (5 g, 36.45mmol), triethylamine (5.7 mL, 72.9 mmol), methylene chloride (80 mL). The solution was cooled down to 0° C. and mesyl chloride (5.7 mL, 72.9 mmol) in methylene chloride (20 mL) was slowly added. The ice bath was removed, and the mixture was stirred at room temperature overnight before being concentrated. The residue was diluted with ethyl acetate, and the organic was washed with water (2×) and brine (1×). It was dried over anhydrous sodium sulfate and concentrated to give methanesulfonic acid 3-pyridin-4-yl-propyl ester as a dark oil (6.52 g).

To a solution of methanesulfonic acid 3-pyridin-4-yl-propyl ester (6.5 g, 30.19 mmol) in methanol (150 mL) was added sodium thiomethoxide (6.35 g, 90.57 mmol, Aldrich). The mixture was stirred at room temperature for 1 h then concentrated in vacuo. The residue was diluted with ethyl acetate and washed with water (2×), brine (1×), dried over anhydrous sodium sulfate and concentrated to give 4-(3-methylsulfanyl-propyl)-pyridine as dark brown oil (2.24 g).

To a solution of 4-(3-methylsulfanyl-propyl)-pyridine (2.24 g, 30 mmol) in methylene chloride (80 mL) cooled to 0° C. was added 3-chloroperoxybenzoic acid (4.67 g, 60 mmol, ~70% w from Aldrich). The ice bath was removed and the reaction mixture was stirred at room temperature overnight. It was diluted with methylene chloride and washed with cold 1N sodium hydroxide (150 mL), water and brine. The organic layer was dried over anhydrous sodium sulfate and concentrated. Purification of the crude residue by flash column chromatography (45 g of silica gel, eluting with 0-10% methanol in ethyl acetate) gave 4-(3-methanesulfonyl-propyl)-pyridine (523 mg).

In a round bottom of flask was charged with 4-(3-methanesulfonyl-propyl)-pyridine (373 mg) and ethanol (5 mL). Hydrochloric acid was added (1 mL, 4N solution in dioxane) with stirring. The mixture was concentrated then the residue was taken in methanol and water. Platinum oxide (21 mg, 0.09 mmol, Aldrich) was added, and the mixture was hydrogenated at 60 psi overnight using a Parr apparatus. Upon completion, the mixture was filtered through Celite and washed thoroughly with methanol. The filtrate was concentrated to give 4-(3-methanesulfonyl-propyl)-piperidine dihydrochloride as a white solid (480.7 mg, 85% pure). The crude product was used without further purification.

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 4-(3-methanesulfonyl-propyl)-piperidine dihydrochloride to give the title compound. HR-MS (ES, m/z) calculated for $C_{38}H_{49}Cl_2N_4O_4S$ [(M+H)⁺] 727.2846, observed 727.2848.

EXAMPLE 73

1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2-(4-methyl-thiazol-2-yl)-ethanone

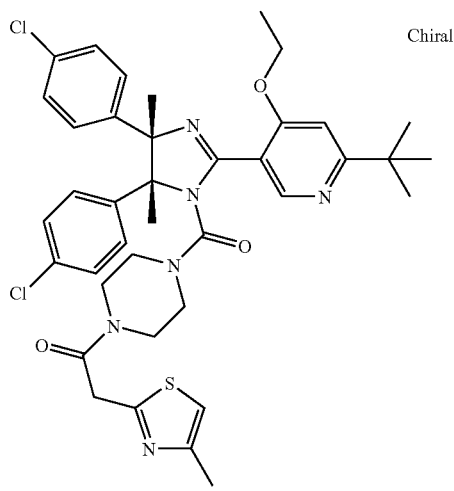 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C(=O)Cc2nc(C)cs2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 2-(4-methyl-thiazol-2-yl)-1-piperazin-1-yl-ethanone (Enamine) to give the title compound. HR-MS (ES, m/z) calculated for $C_{39}H_{45}Cl_2N_6O_3S$ [(M+H)$^+$] 747.2646, observed 747.2642.

EXAMPLE 74

9-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-3,9-diaza-spiro[5.5]undecane-3-carboxylic acid tert-butyl ester

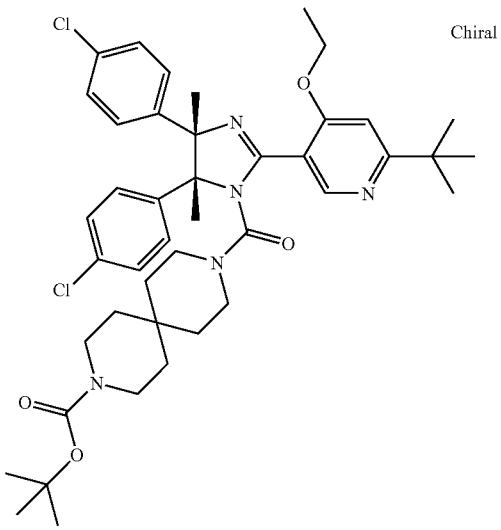 [SMILES: CCOc1cc(C(C)(C)C)ncc1C1=N[C@@](C)(c2ccc(Cl)cc2)[C@@](C)(c2ccc(Cl)cc2)N1C(=O)N1CCC2(CCN(C(=O)OC(C)(C)C)CC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 3,9-diaza-spiro[5.5]undecane-3-carboxylic acid tert-butyl ester (Syntech Labs) to give the title compound. HR-MS (ES, m/z) calculated for $C_{43}H_{56}Cl_2N_5O_4$ [(M+H)$^+$] 776.3704, observed 776.3699.

EXAMPLE 75

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3,9-diaza-spiro[5.5]undec-3-yl)-methanone

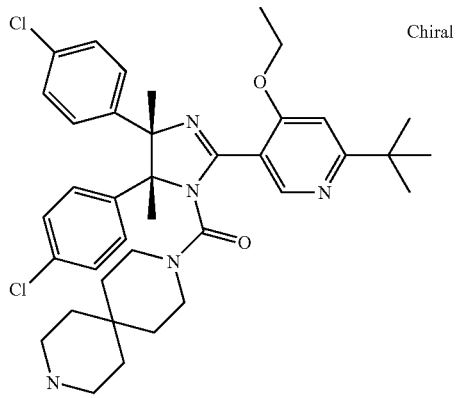 [SMILES: CCOc1cc(C(C)(C)C)ncc1C1=N[C@@](C)(c2ccc(Cl)cc2)[C@@](C)(c2ccc(Cl)cc2)N1C(=O)N1CCC2(CCNCC2)CC1]

9-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-3,9-diaza-spiro[5.5]undecane-3-carboxylic acid tert-butyl ester (example 74) was treated with trifluoroacetic acid to give the title compound. HR-MS (ES, m/z) calculated for $C_{38}H_{48}Cl_2N_5O_2$ [(M+H)$^+$] 676.318, observed 676.3177.

EXAMPLE 76

2-{9-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-3,9-diaza-spiro[5.5]undec-3-yl}-acetamide

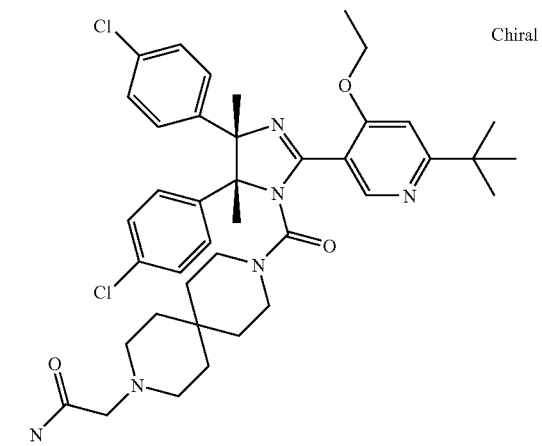 [SMILES: CCOc1cc(C(C)(C)C)ncc1C1=N[C@@](C)(c2ccc(Cl)cc2)[C@@](C)(c2ccc(Cl)cc2)N1C(=O)N1CCC2(CCN(CC(N)=O)CC2)CC1]

The mixture of [(4S,5R)-2-(6-tert-butyl-4-ethoxy-pyridin-3-yl)-4,5-bis-(4-chloro-phenyl)-4,5-dimethyl-4,5-dihydro-imidazol-1-yl]-(3,9-diaza-spiro[5.5]undec-3-yl)-methanone (25 mg, 0.037 mmol, example 75), 2-chloroacetamide (6.9 mg, 0.074 mmol, Aldrich) and triethylamine (1 drop) in dimethylformamide (1 mL) was heated at 160° C. for 10 min using the microwave synthesizer. The mixture was diluted with water, extracted with ethyl ether (2×). The extracts were washed with brine, dried over anhydrous magnesium sulfate and concentrated. The crude was filtered through a plug of silica gel, eluting with 5% methanol-ethyl acetate to give the title product as white solids (24.9 mg). HR-MS (ES, m/z) calculated for $C_{40}H_{51}Cl_2N_6O_3$ [(M+H)$^+$] 733.3394, observed 733.3392.

EXAMPLE 77

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(1,1-dioxo-tetrahydro-1λ6-thiophen-3-yl)-piperazin-1-yl]-methanone

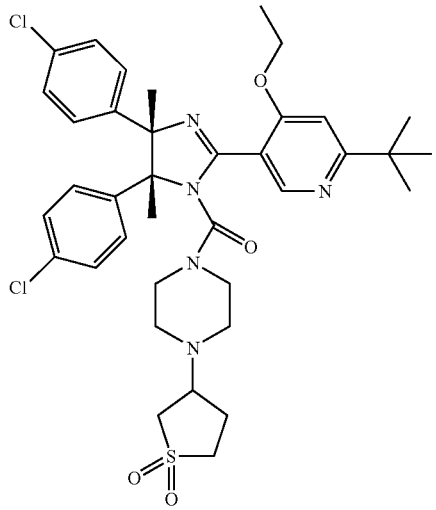 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C2CCS(=O)(=O)C2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-(1,1-dioxo-tetrahydro-1λ$^6$-thiophen-3-yl)-piperazine to give the title compound as a mixture of diastereomers.

The diastereomers can be separated by supercritical fluid chromatography (Berger Instrument Multi-Gram II, Daicel ChiralPak OD-H eluting with 15% acetonitrile in carbon dioxide) to give [(4S,5R)-2-(6-tert-butyl-4-ethoxy-pyridin-3-yl)-4,5-bis-(4-chloro-phenyl)-4,5-dimethyl-4,5-dihydro-imidazol-1-yl]-[4-((R)-1,1-dioxo-tetrahydro-1λ6-thiophen-3-yl)-piperazin-1-yl]-methanone and [(4S,5R)-2-(6-tert-butyl-4-ethoxy-pyridin-3-yl)-4,5-bis-(4-chloro-phenyl)-4,5-dimethyl-4,5-dihydro-imidazol-1-yl]-[4-((S)-1,1-dioxo-tetrahydro-1λ6-thiophen-3-yl)-piperazin-1-yl]-methanone. HR-MS (ES, m/z) calculated for $C_{37}H_{46}Cl_2N_5O_4S$ [(M+H)$^+$] 726.2642, observed 726.2645.

EXAMPLE 78

3-{4-[(4S,5R)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperazin-1-yl}-propane-1-sulfonic acid amide

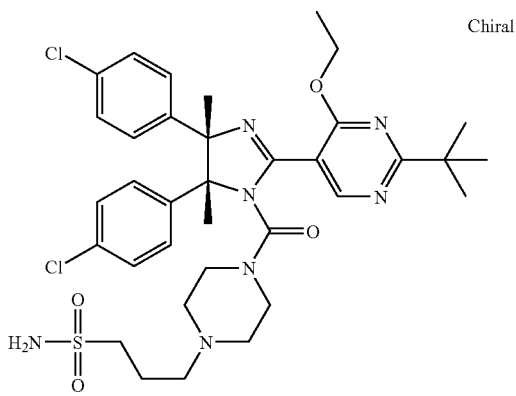 [SMILES: CCOc1nc(C(C)(C)C)ncc1C1=N[C@@](C)(c2ccc(Cl)cc2)[C@@](C)(c2ccc(Cl)cc2)N1C(=O)N1CCN(CCCS(N)(=O)=O)CC1]

In a manner analogous to the method described in example 3, (4S,5R)-2-(2-tert-butyl-4-ethoxy-pyrimidin-5-yl)-4,5-bis-(4-chloro-phenyl)-4,5-dimethyl-4,5-dihydro-imidazole-1-carbonyl chloride (example 2) was reacted with 3-piperazin-1-yl-propane-1-sulfonic acid amide dihydrochloride (example 55) to give the title compound. HR-MS (ES, m/z) calculated for $C_{35}H_{46}Cl_2N_7O_4S$ [(M+H)$^+$] 730.2704, observed 730.271.

EXAMPLE 79

Rac-[(4S*,5R*)-2-(2-tert-Butyl-4-ethoxy-pyrimidin-5-yl)-4,5-bis-(4-chloro-phenyl)-4,5-dimethyl-4,5-dihydro-imidazol-1-yl]-piperidin-1-yl-methanone

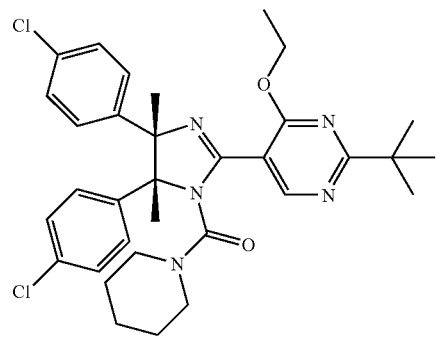 [SMILES: CCOc1nc(C(C)(C)C)ncc1C1=N[C@@](C)(c2ccc(Cl)cc2)[C@@](C)(c2ccc(Cl)cc2)N1C(=O)N1CCCCC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with piperidine (Aldrich) to give the title compound. HR-MS (ES, m/z) calculated for $C_{33}H_{40}Cl_2N_5O_2$ [(M+H)$^+$] 608.2554, observed 608.2551.

EXAMPLE 80

2-{1-[(4S,5R)-2-(2-tert-Butyl-4-ethoxy-pyrimidin-5-yl)-4,5-bis-(4-chloro-phenyl)-4,5-dimethyl-4,5-dihydro-imidazole-1-carbonyl]-piperidin-4-yl}-acetamide

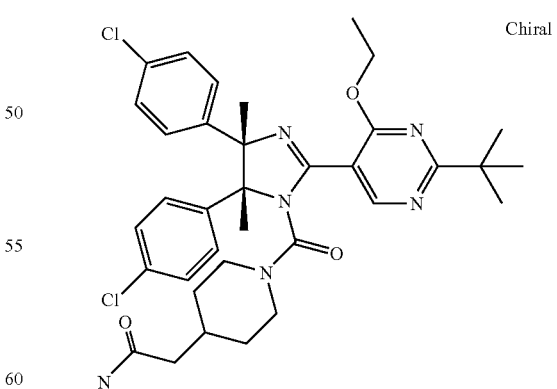

In a manner analogous to the method described in example 3, (4S,5R)-2-(2-tert-butyl-4-ethoxy-pyrimidin-5-yl)-4,5-bis-(4-chloro-phenyl)-4,5-dimethyl-4,5-dihydro-imidazole-1-carbonyl chloride (example 2) was reacted with 4-piperidine-acetamide (Chembridge) to give the title compound. HR-MS (ES, m/z) calculated for $C_{35}H_{43}Cl_2N_6O_3$ [(M+H)$^+$] 665.2768, observed 665.2767.

EXAMPLE 81

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(2-methanesulfonyl-ethyl)-piperidin-1-yl]-methanone

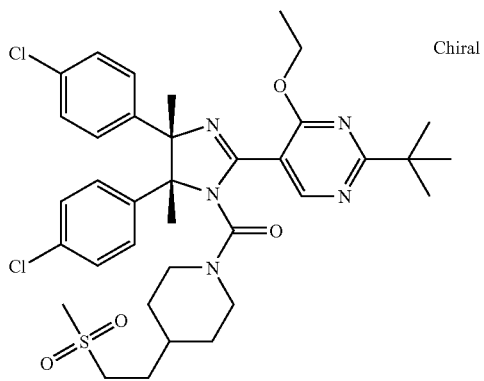 [SMILES: CCOc1nc(C(C)(C)C)ncc1C1=N[C@@](C)(c2ccc(Cl)cc2)[C@@](C)(c2ccc(Cl)cc2)N1C(=O)N1CCC(CCS(C)(=O)=O)CC1]

In a manner analogous to the method described in example 3, (4S,5R)-2-(2-tert-butyl-4-ethoxy-pyrimidin-5-yl)-4,5-bis-(4-chloro-phenyl)-4,5-dimethyl-4,5-dihydro-imidazole-1-carbonyl chloride (example 2) was reacted with 4-(2-methanesulfonyl-ethyl)-piperidine hydrochloride (example 53) to give the title compound. HR-MS (ES, m/z) calculated for $C_{36}H_{46}Cl_2N_5O_4S$ [(M+H)$^+$] 714.2642, observed 714.2644.

EXAMPLE 82

Rac-[(4S*,5R*)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(1,2-dihydroxy-ethyl)-piperidin-1-yl]-methanone

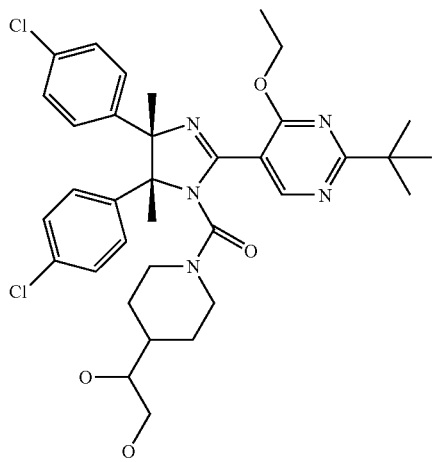 [SMILES: CCOc1nc(C(C)(C)C)ncc1C1=N[C@@](C)(c2ccc(Cl)cc2)[C@@](C)(c2ccc(Cl)cc2)N1C(=O)N1CCC(C(O)CO)CC1]

In a manner analogous to the method described in example 3, rac-(4S*,5R*)-2-(2-tert-butyl-4-ethoxy-pyrimidin-5-yl)-4,5-bis-(4-chloro-phenyl)-4,5-dimethyl-4,5-dihydro-imidazole-1-carbonyl chloride was reacted with 1-piperidin-4-yl-ethane-1,2-diol (prepared from 4-vinyl-pyridine using procedure reported by Aaron, H. S. et al. *J. Org. Chem.* 1965, 30, 1331-1333) to give the title compound as a mixture of diastereomers. HR-MS (ES, m/z) calculated for $C_{35}H_{44}Cl_2N_5O_4$ [(M+H)$^+$] 668.2765, observed 668.2767.

EXAMPLE 83

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-(4-methanesulfonylmethyl-piperidin-1-yl)-methanone

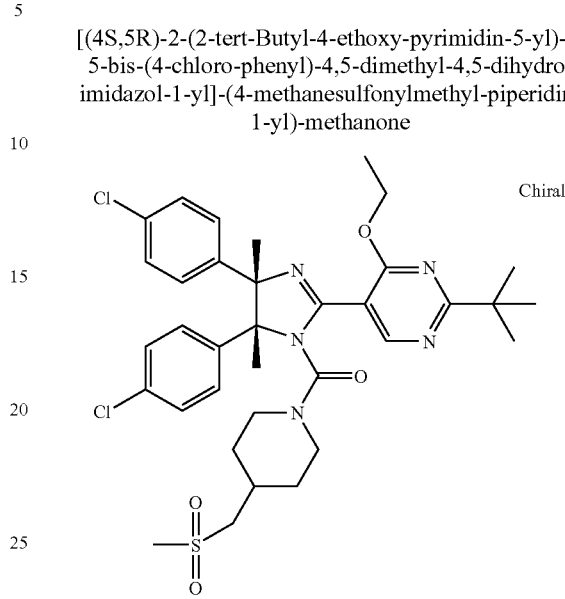

In a manner analogous to the method described in example 3, (4S,5R)-2-(2-tert-butyl-4-ethoxy-pyrimidin-5-yl)-4,5-bis-(4-chloro-phenyl)-4,5-dimethyl-4,5-dihydro-imidazole-1-carbonyl chloride (example 51) was reacted with 4-methanesulfonylmethyl-piperidine (example 52) to give the title compound. HR-MS (ES, m/z) calculated for $C_{35}H_{44}Cl_2N_5O_4S$ [(M+H)$^+$] 700.2486, observed 700.2485.

EXAMPLE 84

[(4S,5R)-2-(2-tert-Butyl-4-ethoxy-pyrimidin-5-yl)-4,5-bis-(4-chloro-phenyl)-4,5-dimethyl-4,5-dihydro-imidazol-1-yl]-[4-(3-methanesulfonyl-propyl)-piperidin-1-yl]-methanone

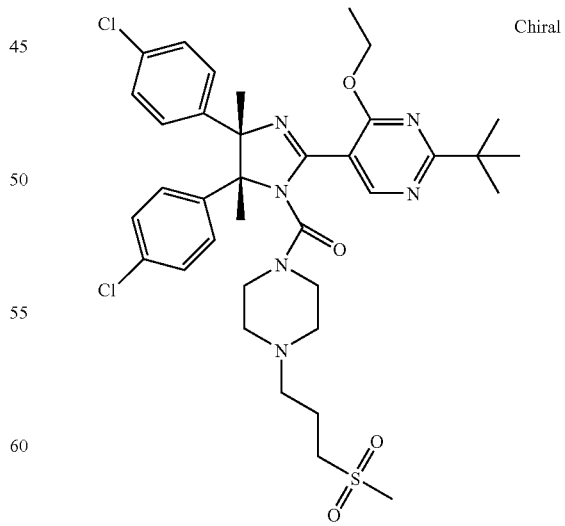

In a manner analogous to the method described in example 3, (4S,5R)-2-(2-tert-butyl-4-ethoxy-pyrimidin-5-yl)-4,5-bis-(4-chloro-phenyl)-4,5-dimethyl-4,5-dihydro-imidazole-1- carbonyl chloride was reacted with 4-(3-methanesulfonyl-propyl)-piperidine dihydrochloride (example 72) to give the title compound as a racemic mixture. HR-MS (ES, m/z) calculated for $C_{37}H_{48}Cl_2N_5O_4S$ [(M+H)$^+$] 728.2799, observed 728.2797.

EXAMPLE 85

Rac-[(4S*,5R*)-4,5-Bis-(4-chloro-phenyl)-2-(3,6-dimethoxy-pyridazin-4-yl)-4,5-dimethyl-4,5-dihydro-imidazol-1-yl]-[4-(3-methanesulfonyl-propyl)-piperazin-1-yl]-methanone

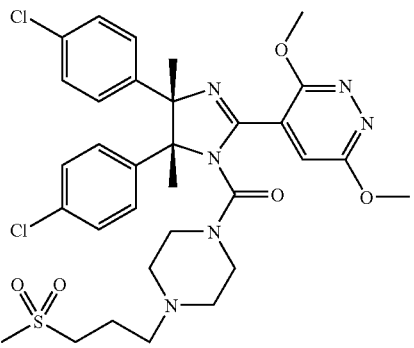

In a manner analogous to the method described in example 6, meso-2,3-Bis-(4-chlorophenyl)-2,3-butanediamine (1.838 g, 5.95 mmol, prepared as described in Ding, Q. et al. WO2007063013) was reacted with 3,6-dimethoxy-pyridazine-4-carboxylic acid methyl ester (prepared from 3,6-dimethoxy-pyridazine-4-carboxylic acid, Alfa) to give rac-4-[(4S*,5R*)-4,5-Bis-(4-chloro-phenyl)-4,5-dimethyl-4,5-dihydro-1H-imidazol-2-yl]-3,6-dimethoxy-pyridazine. The imidazoline was then converted to the corresponding carbamoyl chloride in a similar manner as described in example 2.

In a manner analogous to the method described in examples 3, rac-(4S*,5R*)-4,5-bis-(4-chloro-phenyl)-2-(3,6-dimethoxy-pyridazin-4-yl)-4,5-dimethyl-4,5-dihydro-imidazole-1-carbonyl chloride was coupled with 4-[3-(methylsulfonyl)propyl]-piperazine (prepared as described in Fotouhi, N. et al. WO 2005110996) to give the title compound. HR-MS (ES, m/z) calculated for $C_{32}H_{39}Cl_2N_6O_5S$ [(M+H)$^+$] 689.2074, observed 689.2079.

EXAMPLE 86

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-ethanesulfonyl-piperazin-1-yl)-methanone

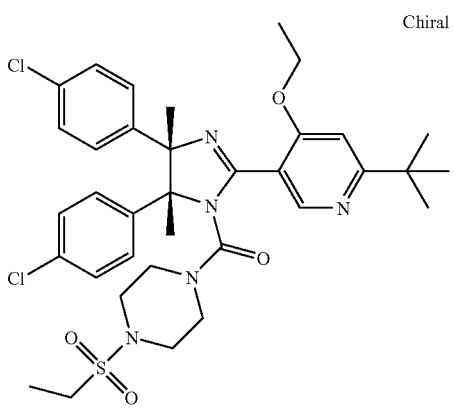 [SMILES: CCOc1cc(C(C)(C)C)ncc1C1=N[C@@](C)(c2ccc(Cl)cc2)[C@@](C)(c2ccc(Cl)cc2)N1C(=O)N1CCN(S(=O)(=O)CC)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-ethanesulfonyl-piperazine (Aldrich) to give the title compound. HR-MS (ES, m/z) calculated for $C_{35}H_{44}Cl_2N_5O_4S$ [(M+H)$^+$] 700.2486, observed 700.2486.

EXAMPLE 87

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-hydroxy-ethyl)-piperidin-1-yl]-methanone

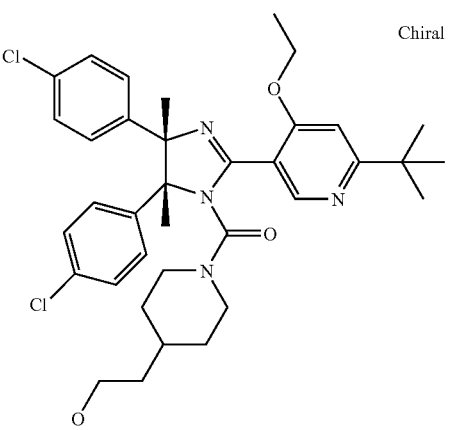 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CCO)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 2-piperidin-4-yl-ethanol (Aldrich) to give the title compound. HR-MS (ES, m/z) calculated for $C_{36}H_{45}Cl_2N_4O_3$ [(M+H)$^+$] 651.2863, observed 651.2863.

EXAMPLE 88

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methoxy-ethyl)-piperazin-1-yl]-methanone

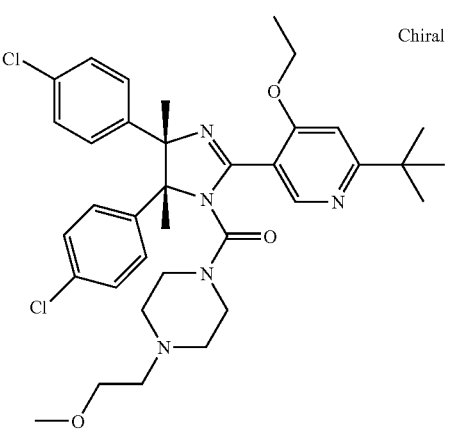 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CCOC)CC1]

In a manner analogous to the method described in examples 8, (4S,5R)-2-(6-tert-butyl-4-ethoxy-pyridin-3-yl)-

4,5-bis-(4-chloro-phenyl)-4,5-dimethyl-4,5-dihydro-imidazole-1-carbonyl chloride (example 51) was coupled with 1-(2-methoxy-ethyl)-piperazine (Oakwood) to give the title compound. HR-MS (ES, m/z) calculated for $C_{36}H_{46}Cl_2N_5O_3$ [(M+H)$^+$] 666.2972, observed 666.2971.

EXAMPLE 89

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-pyrrolidin-1-yl-piperidin-1-yl)-methanone

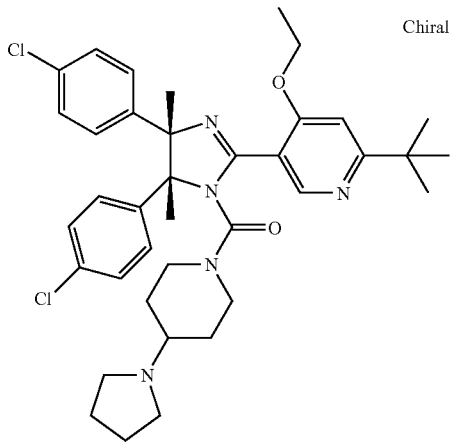 [SMILES: CCOc1cc(C(C)(C)C)ncc1C1=N[C@@](C)(c2ccc(Cl)cc2)[C@@](C)(c2ccc(Cl)cc2)N1C(=O)N1CCC(N2CCCC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 4-pyrrolidin-1-yl-piperidine (Aldrich) to give the title compound. HR-MS (ES, m/z) calculated for $C_{38}H_{48}Cl_2N_5O_2$ [(M+H)$^+$] 676.318, observed 676.3176.

EXAMPLE 90

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-isopropyl-piperazin-1-yl)-methanone

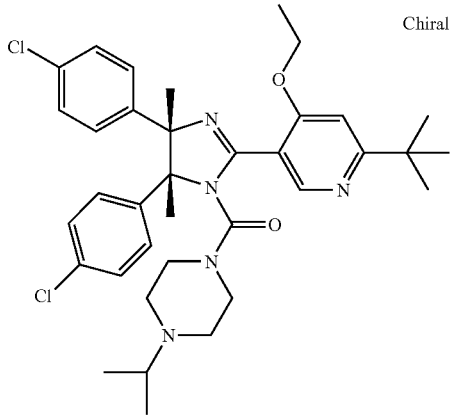 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C(C)C)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-isopropyl-piperazine (Oakwood) to give the title compound. HR-MS (ES, m/z) calculated for $C_{36}H_{46}Cl_2N_5O_2$ [(M+H)$^+$] 650.3023, observed 650.3022.

EXAMPLE 91

[1,4']Bipiperidinyl-1'-yl-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone

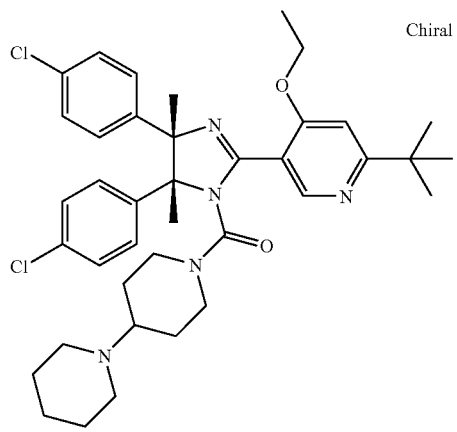 [SMILES: CCOc1cc(C(C)(C)C)ncc1C1=N[C@@](C)(c2ccc(Cl)cc2)[C@@](C)(c2ccc(Cl)cc2)N1C(=O)N1CCC(N2CCCCC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with [1,4']-bipiperidinyl (Aldrich) to give the title compound. HR-MS (ES, m/z) calculated for $C_{39}H_{50}Cl_2N_5O_2$ [(M+H)$^+$] 690.3336, observed 690.334.

EXAMPLE 92

1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-ethanone

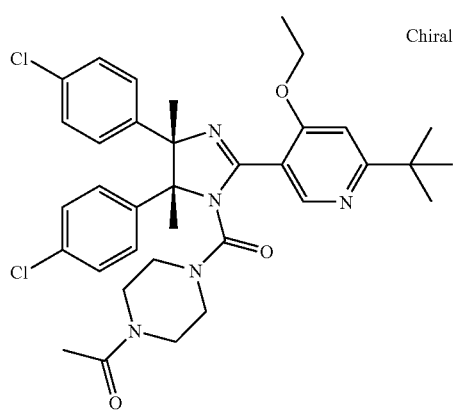 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C(C)=O)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-acetyl-piperazine (Aldrich) to give the title compound. HR- MS (ES, m/z) calculated for $C_{35}H_{42}Cl_2N_5O_3$ $[(M+H)^+]$ 650.2659, observed 650.2662.

EXAMPLE 93

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-dimethylamino-piperidin-1-yl)-methanone

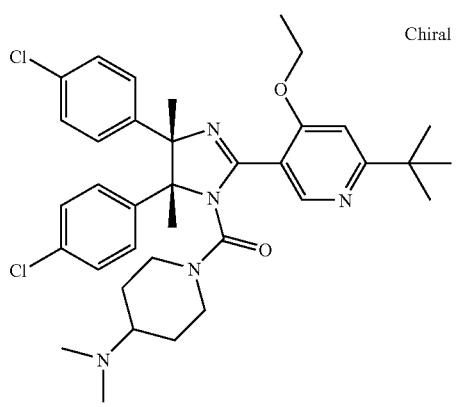 [SMILES: CCOc1cc(C(C)(C)C)ncc1C1=N[C@@](C)(c2ccc(Cl)cc2)[C@@](C)(c2ccc(Cl)cc2)N1C(=O)N1CCC(N(C)C)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 4-dimethylamino-piperidine (Oakwood) to give the title compound. HR-MS (ES, m/z) calculated for $C_{36}H_{46}Cl_2N_5O_2$ $[(M+H)^+]$ 650.3023, observed 650.3027.

EXAMPLE 94

{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride

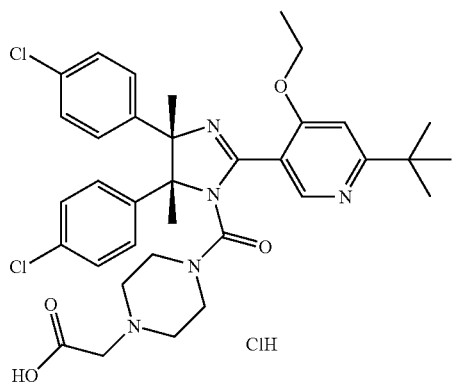 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)O)CC1 ; Cl]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (309 mg, 0.55 mmol, example 51) was coupled with piperazine-1-carboxylic acid tert-butyl ester dihydrochloric acid salt (224 mg, 0.83 mmol, Lancaster) in the presence of triethylamine (0.69 mL, 4.95 mmol, Fluka) to give {4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid tert-butyl ester. {4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid tert-butyl ester was either reacted with lithium hydroxide (2N solution) in methanol and tetrahydrofuran at 50° C. for 4 h or with 1N hydrochloric acid at 50° C. for 2.5 h to give the title compound. HR-MS (ES, m/z) calculated for $C_{35}H_{42}Cl_2N_5O_4$ $[(M+H)^+]$ 666.2609, observed 666.2611.

EXAMPLE 95

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(tetrahydro-furan-2-carbonyl)-piperazin-1-yl]-methanone

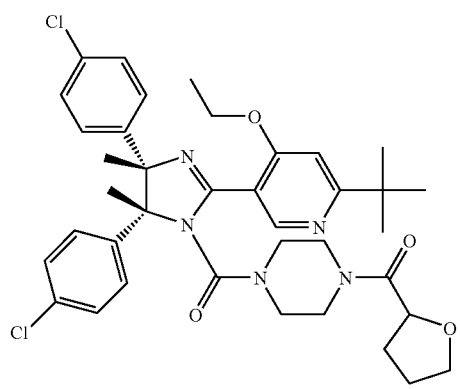 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C(=O)C2CCCO2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with piperazin-1-yl-(tetrahydro-furan-2-yl)-methanone (Alfa) to give the title compound as a mixture of diastereomers. HR-MS (ES, m/z) calculated for $C_{38}H_{46}Cl_2N_5O_4$ $[(M+H)^+]$ 706.2922, observed 706.2918.

EXAMPLE 96

4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazine-1-carboxylic acid dimethylamide

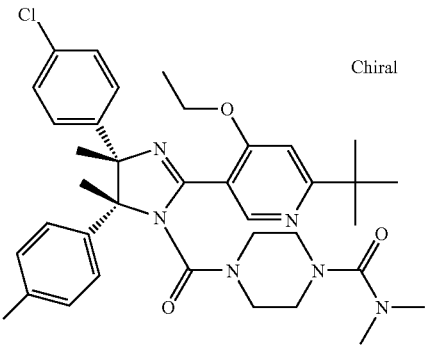

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with piperazine-1-carboxylic acid dimethylamide (Oakwood) to give

EXAMPLE 97

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3-methoxy-propyl)-piperazin-1-yl]-methanone

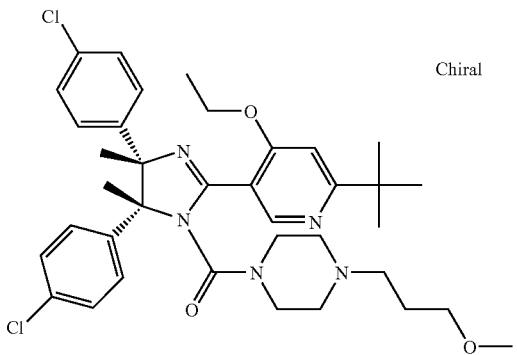 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CCCOC)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-(3-methoxy-propyl)-piperazine (Oakwood) to give the title compound. HR-MS (ES, m/z) calculated for $C_{37}H_{48}Cl_2N_5O_3$ [(M+H)$^+$] 680.3129, observed 680.3133.

EXAMPLE 98

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-(1,1-dioxo-1λ6-thiomorpholin-4-yl)-ethanone

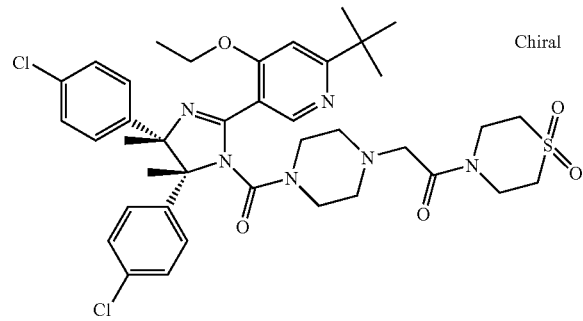 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)N2CCS(=O)(=O)CC2)CC1]

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with thiomorpholine 1,1-dioxide (Syntech Development) to give the title compound. HR-MS (ES, m/z) calculated for $C_{39}H_{49}Cl_2N_6O_5S$ [(M+H)$^+$] 783.2857, observed 783.2856.

EXAMPLE 99

4-(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetyl)-piperazin-2-one

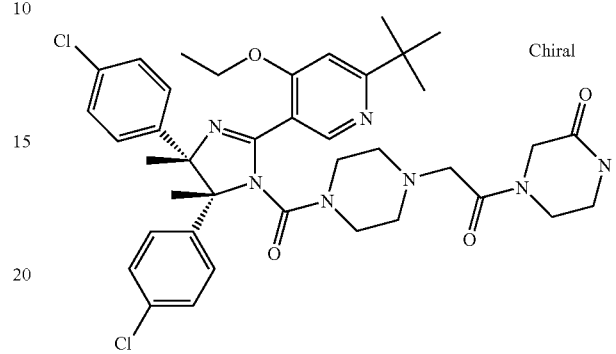

{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride salt (31.5 mg, 0.47 mmol, example 99), O-(7-azabenzotriazol-1-yl)-N,N,N',N'-tetramethyluronium hexafluorophosphate (HATU, 19.7 mg, 0.052 mmol, Advchemtech), piperazin-2-one (12 mg, ) and triethylamine (0.05 mL) was mixed in dichloromethane (2 ml) and stirred for 2 h. The mixture was diluted with dichloromethane (5 mL) and was washed with sodium hydroxide (0.1 N solution), saturated sodium chloride solution and water. Dichloromethane solution was dried over anhydrous magnesium sulfate. The solids were filtered off, and the filtrate was concentrated in vacuo. Purification of the crude residue by preparative HPLC (reversed phase, eluting with acetonitrile and water) gave the title compound (20.7 mg). HR-MS (ES, m/z) calculated for $C_{39}H_{48}Cl_2N_7O_4$ [(M+H)$^+$] 748.314, observed 748.3138.

EXAMPLE 100

1-(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetyl)-[1,4]diazepan-5-one

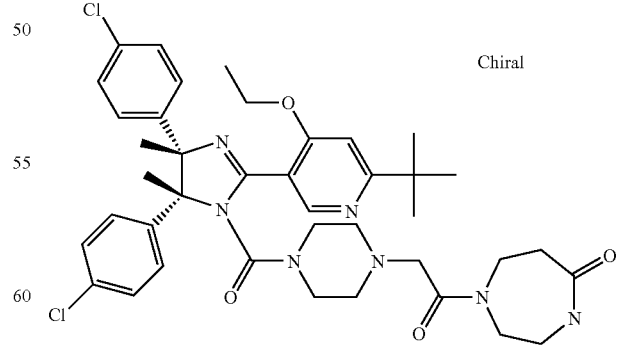

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with [1,4]diazepan-5-one (Oakwood Products) to give the title compound. HR-MS (ES, m/z) calculated for $C_{40}H_{50}Cl_2N_7O_4$ [(M+H)$^+$] 762.3296, observed 762.3297.

EXAMPLE 101

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-hydroxy-piperidin-1-yl)-methanone

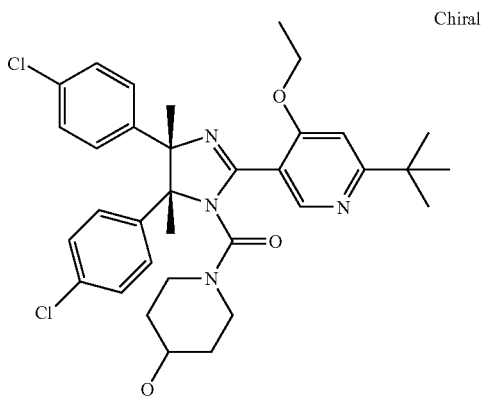 [SMILES: CCOc1cc(C(C)(C)C)ncc1C1=N[C@@](C)(c2ccc(Cl)cc2)[C@@](C)(c2ccc(Cl)cc2)N1C(=O)N1CCC(O)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 4-hydroxypiperidine (Aldrich) to give the title compound. HR-MS (ES, m/z) calculated for $C_{34}H_{41}Cl_2N_4O_3$ [(M+H)$^+$] 623.255, observed 623.2551.

EXAMPLE 102

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3-hydroxy-piperidin-1-yl)-methanone

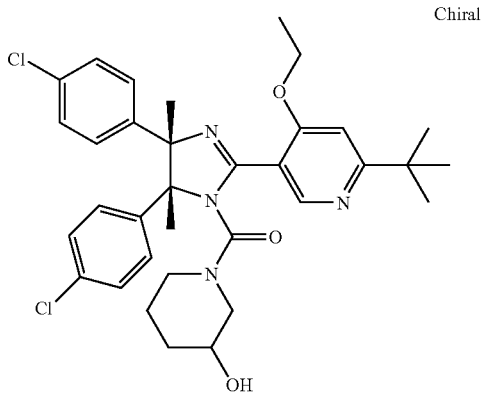 [SMILES: CCOc1cc(C(C)(C)C)ncc1C1=N[C@@](C)(c2ccc(Cl)cc2)[C@@](C)(c2ccc(Cl)cc2)N1C(=O)N1CCCC(O)C1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 3-hydroxypiperidine (Aldrich) to give the title compound. HR-MS (ES, m/z) calculated for $C_{34}H_{41}Cl_2N_4O_3$ [(M+H)$^+$] 623.255, observed 623.2547.

EXAMPLE 103

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-hydroxymethyl-piperidin-1-yl)-methanone

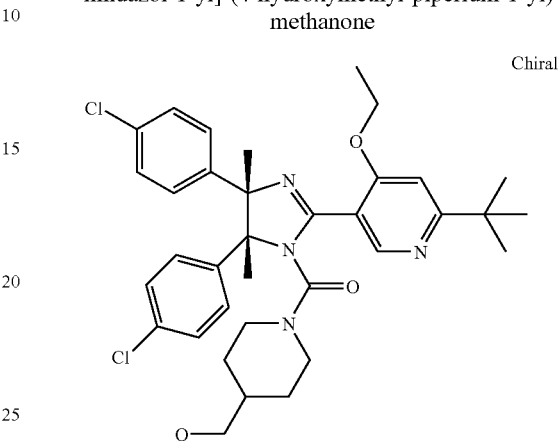

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with piperidin-4-yl-methanol (Lancaster) to give the title compound. HR-MS (ES, m/z) calculated for $C_{35}H_{43}Cl_2N_4O_3$ [(M+H)$^+$] 637.2707, observed 637.2708.

EXAMPLE 104

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-pyrrolidin-1-yl-ethanone

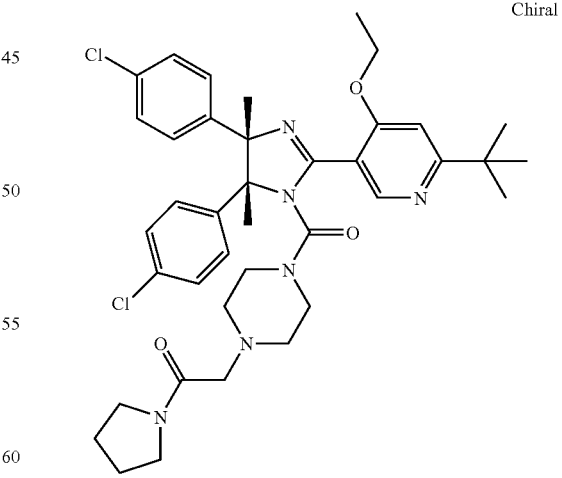

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 2-piperazin-1-yl-1-pyrrolidin-1-yl-ethanone (Oakwood) to give the title compound. HR-MS (ES, m/z) calculated for $C_{39}H_{49}Cl_2N_6O_3$ [(M+H)$^+$] 719.3238, observed 719.3242.

EXAMPLE 105

1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-[1,4]diazepan-5-one

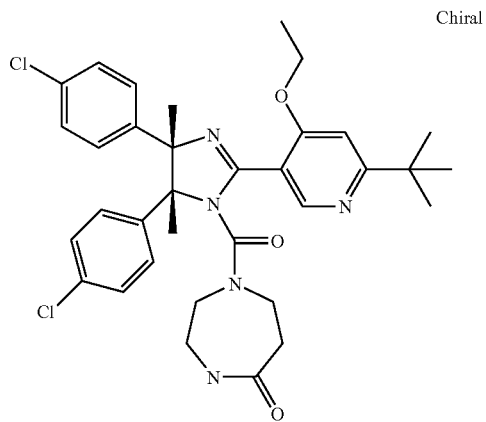 [SMILES: CCOc1cc(C(C)(C)C)ncc1C1=N[C@@](C)(c2ccc(Cl)cc2)[C@@](C)(c2ccc(Cl)cc2)N1C(=O)N1CCNC(=O)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with [1,4]-diazepan-5-one (Oakwood) to give the title compound. HR-MS (ES, m/z) calculated for $C_{34}H_{40}Cl_2N_5O_3$ [(M+H)$^+$] 636.2503, observed 636.2504.

EXAMPLE 106

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-((R)-3-methyl-piperazin-1-yl)-methanone

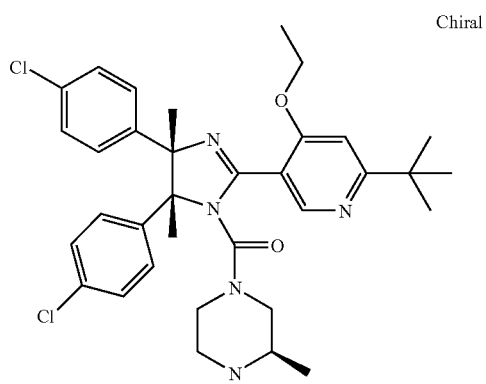 [SMILES: CCOc1cc(C(C)(C)C)ncc1C1=N[C@@](C)(c2ccc(Cl)cc2)[C@@](C)(c2ccc(Cl)cc2)N1C(=O)N1CCN[C@H](C)C1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with (R)-2-methyl-piperazine (Aldrich) to give the title compound. HR-MS (ES, m/z) calculated for $C_{34}H_{42}Cl_2N_5O_2$ [(M+H)$^+$] 622.271, observed 622.2714.

EXAMPLE 107

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2,3-dihydroxy-propyl)-acetamide

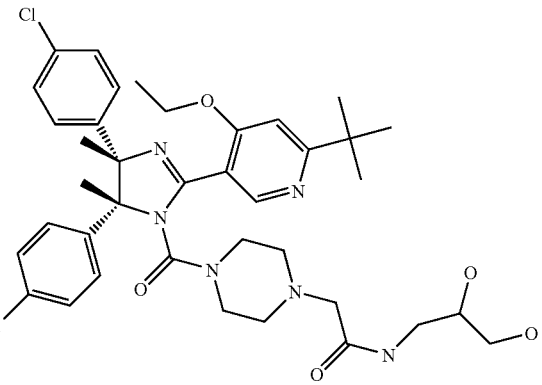

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with 3-amino-propane-1,2-diol (Aldrich) to give the title compound as a mixture of diastereomers. HR-MS (ES, m/z) calculated for $C_{38}H_{49}Cl_2N_6O_5$ [(M+H)$^+$] 739.3136, observed 739.3139.

EXAMPLE 108

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-isopropyl-N-methyl-acetamide

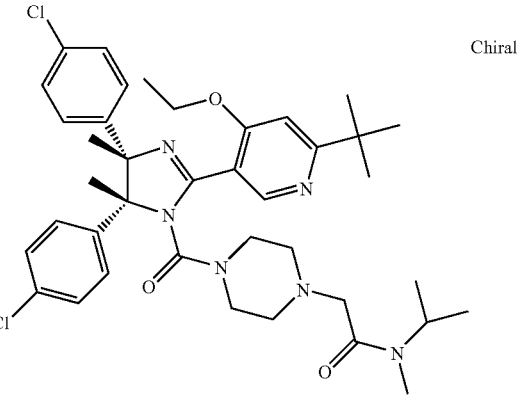

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with isopropyl-methylamine (Aldrich) to give the title compound. HR-MS (ES, m/z) calculated for $C_{39}H_{51}Cl_2N_6O_3$ [(M+H)$^+$] 721.3394, observed 721.3399.

EXAMPLE 109

N-tert-Butyl-2-{4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetamide

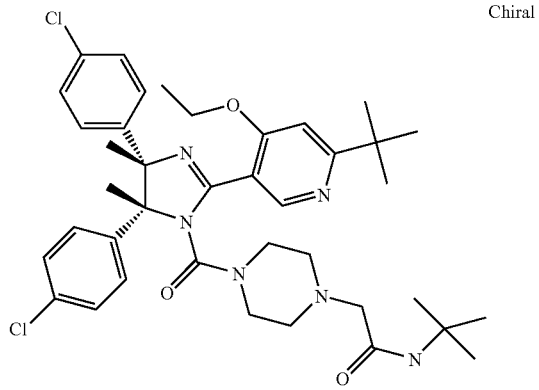 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)NC(C)(C)C)CC1]

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with tert-butylamine (Aldrich) to give the title compound. HR-MS (ES, m/z) calculated for $C_{39}H_{51}Cl_2N_6O_3$ [(M+H)$^+$] 721.3394, observed 721.3399.

EXAMPLE 110

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-methanesulfonyl-piperazin-1-yl)-methanone

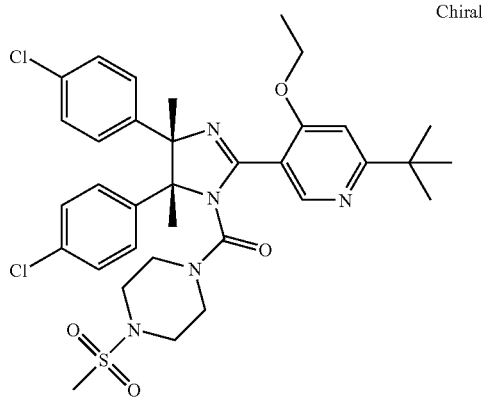 [SMILES: CCOc1cc(C(C)(C)C)ncc1C1=N[C@@](C)(c2ccc(Cl)cc2)[C@@](C)(c2ccc(Cl)cc2)N1C(=O)N1CCN(S(C)(=O)=O)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-methanesulfonyl-piperazine (Astatech) to give the title compound. HR-MS (ES, m/z) calculated for $C_{34}H_{42}Cl_2N_5O_4S$ [(M+H)$^+$] 686.2329, observed 686.2329.

EXAMPLE 111

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-{4-[2-(2-hydroxy-ethoxy)-ethyl]-piperazin-1-yl}-methanone

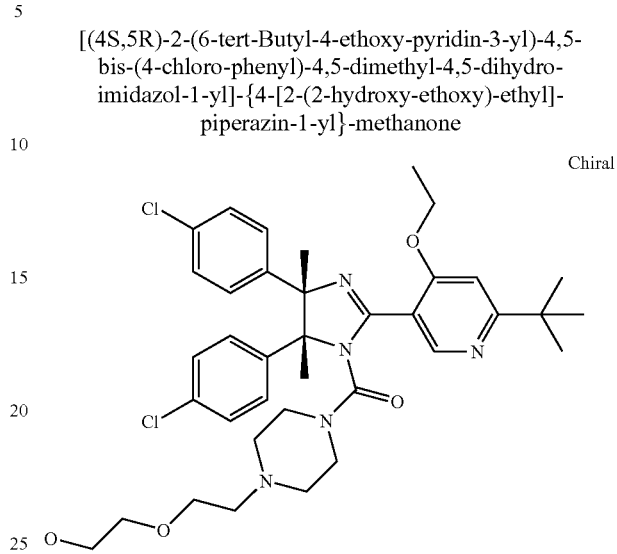

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 2-(2-piperazin-1-yl-ethoxy)-ethanol (Aldrich) to give the title compound. HR-MS (ES, m/z) calculated for $C_{37}H_{48}Cl_2N_5O_4$ [(M+H)$^+$] 696.3078, observed 696.3076.

EXAMPLE 112

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-(4-methyl-piperazin-1-yl)-ethanone

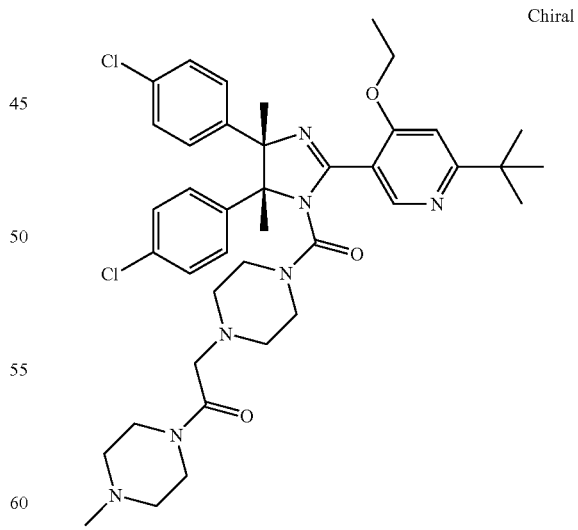

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-(4-methylpiperazin-1-yl)-2-piperazin-1-yl-ethanone (Ibscreen-BB) to give the title compound. HR-MS (ES, m/z) calculated for $C_{40}H_{52}Cl_2N_7O_3$ [(M+H)$^+$] 748.3503, observed 748.3504.

EXAMPLE 113

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-cyclopropanecarbonyl-piperazin-1-yl)-methanone

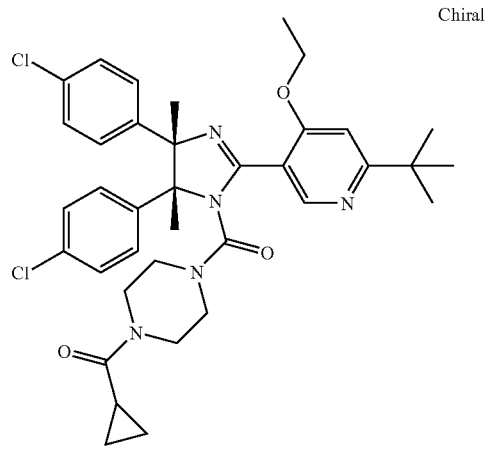 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C(=O)C2CC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with piperazine-cyclopropanecarboxylic acid (Aldrich) to give the title compound. HR-MS (ES, m/z) calculated for $C_{37}H_{44}Cl_2N_5O_3$ [(M+H)$^+$] 676.2816, observed 676.2814.

EXAMPLE 114

4-[4-(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetyl)-piperazin-1-yl]-benzonitrile

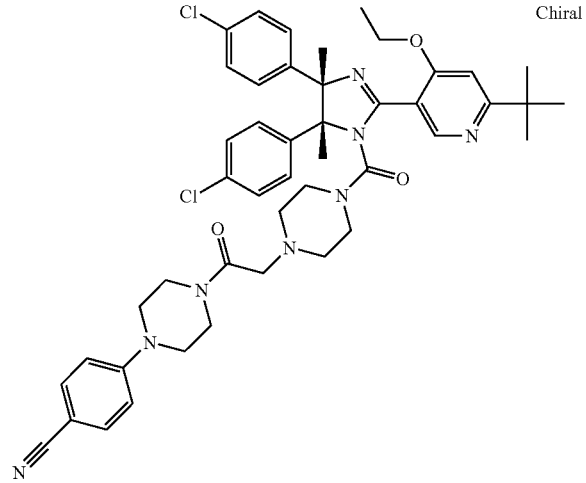 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)N2CCN(c3ccc(C#N)cc3)CC2)CC1]

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with 4-piperazin-1-yl-benzonitrile (Fluka) to give the title compound. HR-MS (ES, m/z) calculated for $C_{46}H_{53}Cl_2N_8O_3$ [(M+H)$^+$] 835.3612, observed 835.3611.

EXAMPLE 115

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-hydroxy-1,1-dimethyl-ethyl)-acetamide

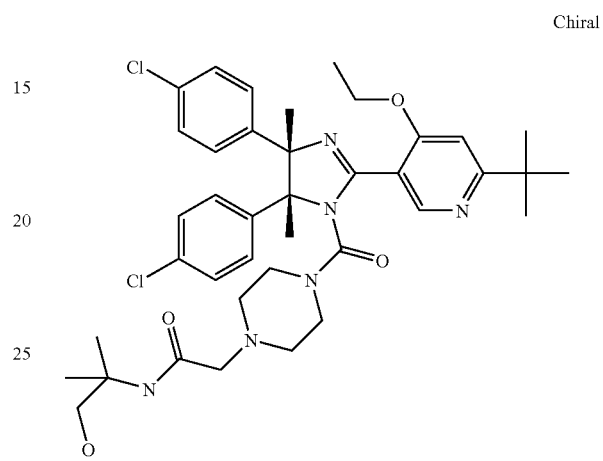

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with 2-amino-2-methyl-propan-1-ol (Aldrich) to give the title compound. HR-MS (ES, m/z) calculated for $C_{39}H_{51}Cl_2N_6O_4$ [(M+H)$^+$] 737.3344, observed 737.3342.

EXAMPLE 116

2-{4-[(4S,5R)-2-(6-tert-Butyl-4-ethoxy-pyridin-3-yl)-4,5-bis-(4-chloro-phenyl)-4,5-dihydro-imidazole-1-carbonyl]-piperazin-1-yl}-N-(2-hydroxy-1-hydroxymethyl-1-methyl-ethyl)-acetamide

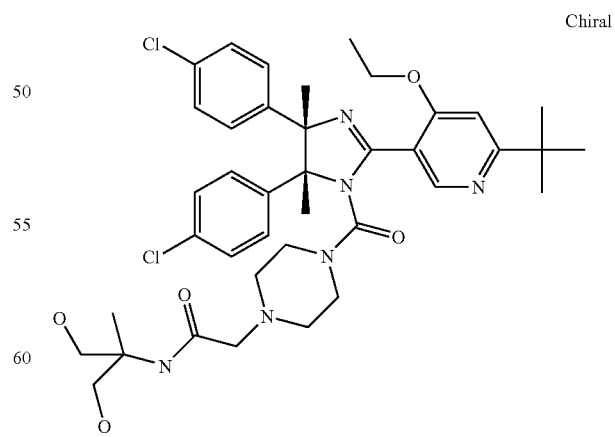

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydroimidazole-1-carbonyl]-piperazin-1-yl}-acetic acid hydrochloride (example 94) was coupled with 2-amino-2-methyl-propane-1,3-diol (Fluka) to give the title compound. HR-MS (ES, m/z) calculated for $C_{39}H_{51}Cl_2N_6O_5$ [(M+H)$^+$] 753.3293, observed 753.3292.

EXAMPLE 117

4-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-piperazin-2-one

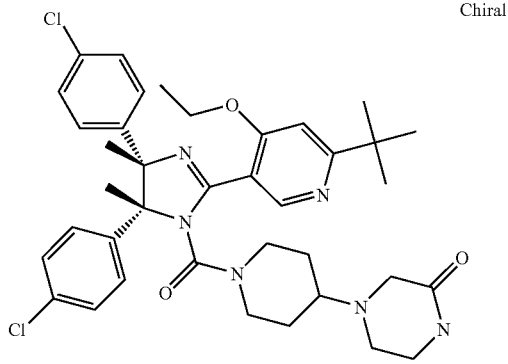 [SMILES: CCOc1cc(C(C)(C)C)ncc1C1=N[C@@](C)(c2ccc(Cl)cc2)[C@@](C)(c2ccc(Cl)cc2)N1C(=O)N1CCC(N2CCNC(=O)C2)CC1]

The mixture of piperazin-2-one (1.11 g, 11.1 mmol, Aldrich), 4-oxo-piperidine-1-carboxylic acid tert-butyl ester (2.43 g, 12.21 mmol, Aldrich) and sodium triacetoxyborohydride (2.59 g, 12.21 mmol, Aldrich) in dichloromethane (50 mL) was stirred at ambient temperature for 2 h. After the aqueous work up, the crude residue was purified by flash column chromatography (silica gel, Isco system, eluting with ethyl acetate and hexane) to give 4-(3-oxo-piperazin-1-yl)-piperidine-1-carboxylic acid tert-butyl ester (1.78 g).

4-(3-Oxo-piperazin-1-yl)-piperidine-1-carboxylic acid tert-butyl ester (660 mg) was dissolved in methanol (5 mL) and 1 N hydrochloric acid (10 mL) was added. The mixture was stirred at 50° C. for 2 h. After removal of all solvents, acetonitrile (2×10 mL) was added and removed twice. The residue was then lyophilized to give 4-(3-oxo-piperazin-1-yl)-piperidine hydrochloride (665.8 mg).

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 4-(3-oxo-piperazin-1-yl)-piperidine hydrochloride to give the title compound. HR-MS (ES, m/z) calculated for $C_{38}H_{47}Cl_2N_6O_3$ [(M+H)$^+$] 705.3081, observed 705.3081.

EXAMPLE 118

4-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-methyl-piperazin-2-one

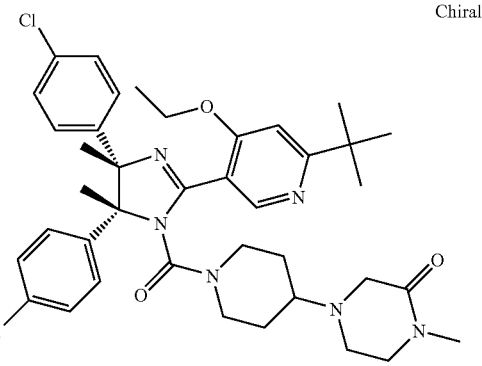

4-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-piperazin-2-one (61.8 mg, example 117) was dissolved in N,N-dimethylformamide (1 mL), sodium hydride (60% in mineral oil, 20 mg, Aldrich) was added. After stirring for 5 min, methyl iodide (0.03 mL, Aldrich) was added. The mixture was stirred at ambient temperature for 3 h, and the crude product was purified on a HPLC (reversed phase, eluting with acetonitrile and water) to give the title product (34 mg). HR-MS (ES, m/z) calculated for $C_{39}H_{49}Cl_2N_6O_3$ [(M+H)$^+$] 719.3238, observed 719.3242.

EXAMPLE 119

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3,4-dihydroxy-butyl)-piperazin-1-yl]-methanone

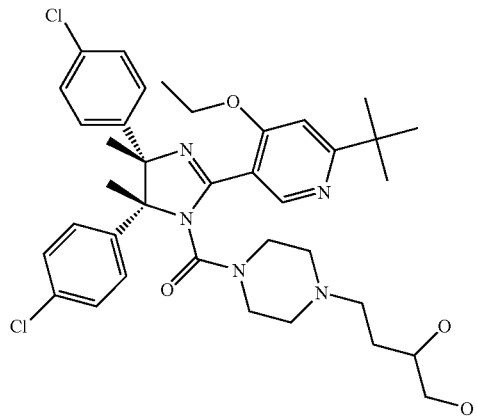 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CCC(O)CO)CC1]

Piperazine-1-carboxylic acid tert-butyl ester (1.17 g, 6.28 mmol, Lancaster) and toluene-4-sulfonic acid 2-(2,2-dimethyl-[1,3]dioxolan-4-yl)-ethyl ester (1.98 g, 6.6 mmol, prepared from (2,2-dimethyl-[1,3]dioxolan-4-yl)-ethanol and tosyl chloride) and potassium carbonate (1 g, Fisher) were stirred in acetonitrile (22 mL) overnight at room temperature. After aqueous workup, the residue was purified by flash column chromatography to give 4-(3,4-dihydroxy-butyl)-piperazine-1-carboxylic acid tert-butyl ester (0.52g), which was deprotected with 1 N hydrochloric acid in methanol at 50° C. to give 4-piperazin-1-yl-butane-1,2-diol hydrochloride (360 mg).

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 4-piperazin-1-yl-butane-1,2-diol hydrochloride to give the title compound. HR-MS (ES, m/z) calculated for $C_{37}H_{48}Cl_2N_5O_4$ [(M+H)$^+$] 696.3078, observed 696.3074.

EXAMPLE 120

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(1,1-dioxo-1λ6-thiomorpholin-4-yl)-methanone

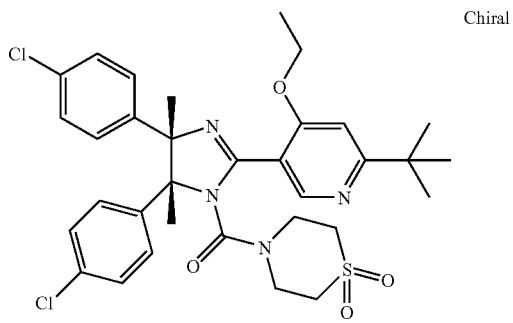 [SMILES: CCOc1cc(C(C)(C)C)ncc1C1=N[C@@](C)(c2ccc(Cl)cc2)[C@@](C)(c2ccc(Cl)cc2)N1C(=O)N1CCS(=O)(=O)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with thiomorpholine 1,1-dioxide (Syntech) to give the title compound. HR-MS (ES, m/z) calculated for $C_{33}H_{39}Cl_2N_4O_4S$ [(M+H)$^+$] 657.2064, observed 657.2067.

EXAMPLE 121

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-piperidin-1-yl-ethanone

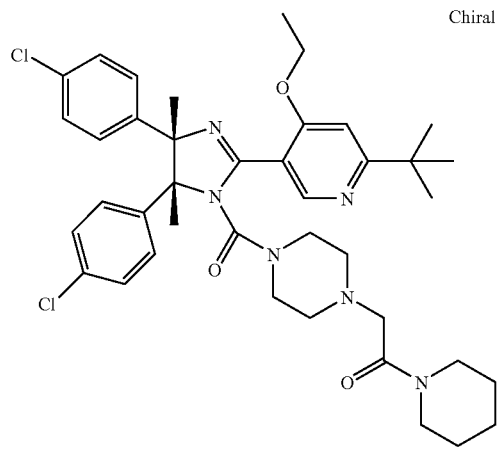 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)N2CCCCC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 2-piperazin-1-yl-1-piperidin-1-yl-ethanone (Oakwood) to give the title compound. HR-MS (ES, m/z) calculated for $C_{40}H_{51}Cl_2N_6O_3$ [(M+H)$^+$] 733.3394, observed 733.3392.

EXAMPLE 122

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-hydroxy-ethyl)-acetamide

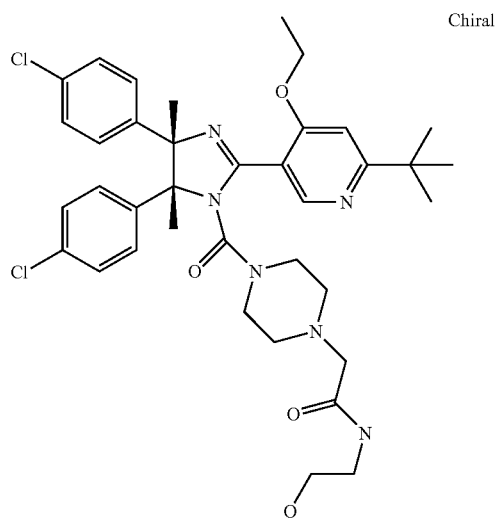 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)NCCO)CC1]

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with 2-amino-ethanol (Aldrich) to give the title compound. HR-MS (ES, m/z) calculated for $C_{37}H_{47}Cl_2N_6O_4$ [(M+H)$^+$] 709.3031, observed 709.3029.

EXAMPLE 123

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-[1,4]dioxan-2-ylmethyl-acetamide

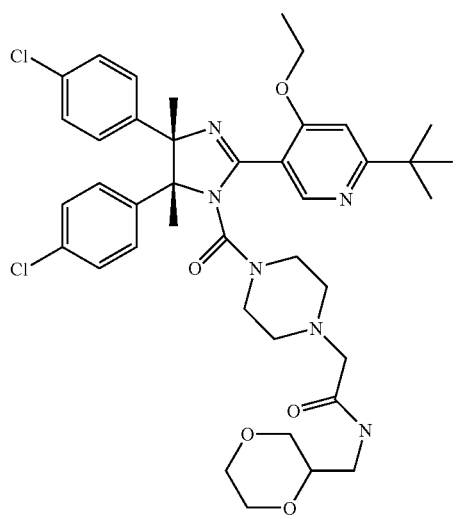 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)NCC2COCCO2)CC1]

In a manner analogous to the method described in examples 99, {4-[(4S,5R)-2-(6-tert-butyl-4-ethoxy-pyridin- 3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with [1,4]-dioxan-2-yl-methylamine (Matrix Scientific) to give the title compound. HR-MS (ES, m/z) calculated for $C_{40}H_{51}Cl_2N_6O_5$ [(M+H)$^+$] 765.3293, observed 765.3289.

EXAMPLE 124

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3-hydroxy-pyrrolidin-1-yl)-methanone

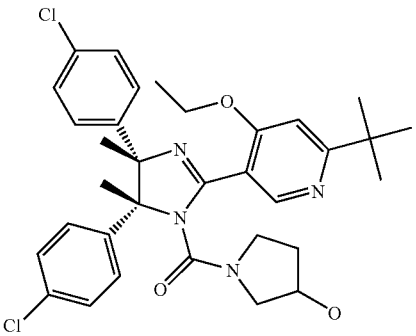 [SMILES: CCOc1cc(C(C)(C)C)ncc1C1=N[C@@](C)(c2ccc(Cl)cc2)[C@@](C)(c2ccc(Cl)cc2)N1C(=O)N1CCC(O)C1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with pyrrolidin-3-ol (Aldrich) to give the title compound as a mixture of diastereomers. HR-MS (ES, m/z) calculated for $C_{33}H_{39}Cl_2N_4O_3$ [(M+H)$^+$] 609.2394, observed 609.2393.

EXAMPLE 125

{(S)-1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-pyrrolidin-3-yl}-carbamic acid tert-butyl ester

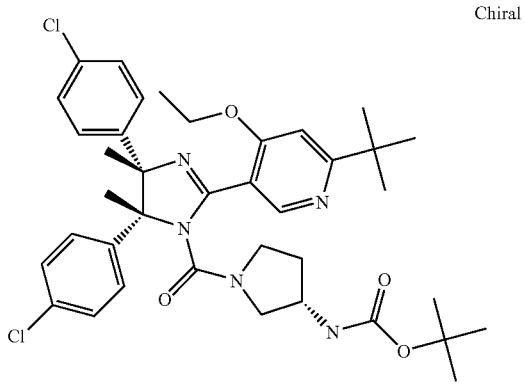 [SMILES: CCOc1cc(C(C)(C)C)ncc1C1=N[C@@](C)(c2ccc(Cl)cc2)[C@@](C)(c2ccc(Cl)cc2)N1C(=O)N1CC[C@H](NC(=O)OC(C)(C)C)C1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with (S)-pyrrolidin-3-yl-carbamic acid tert-butyl ester (Aldrich) to give the title compound. HR-MS (ES, m/z) calculated for $C_{38}H_{48}Cl_2N_5O_4$ [(M+H)$^+$] 708.3078, observed 708.3081.

EXAMPLE 126

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-thiazol-5-yl-acetamide

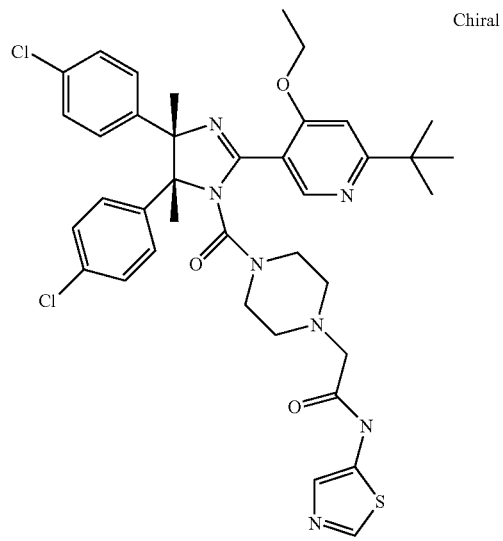 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)Nc2cncs2)CC1]

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with thiophen-2-ylamine (Aldrich) to give the title compound. HR-MS (ES, m/z) calculated for $C_{38}H_{44}Cl_2N_7O_3S$ [(M+H)$^+$] 748.2598, observed 748.2594.

EXAMPLE 127

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-3-yl-acetamide

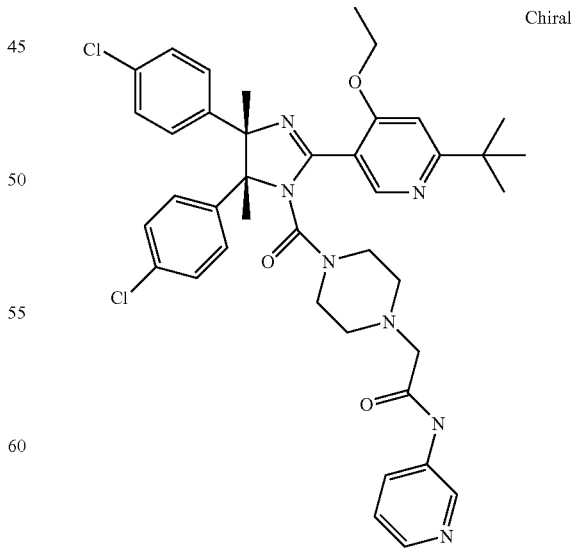

In a manner analogous to the method described in examples 99, {4-[(4S,5R)-2-(6-tert-butyl-4-ethoxy-pyridin- 3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with pyridin-3-ylamine (Aldrich) to give the title compound. HR-MS (ES, m/z) calculated for $C_{40}H_{46}Cl_2N_7O_3$ [(M+H)$^+$] 742.3034, observed 742.3034.

EXAMPLE 128

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-phenyl-acetamide Chiral

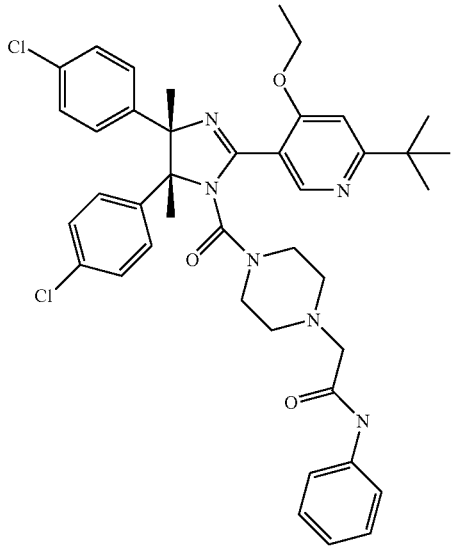

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with aniline to give the title compound. HR-MS (ES, m/z) calculated for $C_{41}H_{47}Cl_2N_6O_3$ [(M+H)$^+$] 741.3081, observed 741.3079.

EXAMPLE 129

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-4-yl-acetamide Chiral

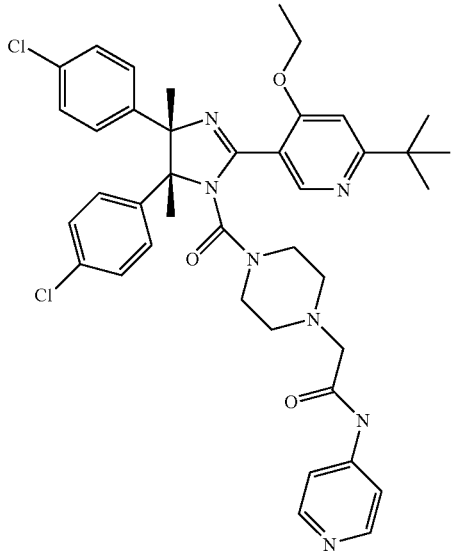

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with pyridin-4-ylamine (Aldrich) to give the title compound. HR-MS (ES, m/z) calculated for $C_{40}H_{46}Cl_2N_7O_3$ [(M+H)$^+$] 742.3034, observed 742.3036.

EXAMPLE 130

(3-Amino-pyrrolidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone

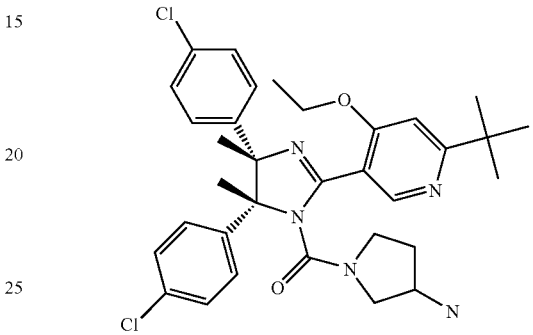

{(S)-1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-pyrrolidin-3-yl}-carbamic acid tert-butyl ester (12.6 mg, example 125) was diluted with methanol (1.5 mL) and trifluoroacetic acid (0.1 mL). The mixture was stirred at 75-80° C. for 1 h. Thionyl chloride (0.3 mL) was added dropwise and the mixture was stirred at 80° C. for 1 h. The mixture was then concentrated and diluted with methanol (2 mL) and neutralized with 15% solution of sodium hydroxide. Purification of the crude product on a preparative HPLC (reversed phase, eluting with acetonitrile and water) gave the title product as a mixture of diastereomers (5.4 mg). HR-MS (ES, m/z) calculated for $C_{33}H_{40}Cl_2N_5O_2$ [(M+H)$^+$] 608.2554, observed 608.2554.

EXAMPLE 131

N-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-pyrrolidin-3-yl}-oxalamide

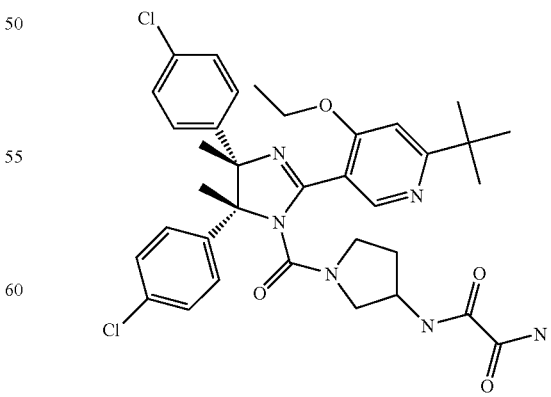

In a manner analogous to the method described in examples 99, (3-amino-pyrrolidin-1-yl )-[(4S,5R)-2-(6-tertbutyl-4-ethoxy-pyridin-3-yl)-4,5-bis-(4-chloro-phenyl)-4,5-dimethyl-4,5-dihydro-imidazol-1-yl]-methanone was coupled with oxalamic acid (Aldrich) to give the title product. HR-MS (ES, m/z) calculated for $C_{35}H_{41}Cl_2N_6O_4$ [(M+H)$^+$] 679.2561, observed 679.2561.

EXAMPLE 132

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(2,3,4,5-tetrahydro-benzo[b][1,4]diazepin-1-yl)-methanone

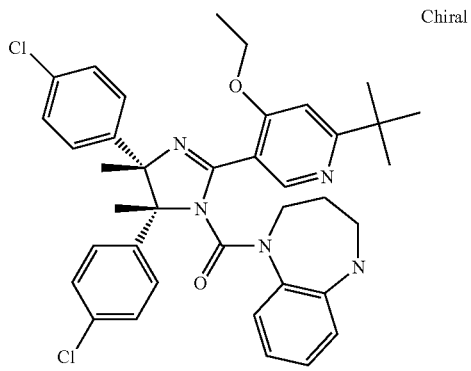 [SMILES: CCOc1cc(C(C)(C)C)ncc1C1=N[C@@](C)(c2ccc(Cl)cc2)[C@@](C)(c2ccc(Cl)cc2)N1C(=O)N1CCCNc2ccccc21]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 2,3,4,5-tetrahydro-1H-benzo[b][1,4]diazepine (Aldrich) to give the title compound. HR-MS (ES, m/z) calculated for $C_{38}H_{42}Cl_2N_5O_2$ [(M+H)$^+$] 670.271, observed 670.2712.

EXAMPLE 133

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-(3-hydroxy-azetidin-1-yl)-ethanone

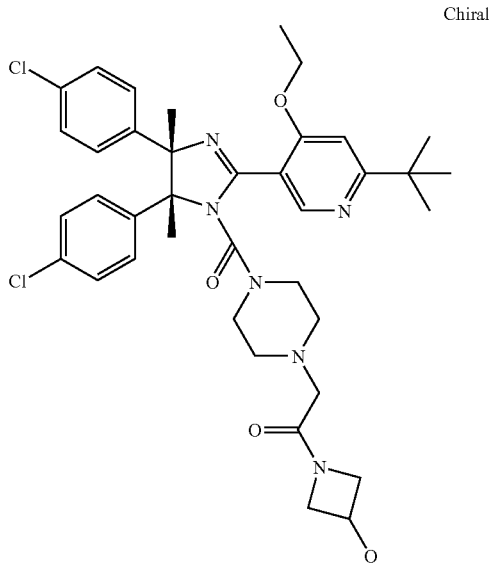 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)N2CC(O)C2)CC1]

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with azetidin-3-ol (Oakwood) to give the title compound. HR-MS (ES, m/z) calculated for $C_{38}H_{47}Cl_2N_6O_4$ [(M+H)$^+$] 721.3031, observed 721.3034.

EXAMPLE 134

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(tetrahydro-pyran-4-yl)-acetamide

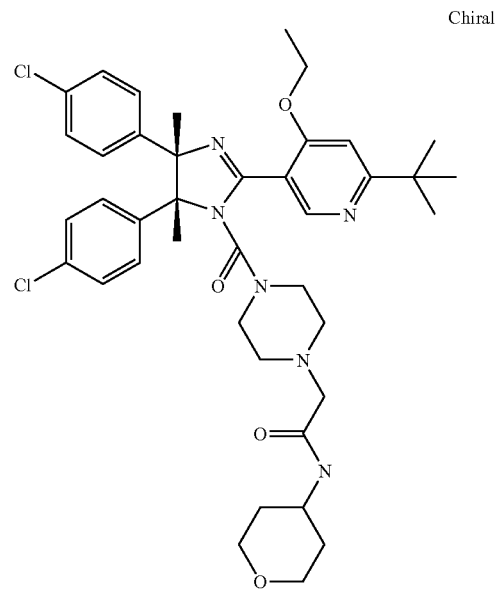 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)NC2CCOCC2)CC1]

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with tetrahydro-pyran-4-ylamine (Matrix Scientific) to give the title compound. HR-MS (ES, m/z) calculated for $C_{40}H_{51}Cl_2N_6O_4$ [(M+H)$^+$] 749.3344, observed 749.3343.

EXAMPLE 135

(1S,5R)-3-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-3-aza-bicyclo[3.1.0]hexane-6-carboxylic acid ethyl ester

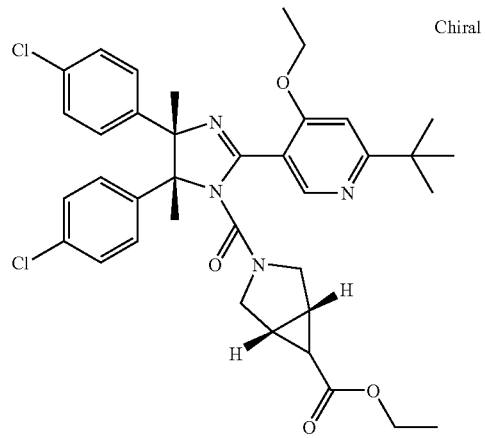 [SMILES: CCOC(=O)C1[C@H]2CN(C(=O)N3C(c4cnc(C(C)(C)C)cc4OCC)=N[C@@](C)(c4ccc(Cl)cc4)[C@@]3(C)c3ccc(Cl)cc3)C[C@@H]12]

In a manner analogous to the method described in examples 8, (4S,5R)-2-(6-tert-butyl-4-ethoxy-pyridin-3-yl)-

4,5-bis-(4-chloro-phenyl)-4,5-dimethyl-4,5-dihydro-imidazole-1-carbonyl chloride (example 51) was coupled with (1S, 5R)-3-aza-bicyclo-[3.1.0]hexane-6-carboxylic acid ethyl ester (Tyger Scientific) to give the title compound. HR-MS (ES, m/z) calculated for $C_{37}H_{43}Cl_2N_4O_4$ $[(M+H)^+]$ 677.2656, observed 677.2655.

EXAMPLE 136

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N,N-bis-(2-methoxy-ethyl)-acetamide

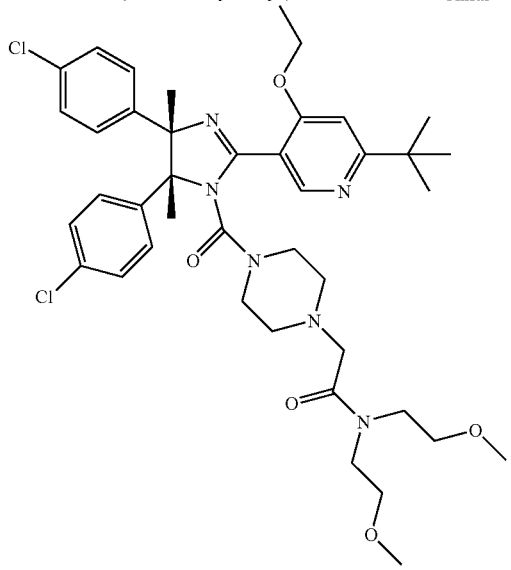

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with bis-(2-methoxy-ethyl)-amine (Aldrich) to give the title compound. HR-MS (ES, m/z) calculated for $C_{41}H_{55}Cl_2N_6O_5$ $[(M+H)^+]$ 781.3606, observed 781.3603.

EXAMPLE 137

1-Azetidin-1-yl-2-{4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-ethanone

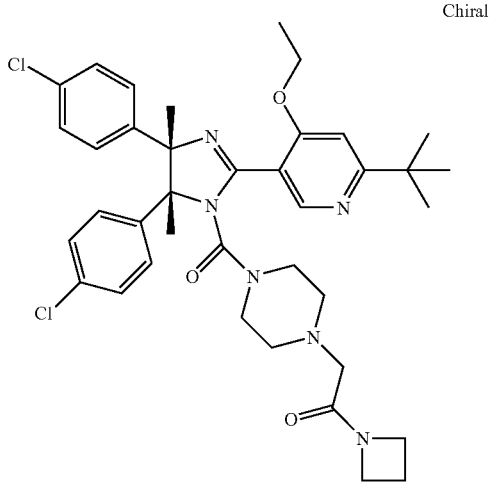 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)N2CCC2)CC1]

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with azetidine (Aldrich) to give the title compound. HR-MS (ES, m/z) calculated for $C_{38}H_{47}Cl_2N_6O_3$ $[(M+H)^+]$ 705.3081, observed 705.3081.

EXAMPLE 138

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N,N-bis-(2-hydroxy-ethyl)-acetamide

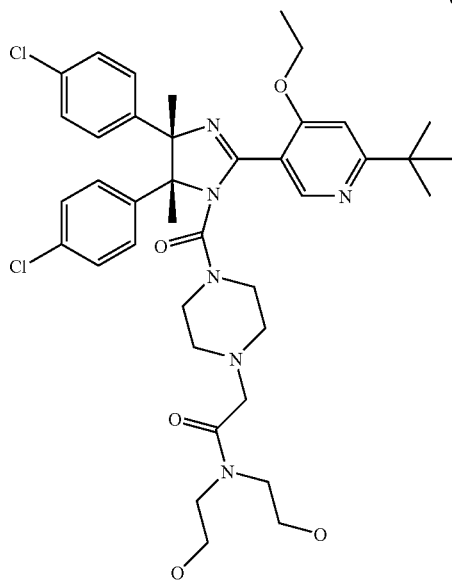

In a manner analogous to the method described in examples 99, {4-[(4S,5R)-2-(6-tert-butyl-4-ethoxy-pyridin3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with 2-(2-hydroxy-ethylamino)-ethanol (Aldrich) to give the title compound. HR-MS (ES, m/z) calculated for $C_{39}H_{51}Cl_2N_6O_5$ $[(M+H)^+]$ 753.3293, observed 753.3294. -

EXAMPLE 139

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-[2-(4-methoxy-phenyl)-ethyl]-acetamide

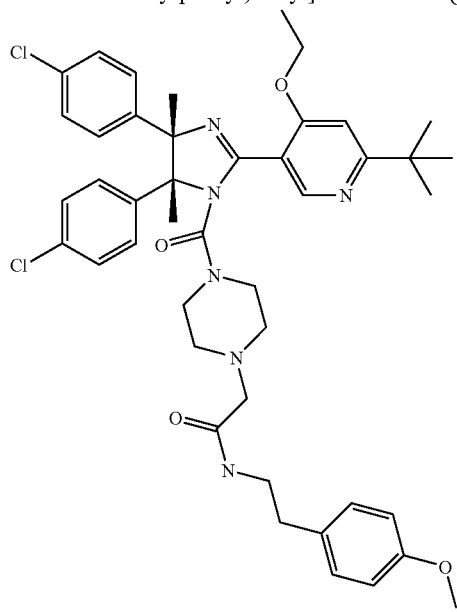

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with 2-(4-methoxyphenyl)-ethylamine (Aldrich) to give the title compound. HR-MS (ES, m/z) calculated for $C_{44}H_{53}Cl_2N_6O_4$ [(M+H)$^+$] 799.35, observed 799.3501.

EXAMPLE 140

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-[2-(2-methoxy-phenyl)-ethyl]-acetamide

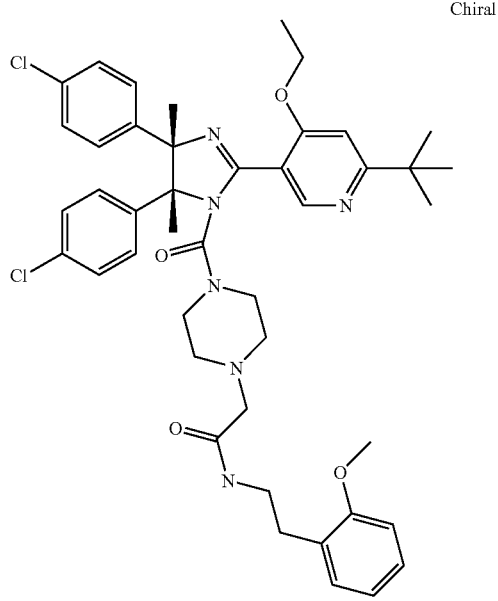 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)NCCc2ccccc2OC)CC1]

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with 2-(2-methoxyphenyl)-ethylamine (Fluka) to give the title compound. HR-MS (ES, m/z) calculated for $C_{44}H_{53}Cl_2N_6O_4$ [(M+H)$^+$] 799.35, observed 799.3496.

EXAMPLE 141

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(7,8-dimethoxy-1,2,3,5-tetrahydro-benzo[e][1,4]diazepin-4-yl)-methanone and [(4S,5R)-2-(6-tert-butyl-4-ethoxy-pyridin-3-yl)-4,5-bis-(4-chloro-phenyl)-4,5-dimethyl-4,5-dihydro-imidazol-1-yl]-(7,8-dimethoxy-2,3,4,5-tetrahydro-benzo[e][1,4]diazepin-1-yl)-methanone

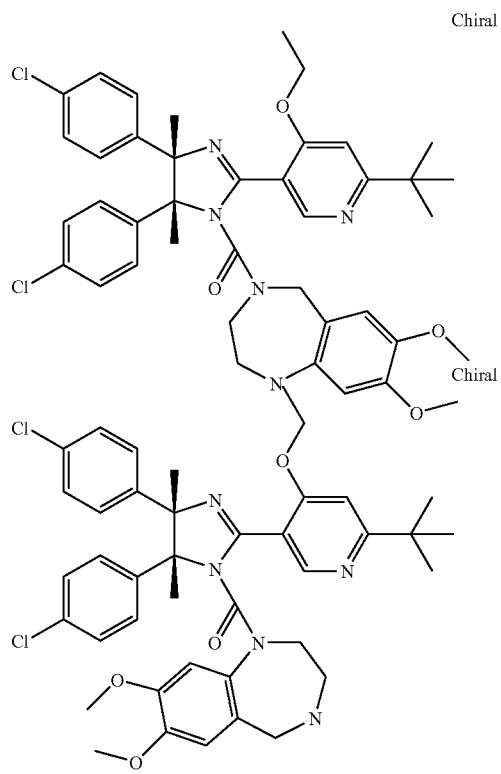

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 7,8-dimethoxy-2,3,4,5-tetrahydro-1H-benzo[e][1,4]diazepine (Oakwood) to give the title compounds. HR-MS (ES, m/z) calculated for $C_{40}H_{46}Cl_2N_5O_4$ [(M+H)$^+$] 730.2922, observed 730.2922.

EXAMPLE 142

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[(1S,5R)-6-(3-hydroxy-azetidine-1-carbonyl)-3-aza-bicyclo[3.1.0]hex-3-yl]-methanone

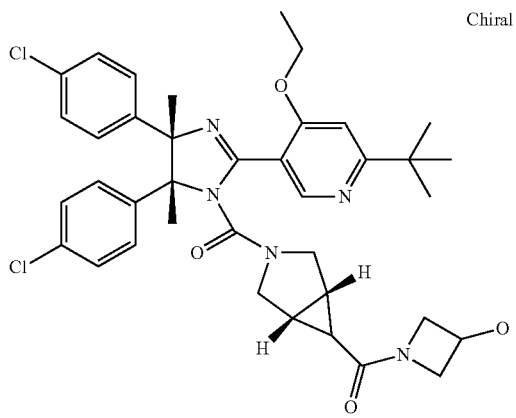 [SMILES: CCOc1cc(C(C)(C)C)ncc1C1=N[C@@](C)(c2ccc(Cl)cc2)[C@@](C)(c2ccc(Cl)cc2)N1C(=O)N1C[C@@H]2C(C(=O)N3CC(O)C3)[C@@H]2C1]

In a manner analogous to the method described in examples 99, (1S,5R)-3-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-3-aza-bicyclo[3.1.0]hexane-6-carboxylic acid (prepared from the ethyl ester, example 135) was coupled with azetidin-3-ol (Oakwood) to give the title compound. HR-MS (ES, m/z) calculated for $C_{38}H_{44}Cl_2N_5O_4$ [(M+H)$^+$] 704.2765, observed 704.2764.

EXAMPLE 143

(1S,5R)-3-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-3-aza-bicyclo[3.1.0]hexane-6-carboxylic acid (2-hydroxy-ethyl)-amide

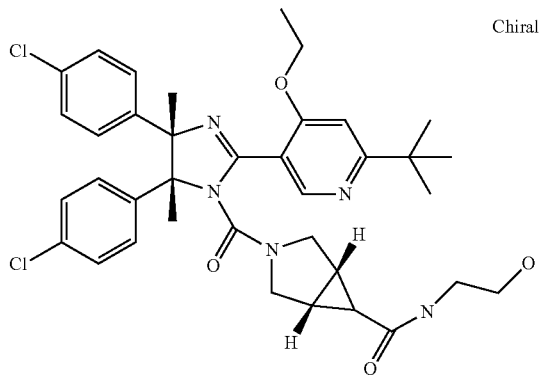 [SMILES: CCOc1cc(C(C)(C)C)ncc1C1=N[C@@](C)(c2ccc(Cl)cc2)[C@@](C)(c2ccc(Cl)cc2)N1C(=O)N1C[C@@H]2C(C(=O)NCCO)[C@@H]2C1]

In a manner analogous to the method described in examples 99, (1S,5R)-3-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-3-aza-bicyclo[3.1.0]hexane-6-carboxylic acid (prepared from the ethyl ester, example 135) was coupled with 2-aminoethanol (Aldrich) to give the title compound. HR-MS (ES, m/z) calculated for $C_{37}H_{44}Cl_2N_5O_4$ [(M+H)$^+$] 692.2765, observed 692.2768.

EXAMPLE 144

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[(1S,5R)-6-(3-hydroxy-pyrrolidine-1-carbonyl)-3-aza-bicyclo[3.1.0]hex-3-yl]-methanone

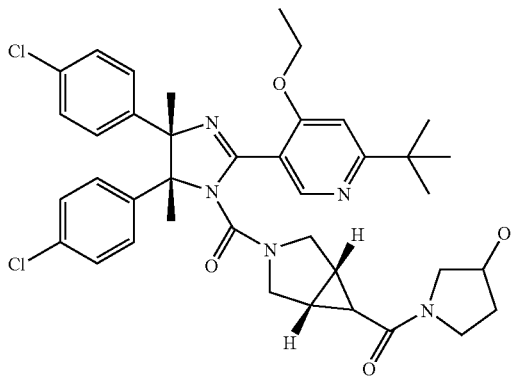 [SMILES: CCOc1cc(C(C)(C)C)ncc1C1=N[C@@](C)(c2ccc(Cl)cc2)[C@@](C)(c2ccc(Cl)cc2)N1C(=O)N1C[C@@H]2C(C(=O)N3CCC(O)C3)[C@@H]2C1]

In a manner analogous to the method described in examples 99, (1S,5R)-3-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-3-aza-bicyclo[3.1.0]hexane-6-carboxylic acid (prepared from the ethyl ester, example 135) was coupled with pyrrolidin-3-ol (Aldrich) to give the title compound as a mixture of diastereomers. HR-MS (ES, m/z) calculated for $C_{39}H_{46}Cl_2N_5O_4$ [(M+H)$^+$] 718.2922, observed 718.2921.

EXAMPLE 145

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-methyl-[1,4]diazepan-1-yl)-methanone

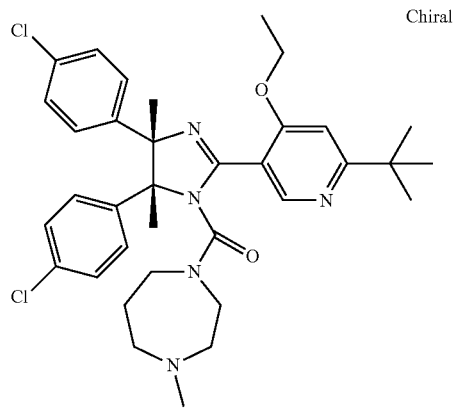 [SMILES: CCOc1cc(C(C)(C)C)ncc1C1=N[C@@](C)(c2ccc(Cl)cc2)[C@@](C)(c2ccc(Cl)cc2)N1C(=O)N1CCCN(C)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-methyl-[1,4]diazepane (Aldrich) to give the title compound. HR-MS (ES, m/z) calculated for $C_{35}H_{44}Cl_2N_5O_2$ [(M+H)$^+$] 636.2867, observed 636.287.

EXAMPLE 146

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-[1,4]diazepan-1-yl}-acetamide

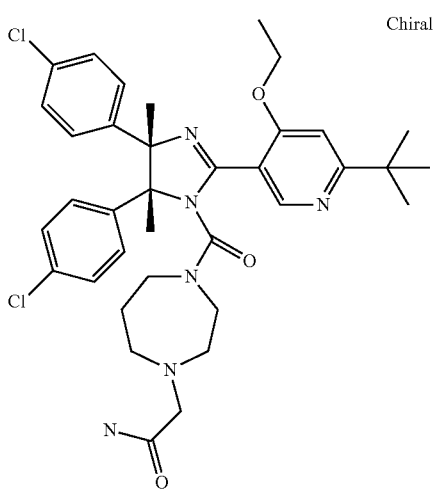 [SMILES: CCOc1cc(C(C)(C)C)ncc1C1=N[C@@](C)(c2ccc(Cl)cc2)[C@@](C)(c2ccc(Cl)cc2)N1C(=O)N1CCCN(CC(N)=O)CC1]

Ethyl bromoacetate (3.7 g, 18.4 mmol, Aldrich) was added in portions to a solution of homopiperazine (2.76 g, 27.6 mmol, Avocado) in N,N-dimethylformamide (15 mL) at room temperature over 1.5 h. The mixture was then stirred for additional 4 h followed by an aqueous workup. The crude was purified by column flash chromatography to give homopiperazine-acetic acid ethyl ester (471 mg).

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with homopiperazine-acetic acid ethyl ester to give 2-{4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-[1,4]diazepan-1-yl}-acetic acid ethyl ester. The ester was hydrolyzed, then the corresponding acid was treated with amonium chloride to give the title compound. HR-MS (ES, m/z) calculated for $C_{36}H_{45}Cl_2N_6O_3$ [(M+H)$^+$] 679.2925, observed 679.2927.

EXAMPLE 147

4-(2-{4-[(4S,5R)-2-(6-tert-Butyl-4-ethoxy-pyridin-3-yl)-4,5-bis-(4-chloro-phenyl-4,5-dimethyl-4,5-dihydro-imidazole-1-carbonyl]-[1,4]diazepan-1-yl}-acetyl)-piperazin-2-one

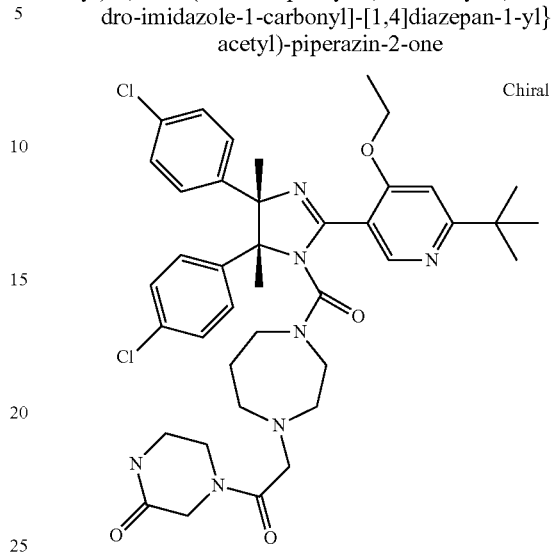

In a manner analogous to the method described in examples 99, 2-{4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-[1,4]diazepan-1-yl}-acetic acid (example 146) was coupled with 2-piperazinone (Alfa) to give the title compound. HR-MS (ES, m/z) calculated for $C_{40}H_{50}Cl_2N_7O_4$ [(M+H)$^+$] 762.3296, observed 762.3295.

EXAMPLE 148

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(6-methoxy-2-methyl-pyridin-3-yl)-acetamide

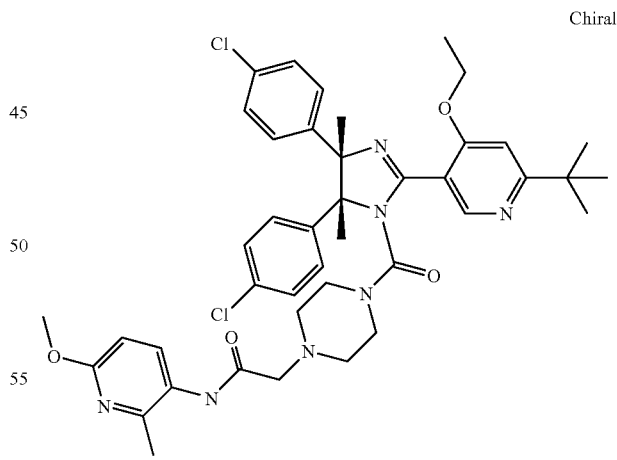

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with (6-methoxy-2-methyl-pyridin-3-yl)-methyl-amine (Asychem) to give the title compound. HR-MS (ES, m/z) calculated for $C_{42}H_{50}Cl_2N_7O_4$ [(M+H)$^+$] 786.3296, observed 786.3289.

EXAMPLE 149

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-methyl-pyridin-3-yl)-acetamide

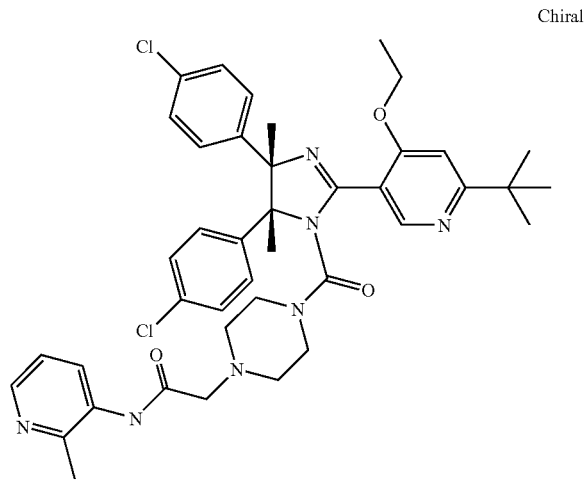 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)Nc2cccnc2C)CC1]

Chiral

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with 2-methyl-pyridin-3-ylamine (Aldrich) to give the title compound. HR-MS (ES, m/z) calculated for $C_{41}H_{48}Cl_2N_7O_3$ $[(M+H)^+]$ 756.319, observed 756.3195.

EXAMPLE 150

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-methoxy-pyridin-3-yl)-acetamide

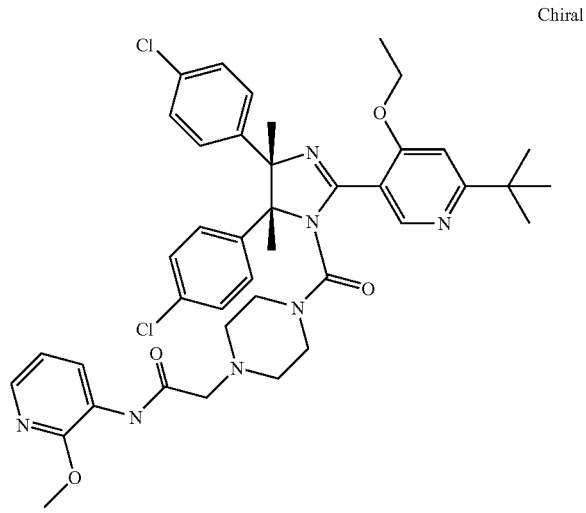 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)Nc2cccnc2OC)CC1]

Chiral

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with 2-methoxy-pyridin-3-ylamine (Fluorochem) to give the title compound. HR-MS (ES, m/z) calculated for $C_{41}H_{48}Cl_2N_7O_4$ $[(M+H)^+]$ 772.314, observed 772.3138.

EXAMPLE 151

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-ethyl-N-pyridin-3-yl-acetamide

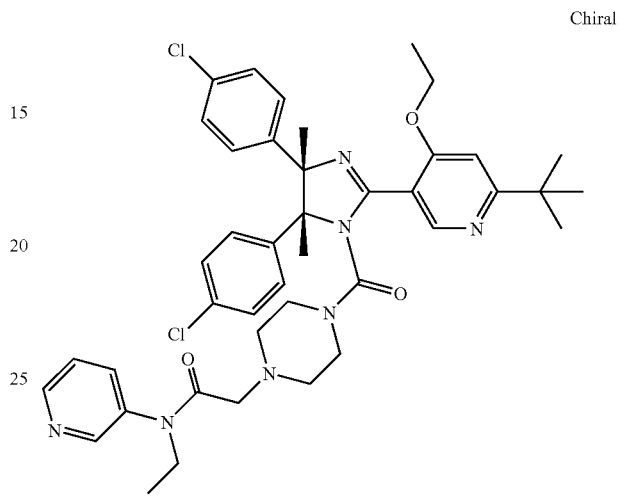

Chiral

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-3-yl-acetamide (example 127) was treated with ethyl iodide (Aldrich) and sodium hydride to give the title compound. HR-MS (ES, m/z) calculated for $C_{42}H_{50}Cl_2N_7O_3$ $[(M+H)^+]$ 770.3347, observed 770.3347.

EXAMPLE 152

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2,6-dimethyl-pyridin-3-yl)-acetamide

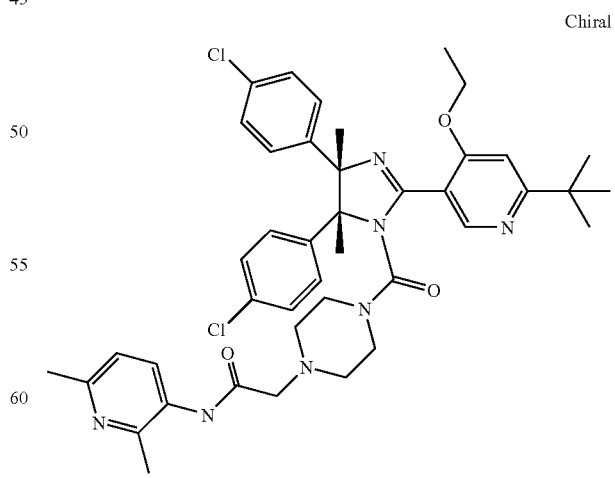

Chiral

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydroimidazole-1-carbonyl]-piperazin-1-yl}-acetic acid hydrochloride (example 94) was coupled with 2,6-dimethyl-pyridin-3-ylamine (Alfa) to give the title compound. HR-MS (ES, m/z) calculated for $C_{42}H_{50}Cl_2N_7O_3$ [(M+H)$^+$] 770.3347, observed 770.3351.

EXAMPLE 153

(S)-4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazine-2-carboxylic acid tert-butylamide

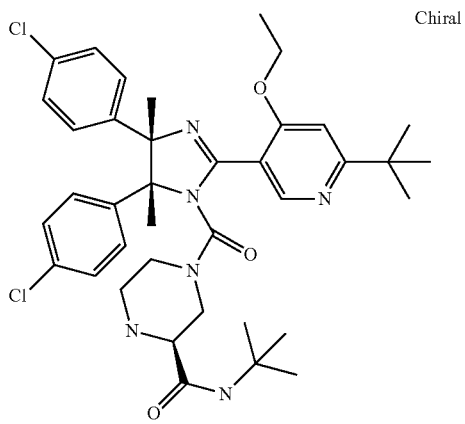 [SMILES: CCOc1cc(C(C)(C)C)ncc1C1=N[C@@](C)(c2ccc(Cl)cc2)[C@@](C)(c2ccc(Cl)cc2)N1C(=O)N1CCN[C@H](C(=O)NC(C)(C)C)C1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with (S)-piperazine-2-carboxylic acid tert-butylamide (Wako) to give the title compound. HR-MS (ES, m/z) calculated for $C_{38}H_{49}Cl_2N_6O_3$ [(M+H)$^+$] 707.3238, observed 707.3239.

EXAMPLE 154

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(4-methyl-piperazin-1-yl)-piperidin-1-yl]-methanone

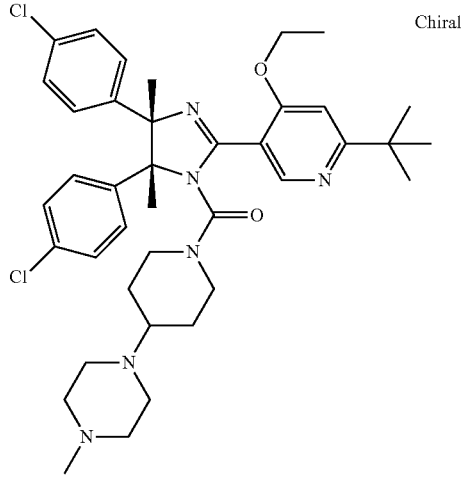 [SMILES: CCOc1cc(C(C)(C)C)ncc1C1=N[C@@](C)(c2ccc(Cl)cc2)[C@@](C)(c2ccc(Cl)cc2)N1C(=O)N1CCC(N2CCN(C)CC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-methyl-4-piperidin-4-yl-piperazine (Oakwood) to give the title compound. HR-MS (ES, m/z) calculated for $C_{39}H_{51}Cl_2N_6O_2$ [(M+H)$^+$] 705.3445, observed 705.3445.

EXAMPLE 155

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-morpholin-4-yl-piperidin-1-yl)-methanone

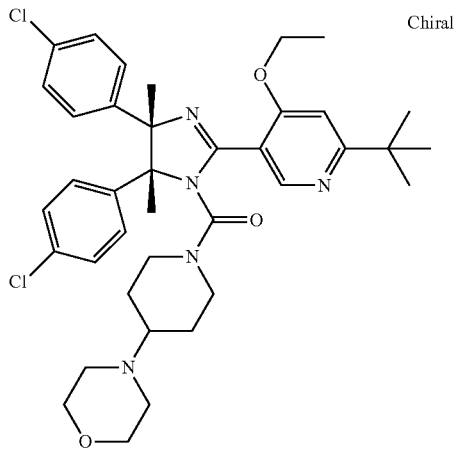 [SMILES: CCOc1cc(C(C)(C)C)ncc1C1=N[C@@](C)(c2ccc(Cl)cc2)[C@@](C)(c2ccc(Cl)cc2)N1C(=O)N1CCC(N2CCOCC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 4-piperidin-4-yl-morpholine (Aldrich) to give the title compound. HR-MS (ES, m/z) calculated for $C_{38}H_{48}Cl_2N_5O_3$ [(M+H)$^+$] 692.3129, observed 692.3123.

EXAMPLE 156

N-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide

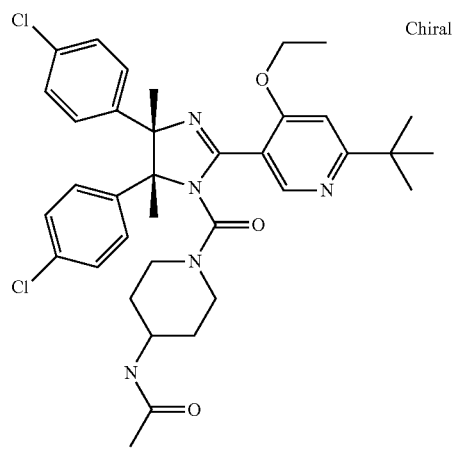 [SMILES: CCOc1cc(C(C)(C)C)ncc1C1=N[C@@](C)(c2ccc(Cl)cc2)[C@@](C)(c2ccc(Cl)cc2)N1C(=O)N1CCC(NC(C)=O)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with N-piperidin-4-yl-acetamide (TCI) to give the title compound. HR-MS (ES, m/z) calculated for $C_{36}H_{44}Cl_2N_5O_3$ $[(M+H)^+]$ 664.2816, observed 664.2813.

EXAMPLE 157

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-methyl-[1,4']bipiperidinyl-1'-yl)-methanone

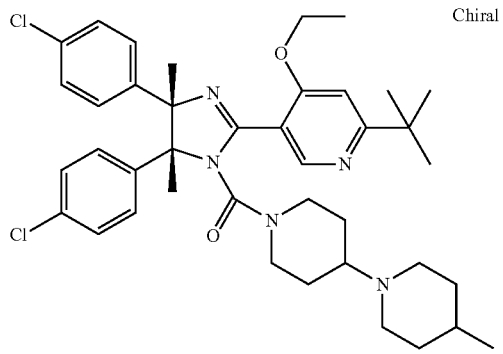 [SMILES: CCOc1cc(C(C)(C)C)ncc1C1=N[C@@](C)(c2ccc(Cl)cc2)[C@@](C)(c2ccc(Cl)cc2)N1C(=O)N1CCC(N2CCC(C)CC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 4-methyl-[1,4']bipiperidinyl (Aldrich) to give the title compound. HR-MS (ES, m/z) calculated for $C_{40}H_{52}Cl_2N_5O_2$ $[(M+H)^+]$ 704.3493, observed 704.3492.

EXAMPLE 158

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(4-ethyl-piperazin-1-yl)-piperidin-1-yl]-methanone

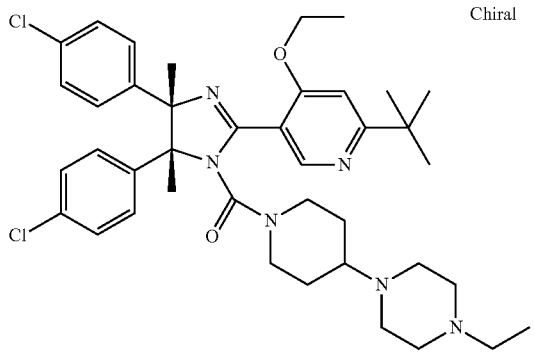 [SMILES: CCOc1cc(C(C)(C)C)ncc1C1=N[C@@](C)(c2ccc(Cl)cc2)[C@@](C)(c2ccc(Cl)cc2)N1C(=O)N1CCC(N2CCN(CC)CC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-ethyl-4-piperidin-4-yl-piperazine (Matrix) to give the title compound. HR-MS (ES, m/z) calculated for $C_{40}H_{53}Cl_2N_6O_2$ $[(M+H)^+]$ 719.3602, observed 719.3606.

EXAMPLE 159

N-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-methanesulfonamide

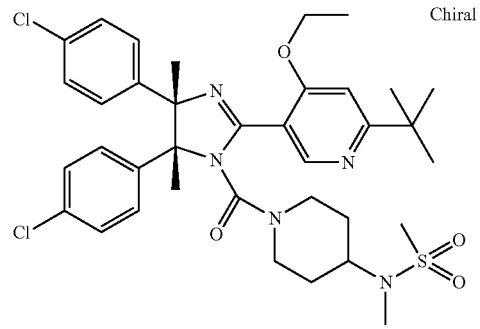 [SMILES: CCOc1cc(C(C)(C)C)ncc1C1=N[C@@](C)(c2ccc(Cl)cc2)[C@@](C)(c2ccc(Cl)cc2)N1C(=O)N1CCC(N(C)S(C)(=O)=O)CC1]

To a solution of 4-methylamino-piperidine-1-carboxylic acid tert-butyl ester (1.20 g, 5.58 mmole, Astatech) and triethylamine (3.2 mL, 22.95 mmole) in dichloromethane (70 mL) at 0° C. was added methanesulfonyl chloride (724 mg, 6.287 mmole, Aldrich). The mixture was allowed to stir for 30 min before washed successively with aqueous sodium bicarbonate and water and concentrated to dryness. The residue was taken up in dichloromethane (20 mL), treated with trifluoroacetic acid (20 mL) and allowed to stir for 3 h before it was concentrated to dryness. The residue was dissolved in dichloromethane, washes with aqueous sodium bicarbonate and concentrated to give N-methyl-N-piperidin-4-yl-methanesulfonamide (1.61 g) which was used without further purification.

In a manner analogous to the method described in example 8, N-Methyl-N-piperidin-4-yl-methanesulfonamide from above was reacted with (4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl chloride (example 51) to give the title compound. HR-MS (ES, m/z) calculated for $C_{36}H_{46}Cl_2N_5O_4S$ $[(M+H)^+]$ 714.2642, observed 714.2636.

EXAMPLE 160

N-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-methanesulfonamide

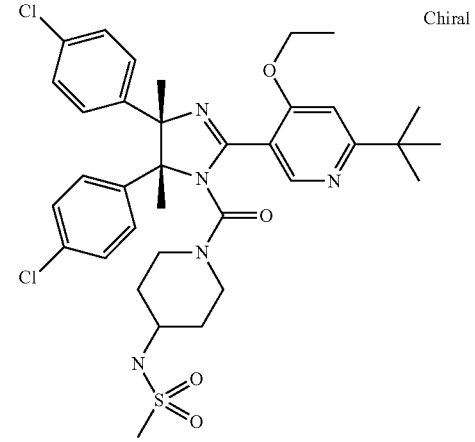 [SMILES: CCOc1cc(C(C)(C)C)ncc1C1=N[C@@](C)(c2ccc(Cl)cc2)[C@@](C)(c2ccc(Cl)cc2)N1C(=O)N1CCC(NS(C)(=O)=O)CC1]

A solution of (4-amino-piperidin-1-yl)-[(4S,5R)-2-(6-tert-butyl-4-ethoxy-pyridin-3-yl)-4,5-bis-(4-chloro-phenyl)-4,5- dimethyl-4,5-dihydro-imidazol-1-yl]-methanone (87 mg, 0.139 mmole, example 204) in dichloromethane (5 mL) was treated with methanesulfonyl chloride (31.8 mg, 0.277 mmole, Aldrich) at 0° C. and allowed to stir for 1 h before diluted with dichloromethane (60 mL), washed with aqueous sodium carbonate (15 mL), water (15 mL) and concentrated. The residue was purified by flash column chromatography (silica gel, eluting with a gradient of 1% to 10% methanol in dichloromethane) to give the title compound (83.8 mg). HR-MS (ES, m/z) calculated for $C_{35}H_{44}Cl_2N_5O_4S$ [(M+H)$^+$] 700.2486, observed 700.2482.

EXAMPLE 161

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methanesulfonyl-ethylamino)-piperidin-1-yl]-methanone

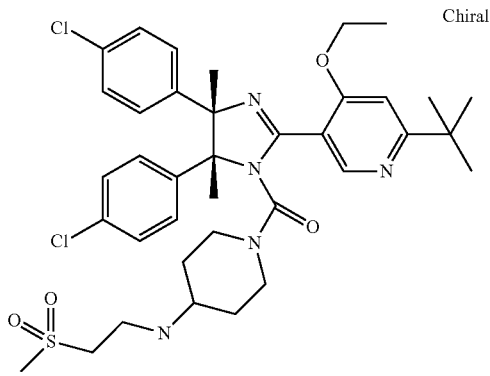 [SMILES: CCOc1cc(C(C)(C)C)ncc1C1=N[C@@](C)(c2ccc(Cl)cc2)[C@@](C)(c2ccc(Cl)cc2)N1C(=O)N1CCC(NCCS(C)(=O)=O)CC1]

To a solution of 1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-one (64.6 mg, 0.104 mmole, example 209) and 2-aminoethyl methylsulfone hydrochloride (17.9 mg, 0.112 mmole, Array) in dichloromethane (3 mL) were added sodium acetate (21.1 mg, 0.257 mmole) and sodium triacetoxyborohydride (40.1 mg, 0.189 mmole). The mixture was stirred at room temperature overnight before saturated solution of sodium bicarbonate (3 mL) was added. After stirred for 1 h, the mixture was extracted with dichloromethane (2×10 mL). The combined organic extracts were washed with brine, dried over sodium sulfate and concentrated to dryness. The crude product was purified by flash column chromatography (silica gel, eluting with a gradient of 1% to 10% methanol in dichloromethane) to give the title compound (56.7 mg, 75% yield). HR-MS (ES, m/z) calculated for $C_{37}H_{48}Cl_2N_5O_4S$ [(M+H)$^+$] 728.2799, observed 728.2796.

EXAMPLE 162

{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid methyl ester

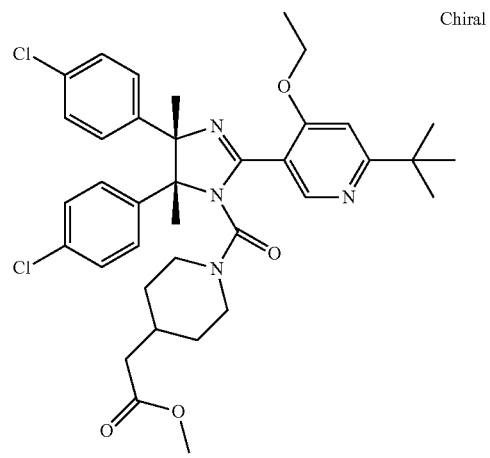 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)OC)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with piperidin-4-yl-acetic acid methyl ester (Astatech) to give the title compound. HR-MS (ES, m/z) calculated for $C_{37}H_{45}Cl_2N_4O_4$ [(M+H)$^+$] 679.2813, observed 679.2808.

EXAMPLE 163

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-pyrrolidin-1-yl-ethanone

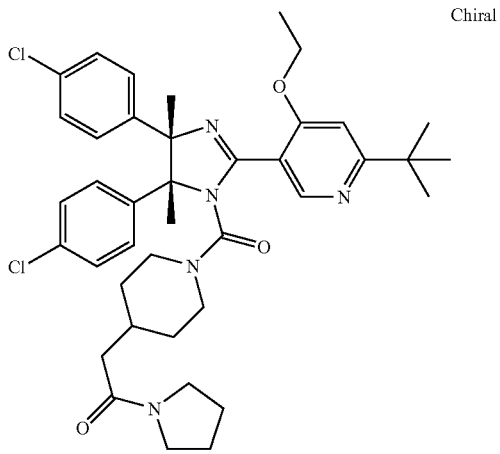 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCCC2)CC1]

{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid methyl ester (519 mg, 0.763 mmole, example 162) in methanol (4 mL) and tetrahydrofuran (4 mL) was treated with lithium hydroxide (36 mg) in water (4 mL) and allowed to stir at room temp. for 3 h. The mixture was neutralized with 1N hydrochloric acid and extracted with ethyl acetate. The organic extracts were washed with brine, dried over anhydrous sodium sulfate. The solids were filtered off, and the filtrate was concentrated to give {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid (482 mg) which was used without purification.

To a suspension of {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid (75.0 mg, 0.112 mmole) in dimethylformamide (6 mL) were added successively 1-hydroxybenzotriazole (23.0 mg, 0.169 mmole, Chem-Impex), N,N,N',N'-tetramethyl-O-(1H-benzotriazol-1-yl)uranium hexafluorophosphate (64.0 mg, 0.169 mmole, Aldrich) and diisopropylethylamine (58 mg, 0.448 mmole). The mixture was stirred for 15 min before pyrrolidine (12.0 mg, 0.169 mmole, Aldrich) was added. The reaction mixture was allowed to stir for 2 h before concentrated under reduced pressure. The residue was dissolved in ethyl acetate and washed with 1 N sodium hydroxide, brine, dried and concentrated. The crude residue was purified by flash column chromatography (silica gel, eluting with a gradient of 1-10% methanol in methylene chloride) to give the title compound (71.8 mg, 89% yield). HR-MS (ES, m/z) calculated for $C_{40}H_{50}Cl_2N_5O_3$ $[(M+H)^+]$ 718.3285, observed 718.328.

EXAMPLE 164

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-dimethyl-acetamide

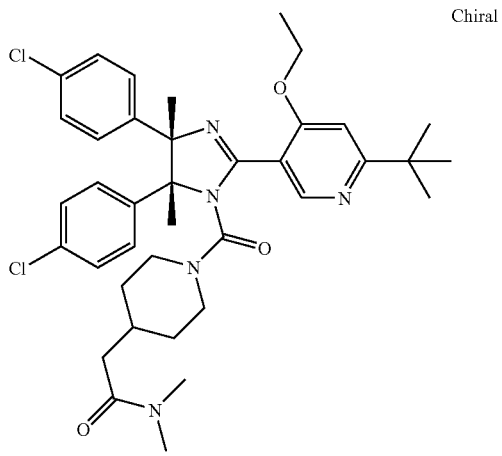 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)C)CC1]

In a manner analogous to the method described in example 163, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with dimethylamine (Aldrich) to give the title compound. HR-MS (ES, m/z) calculated for $C_{38}H_{48}Cl_2N_5O_3$ $[(M+H)^+]$ 692.3129, observed 692.3129.

EXAMPLE 165

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-diethylamino-piperidin-1-yl)-methanone

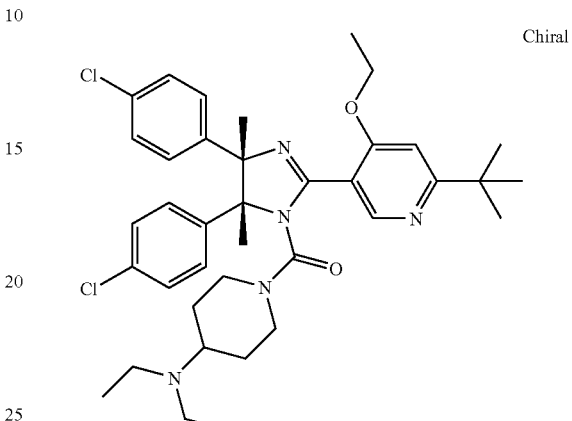

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with diethyl-4-piperidinylamine (Astatech) to give the title compound. HR-MS (ES, m/z) calculated for $C_{38}H_{50}Cl_2N_5O_2$ $[(M+H)^+]$ 678.3336, observed 678.3335.

EXAMPLE 166

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-{4-[(2-methanesulfonyl-ethyl)-methyl-amino]-piperidin-1-yl}-methanone

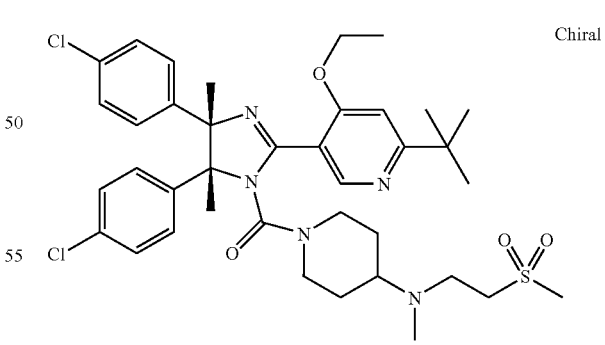

In a manner analogous to the method described in example 161, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-one (example 209) was coupled with 2-(methylamino)-1-(methylsulfonyl)ethane (Array) to give the title compound. HR-MS (ES, m/z) calculated for $C_{38}H_{50}Cl_2N_5O_4S$ $[(M+H)^+]$ 742.2955, observed 742.2957.

EXAMPLE 167

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-hydroxy-ethyl)-acetamide

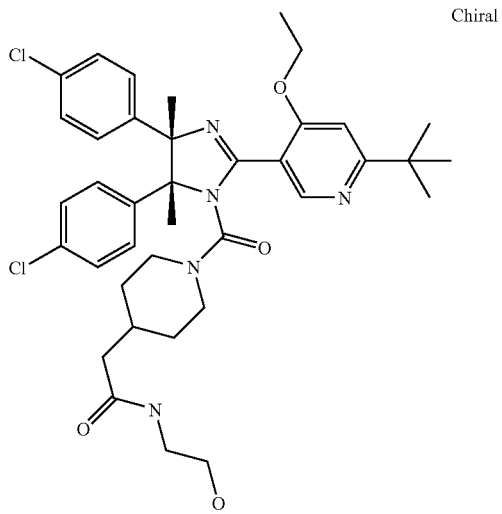 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCCO)CC1]

In a manner analogous to the method described in example 163, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with 2-hydroxylethylamine (Aldrich) to give the title compound. HR-MS (ES, m/z) calculated for $C_{38}H_{48}Cl_2N_5O_4$ [(M+H)$^+$] 708.3078, observed 708.3074.

EXAMPLE 168

1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-methyl-urea

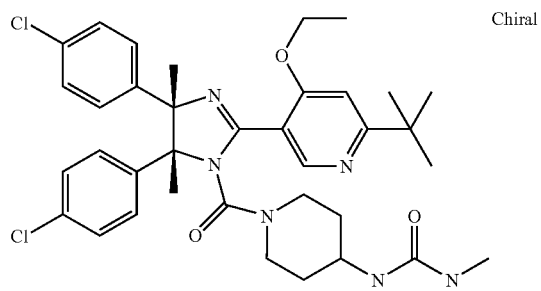 [SMILES: CCOc1cc(C(C)(C)C)ncc1C1=N[C@@](C)(c2ccc(Cl)cc2)[C@@](C)(c2ccc(Cl)cc2)N1C(=O)N1CCC(NC(=O)NC)CC1]

In a manner similar to the method described in example 160, (4-amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with methyl isocyanate (Aldrich) to give the title compound. HR-MS (ES, m/z) calculated for $C_{36}H_{45}Cl_2N_6O_3$ [(M+H)$^+$] 679.2925, observed 679.2929.

EXAMPLE 169

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(pyrrolidine-1-carbonyl)-piperidin-1-yl]-methanone

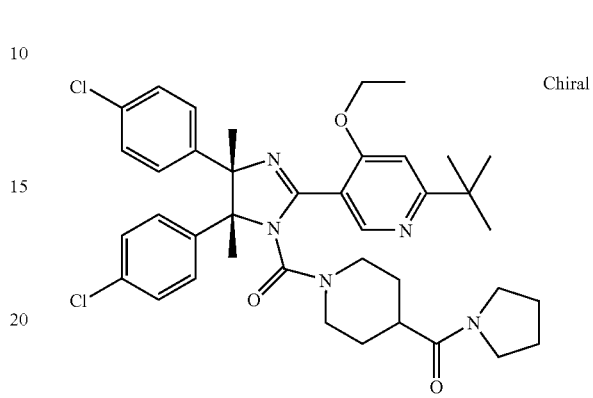

In a manner analogous to the method described in example 163,1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid was coupled with pyrrolidine (Aldrich) to give the title compound. HR-MS (ES, m/z) calculated for $C_{39}H_{48}Cl_2N_5O_3$ [(M+H)$^+$] 704.3129, observed 704.3131.

EXAMPLE 170

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(piperazine-1-carbonyl)-piperidin-1-yl]-methanone

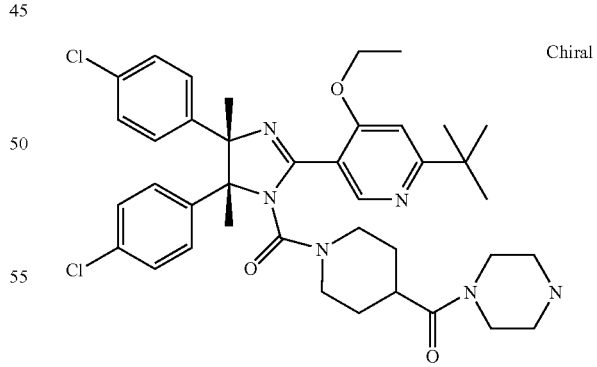

In a manner analogous to the method described in example 163, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid was reacted with piperazine (Aldrich) to give the title compound. HR-MS (ES, m/z) calculated for $C_{39}H_{49}Cl_2N_6O_3$ [(M+H)$^+$] 719.3238, observed 719.3243.

EXAMPLE 171

1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-3-methylsulfanyl-propan-1-one

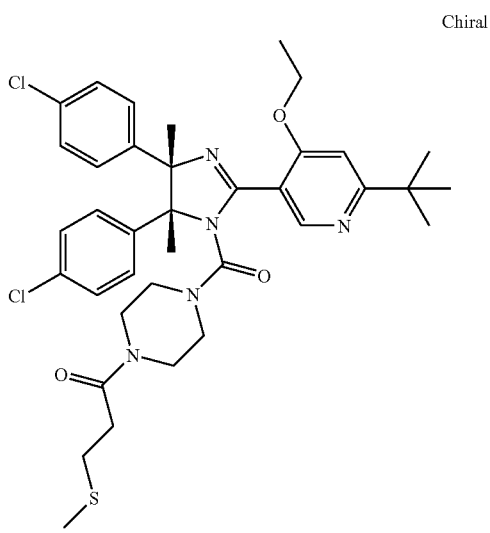 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C(=O)CCSC)CC1]

In a manner analogous to the method described in example 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was reacted with piperazine (Aldrich) to give [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-piperazin-1-yl-methanone.

To a solution of 3-(methylthio)propionic acid (30.8 mg, 0.256 mmole, Lancaster) in dimethylformamide (10 mL) were added successively 1-hydroxybenzotriazole (46.3 mg, 0.342 mmole, Chem-Impex), N,N,N',N'-tetramethyl-O-(1H-Benzotriazol-1-yl)uranium hexafluorophosphate (130.0 mg, 0.343 mmole, Aldrich) and diisopropylethylamine (111.0 mg, 0.857 mmole). The mixture was stirred for 15 min before [(4S,5R)-2-(6-tert-butyl-4-ethoxy-pyridin-3-yl)-4,5-bis-(4-chloro-phenyl)-4,5-dimethyl-4,5-dihydro-imidazol-1-yl]-piperazin-1-yl-methanone (104.4 mg, 0.171 mmole) was added. The reaction mixture was allowed to stir for 1 h before concentrated under reduced pressure. The residue was dissolved in ethyl acetate and washed with 1 N sodium hydroxide, brine, dried and concentrated. The crude residue was purified by flash column chromatography (silica gel, eluting with a gradient of 1-10% methanol in methylene chloride) to give the title compound (108.7 mg, 89% yield). HR-MS (ES, m/z) calculated for $C_{37}H_{46}Cl_2N_5O_3S$ $[(M+H)^+]$ 710.2693, observed 710.2691.

EXAMPLE 172

1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-3-methanesulfonyl-propan-1-one

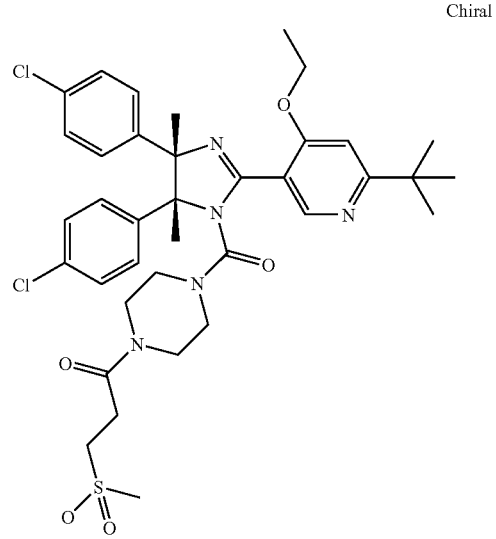

To a solution of 1-{4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-3-methylsulfanyl-propan-1-one (92.3 mg, 0.129 mmole, example 171) in dichloromethane (8 mL) was added 3-chloroperoxybenzoic acid (72.5 mg, 0.324 mmole, Aldrich, max. 77%). The mixture was allowed to stir at 0° C. for 1.5 h before diluted with dichloromethane and washed successively with 10% aqueous sodium thiosulfate, saturated aqueous sodium carbonate, water and concentrated. The crude product was purified by flash column chromatography (silica gel, eluting with a gradient of 1-10% methanol in methylene chloride) to give the title compound (73.3 mg, 76%). HR-MS (ES, m/z) calculated for $C_{37}H_{46}Cl_2N_5O_5S$ $[(M+H)^+]$ 742.2591, observed 742.2591

EXAMPLE 173

1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid (2-methanesulfonyl-ethyl)-amide

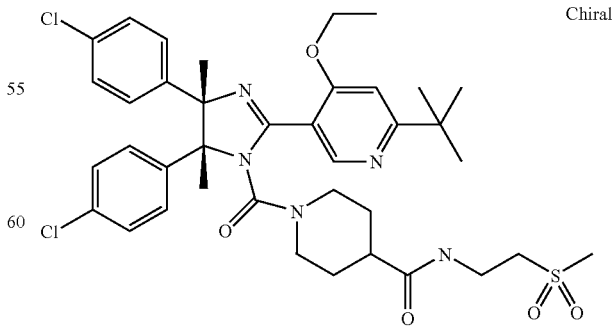

In a manner analogous to the method described in example 163, 1-[(4S,5R)-2-(6-tert-butyl-4-ethoxy-pyridin-3-yl)-4,5-.

bis-(4-chloro-phenyl)-4,5-dimethyl-4,5-dihydro-imidazole-1-carbonyl]-piperidine-4-carboxylic acid, was coupled with 2-aminoethyl methylsulfone hydrochloride (Array) to give the title compound. HR-MS (ES, m/z) calculated for $C_{38}H_{48}Cl_2N_5O_5S$ $[(M+H)^+]$ 756.2748, observed 756.2749.

EXAMPLE 174

1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid (2-methanesulfonyl-ethyl)-methyl-amide

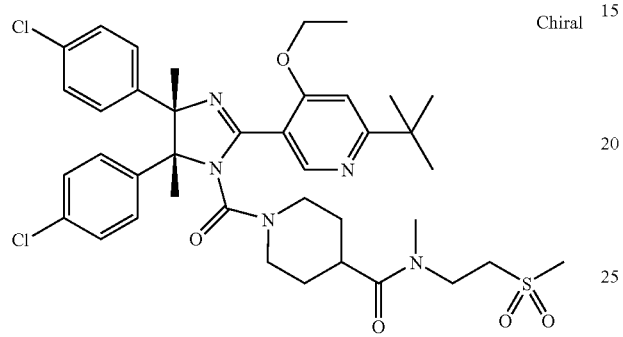

In a manner analogous to the method described in example 163, 1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid was coupled with (2-methanesulfonylethyl)-methylamine hydrochloride (Array) to give the title compound. HR-MS (ES, m/z) calculated for $C_{39}H_{50}Cl_2N_5O_5S$ $[(M+H)^+]$ 770.2904, observed 770.2905.

EXAMPLE 175

1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid (2-hydroxy-ethyl)-amide

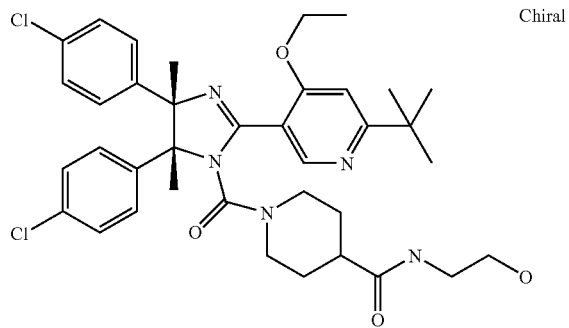 [SMILES: CCOc1cc(C(C)(C)C)ncc1C1=N[C@@](C)(c2ccc(Cl)cc2)[C@@](C)(c2ccc(Cl)cc2)N1C(=O)N1CCC(C(=O)NCCO)CC1]

In a manner analogous to the method described in example 163, 1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid was coupled with ethanolamine (Aldrich) to give the title compound. HR-MS (ES, m/z) calculated for $C_{37}H_{46}Cl_2N_5O_4$ $[(M+H)^+]$ 694.2922, observed 694.2918.

EXAMPLE 176

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(1,1-dioxo-1λ6-thiomorpholine-4-carbonyl)-piperidin-1-yl]-methanone

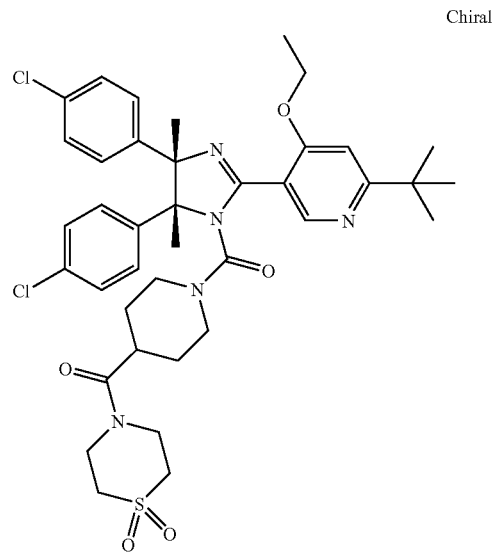 [SMILES: CCOc1cc(C(C)(C)C)ncc1C1=N[C@@](C)(c2ccc(Cl)cc2)[C@@](C)(c2ccc(Cl)cc2)N1C(=O)N1CCC(C(=O)N2CCS(=O)(=O)CC2)CC1]

In a manner analogous to the method described in example 163, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid was coupled with thiomorpholine 1,1-dioxide (Aldrich) to give the title compound. HR-MS (ES, m/z) calculated for $C_{39}H_{48}Cl_2N_5O_5S$ $[(M+H)^+]$ 768.2748, observed 768.2748.

EXAMPLE 177

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methanesulfonyl-ethoxy)-piperidin-1-yl]-methanone

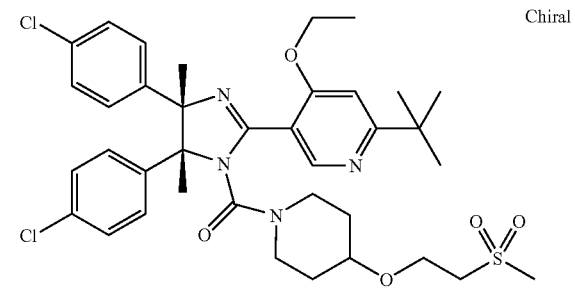 [SMILES: CCOc1cc(C(C)(C)C)ncc1C1=N[C@@](C)(c2ccc(Cl)cc2)[C@@](C)(c2ccc(Cl)cc2)N1C(=O)N1CCC(OCCS(C)(=O)=O)CC1]

To a stirred solution of [(4S,5R)-2-(6-tert-butyl-4-ethoxy-pyridin-3-yl)-4,5-bis-(4-chloro-phenyl)-4,5-dimethyl-4,5-dihydro-imidazol-1-yl]-(4-hydroxy-piperidin-1-yl)-methanone (94.8 mg, 0.152 mmole, example 101) was added sodium hydride (9.3 mg, 0.232 mmole, 60%, Aldrich) followed by methyl vinyl sulfone (0.04 mL, 0.448 mmole, Aldrich). The mixture was allowed to stir at room temp for 2.5 h before quenched with aqueous ammonium chloride and extracted with dichloromethane. The organic extracts were washed with brine and concentrated to dryness. The crude product was purified by flash column chromatography (silica gel, eluting a gradient of 1-10% methanol in methylene chloride) to give the title compound (93.4 mg, 84% yield). HR-MS (ES, m/z) calculated for $C_{37}H_{47}Cl_2N_4O_5S$ $[(M+H)^+]$ 729.2639, observed 729.2641.

EXAMPLE 178

Rac-4-[(4S*,5R*)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-2-one

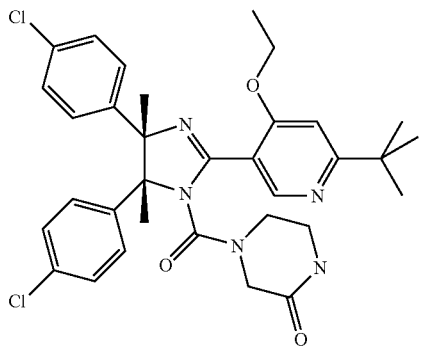 [SMILES: CCOc1cc(C(C)(C)C)ncc1C1=N[C@@](C)(c2ccc(Cl)cc2)[C@@](C)(c2ccc(Cl)cc2)N1C(=O)N1CCNC(=O)C1]

In a manner analogous to the method described in examples 8, rac-(4S*,5R*)-2-(6-tert-butyl-4-ethoxy-pyridin-3-yl)-4,5-bis-(4-chloro-phenyl)-4,5-dimethyl-4,5-dihydro-imidazole-1-carbonyl chloride was coupled with 2-piperazinone (Alfa) to give the title compound. HR-MS (ES, m/z) calculated for $C_{33}H_{38}Cl_2N_5O_3$ $[(M+H)^+]$ 622.2346, observed 622.2341.

EXAMPLE 179

Rac-[(4S*,5R*)-2-(6-tert-Butyl-4-ethoxy-pyridin-3-yl)-4,5-bis-(4-chloro-phenyl)-4,5-dimethyl-4,5-dihydro-imidazol-1-yl]-[4-(morpholine-4-carbonyl)-piperazin-1-yl]-methanone

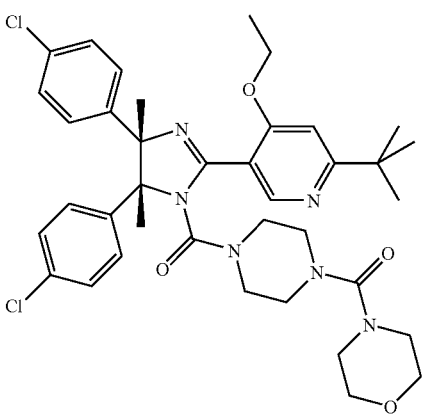 [SMILES: CCOc1cc(C(C)(C)C)ncc1C1=N[C@@](C)(c2ccc(Cl)cc2)[C@@](C)(c2ccc(Cl)cc2)N1C(=O)N1CCN(C(=O)N2CCOCC2)CC1]

In a manner analogous to the method described in examples 8, rac-(4S*,5R*)-2-(6-tert-butyl-4-ethoxy-pyridin-3-yl)-4,5-bis-(4-chloro-phenyl)-4,5-dimethyl-4,5-dihydro-imidazole-1-carbonyl chloride was coupled with morpholin-4-yl-piperazin-1-yl-methanone (Oakwood) to give the title compound. HR-MS (ES, m/z) calculated for $C_{38}H_{47}Cl_2N_6O_4$ $[(M+H)^+]$ 721.3031, observed 721.3031.

EXAMPLE 180

4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-2-one

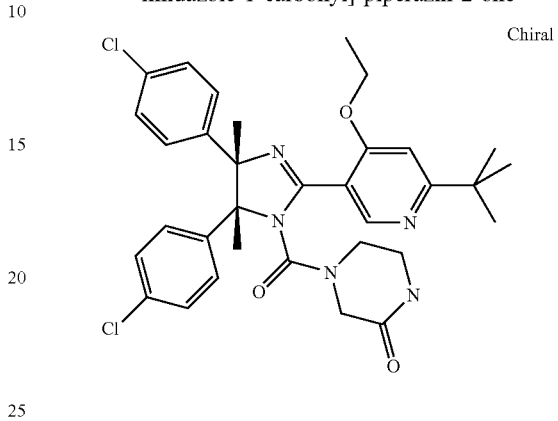

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 2-piperazinone (Alfa) to give the title compound. HR-MS (ES, m/z) calculated for $C_{33}H_{38}Cl_2N_5O_3$ $[(M+H)^+]$ 622.2346, observed 622.2346.

EXAMPLE 181

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide

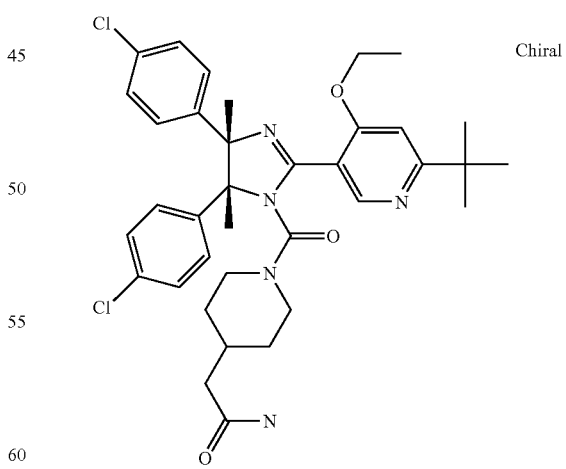

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 2-piperidin-4-yl-acetamide (ChemBridge) to give the title compound. HR-MS (ES, m/z) calculated for $C_{36}H_{44}Cl_2N_5O_3$ [(M+H)$^+$] 664.2816, observed 664.2818.

EXAMPLE 182

Rac-1-{1-[(4S*,5R*)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-[1,4]diazepan-5-one

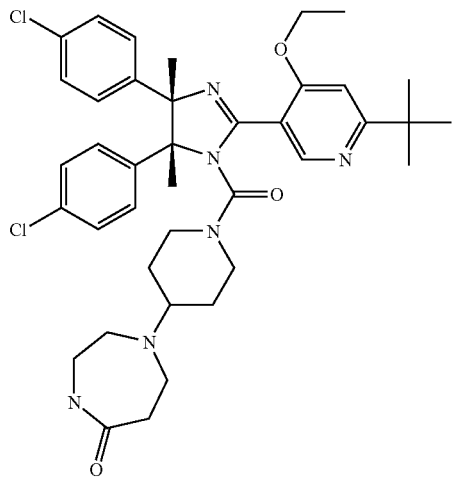 [SMILES: CCOc1cc(C(C)(C)C)ncc1C1=N[C@@](C)(c2ccc(Cl)cc2)[C@@](C)(c2ccc(Cl)cc2)N1C(=O)N1CCC(N2CCNC(=O)CC2)CC1]

In a manner analogous to the method described in examples 8, rac-(4S*,5R*)-2-(6-tert-butyl-4-ethoxy-pyridin-3-yl)-4,5-bis-(4-chloro-phenyl)-4,5-dimethyl-4,5-dihydro-imidazole-1-carbonyl chloride was coupled with 1-piperidin-4-yl-[1,4]diazepan-5-one (ChemBridge) to give the title compound. HR-MS (ES, m/z) calculated for $C_{39}H_{49}Cl_2N_6O_3$ [(M+H)$^+$] 719.3238, observed 719.3243.

EXAMPLE 183

1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-[1,4]diazepan-5-one

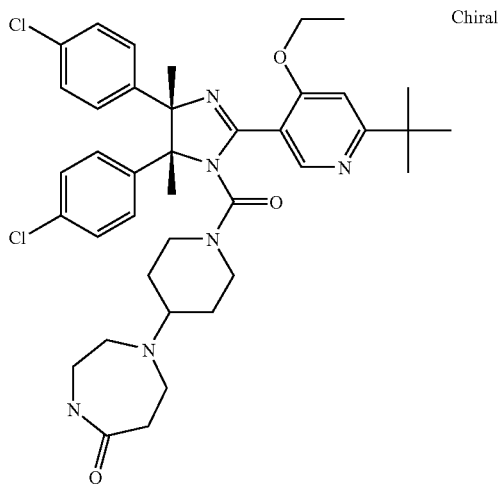 [SMILES: CCOc1cc(C(C)(C)C)ncc1C1=N[C@@](C)(c2ccc(Cl)cc2)[C@@](C)(c2ccc(Cl)cc2)N1C(=O)N1CCC(N2CCNC(=O)CC2)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1-piperidin-4-yl-[1,4]diazepan-5-one (ChemBridge) to give the title compound. HR-MS (ES, m/z) calculated for $C_{39}H_{49}Cl_2N_6O_3$ [(M+H)$^+$] 719.3238, observed 719.3241.

EXAMPLE 184

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-2-yl-acetamide

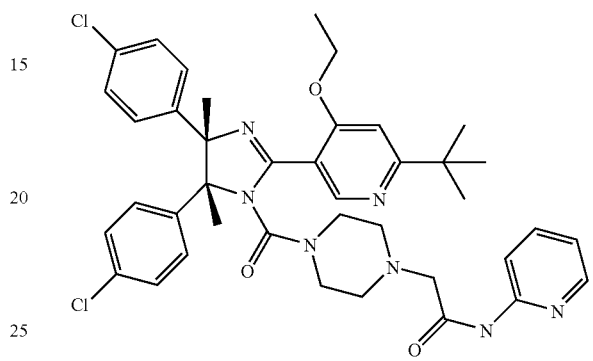

In a manner analogous to the method described in examples 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride (example 94) was coupled with 2-aminopyridine (Aldrich) to give the title compound. HR-MS (ES, m/z) calculated for $C_{40}H_{46}Cl_2N_7O_3$ [(M+H)$^+$] 742.3034, observed 742.3032.

EXAMPLE 185

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-piperazin-1-yl-methanone

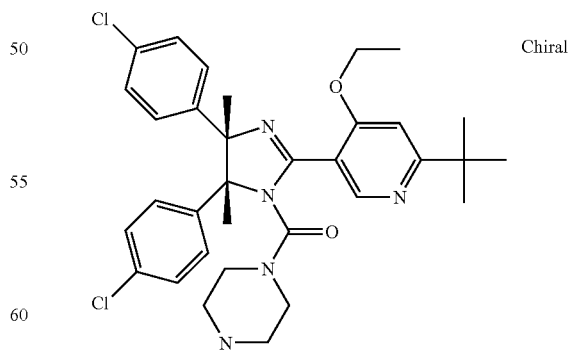

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with piperazine (Aldrich) to give the title compound. HR-MS (ES, m/z) calculated for $C_{33}H_{40}Cl_2N_5O_2$ [(M+H)$^+$] 608.2554, observed 608.2554.

EXAMPLE 186

(4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid ((S)-3,4-dihydroxy-butyl)-amide

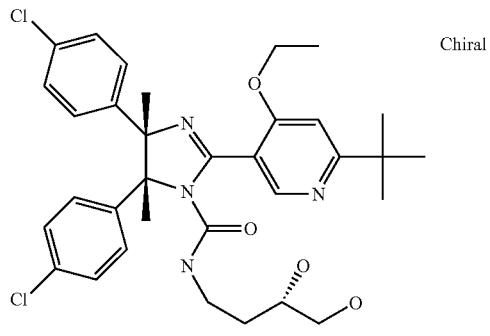 [SMILES: CCOc1cc(C(C)(C)C)ncc1C1=N[C@@](C)(c2ccc(Cl)cc2)[C@@](C)(c2ccc(Cl)cc2)N1C(=O)NCC[C@H](O)CO]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with (S)-4-amino-butane-1,2-diol (prepared from (4S)-(+)-4-(2-hydroxyethyl)-2,2-dimethyl-1,3-dioxolane (Aldrich) to give the title compound. HR-MS (ES, m/z) calculated for C33H41Cl2N4O4 [(M+H)$^+$] 627.25, observed 627.2497.

EXAMPLE 187

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3,6-dihydro-2H-pyridin-1-yl)-methanone

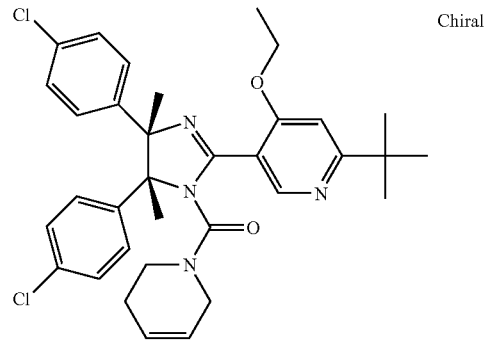 [SMILES: CCOc1cc(C(C)(C)C)ncc1C1=N[C@@](C)(c2ccc(Cl)cc2)[C@@](C)(c2ccc(Cl)cc2)N1C(=O)N1CC=CCC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 1,2,3,6-tetrahydro-pyridine (Aldrich) to give the title compound. HR-MS (ES, m/z) calculated for C34H39Cl2N4O2 [(M+H)$^+$] 605.2445, observed 605.2446.

EXAMPLE 188

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3,4-dihydroxy-piperidin-1-yl)-methanone

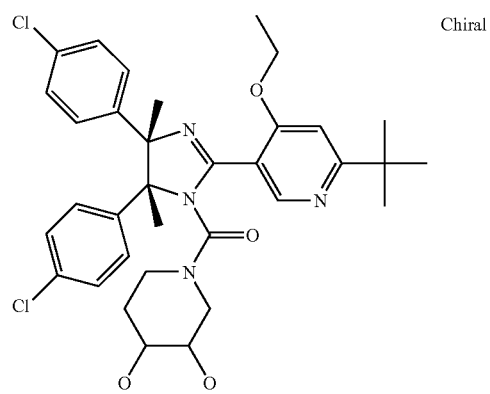 [SMILES: CCOc1cc(C(C)(C)C)ncc1C1=N[C@@](C)(c2ccc(Cl)cc2)[C@@](C)(c2ccc(Cl)cc2)N1C(=O)N1CCC(O)C(O)C1]

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3,6-dihydro-2H-pyridin-1-yl)-methanone (example 187) was reacted with osmium tetroxide in the presence of N-methylmorpholine oxide to give the title compound. HR-MS (ES, m/z) calculated for $C_{34}H_{41}Cl_2N_4O_4$ [(M+H)$^+$] 639.2500, observed 639.2500.

EXAMPLE 189

(4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid methyl-((2S,3R,4R,5R)-2,3,4,5,6-pentahydroxy-hexyl)-amide

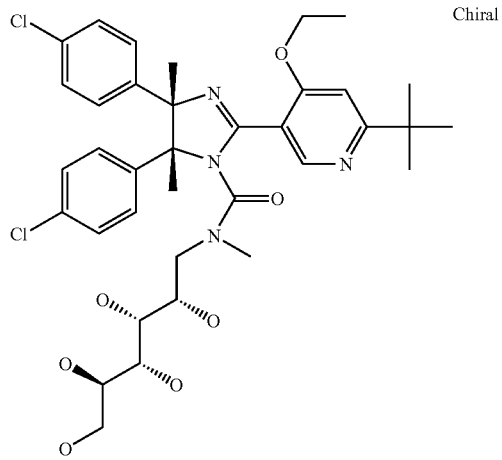 [SMILES: CCOc1cc(C(C)(C)C)ncc1C1=N[C@@](C)(c2ccc(Cl)cc2)[C@@](C)(c2ccc(Cl)cc2)N1C(=O)N(C)C[C@H](O)[C@@H](O)[C@H](O)[C@H](O)CO]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with (2R,3R,4R,5S)-6-methylamino-hexane-1,2,3,4,5-pentaol (Aldrich) to give the title compound. HR-MS (ES, m/z) calculated for $C_{36}H_{47}Cl_2N_4O_7$ [(M+H)$^+$] 717.2817, observed 717.2813.

EXAMPLE 190

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-2-ylmethyl-acetamide

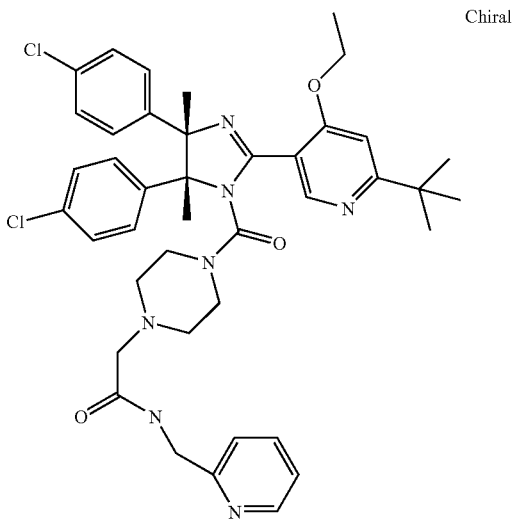 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)NCc2ccccn2)CC1]

In a manner analogous to the method described in example 99, {4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid was coupled with 2-(Aminomethyl)pyridine (Aldrich) to give the title compound. HR-MS (ES, m/z) calculated for $C_{41}H_{48}Cl_2N_7O_3$ [(M+H)$^+$] 756.319, observed 756.3194.

EXAMPLE 191

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-3-ylmethyl-acetamide

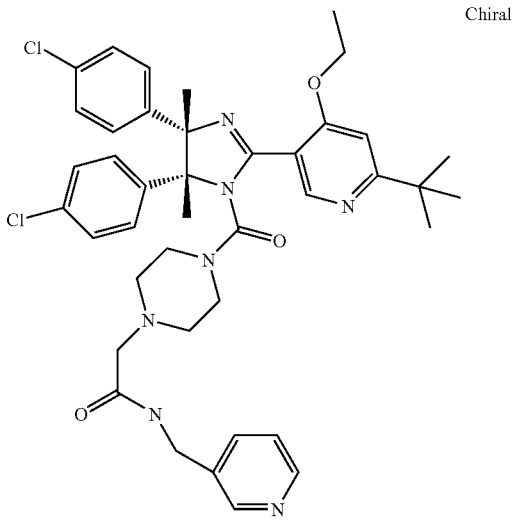 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)NCc2cccnc2)CC1]

In a manner analogous to the method described in example 99, {4-[(4S,5R)-2-(6-tert-Butyl-4-ethoxy-pyridin-3-yl)-4,5- bis-(4-chloro-phenyl)-4,5-dimethyl-4,5-dihydro-imidazole-1-carbonyl]-piperazin-1-yl}-acetic acid was coupled with 3-(Aminomethyl)pyridine (Aldrich) to give the title compound. HR-MS (ES, m/z) calculated for $C_{41}H_{48}Cl_2N_7O_3$ [(M+H)$^+$] 756.319, observed 756.3195.

EXAMPLE 192

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-4-ylmethyl-acetamide

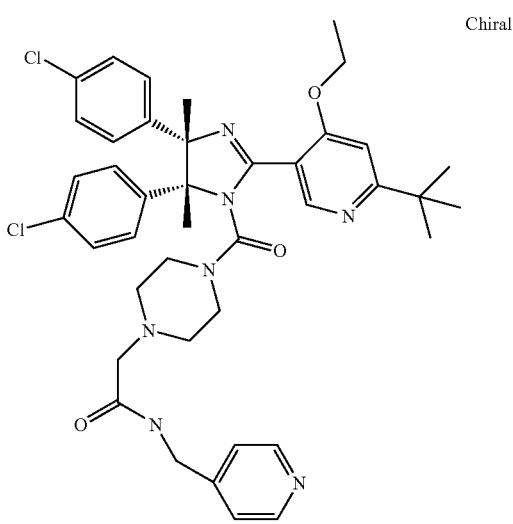 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)NCc2ccncc2)CC1]

In a manner analogous to the method described in example 99, {4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid was coupled with 4-(Aminomethyl)pyridine (Aldrich) to give the title compound. HR-MS (ES, m/z) calculated for $C_{41}H_{48}Cl_2N_7O_3$ [(M+H)$^+$] 756.319, observed 756.3194.

EXAMPLE 193

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-furan-2-ylmethyl-acetamide

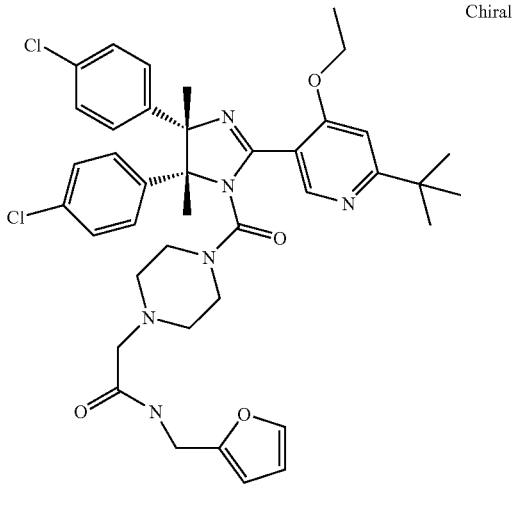 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)NCc2ccco2)CC1]

In a manner analogous to the method described in example 99, {4-[(4S,5R)-2-(6-tert-Butyl-4-ethoxy-pyridin-3-yl)-4,5- bis-(4-chloro-phenyl)-4,5-dimethyl-4,5-dihydro-imidazole-1-carbonyl]-piperazin-1-yl}-acetic acid was coupled with furfurylamine (Acros Organics) to give the title compound. HR-MS (ES, m/z) calculated for $C_{40}H_{47}Cl_2N_6O_4$ $[(M+H)^+]$ 745.3031, observed 745.3028.

EXAMPLE 194

{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid

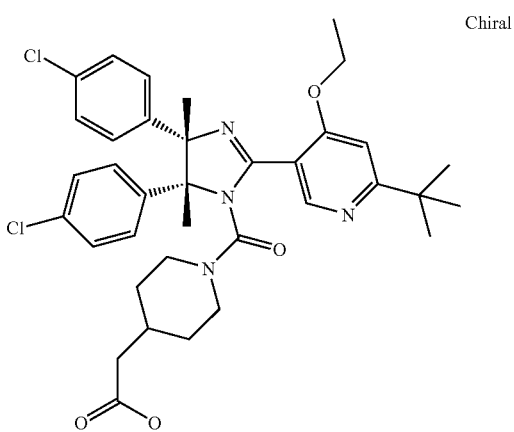 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)O)CC1]

{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid methyl ester (example 162) was hydrolyzed using lithium hydroxide in methanol/tetrahydrofuran and water to give the title compound. HR-MS (ES, m/z) calculated for $C_{36}H_{43}Cl_2N_4O_4$ $[(M+H)^+]$ 665.2656, observed 665.2656.

EXAMPLE 195

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-pyridin-2-ylmethyl-acetamide

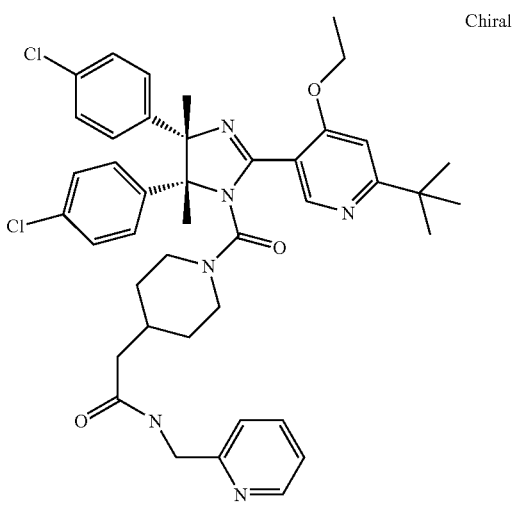 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCc2ccccn2)CC1]

In a manner analogous to the method described in example 163, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 2-(aminomethyl)pyridine (Aldrich) to give the title compound. HR-MS (ES, m/z) calculated for $C_{42}H_{49}Cl_2N_6O_3$ $[(M+H)^+]$ 755.3238, observed 755.3238.

EXAMPLE 196

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-pyridin-3-yl-acetamide

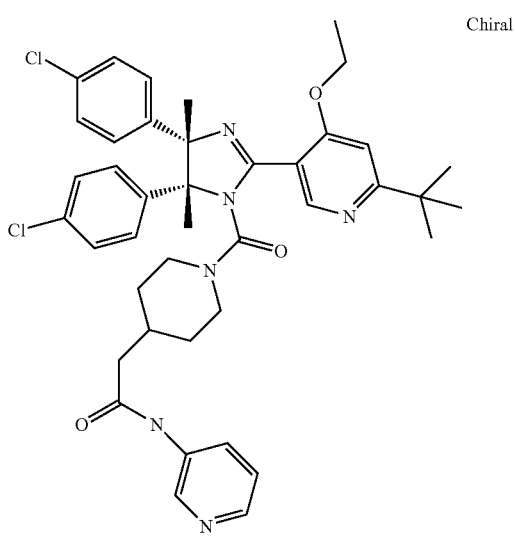 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)Nc2cccnc2)CC1]

In a manner analogous to the method described in example 163, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 3-aminopyridine (Aldrich) to give the title compound. HR-MS (ES, m/z) calculated for $C_{41}H_{47}Cl_2N_6O_3$ $[(M+H)^+]$ 741.3081, observed 741.3083.

EXAMPLE 197

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-methyl-piperazin-1-yl)-ethanone

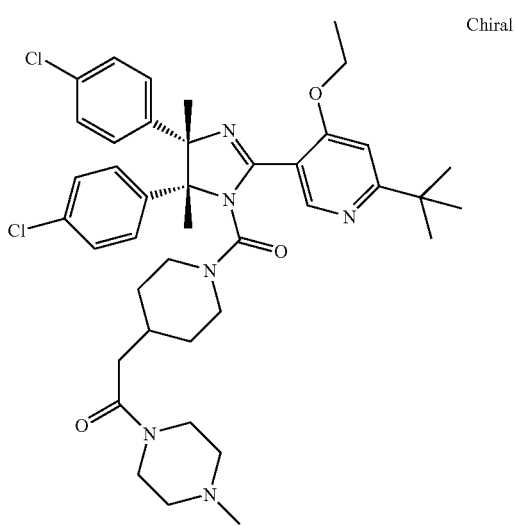 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCN(C)CC2)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with N-methylpiperazine (Aldrich) to give the title compound. HR-MS (ES, m/z) calculated for $C_{41}H_{53}Cl_2N_6O_3$ [(M+H)$^+$] 747.3551, observed 747.3554.

EXAMPLE 198

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-bis-(2-methoxy-ethyl)-acetamide

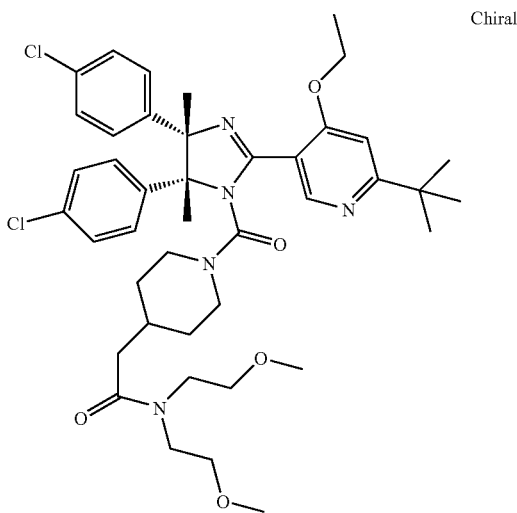 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(CCOC)CCOC)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with bis-(2-methoxy-ethyl)-amine (Aldrich) to give the title compound. HR-MS (ES, m/z) calculated for $C_{42}H_{56}Cl_2N_5O_5$ [(M+H)$^+$] 780.3653, observed 780.3657.

EXAMPLE 199

4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazine-1-sulfonic acid dimethylamide

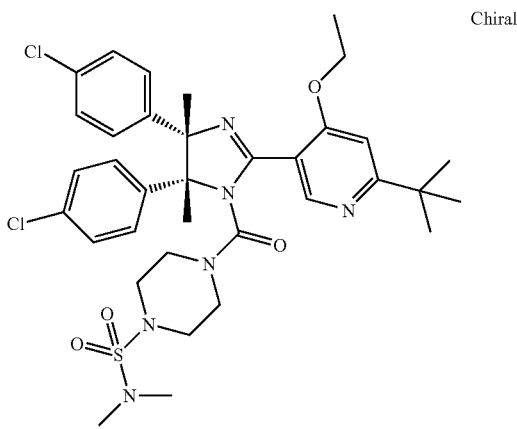 [SMILES: CCOc1cc(C(C)(C)C)ncc1C1=N[C@@](C)(c2ccc(Cl)cc2)[C@@](C)(c2ccc(Cl)cc2)N1C(=O)N1CCN(S(=O)(=O)N(C)C)CC1]

In a manner analogous to the method described in example 3, (4S,5R)-2-(2-tert-butyl-4-ethoxy-pyrimidin-5-yl)-4,5-bis-(4-chloro-phenyl)-4,5-dimethyl-4,5-dihydro-imidazole-1-carbonyl chloride (example 2) was reacted with piperazine-1-sulfonic acid dimethylamide (Oakwood) to give the title compound. HR-MS (ES, m/z) calculated for $C_{35}H_{45}Cl_2N_6O_4S$ [(M+H)$^+$] 715.2595, observed 715.2594.

EXAMPLE 200

(4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid (2-hydroxy-ethyl)-amide

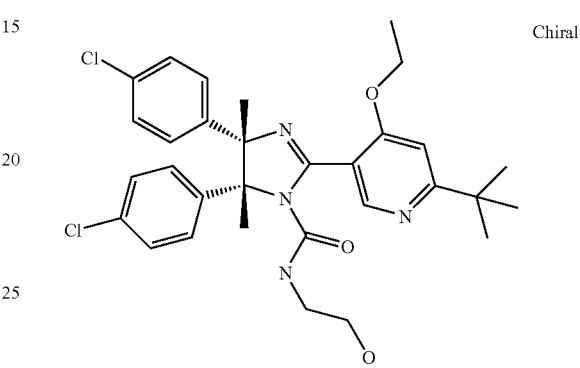

In a manner analogous to the method described in example 3, (4S,5R)-2-(2-tert-butyl-4-ethoxy-pyrimidin-5-yl)-4,5-bis-(4-chloro-phenyl)-4,5-dimethyl-4,5-dihydro-imidazole-1-carbonyl chloride (example 2) was reacted with 2-aminoethanol (Aldrich) to give the title compound. HR-MS (ES, m/z) calculated for $C_{31}H_{37}Cl_2N_4O_3$ [(M+H)$^+$] 583.2237, observed 583.2241.

EXAMPLE 201

(4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid (2-hydroxy-ethyl)-methyl-amide

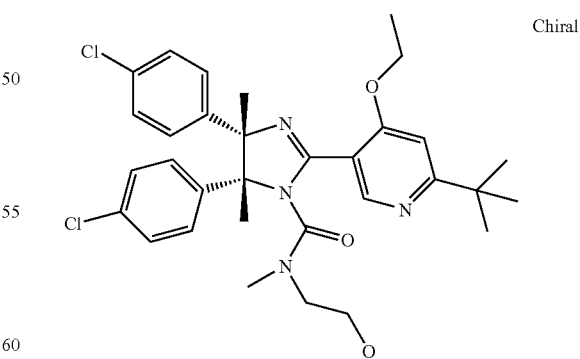

In a manner analogous to the method described in example 3, (4S,5R)-2-(2-tert-butyl-4-ethoxy-pyrimidin-5-yl)-4,5-bis-(4-chloro-phenyl)-4,5-dimethyl-4,5-dihydro-imidazole-1-carbonyl chloride (example 2) was reacted with 2-(methylamino)ethanol (Acros Organics) to give the title compound.

HR-MS (ES, m/z) calculated for $C_{32}H_{39}Cl_2N_4O_3$ [(M+H)$^+$] 597.2394, observed 597.2393.

EXAMPLE 202

(4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid bis-(2-methoxy-ethyl)-amide

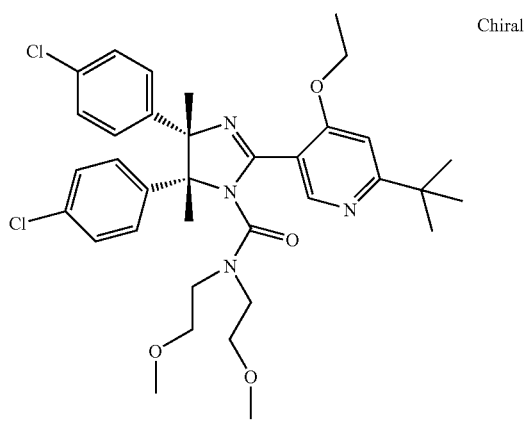 [SMILES: CCOc1cc(C(C)(C)C)ncc1C1=N[C@@](C)(c2ccc(Cl)cc2)[C@@](C)(c2ccc(Cl)cc2)N1C(=O)N(CCOC)CCOC]

In a manner analogous to the method described in example 3, (4S,5R)-2-(2-tert-butyl-4-ethoxy-pyrimidin-5-yl)-4,5-bis-(4-chloro-phenyl)-4,5-dimethyl-4,5-dihydro-imidazole-1-carbonyl chloride (example 2) was reacted with bis-(2-methoxy-ethyl)-amine (Aldrich) to give the title compound. HR-MS (ES, m/z) calculated for $C_{35}H_{45}Cl_2N_4O_4$ [(M+H)$^+$] 655.2813, observed 655.2813.

EXAMPLE 203

{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-carbamic acid tert-butyl ester

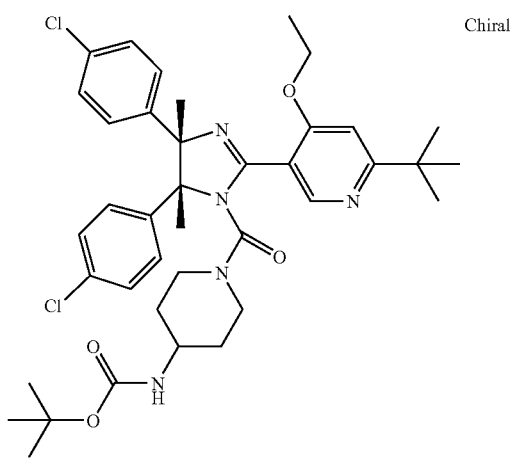 [SMILES: CCOc1cc(C(C)(C)C)ncc1C1=N[C@@](C)(c2ccc(Cl)cc2)[C@@](C)(c2ccc(Cl)cc2)N1C(=O)N1CCC(NC(=O)OC(C)(C)C)CC1]

In a manner analogous to the method described in example 3, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was reacted with piperidin-4-yl-carbamic acid tert-butyl ester (Aldrich) to give the title compound. HR-MS (ES, m/z) calculated for $C_{39}H_{50}Cl_2N_5O_4$ [(M+H)$^+$] 722.3235, observed 722.3233.

EXAMPLE 204

(4-Amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone

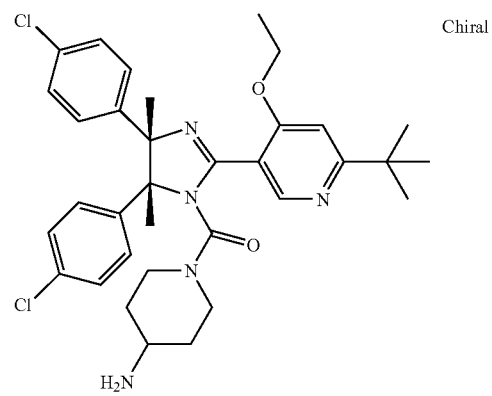

A solution of {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-carbamic acid tert-butyl ester (220 mg, 0.304 mmole, example 203) in dichloromethane (6 mL) was treated with trifluoroacetic acid (6 mL) at 0° C. and allowed to stir for 2 h before concentrated to dryness under reduced pressure. The residue was then taken up in dichloromethane (100 mL), washed with aqueous sodium carbonate (2×15 mL), water (15 mL) and concentrated to give the title compound (174 mg). HR-MS (ES, m/z) calculated for $C_{34}H_{42}Cl_2N_5O_2$ [(M+H)$^+$] 622.2710, observed 622.2714.

EXAMPLE 205

4-{[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-amino}-piperidine-1-carboxylic acid tert-butyl ester

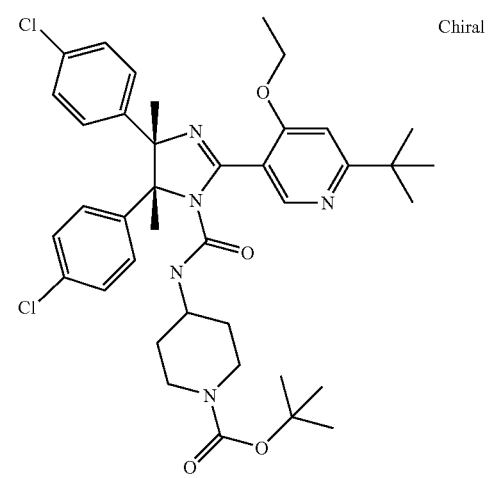 [SMILES: CCOc1cc(C(C)(C)C)ncc1C1=N[C@@](C)(c2ccc(Cl)cc2)[C@@](C)(c2ccc(Cl)cc2)N1C(=O)NC1CCN(C(=O)OC(C)(C)C)CC1]

In a manner analogous to the method described in example 3, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was reacted with 4-aminopiperidine-1-carboxylic acid tert-butyl ester (Aldrich) to give the title compound. HR-MS (ES, m/z) calculated for $C_{39}H_{50}Cl_2N_5O_4$ $[(M+H)^+]$ 722.3235, observed 722.3235.

EXAMPLE 206

(4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid (1-methanesulfonyl-piperidin-4-yl)-amide

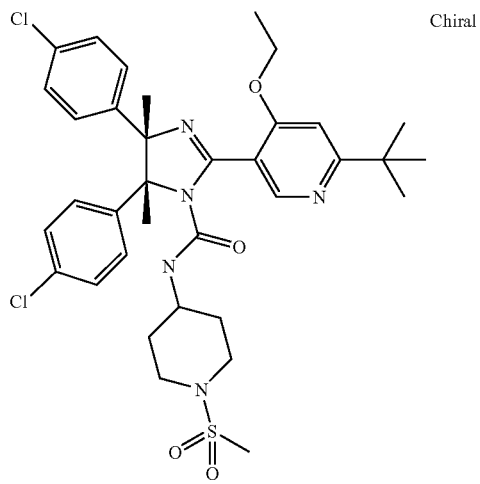 [SMILES: CCOc1cc(C(C)(C)C)ncc1C1=N[C@@](C)(c2ccc(Cl)cc2)[C@@](C)(c2ccc(Cl)cc2)N1C(=O)NC1CCN(S(C)(=O)=O)CC1]

A solution of 4-{[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-amino}-piperidine-1-carboxylic acid tert-butyl ester (640 mg, 0.885 mmole, example 205) in dichloromethane (6 mL) was treated with trifluoroacetic acid (6 mL) at 0° C. and allowed to stir for 2 h before concentrated to dryness under reduced pressure. The residue was then taken up in dichloromethane (100 mL), washed with aqueous sodium carbonate (2×15 mL), water (15 mL) and concentrated to give (4S,5R)-2-(6-tert-butyl-4-ethoxy-pyridin-3-yl)-4,5-bis-(4-chloro-phenyl)-4,5-dimethyl-4,5-dihydro-imidazole-1-carboxylic acid piperidin-4-yl amide (533.3 mg) which was used without purification.

(4S,5R)-2-(6-tert-butyl-4-ethoxy-pyridin-3-yl)-4,5-bis-(4-chloro-phenyl)-4,5-dimethyl-4,5-dihydro-imidazole-1-carboxylic acid piperidin-4-yl amide (56.5 mg, 0.091 mmole) in dichloromethane (6 mL) was treated with methanesulfonyl chloride (26.0 mg, 0.226 mmole, Aldrich) at 0° C. and allowed to stir for 1 h before diluted with dichloromethane (60 mL), washed with aqueous sodium carbonate (15 mL), water (15 mL) and concentrated. The residue was purified by flash column chromatography (silica gel, eluting with a gradient of 1-10% methanol in dichloromethane) to give the title compound (59.5 mg). HR-MS (ES, m/z) calculated for $C_{35}H_{44}Cl_2N_5O_4S$ $[(M+H)^+]$ 700.2486, observed 700.2482.

EXAMPLE 207

4-{[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-amino}-piperidine-1-carboxylic acid ethylamide

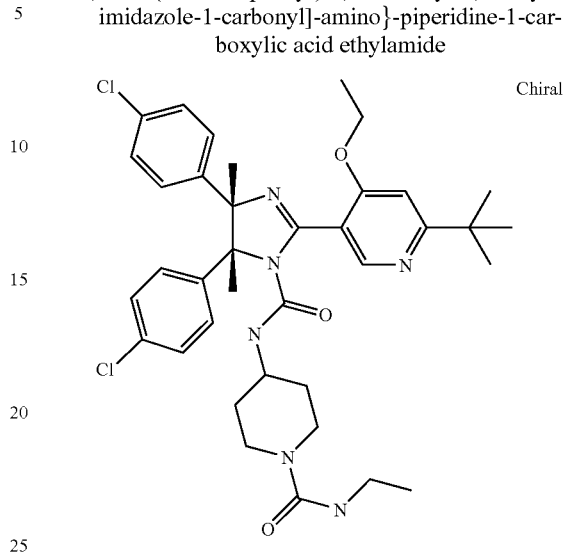

A mixture of (4S,5R)-2-(6-tert-butyl -4-ethoxy-pyridin-3-yl)-4,5-bis-(4-chloro-phenyl)-4,5-dimethyl-4,5-dihydro-imidazole-1-carboxylic acid piperidin-4-yl amide (51.2 mg, 0.082 mmole, example 205) and ethyl isocyanate (12.0 mg, 0.169 mmole, Aldrich) in dichloromethane (4 mL) was stirred at room temperature for 2 h before concentrated to dryness. The residue was purified by flash column chromatography (silica gel, eluting with a gradient of 1-10% methanol in dichloromethane) to give the title compound (44.6 mg, 78% yield). HR-MS (ES, m/z) calculated for $C_{37}H_{47}Cl_2N_6O_3$ $[(M+H)^+]$ 693.3081, observed 693.3081.

EXAMPLE 208

(4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid (1-carbamoylmethyl-piperidin-4-yl)-amide

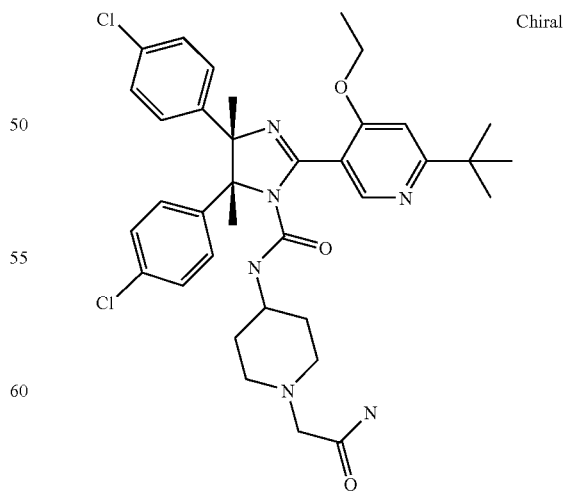

To a mixture of (4S,5R)-2-(6-tert-butyl-4-ethoxy-pyridin-3-yl)-4,5-bis-(4-chloro-phenyl)-4,5-dimethyl-4,5-dihydroimidazole-1-carboxylic acid piperidin-4-yl amide (50.0 mg, 0.081 mmole, example 205) and potassium carbonate (22.4 mg, 0.162 mmole) in N,N-dimethylformamide (4 mL) was added iodoacetamide (29.8 mg, 0.162 mmole, Aldrich). The mixture was stirred at room temperature overnight and diluted with ethyl acetate, washed with water, brine and concentrated. The crude product was purified by flash column chromatography (silica gel, eluting with a gradient of 1-10% methanol in dichloromethane) to give the title compound (40.5 mg, 74% yield). HR-MS (ES, m/z) calculated for $C_{36}H_{45}Cl_2N_6O_3$ [(M+H)$^+$] 679.2925, observed 679.2924.

EXAMPLE 209

1-[(4S,5R)-2-(6-tert-Butyl-4-ethoxy-pyridin-3-yl)-4, 5-bis-(4-chloro-phenyl)-4,5-dimethyl-4,5-dihydro-imidazole-1-carbonyl]-piperidin-4-one

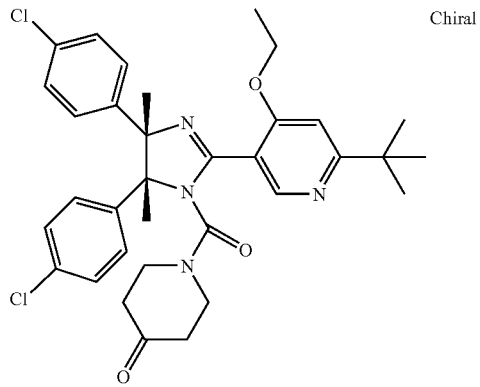 [SMILES: CCOc1cc(C(C)(C)C)ncc1C1=N[C@@](C)(c2ccc(Cl)cc2)[C@@](C)(c2ccc(Cl)cc2)N1C(=O)N1CCC(=O)CC1]

In a manner analogous to the method described in example 3, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was reacted with piperidin-4-one (Aldrich) to give the title compound. HR-MS (ES, m/z) calculated for $C_{34}H_{39}Cl_2N_4O_3$ [(M+H)$^+$] 621.2394, observed 621.2395.

EXAMPLE 210

1-[(4S,5R)-2-(6-tert-Butyl-4-ethoxy-pyridin-3-yl)-4, 5-bis-(4-chloro-phenyl)-4,5-dimethyl-4,5-dihydro-imidazole-1-carbonyl]-piperidine-4-carboxylic acid methyl ester

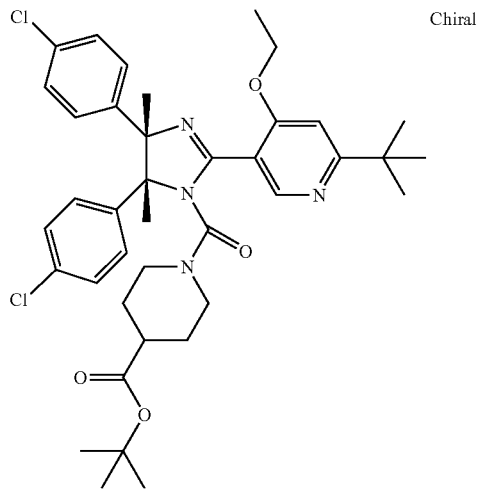 [SMILES: CCOc1cc(C(C)(C)C)ncc1C1=N[C@@](C)(c2ccc(Cl)cc2)[C@@](C)(c2ccc(Cl)cc2)N1C(=O)N1CCC(C(=O)OC(C)(C)C)CC1]

In a manner analogous to the method described in example 3, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was reacted with piperidine-4-carboxylic acid methyl ester (Aldrich) to give title compound. HR-MS (ES, m/z) calculated for $C_{36}H_{43}Cl_2N_4O_4$ [(M+H)$^+$] 665.2656, observed 665.2652.

EXAMPLE 211

1-[(4S,5R)-2-(6-tert-Butyl-4-ethoxy-pyridin-3-yl)-4, 5-bis-(4-chloro-phenyl)-4,5-dimethyl-4,5-dihydro-imidazole-1-carbonyl]-piperidine-4-carboxylic acid

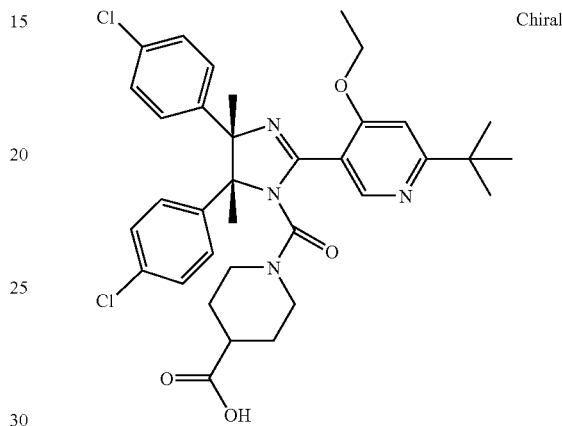

A mixture of 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid methyl ester (575 mg, 0.864 mmole, example 210) and lithium hydroxide hydrate (217 mg, 5.179 mmole) in water (20 mL) and tetrahydrofuran (20 mL) was stirred at room temperature for 4 h before neutralized with 1N hydrochloric acid and extracted with ethyl acetate. The organic extracts were washed with brine and dried over sodium sulfate and concentrated to give the title compound (552.5 mg, 98%). HR-MS (ES, m/z) calculated for $C_{35}H_{41}Cl_2N_4O_4$ [(M+H)$^+$] 651.2500, observed 651.2498.

EXAMPLE 212

3-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yloxy}-propionamide

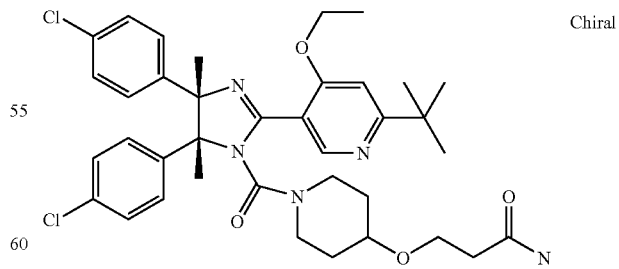

In a manner similar to the method described in example 177, [(4S,5R)-2-(6-tert-butyl-4-ethoxy-pyridin-3-yl)-4,5-bis-(4-chloro-phenyl)-4,5-dimethyl-4,5-dihydro-imidazol-1-yl]-(4-hydroxy-piperidin-1-yl)-methanone (example 101) was reacted with acrylamide (Promega) to give the title compound. HR-MS (ES, m/z) calculated for $C_{37}H_{46}Cl_2N_5O_4$ [(M+H)$^+$] 694.2922, observed 694.2918.

EXAMPLE 213

3-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yloxy}-propionitrile

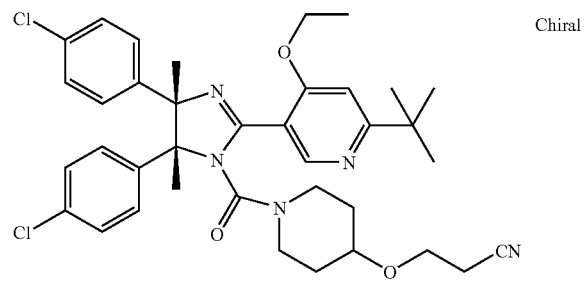 [SMILES: CCOc1cc(C(C)(C)C)ncc1C1=N[C@@](C)(c2ccc(Cl)cc2)[C@@](C)(c2ccc(Cl)cc2)N1C(=O)N1CCC(OCCC#N)CC1]

In a manner similar to the method described in example 177, [(4S,5R)-2-(6-tert-butyl-4-ethoxy-pyridin-3-yl)-4,5-bis-(4-chloro-phenyl)-4,5-dimethyl-4,5-dihydro-imidazol-1-yl]-(4-hydroxy-piperidin-1-yl)-methanone (example 101) was reacted with acrylonitrile (Aldrich) to give the title compound. HR-MS (ES, m/z) calculated for $C_{37}H_{44}Cl_2N_5O_3$ [(M+H)$^+$] 676.2816, observed 676.2815.

EXAMPLE 214

1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-isopropyl-urea

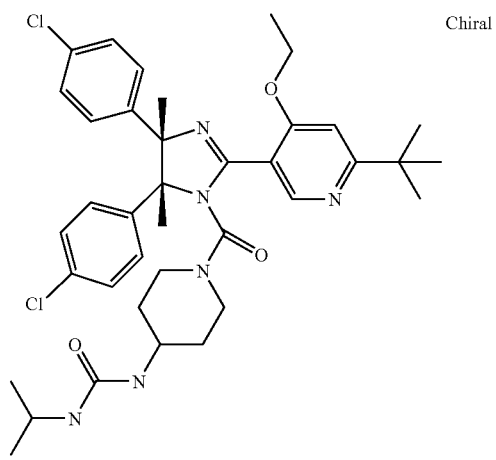 [SMILES: CCOc1cc(C(C)(C)C)ncc1C1=N[C@@](C)(c2ccc(Cl)cc2)[C@@](C)(c2ccc(Cl)cc2)N1C(=O)N1CCC(NC(=O)NC(C)C)CC1]

In a manner similar to the method described in example 160, (4-Amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with isopropyl isocyanate (Aldrich) to give the title compound. HR-MS (ES, m/z) calculated for $C_{38}H_{49}Cl_2N_6O_3$ [(M+H)$^+$] 707.3238, observed 707.3236

EXAMPLE 215

1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-pyridin-3-yl-urea

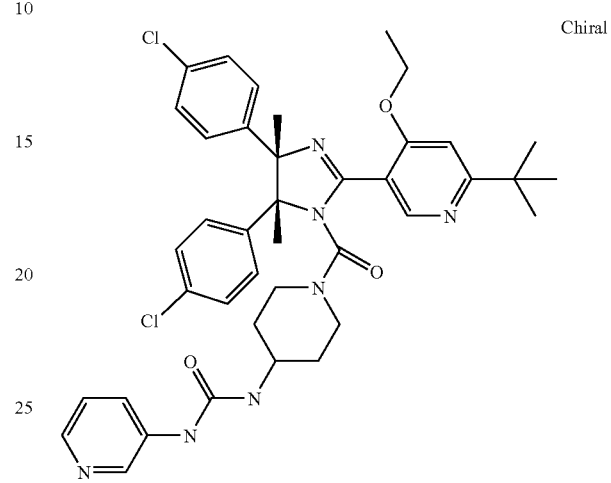

In a manner similar to the method described in example 160, (4-Amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with pyridine-3-isocyanate (Oakwood Products) to give the title compound. HR-MS (ES, m/z) calculated for $C_{40}H_{46}Cl_2N_7O_3$ [(M+H)$^+$] 742.3034, observed 742.3029.

EXAMPLE 216

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-acetamide

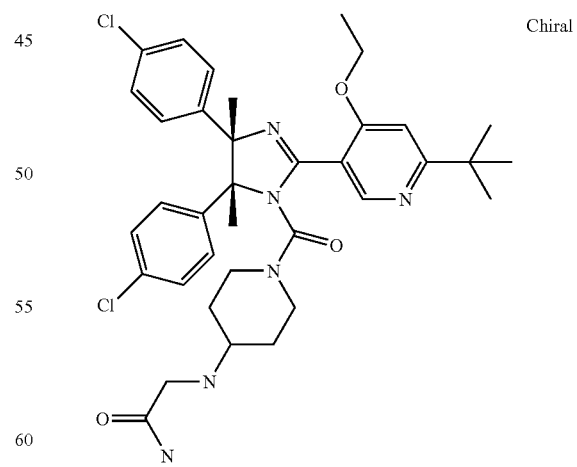

In a manner similar to the method described in example 160, (4-Amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with iodoacetamide (Aldrich) to give the title compound. HR-MS (ES, m/z) calculated for $C_{36}H_{45}Cl_2N_6O_3$ [(M+H)$^+$] 679.2925, observed 679.2926.

EXAMPLE 217

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-((R)-3-methoxy-pyrrolidin-1-yl)-ethanone

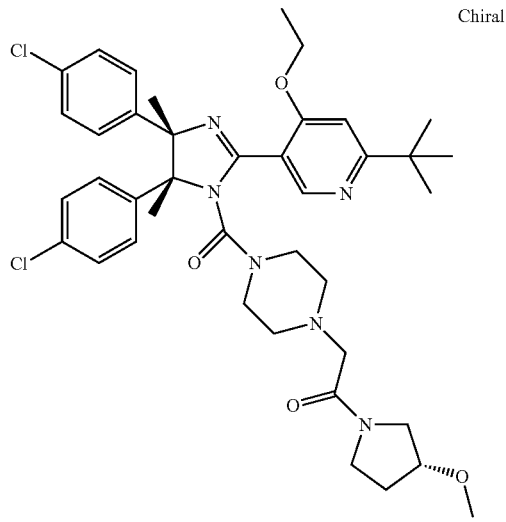 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)N2CC[C@@H](OC)C2)CC1]

In a manner analogous to the method described in example 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid was coupled with (R)-3-methoxy-pyrrolidine (Aldrich) to give the title compound. HR-MS (ES, m/z) calculated for $C_{40}H_{51}Cl_2N_6O_4$ [(M+H)$^+$] 749.3344, observed 749.3337.

EXAMPLE 218

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-((S)-3-methoxy-pyrrolidin-1-yl)-ethanone

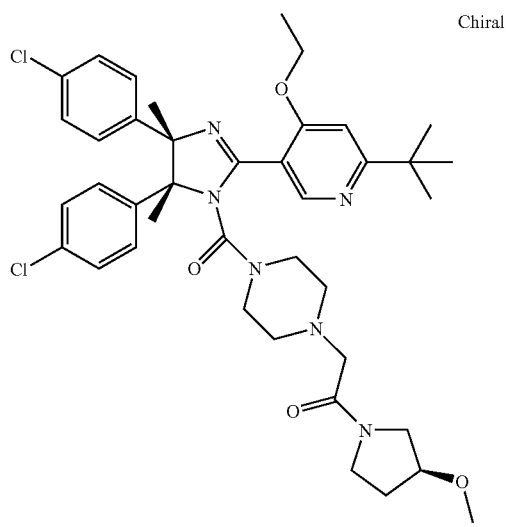 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)N2CC[C@H](OC)C2)CC1]

In a manner analogous to the method described in example 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid was coupled with (S)-3-methoxy-pyrrolidine (Aldrich) to give the title compound. HR-MS (ES, m/z) calculated for $C_{40}H_{51}Cl_2N_6O_4$ [(M+H)$^+$] 749.3344, observed 749.3340.

EXAMPLE 219

1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-ethyl-urea

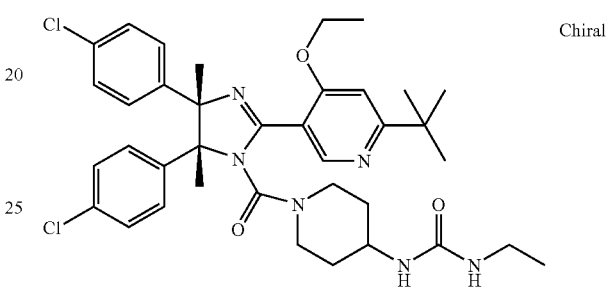

In a manner similar to the method described in example 160, (4-amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with ethyl isocyanate (Aldrich) to give the title compound. HR-MS (ES, m/z) calculated for $C_{37}H_{47}Cl_2N_6O_3$ [(M+H)$^+$] 693.3091, observed 693.3078.

EXAMPLE 220

1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-phenyl-urea

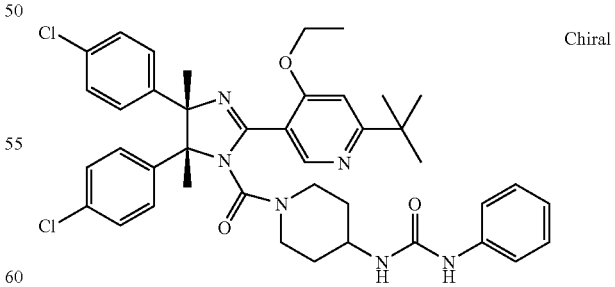

In a manner similar to the method described in example 160, (4-amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with phenyl isocyanate (Aldrich) to give the title

EXAMPLE 221

(4-{[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-amino}-piperidin-1-yl)-acetic acid ethyl ester

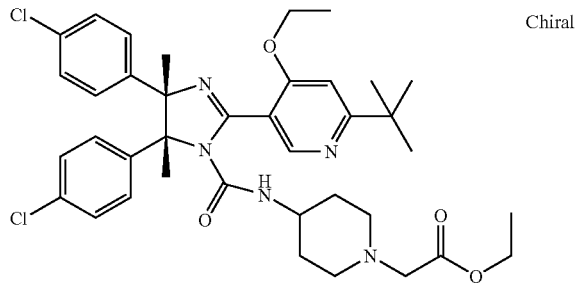 [SMILES: CCOC(=O)CN1CCC(NC(=O)N2C(c3cnc(C(C)(C)C)cc3OCC)=N[C@@](C)(c3ccc(Cl)cc3)[C@@]2(C)c2ccc(Cl)cc2)CC1]

In a manner analogous to the method described in example 146, (4S,5R)-2-(6-tert-butyl-4-ethoxy-pyridin-3-yl)-4,5-bis-(4-chloro-phenyl)-4,5-dimethyl-4,5-dihydro-imidazole-1-carboxylic acid piperidin-4-yl amide (example 206) was reacted with ethyl bromoacetate (Aldrich) to give the title compound. HR-MS (ES, m/z) calculated for $C_{38}H_{48}Cl_2N_5O_4$ [(M+H)$^+$] 708.3078, observed 708.3074.

EXAMPLE 222

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[(1S,5R)-6-((R)-3-methoxy-pyrrolidine-1-carbonyl)-3-aza-bicyclo[3.1.0]hex-3-yl]-methanone

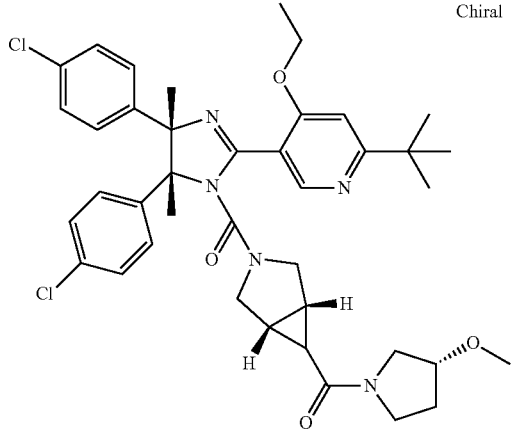 [SMILES: CCOc1cc(C(C)(C)C)ncc1C1=N[C@@](C)(c2ccc(Cl)cc2)[C@@](C)(c2ccc(Cl)cc2)N1C(=O)N1C[C@@H]2C(C(=O)N3CC[C@@H](OC)C3)[C@@H]2C1]

In a manner analogous to the method described in examples 99, (1S,5R)-3-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-3-aza-bicyclo[3.1.0]hexane-6-carboxylic acid (prepared from the ethyl ester, example 135) was coupled with (R)-3-methoxy-pyrrolidine (Aldrich) to give the title compound. HR-MS (ES, m/z) calculated for $C_{40}H_{48}Cl_2N_5O_4$ [(M+H)$^+$] 708.3078, observed 708.3078.

EXAMPLE 223

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[(1S,5R)-6-((S)-3-methoxy-pyrrolidine-1-carbonyl)-3-aza-bicyclo[3.1.0]hex-3-yl]-methanone

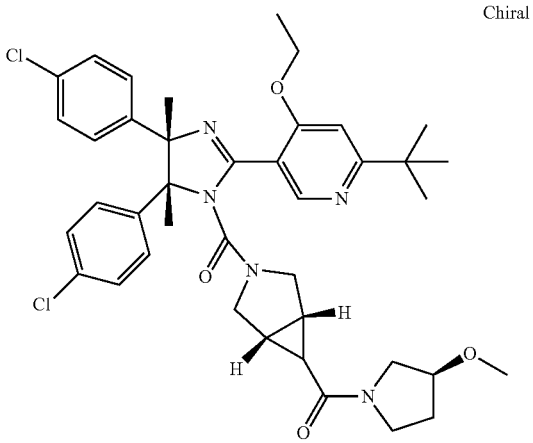 [SMILES: CCOc1cc(C(C)(C)C)ncc1C1=N[C@@](C)(c2ccc(Cl)cc2)[C@@](C)(c2ccc(Cl)cc2)N1C(=O)N1C[C@@H]2C(C(=O)N3CC[C@H](OC)C3)[C@@H]2C1]

In a manner analogous to the method described in examples 99, (1S,5R)-3-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-3-aza-bicyclo[3.1.0]hexane-6-carboxylic acid (prepared from the ethyl ester, example 135) was coupled with (S)-3-methoxy-pyrrolidine (Aldrich) to give the title compound. HR-MS (ES, m/z) calculated for $C_{40}H_{48}Cl_2N_5O_4$ [(M+H)$^+$] 708.3078, observed 708.3072.

EXAMPLE 224

(4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid [1-(2-methanesulfonyl-ethyl)-piperidin-4-yl]-amide

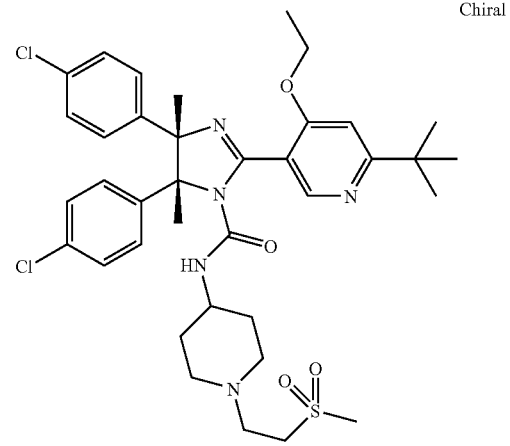 [SMILES: CCOc1cc(C(C)(C)C)ncc1C1=N[C@@](C)(c2ccc(Cl)cc2)[C@@](C)(c2ccc(Cl)cc2)N1C(=O)NC1CCN(CCS(C)(=O)=O)CC1]

(4-Amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204)

was reacted with methyl vinyl sulphone (Aldrich) to give the title compound. LC-MS (ES⁺) 728 [(M+H)⁺].

compound. HR-MS (ES, m/z) calculated for $C_{38}H_{48}Cl_2N_5O_4$ [(M+H)⁺] 708.3078, observed 708.3076.

EXAMPLE 225

1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-cyclopentyl-urea

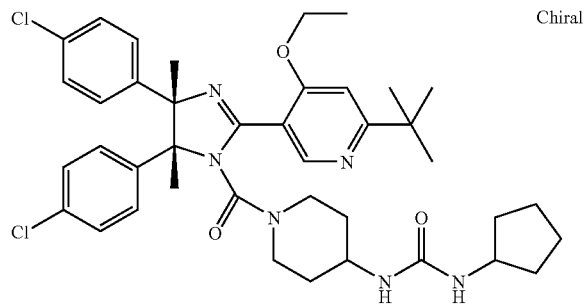 [SMILES: CCOc1cc(C(C)(C)C)ncc1C1=N[C@@](C)(c2ccc(Cl)cc2)[C@@](C)(c2ccc(Cl)cc2)N1C(=O)N1CCC(NC(=O)NC2CCCC2)CC1]

In a manner similar to the method described in example 160, (4-amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with cyclopentyl isocyanate (Aldrich) to give the title compound. LC-MS (ES⁺) 733 [(M+H)⁺].

EXAMPLE 227

1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-pyridin-4-yl-urea

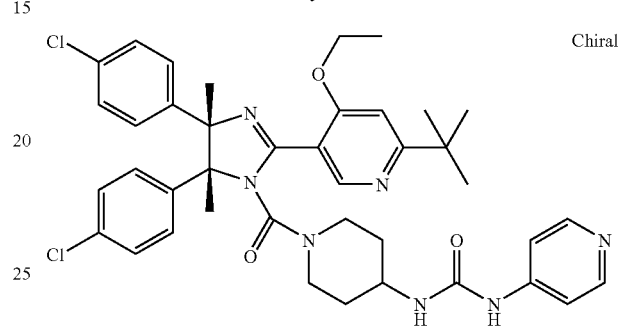

In a manner similar to the method described in example 160, (4-amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with 4-pyridine isocyanate (Princeton) to give the title compound. HR-MS (ES, m/z) calculated for $C_{40}H_{46}Cl_2N_7O_3$ [(M+H)⁺] 742.3034, observed 742.3037.

EXAMPLE 226

{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-acetic acid ethyl ester

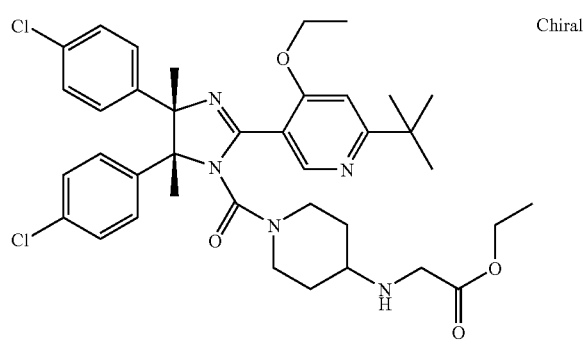 [SMILES: CCOC(=O)CNC1CCN(C(=O)N2C(c3cnc(C(C)(C)C)cc3OCC)=N[C@@](C)(c3ccc(Cl)cc3)[C@@]2(C)c2ccc(Cl)cc2)CC1]

In a manner analogous to the method described in example 146, (4-amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with ethyl bromoacetate (Aldrich) to give the title

EXAMPLE 228

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-N-(2-hydroxy-ethyl)-acetamide

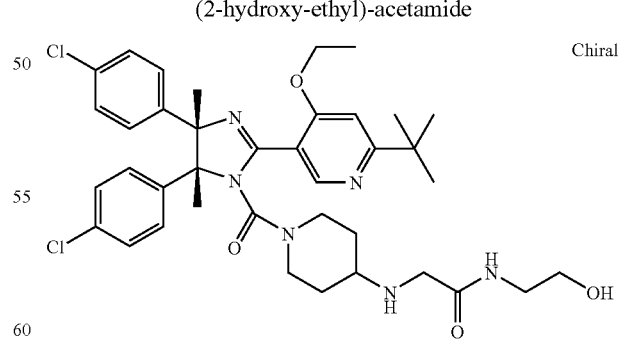

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-ylamino}-acetic acid was reacted with ethanoamine (Aldrich) to give the title compound. HR-MS (ES, m/z) calculated for $C_{38}H_{49}Cl_2N_6O_4$ [(M+H)$^+$] 723.3187, observed 723.3192.

EXAMPLE 229

{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-acetic acid

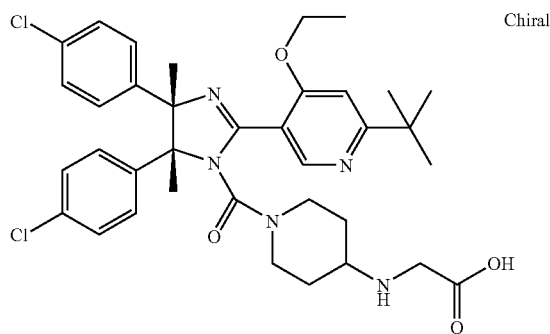 [SMILES: CCOc1cc(C(C)(C)C)ncc1C1=N[C@@](C)(c2ccc(Cl)cc2)[C@@](C)(c2ccc(Cl)cc2)N1C(=O)N1CCC(NCC(=O)O)CC1]

{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-acetic acid ethyl ester (example 226) was saponified to give the title compound. HR-MS (ES, m/z) calculated for $C_{36}H_{44}Cl_2N_5O_4$ [(M+H)$^+$] 680.2765, observed 680.2766.

EXAMPLE 230

Pyrrolidine-1-carboxylic acid {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-amide

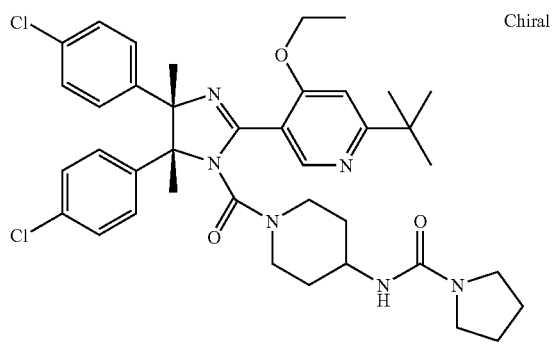 [SMILES: CCOc1cc(C(C)(C)C)ncc1C1=N[C@@](C)(c2ccc(Cl)cc2)[C@@](C)(c2ccc(Cl)cc2)N1C(=O)N1CCC(NC(=O)N2CCCC2)CC1]

(4-Amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with phosgene (Fluka) and pyrrolidine (Aldrich) to give the title product. LC-MS (ES$^+$) 719 [(M+H)$^+$].

EXAMPLE 231

3-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1,1-dimethyl-urea

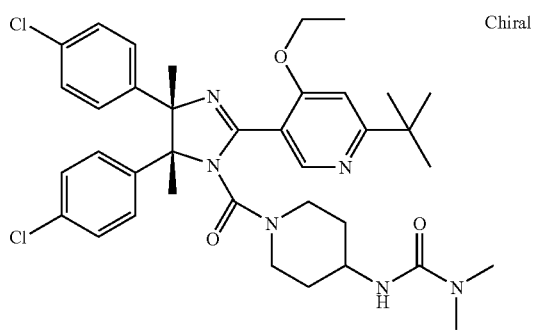 [SMILES: CCOc1cc(C(C)(C)C)ncc1C1=N[C@@](C)(c2ccc(Cl)cc2)[C@@](C)(c2ccc(Cl)cc2)N1C(=O)N1CCC(NC(=O)N(C)C)CC1]

(4-Amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with phosgene (Fluka) and dimethylamine (Aldrich) to give the title product. LC-MS (ES$^+$) 693 [(M+H)$^+$].

EXAMPLE 232

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-bis-(3-methoxy-propyl)-acetamide

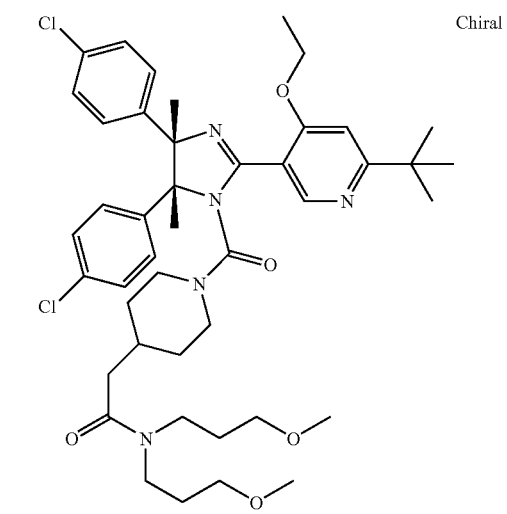 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(CCCOC)CCCOC)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with bis-(3-methoxy-propyl)-amine (prepared from bis-(3-chloro-propyl)-amine and sodium methoxide) to give the title compound. HR-MS (ES, m/z) calculated for $C_{44}H_{59}Cl_2N_5O_5$ [(M+H)$^+$] 808.3966, observed 808.3965.

EXAMPLE 233

3-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-propionic acid

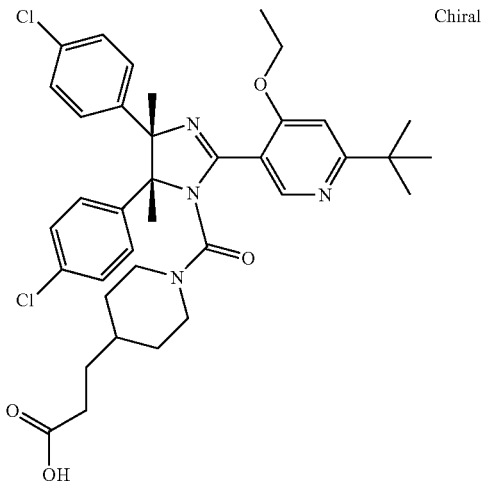 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CCC(=O)O)CC1]

In a manner analogous to the method described in examples 8, (4S,5R)-2-(6-tert-butyl-4-ethoxy-pyridin-3-yl)-4,5-bis-(4-chloro-phenyl)-4,5-dimethyl-4,5-dihydro-imidazole-1-carbonyl chloride (example 51) was coupled with 3-piperidin-4-yl-propionic acid (Astatech) to give the title compound. HR-MS (ES, m/z) calculated for $C_{37}H_{45}Cl_2N_4O_4$ [(M+H)$^+$] 679.2813, observed 679.2814.

EXAMPLE 234

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-bis-(2-ethoxy-ethyl)-acetamide

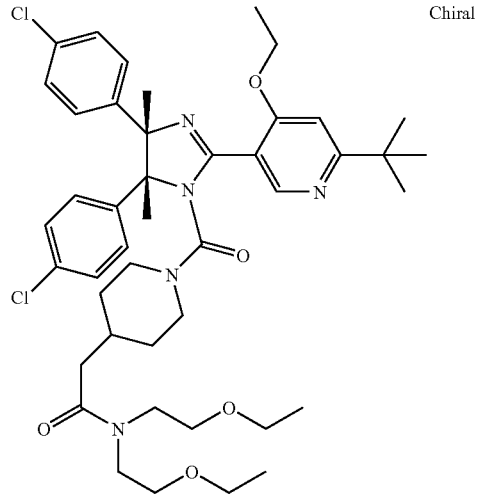 [SMILES: CCOCCN(CCOCC)C(=O)CC1CCN(C(=O)N2C(c3cnc(C(C)(C)C)cc3OCC)=N[C@@](C)(c3ccc(Cl)cc3)[C@@]2(C)c2ccc(Cl)cc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imida-zole-1-carbonyl]-piperidin-4-yl}-acetic acid was coupled with bis-(2-ethoxy-ethyl)-amine (TCI-US) to give the title compound. HR-MS (ES, m/z) calculated for $C_{44}H_{60}Cl_2N_5O_5$ [(M+H)$^+$] 808.3966, observed 808.3968.

EXAMPLE 235

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-bis-(2-isopropoxy-ethyl)-acetamide

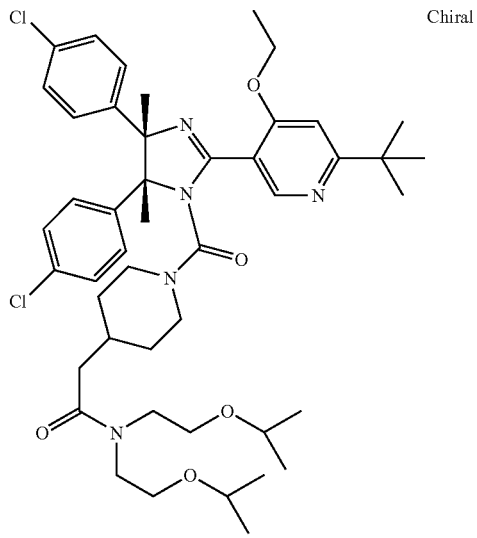 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(CCOC(C)C)CCOC(C)C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imida-zole-1-carbonyl]-piperidin-4-yl}-acetic acid was coupled with bis-(isopropoxy-ethyl)-amine (TCI-US) to give the title compound. HR-MS (ES, m/z) calculated for $C_{46}H_{63}Cl_2N_5O_5$ [(M+H)$^+$] 836.4279, observed 836.4274.

EXAMPLE 236

(4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid [(2R,3R,4S)-3,4-dihydroxy-1-(2-hydroxy-ethyl)-pyrrolidin-2-ylmethyl]-amide

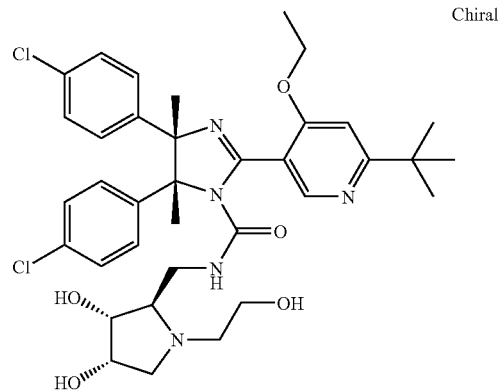 [SMILES: CCOc1cc(C(C)(C)C)ncc1C1=N[C@@](C)(c2ccc(Cl)cc2)[C@@](C)(c2ccc(Cl)cc2)N1C(=O)NC[C@@H]1[C@@H](O)[C@@H](O)CN1CCO]

In a manner analogous to the method described in examples 8, (4S,5R)-2-(6-tert-butyl-4-ethoxy-pyridin-3-yl)-

4,5-bis-(4-chloro-phenyl)-4,5-dimethyl-4,5-dihydro-imidazole-1-carbonyl chloride (example 51) was coupled with (2R,3R,4S)-2-aminomethyl-1-(2-hydroxy-ethyl)-pyrrolidine-3,4-diol (AFID Therapeutics) to give the title compound. HR-MS (ES, m/z) calculated for $C_{36}H_{46}Cl_2N_5O_5$ [(M+H)$^+$] 698.2871, observed 698.2873.

EXAMPLE 237

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N,N-bis-(2-ethoxy-ethyl)-acetamide

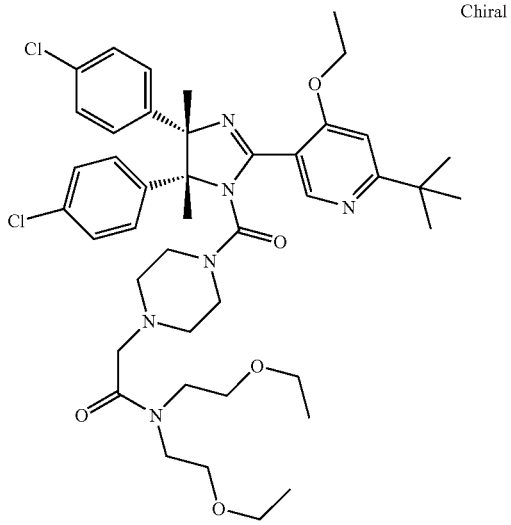 [SMILES: CCOCCN(CCOCC)C(=O)CN1CCN(C(=O)N2C(c3cnc(C(C)(C)C)cc3OCC)=N[C@@](C)(c3ccc(Cl)cc3)[C@@]2(C)c2ccc(Cl)cc2)CC1]

In a manner analogous to the method described in example 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid was coupled with bis-(2-ethoxy-ethyl)-amine (TCI-US) to give the title compound. HR-MS (ES, m/z) calculated for $C_{43}H_{59}Cl_2N_6O_5$ [(M+H)$^+$] 809.3919, observed 809.3118.

EXAMPLE 238

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N,N-bis-(2-isopropoxy-ethyl)-acetamide

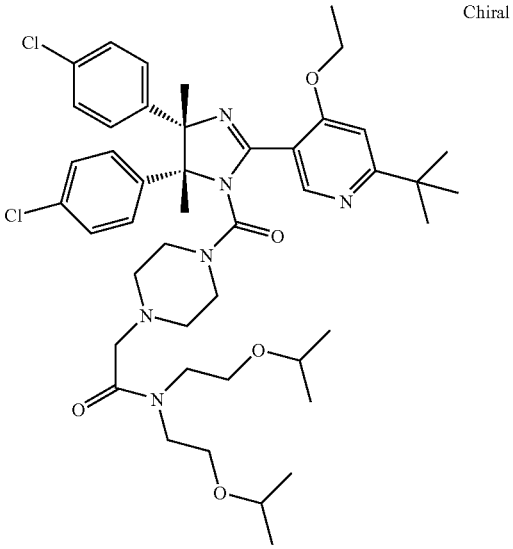 [SMILES: CCOc1cc(C(C)(C)C)ncc1C1=N[C@@](C)(c2ccc(Cl)cc2)[C@@](C)(c2ccc(Cl)cc2)N1C(=O)N1CCN(CC(=O)N(CCOC(C)C)CCOC(C)C)CC1]

In a manner analogous to the method described in example 99, {4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid was coupled with bis-(isopropoxy-ethyl)-amine (TCI-US) to give the title compound. HR-MS (ES, m/z) calculated for $C_{45}H_{62}Cl_2N_6O_5$ [(M+H)$^+$] 837.4232, observed 837.4231.

EXAMPLE 239

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-diethyl-acetamide

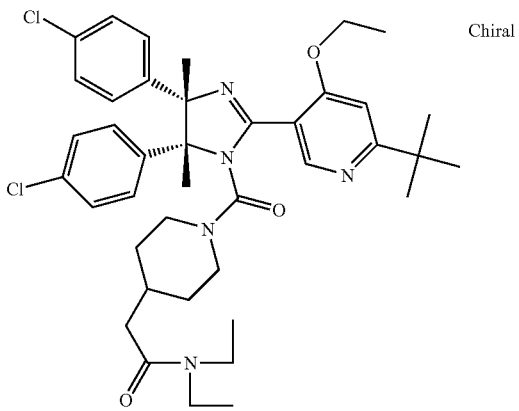 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(CC)CC)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with diethylamine (Aldrich) to give the title compound. HR-MS (ES, m/z) calculated for $C_{40}H_{52}Cl_2N_5O_3$ [(M+H)$^+$] 720.3442, observed 720.3440.

EXAMPLE 240

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-methyl-[1,4]diazepan-1-yl)-ethanone

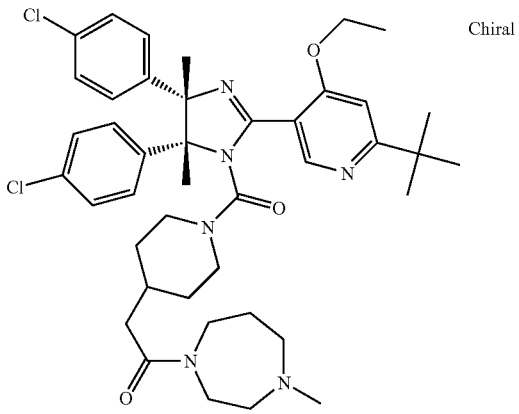 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCCN(C)CC2)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was coupled with 1-methyl-[1,4]diazepane (Aldrich) to give the title compound. HR-MS (ES, m/z) calculated for $C_{42}H_{55}Cl_2N_6O_3$ [(M+H)$^+$] 761.3707, observed 761.3707.

EXAMPLE 241

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(2-methyl-pyrrolidin-1-yl)-ethanone

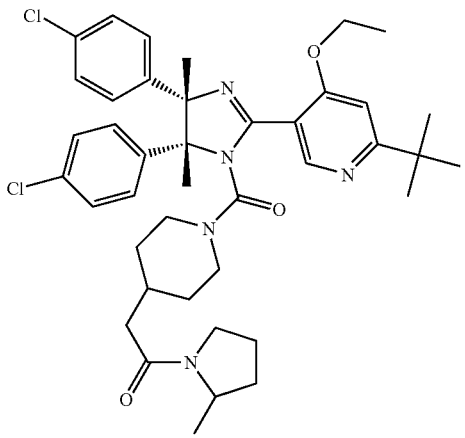 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCCC2C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with 2-methyl-pyrrolidine (Aldrich) to give the title compound as a mixture of diastereomers. HR-MS (ES, m/z) calculated for $C_{41}H_{52}Cl_2N_5O_3$ [(M+H)$^+$] 761.3707, observed 761.3707.

EXAMPLE 242

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-((R)-1-phenyl-ethyl)-acetamide

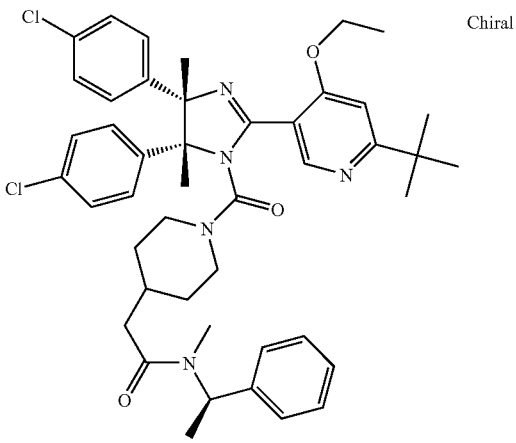 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)[C@H](C)c2ccccc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with methyl-((R)-1-phenyl-ethyl)-amine (Aldrich) to give the title compound. HR-MS (ES, m/z) calculated for $C_{45}H_{54}Cl_2N_5O_3$ [(M+H)$^+$] 782.3598, observed 782.3594.

EXAMPLE 243

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-diisopropyl-acetamide

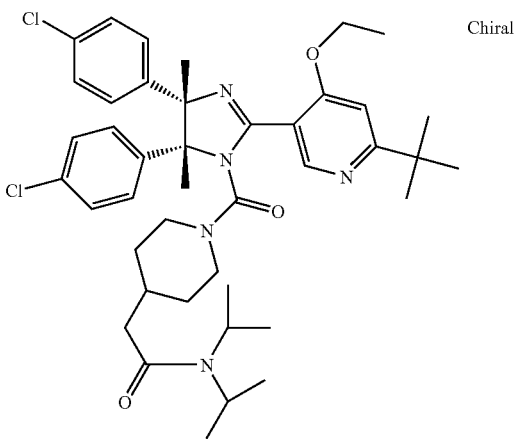 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C(C)C)C(C)C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with diisopropylamine (Aldrich) to give the title compound. HR-MS (ES, m/z) calculated for $C_{42}H_{55}Cl_2N_5O_3$ [(M+H)$^+$] 748.3755, observed 748.3758.

EXAMPLE 244

N-Butyl-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide

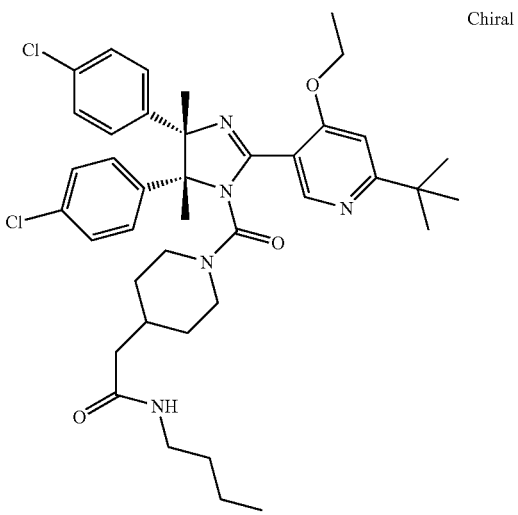 [SMILES: CCCCNC(=O)CC1CCN(C(=O)N2C(c3cnc(C(C)(C)C)cc3OCC)=N[C@@](C)(c3ccc(Cl)cc3)[C@@]2(C)c2ccc(Cl)cc2)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was coupled with n-butylamine (Aldrich) to give the title compound. HR-MS (ES, m/z) calculated for $C_{40}H_{52}Cl_2N_5O_3$ [(M+H)$^+$] 720.3442, observed 720.3438.

EXAMPLE 245

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cyclohexyl-N-isopropyl-acetamide

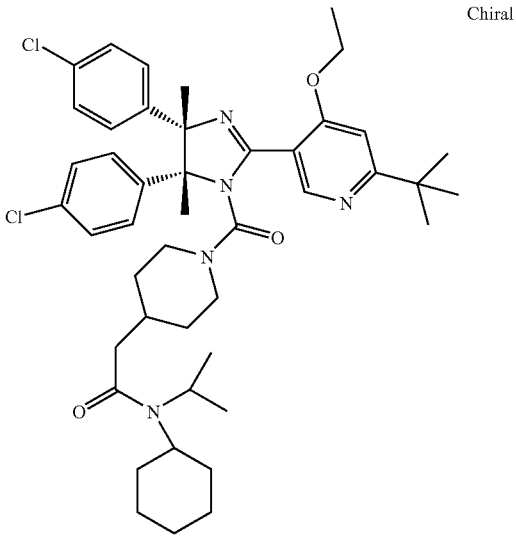 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C(C)C)C2CCCCC2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with N-cyclohexyl-N-isopropylamine (Fluka) to give the title compound. HR-MS (ES, m/z) calculated for $C_{45}H_{60}Cl_2N_5O_3$ [(M+H)$^+$] 788.4068, observed 788.4062.

EXAMPLE 246

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-chloro-benzyl)-acetamide

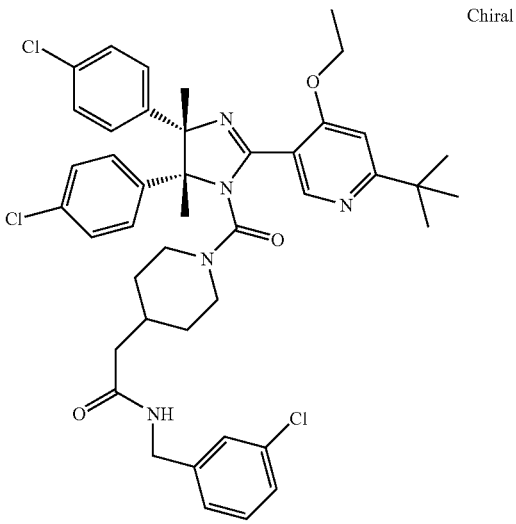 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCc2cccc(Cl)c2)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was coupled with 3-chloro-benzylamine (Avocado) to give the title compound. HR-MS (ES, m/z) calculated for $C_{43}H_{49}Cl_3N_5O_3$ [(M+H)$^+$] 788.2896, observed 788.2890.

EXAMPLE 247

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2,3-difluoro-benzyl)-acetamide

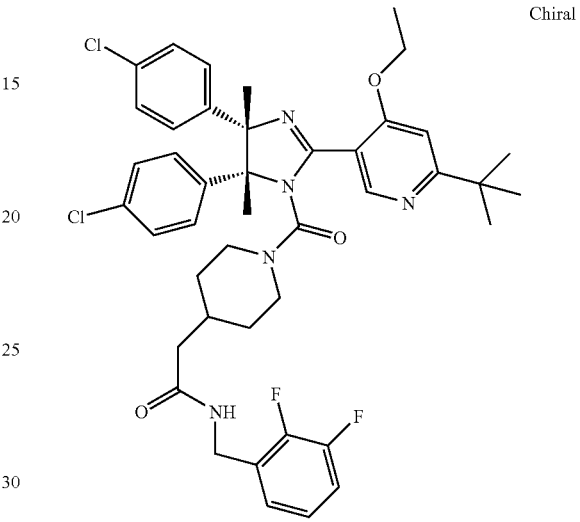

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with 3,4-difluoro-benzylamine (Alfa) to give the title compound. HR-MS (ES, m/z) calculated for $C_{43}H_{48}Cl_2F_2N_5O_3$ [(M+H)$^+$] 790.3097, observed 790.3093.

EXAMPLE 248

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-fluoro-benzyl)-acetamide

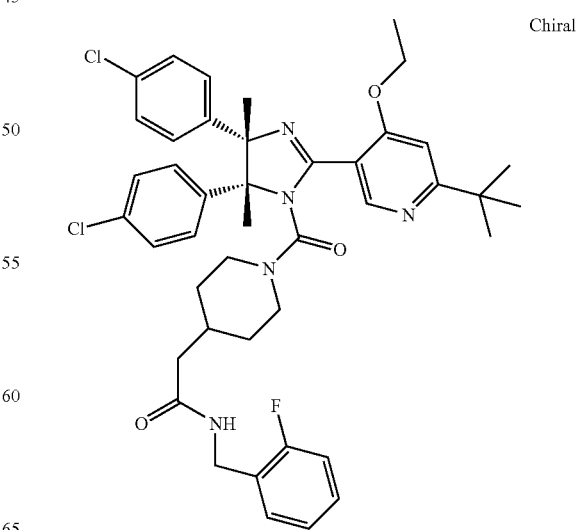

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was coupled with 2-fluoro-benzylamine (Aldrich) to give the title compound. HR-MS (ES, m/z) calculated for $C_{43}H_{49}Cl_2FN_5O_3$ [(M+H)$^+$] 772.3191, observed 772.3185.

EXAMPLE 249

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-propyl)-acetamide

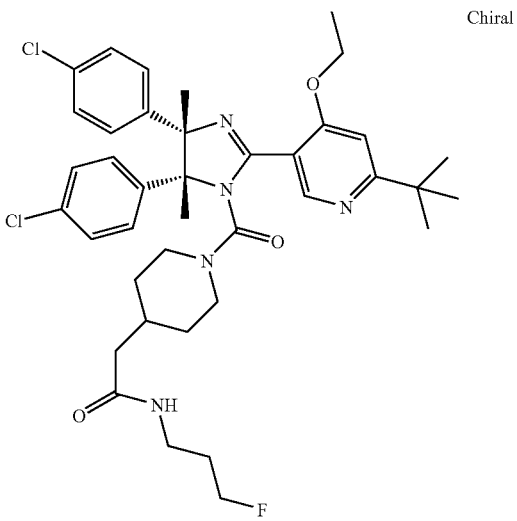 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCCCF)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with 3-fluoro-propylamine (Astatech) to give the title compound. HR-MS (ES, m/z) calculated for $C_{39}H_{49}Cl_2FN_5O_3$ [(M+H)$^+$] 724.3191, observed 724.3190.

EXAMPLE 250

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-piperidin-1-yl-ethanone

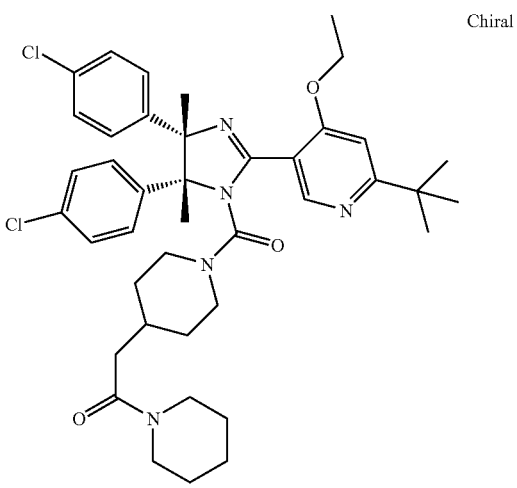 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCCCC2)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was coupled with piperidine (Aldrich) to give the title compound. HR-MS (ES, m/z) calculated for $C_{41}H_{52}Cl_2N_5O_3$ [(M+H)$^+$] 732.3442, observed 732.3440.

EXAMPLE 251

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-isopropyl-N-(2-methoxy-ethyl)-acetamide

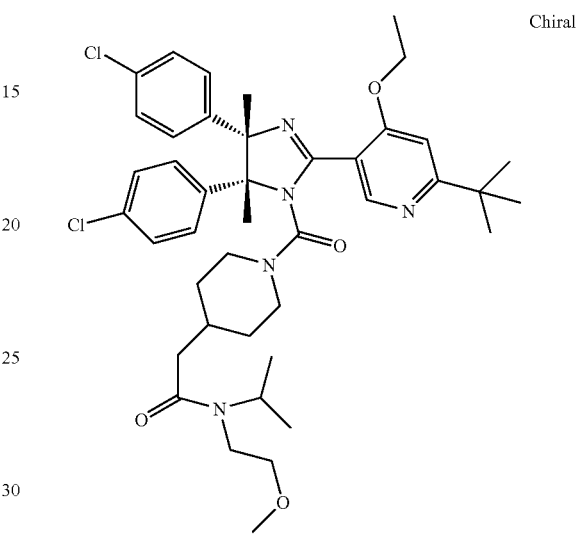

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with N-isopropyl-N-(2-methoxy-ethyl)amine (TCI-US) to give the title compound. HR-MS (ES, m/z) calculated for $C_{42}H_{55}Cl_2N_5O_4$ [(M+H)$^+$] 764.3704, observed 764.3703.

EXAMPLE 252

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[2-(4-fluoro-phenyl)-ethyl]-acetamide

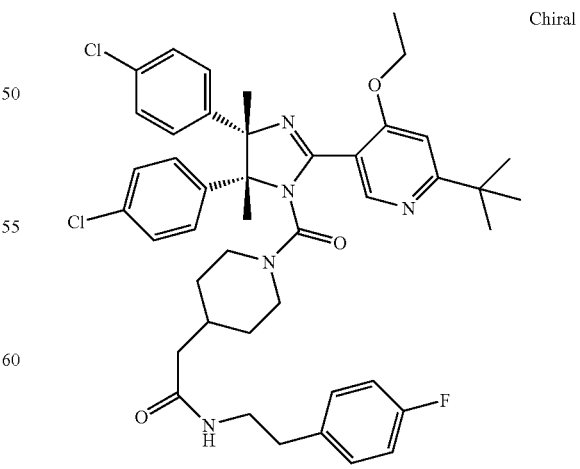

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was coupled with 4-fluorophenyl-ethylamine (Aldrich) to give the title compound. HR-MS (ES, m/z) calculated for $C_{44}H_{51}Cl_2FN_5O_3$ [(M+H)$^+$] 786.3348, observed 786.3345.

EXAMPLE 253

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((S)-1-cyclohexyl-ethyl)-acetamide

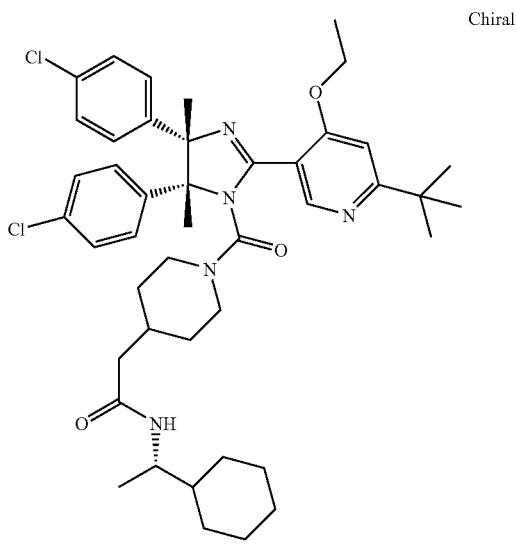 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N[C@@H](C)C2CCCCC2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with N-((S)-1-cyclohexyl-ethyl)amine (Aldrich) to give the title compound. HR-MS (ES, m/z) calculated for $C_{44}H_{58}Cl_2N_5O_3$ [(M+H)$^+$] 774.3911, observed 774.3913.

EXAMPLE 254

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-m-tolyl-acetamide

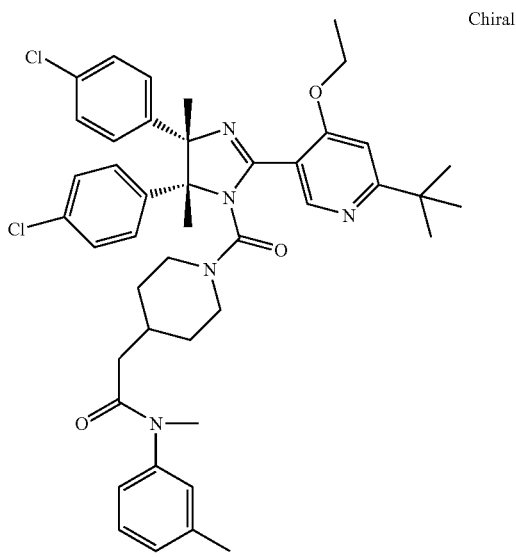 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)c2cccc(C)c2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with N-methyl-N-m-tolylamine (Aldrich) to give the title compound. HR-MS (ES, m/z) calculated for $C_{44}H_{52}Cl_2N_5O_3$ [(M+H)$^+$] 768.3442, observed 768.3440.

EXAMPLE 255

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-isobutyl-piperazin-1-yl)-ethanone

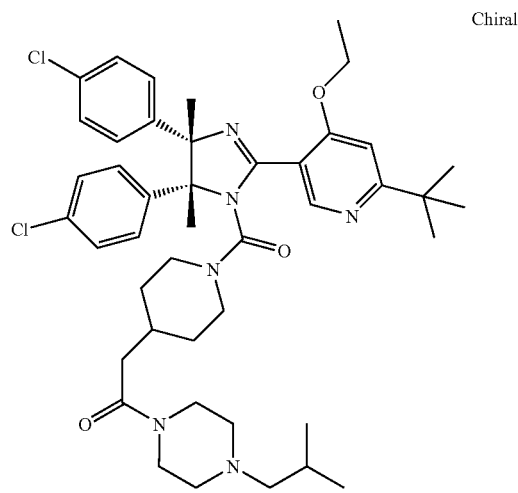 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCN(CC(C)C)CC2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with 4-isopropyl-piperazine (Oakwood) to give the title compound. HR-MS (ES, m/z) calculated for $C_{44}H_{59}Cl_2N_6O_3$ [(M+H)$^+$] 789.4020, observed 789.4016.

EXAMPLE 256

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(1,3-dihydro-isoindol-2-yl)-ethanone

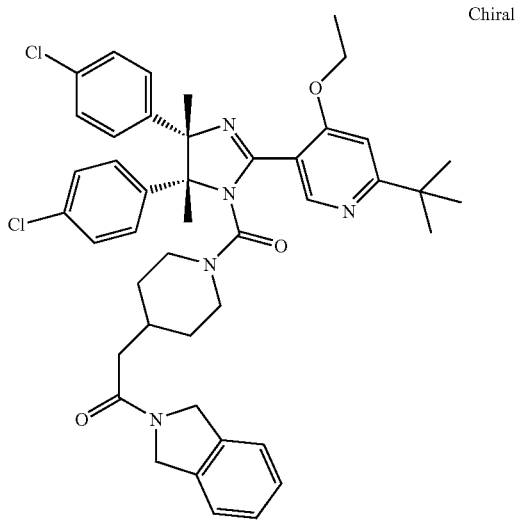 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2Cc3ccccc3C2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with 2,3-dihydro-1H-isoindole (Oakwood) to give the title compound. HR-MS (ES, m/z) calculated for $C_{44}H_{50}Cl_2N_5O_3$ [(M+H)$^+$] 766.3285, observed 766.3286.

EXAMPLE 257

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[(S)-1-(2-fluoro-phenyl)-ethyl]-acetamide

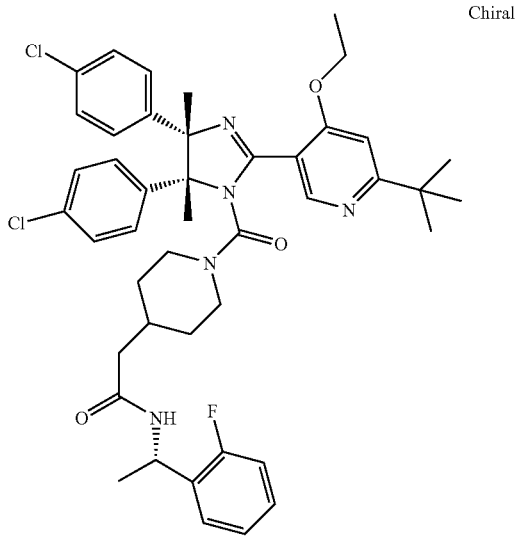 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N[C@@H](C)c2ccccc2F)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with (S)-1-(2-fluoro-phenyl)-ethylamine (Matrix) to give the title compound. HR-MS (ES, m/z) calculated for $C_{44}H_{51}Cl_2FN_5O_3$ [(M+H)$^+$] 786.3348, observed 786.3343.

EXAMPLE 258

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[2-(2,5-dimethyl-phenyl)-ethyl]-acetamide

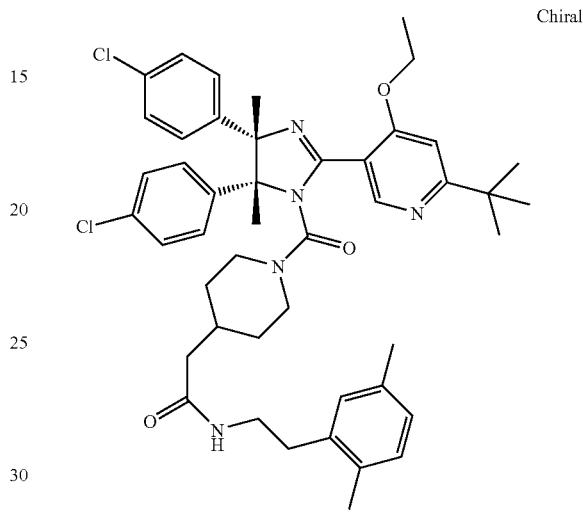

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with 2,5-dimethyl-phenylethylamine (Matrix) to give the title compound. HR-MS (ES, m/z) calculated for $C_{46}H_{56}Cl_2N_5O_3$ [(M+H)$^+$] 796.3755, observed 796.3752.

EXAMPLE 259

N-Butyl-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-N-isopropyl-acetamide

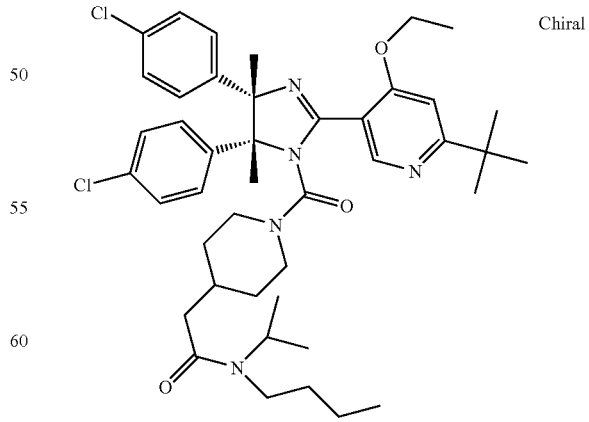

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with n-butyl isopropyl amine (ChemBridge) to give the title compound. HR-MS (ES, m/z) calculated for $C_{43}H_{58}Cl_2N_5O_3$ $[(M+H)^+]$ 762.3911, observed 762.3908.

EXAMPLE 260

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-((S)-1-phenyl-ethyl)-acetamide

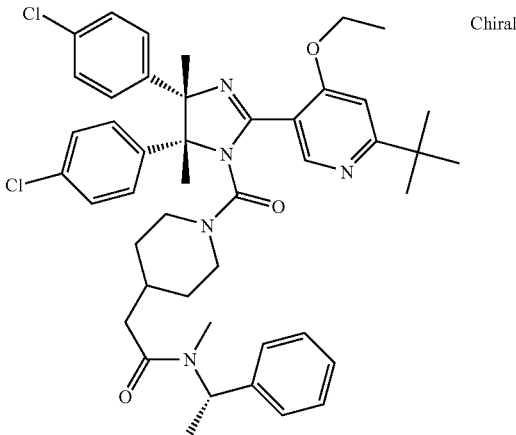 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)[C@@H](C)c2ccccc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with N-methyl-N-((S)-1-phenyl-ethyl)amine (Aldrich) to give the title compound. HR-MS (ES, m/z) calculated for $C_{45}H_{54}Cl_2N_5O_3$ $[(M+H)^+]$ 782.3598, observed 782.3596.

EXAMPLE 261

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methoxy-acetamide

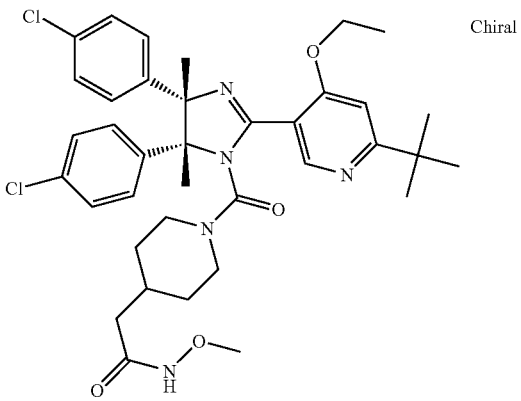 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NOC)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with methoxyamine (Aldrich) to give the title compound. HR-MS (ES, m/z) calculated for $C_{37}H_{46}Cl_2N_5O_4$ $[(M+H)^+]$ 694.2922, observed 694.2919.

EXAMPLE 262

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-fluoro-benzyl)-N-methyl-acetamide

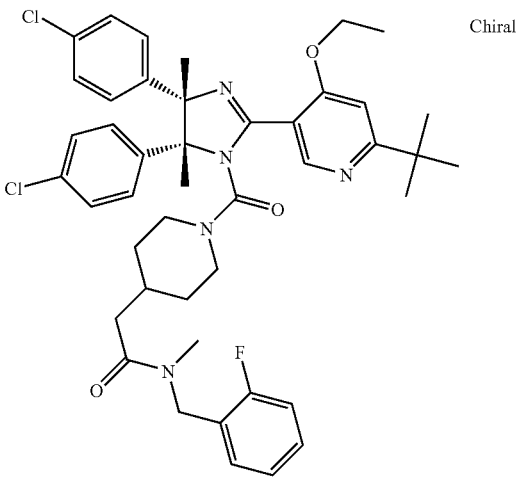 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)Cc2ccccc2F)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was coupled with N-2-fluoro-benzyl N-methyl amine (Aldrich) to give the title compound. HR-MS (ES, m/z) calculated for $C_{44}H_{51}Cl_2FN_5O_3$ $[(M+H)^+]$ 786.3348, observed 786.3345.

EXAMPLE 263

4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazine-1-carboxylic acid amide

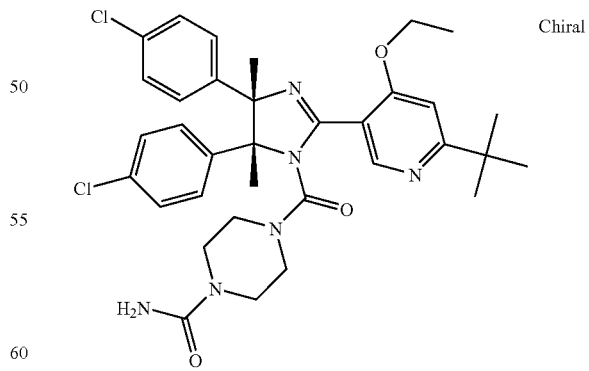

In a manner analogous to the method described in example 160, [(4S,5R)-2-(6-tert-butyl-4-ethoxy-pyridin-3-yl)-4,5-bis-(4-chloro-phenyl)-4,5-dimethyl-4,5-dihydro-imidazol-1-yl]-piperazin-1-yl-methanone (example 185) was reacted with trimethylsilyl isocyanate (TCI-US) to give the title compound. HR-MS (ES, m/z) calculated for $C_{34}H_{41}Cl_2N_6O_3$ [(M+H)$^+$] 651.2612, observed 651.2608.

EXAMPLE 264

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-N-(2,3-dihydroxy-propyl)-acetamide

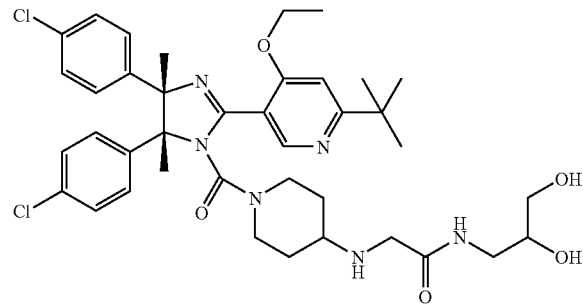 [SMILES: CCOc1cc(C(C)(C)C)ncc1C1=N[C@@](C)(c2ccc(Cl)cc2)[C@@](C)(c2ccc(Cl)cc2)N1C(=O)N1CCC(NCC(=O)NCC(O)CO)CC1]

In a manner analogous to the method described in example 163, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-acetic acid (example 229) was reacted with N-(2,3-dihydroxy-propyl)-amine (Aldrich) to give the title compound as a mixture of diasteromers. HR-MS (ES, m/z) calculated for $C_{39}H_{51}Cl_2N_6O_5$ [(M+H)$^+$] 753.3293, observed 753.3293.

EXAMPLE 265

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(4-methyl-piperazine-1-carbonyl)-piperidin-1-yl]-methanone

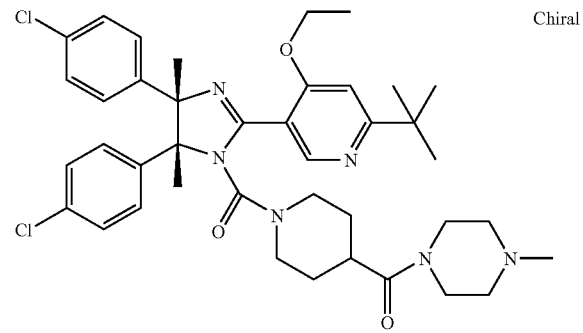 [SMILES: CCOc1cc(C(C)(C)C)ncc1C1=N[C@@](C)(c2ccc(Cl)cc2)[C@@](C)(c2ccc(Cl)cc2)N1C(=O)N1CCC(C(=O)N2CCN(C)CC2)CC1]

In a manner analogous to the method described in example 163,1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid (example 211) was reacted with N-methylpiperazine (Aldrich) to give the title compound. HR-MS (ES, m/z) calculated for $C_{40}H_{51}Cl_2N_6O_3$ [(M+H)$^+$] 733.3394, observed 733.3390.

EXAMPLE 266

1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-(1,1-dioxo-tetrahydro-1λ6-thiophen-3-yl)-urea

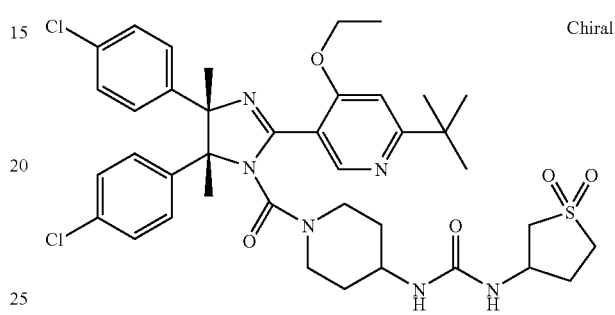

In a manner similar to the method described in example 160, (4-amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with 3-isocyanato-tetrahydro-thiophene 1,1-dioxide (Chembridge) to give a mixture of diasteremers. The diastereomers were separated by supercritical fluid chromatography (Berger Instrument Multi-Gram II, Whelk-O column, eluting with 40% isopropanol in carbon dioxide) to give the title compound as pre-peak. HR-MS (ES, m/z) calculated for $C_{39}H_{49}Cl_2N_6O_5$ [(M+H)$^+$] 783.2857, observed 783.2852.

EXAMPLE 267

1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid cyclopentylamide

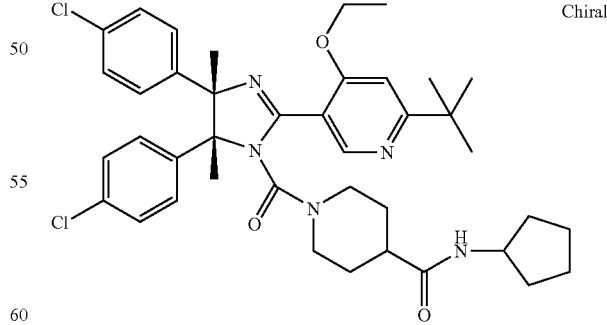

In a manner analogous to the method described in example 163, 1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid (example 211) was reacted with cyclopentylamine (Aldrich) to give the title compound. HR-MS (ES, m/z) calculated for $C_{40}H_{49}Cl_2N_5O_3$ [(M+H)$^+$] 718.3285, observed 718.3288.

EXAMPLE 268

1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-(1,1-dioxo-tetrahydro-1λ6-thiophen-3-yl)-urea

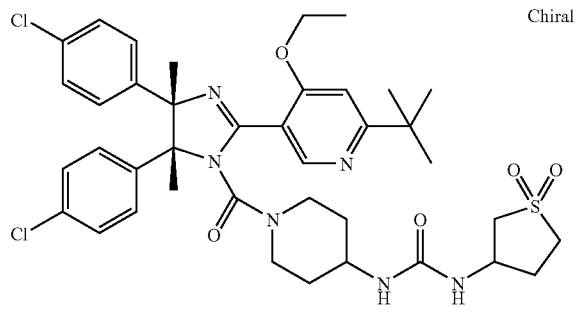 [SMILES: CCOc1cc(C(C)(C)C)ncc1C1=N[C@@](C)(c2ccc(Cl)cc2)[C@@](C)(c2ccc(Cl)cc2)N1C(=O)N1CCC(NC(=O)NC2CCS(=O)(=O)C2)CC1]

In a manner similar to the method described in example 160, (4-amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone (example 204) was reacted with 3-isocyanato-tetrahydro-thiophene 1,1-dioxide (Chembridge) to give a mixture of diasteremers. The diastereomers were separated by supercritical fluid chromatography (Berger Instrument Multi-Gram II, Whelk-O column, eluting with 40% isopropanol in carbon dioxide) to give the title compound as post-peak. HR-MS (ES, m/z) calculated for $C_{39}H_{49}Cl_2N_6O_5$ [(M+H)$^+$] 783.2857, observed 783.2857.

EXAMPLE 269

1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid cyclopentyl-methyl-amide

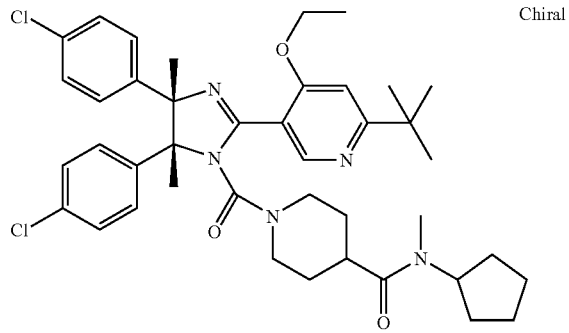 [SMILES: CCOc1cc(C(C)(C)C)ncc1C1=N[C@@](C)(c2ccc(Cl)cc2)[C@@](C)(c2ccc(Cl)cc2)N1C(=O)N1CCC(C(=O)N(C)C2CCCC2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with cyclopentyl-methyl-amine (Aldrich) to give the title compound. HR-MS (ES, m/z) calculated for $C_{41}H_{52}Cl_2N_5O_3$ [(M+H)$^+$] 732.3442, observed 732.3443.

EXAMPLE 270

1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid phenylamide

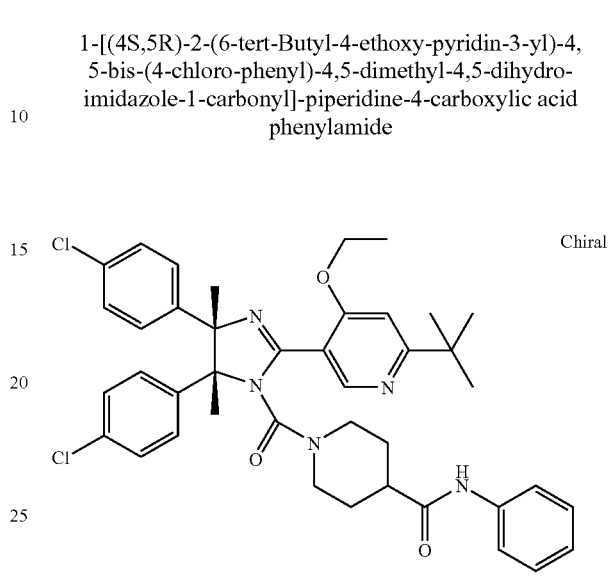

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with aniline (Aldrich) to give the title compound. HR-MS (ES, m/z) calculated for $C_{41}H_{46}Cl_2N_5O_3$ [(M+H)$^+$] 726.2972, observed 726.2969.

EXAMPLE 271

1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid cyclobutylamide

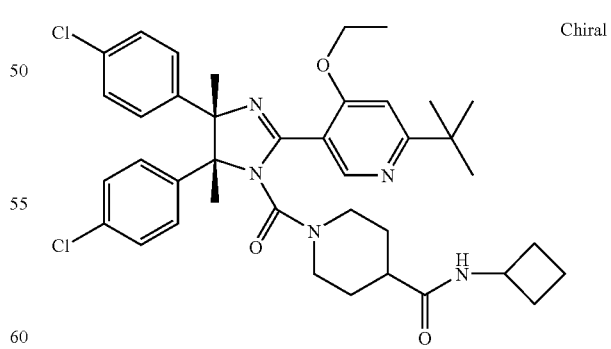

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with cyclobutylamine (Aldrich) to give the title compound.

HR-MS (ES, m/z) calculated for $C_{39}H_{48}Cl_2N_5O_3$ $[(M+H)^+]$ 704.3129, observed 704.3124.

EXAMPLE 272

1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid ([1,4]dioxan-2-ylmethyl)-amide

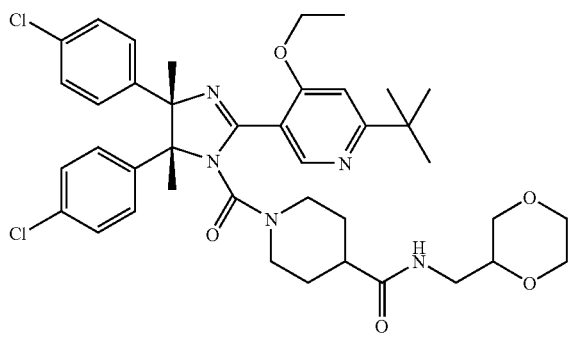 [SMILES: CCOc1cc(C(C)(C)C)ncc1C1=N[C@@](C)(c2ccc(Cl)cc2)[C@@](C)(c2ccc(Cl)cc2)N1C(=O)N1CCC(C(=O)NCC2COCCO2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with [1,4]dioxan-2-yl-methylamine (Aldrich) to give the title compound as a mixture of diastereomers. HR-MS (ES, m/z) calculated for $C_{40}H_{50}Cl_2N_5O_5$ $[(M+H)^+]$ 750.3184, observed 750.3180.

EXAMPLE 273

1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid methylamide

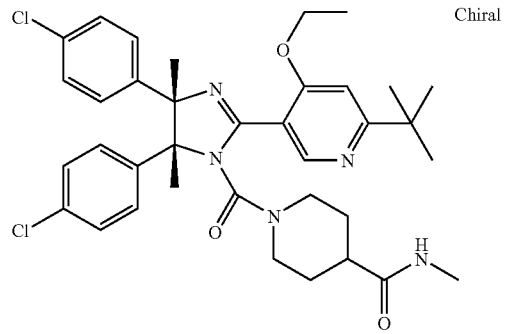 [SMILES: CCOc1cc(C(C)(C)C)ncc1C1=N[C@@](C)(c2ccc(Cl)cc2)[C@@](C)(c2ccc(Cl)cc2)N1C(=O)N1CCC(C(=O)NC)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with methylamine (Aldrich) to give the title compound. HR-MS (ES, m/z) calculated for $C_{36}H_{44}Cl_2N_5O_3$ $[(M+H)^+]$ 664.2816, observed 664.2812.

EXAMPLE 274

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-methoxy-phenyl)-N-methyl-acetamide

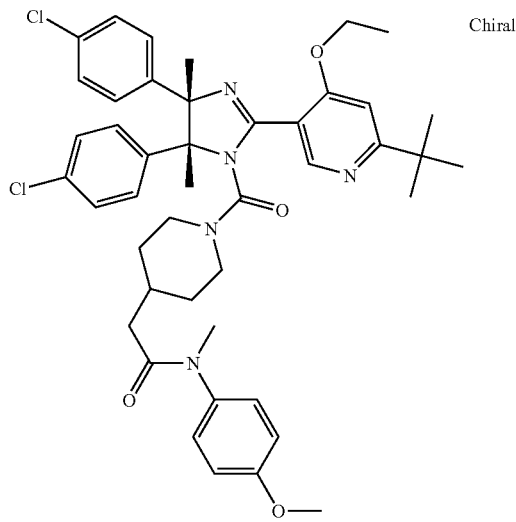 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)c2ccc(OC)cc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with N-(4-methoxy-phenyl)-N-methyl-amine (Aldrich) to give the title compound. LC-MS (ES$^+$) 784 $[(M+H)^+]$.

EXAMPLE 275

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(2-trifluoromethyl-pyrrolidin-1-yl)-ethanone

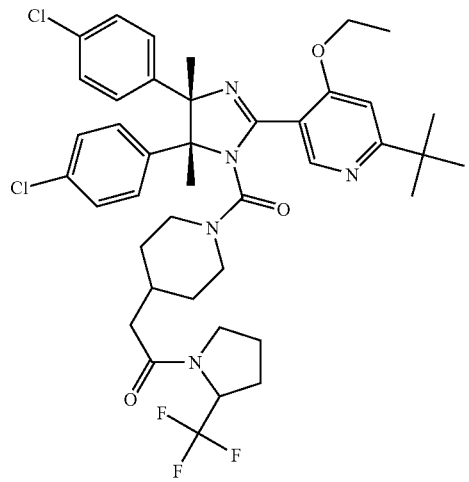 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCCC2C(F)(F)F)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 2-trifluoromethyl-pyrrolidine (Aldrich) to give the title compound. HR-MS (ES, m/z) calculated for $C_{41}H_{49}F_3Cl_2N_5O_3$ $[(M+H)^+]$ 786.3159, observed 786.3157.

EXAMPLE 276

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cycloheptylmethyl-acetamide

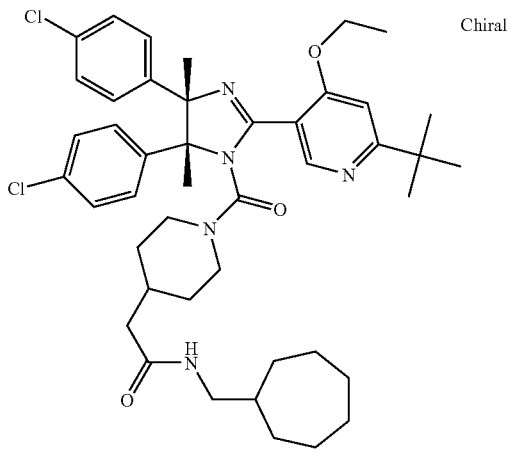 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCC2CCCCCC2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with N-cycloheptylmethyl-amine (Aldrich) to give the title compound. HR-MS (ES, m/z) calculated for $C_{44}H_{58}Cl_2N_5O_3$ $[(M+H)^+]$ 774.3911, observed 774.3909.

EXAMPLE 277

N-But-3-enyl-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide

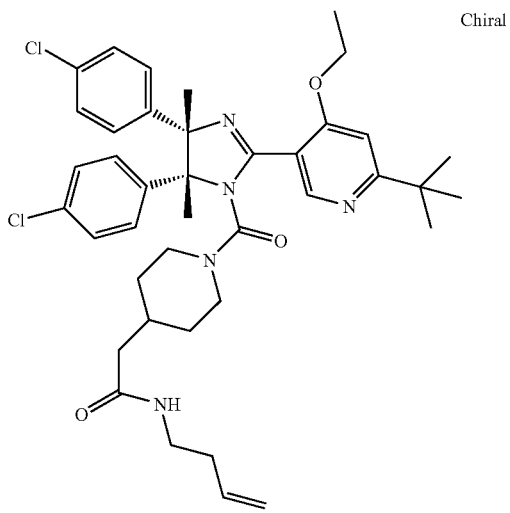 [SMILES: C=CCCNC(=O)CC1CCN(C(=O)N2C(c3cnc(C(C)(C)C)cc3OCC)=N[C@@](C)(c3ccc(Cl)cc3)[C@@]2(C)c2ccc(Cl)cc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with n-but-3-enylamine (Alfa) to give the title compound. LC-MS $(ES^+)$ 718 $[(M+H)^+]$.

EXAMPLE 278

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-propyl-acetamide

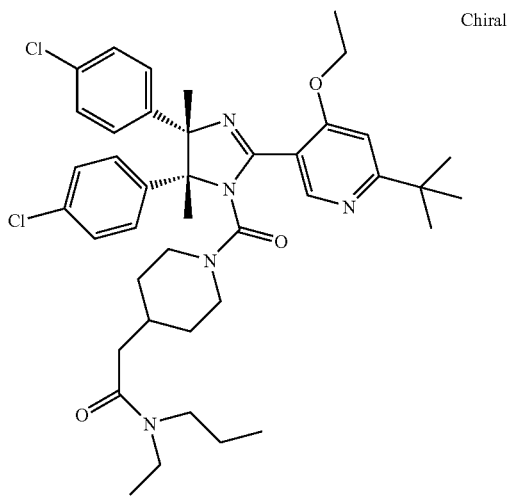 [SMILES: CCCN(CC)C(=O)CC1CCN(C(=O)N2C(c3cnc(C(C)(C)C)cc3OCC)=N[C@@](C)(c3ccc(Cl)cc3)[C@@]2(C)c2ccc(Cl)cc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with N-ethyl-N-propyl-amine (Alfa) to give the title compound. LC-MS $(ES^+)$ 734 $[(M+H)^+]$.

EXAMPLE 279

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-2-methyl-benzyl)-acetamide

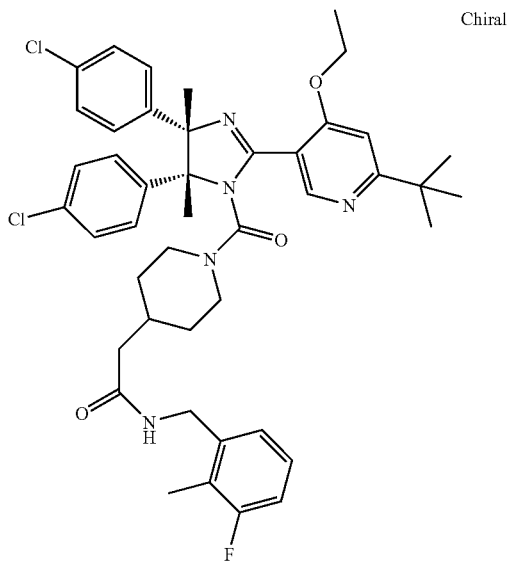 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCc2cccc(F)c2C)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with N-(3-fluoro-2-methyl-benzyl)-amine (Alfa) to give the title compound. LC-MS (ES⁺) 786 [(M+H)⁺].

EXAMPLE 280

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-isopropyl-acetamide

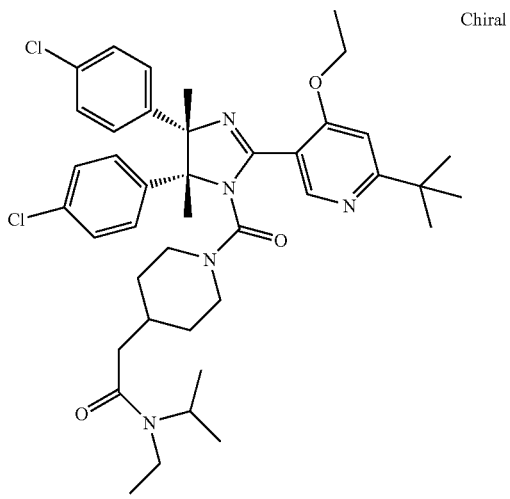 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(CC)C(C)C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with N-ethyl-N-isopropyl-amine (Alfa) to give the title compound. LC-MS (ES⁺) 734 [(M+H)⁺].

EXAMPLE 281

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((S)-1-cyclopropyl-ethyl)-acetamide

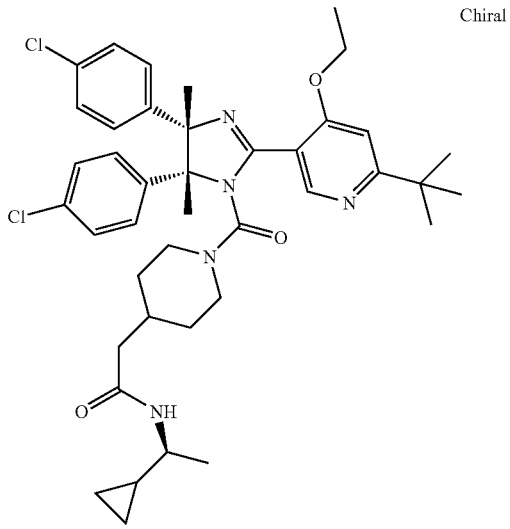 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N[C@@H](C)C2CC2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with N-((S)-1-cyclopropyl-ethyl)-amine (Alfa) to give the title compound. LC-MS (ES⁺) 732 [(M+H)⁺].

EXAMPLE 282

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-acetamide

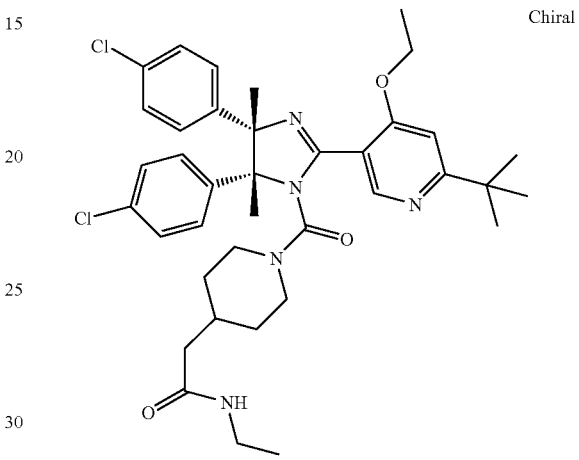

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with ethylamine (Aldrich) to give the title compound. LC-MS (ES⁺) 692 [(M+H)⁺].

EXAMPLE 283

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-methyl-acetamide

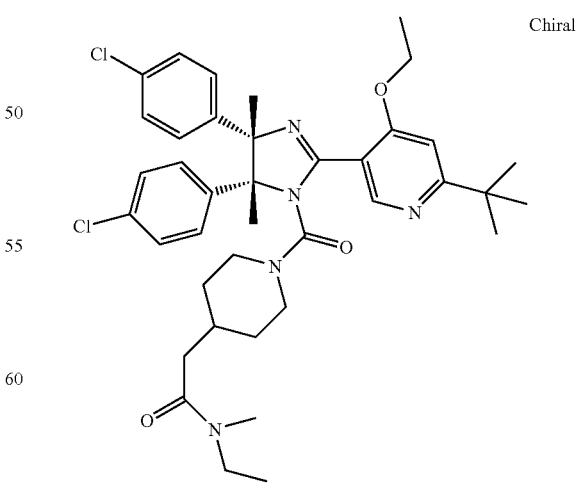

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with N-ethyl-N-methylamine (Aldrich) to give the title compound. LC-MS (ES+) 706 [(M+H)+].

EXAMPLE 284

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-propyl-N-(tetrahydro-pyran-4-yl)-acetamide

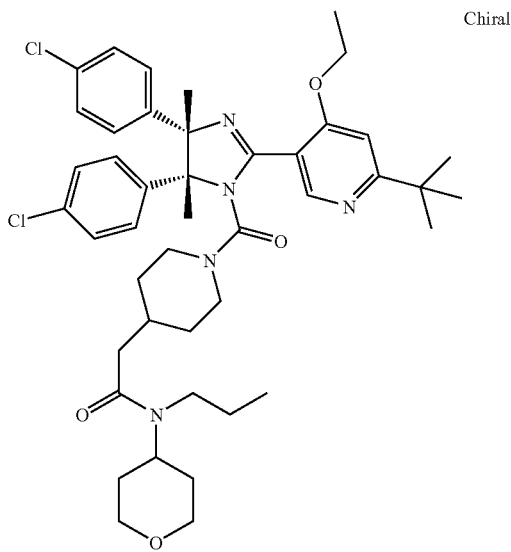 [SMILES: CCCN(C(=O)CC1CCN(C(=O)N2C(c3cnc(C(C)(C)C)cc3OCC)=N[C@@](C)(c3ccc(Cl)cc3)[C@@]2(C)c2ccc(Cl)cc2)CC1)C1CCOCC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with N-propyl-N-(tetrahydro-pyran-4-yl)-amine (Chem Impex) to give the title compound. LC-MS (ES+) 790 [(M+H)+].

EXAMPLE 285

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-m-tolyl-ethyl)-acetamide

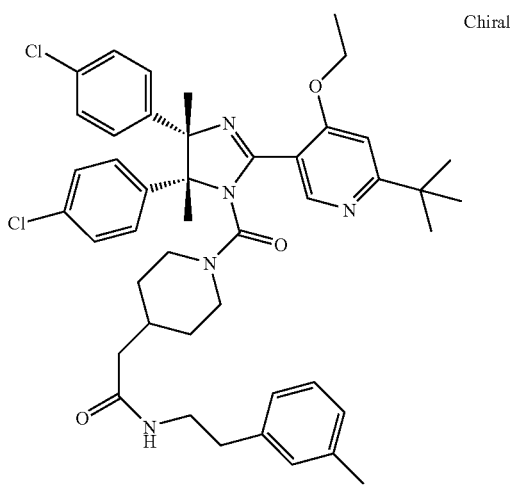 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCCc2cccc(C)c2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with N-(2-m-tolyl-ethyl)-amine (Oakwood) to give the title compound. LC-MS (ES+) 782 [(M+H)+].

EXAMPLE 286

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-dimethylamino-piperidin-1-yl)-ethanone

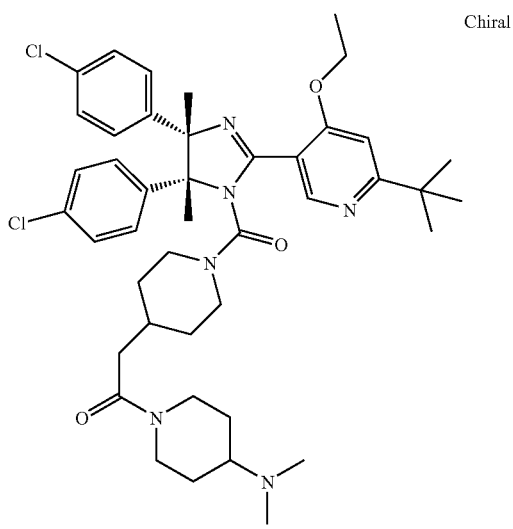 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCC(N(C)C)CC2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 4-dimethylamino-piperidine (Oakwood) to give the title compound. LC-MS (ES+) 775 [(M+H)+].

EXAMPLE 287

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-sec-butyl-phenyl)-acetamide

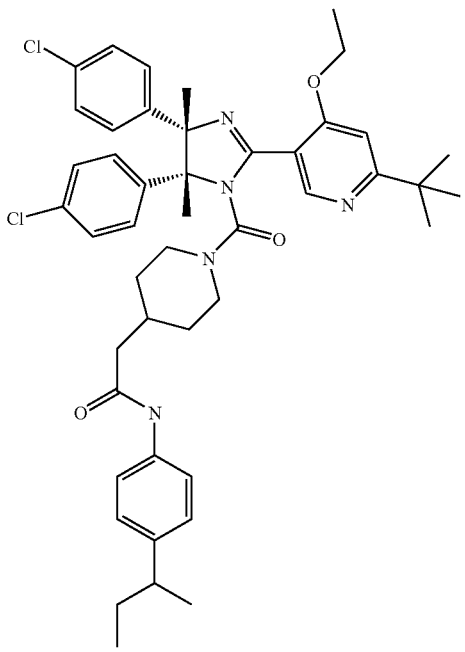 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)Nc2ccc(C(C)CC)cc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with N-(4-sec-butyl-phenyl)-amine (TCI-US) to give the title compound. LC-MS (ES$^+$) 796 [(M+H)$^+$].

EXAMPLE 288

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cyclohexyl-acetamide

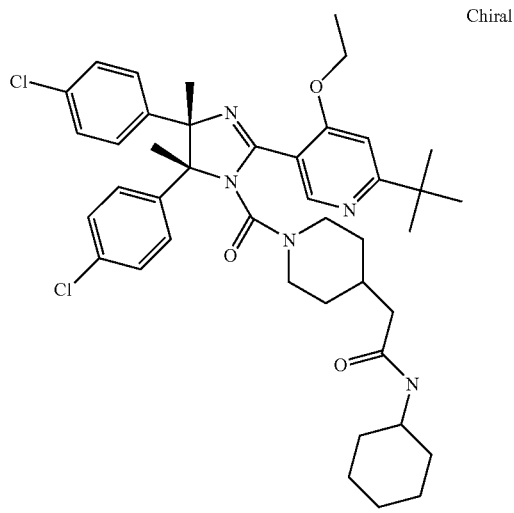 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NC2CCCCC2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with cyclohexylamine (Aldrich) to give the title product. LC-MS (ES$^+$) 746 [(M+H)$^+$].

EXAMPLE 289

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cyclohexylmethyl-acetamide

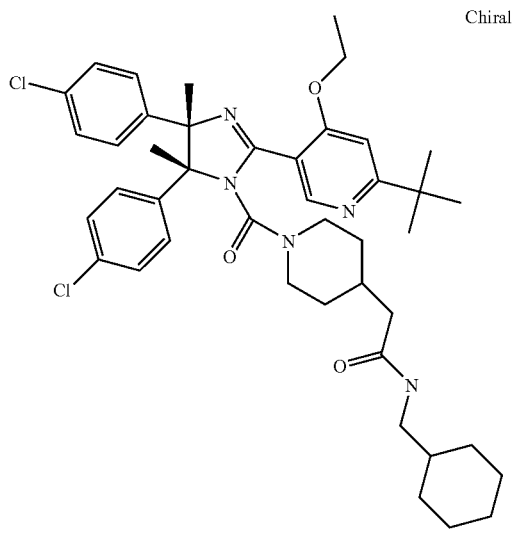 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCC2CCCCC2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with cyclohexane-methylamine (Lancaster) to give the title product. LC-MS (ES$^+$) 760 [(M+H)$^+$].

EXAMPLE 290

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cycloheptyl-acetamide

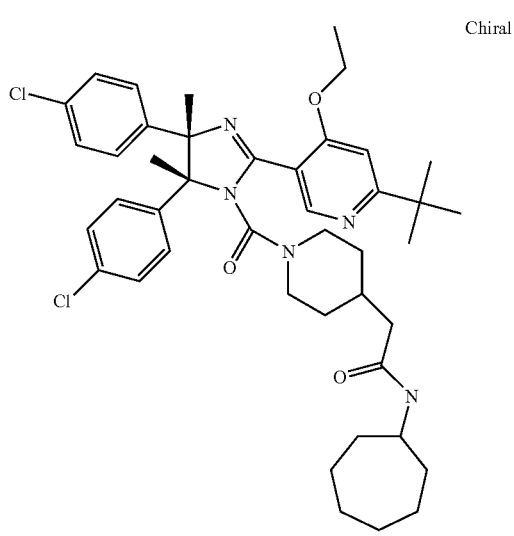 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NC2CCCCCC2)CC1]

In a manner analogous to the method described in example 163, {1-[(4S,5R)-2-(6-tert-butyl-4-ethoxy-pyridin-3-yl)-4,-

5-bis-(4-chloro-phenyl)-4,5-dimethyl-4,5-dihydro-imidazole-1-carbonyl]-piperidin-4-yl}-acetic acid was reacted with cycloheptylamine (Aldrich) to give the title product. LC-MS (ES$^+$) 760 [(M+H)$^+$].

EXAMPLE 291

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(3,4-dihydro-1H-isoquinolin-2-yl)-ethanone

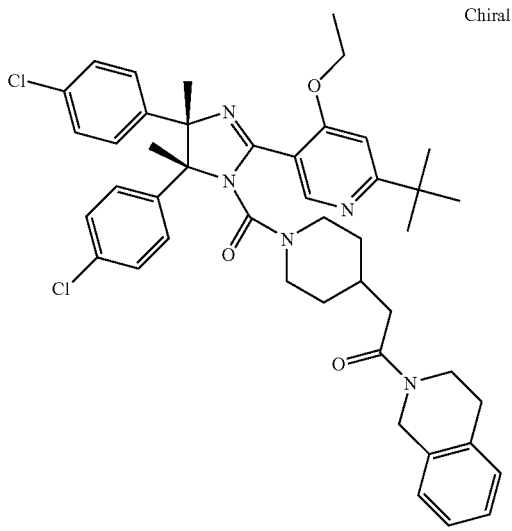 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCc3ccccc3C2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 1,2,3,4-tetrahydroisoquinoline (Aldrich) to give the title product. LC-MS (ES$^+$) 780 [(M+H)$^+$].

EXAMPLE 292

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-fluoro-5-methyl-phenyl)-acetamide

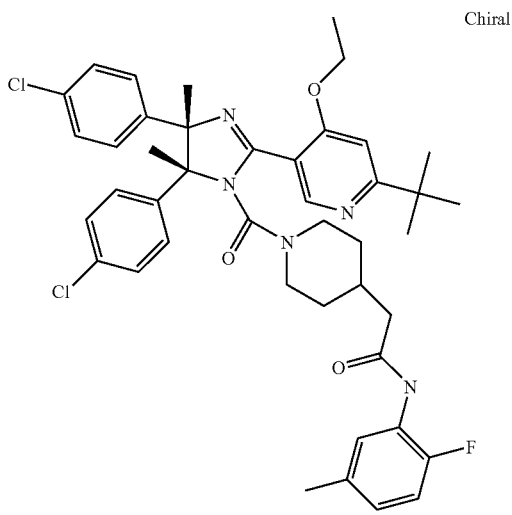 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)Nc2cc(C)ccc2F)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with 2-fluoro-5-methylaniline (Aldrich) to give the title product. LC-MS (ES$^+$) 772 [(M+H)$^+$].

EXAMPLE 293

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-chloro-5-methyl-phenyl)-acetamide

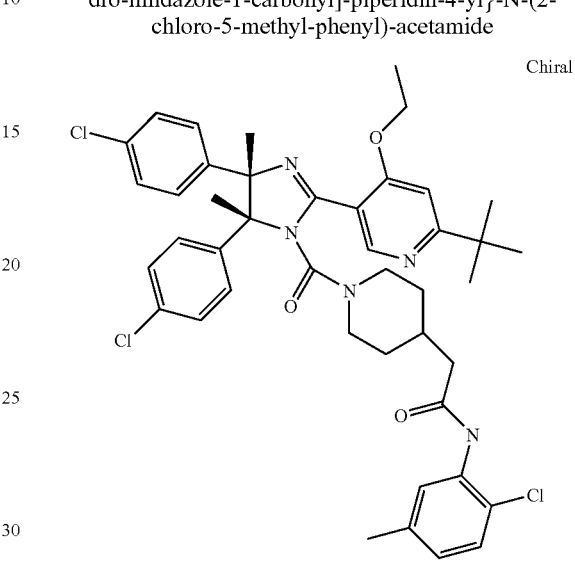

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 2-chloro-5-methylaniline (Aldrich) to give the title product. LC-MS (ES$^+$) 788 [(M+H)$^+$].

EXAMPLE 294

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2,5-dimethyl-phenyl)-acetamide

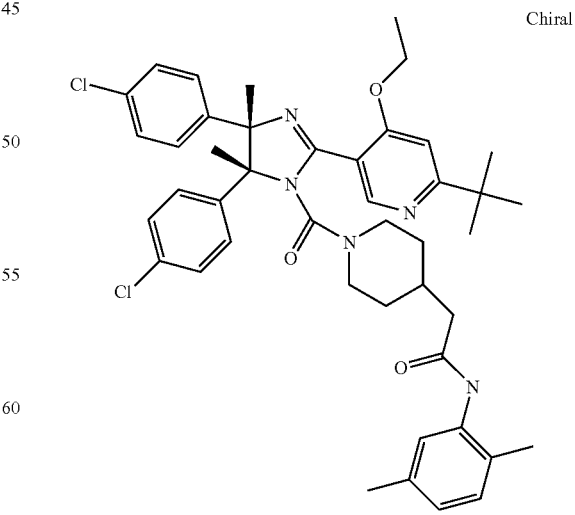

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with 2,5-dimethylaniline (Aldrich) to give the title product. LC-MS (ES+) 768 [(M+H)+].

EXAMPLE 295

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-phenyl)-acetamide

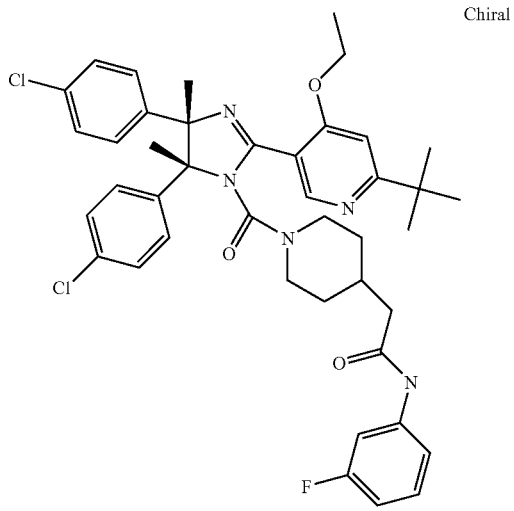 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)Nc2cccc(F)c2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 3-fluoroaniline (Aldrich) to give the title product. LC-MS (ES+) 758 [(M+H)+].

EXAMPLE 296

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-2-methyl-phenyl)-acetamide

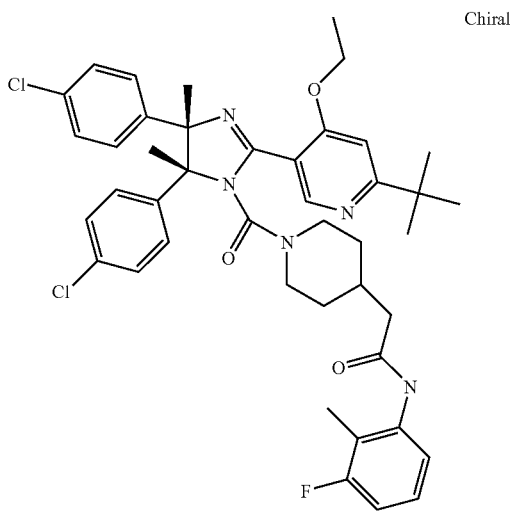 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)Nc2cccc(F)c2C)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with 3-fluoro-2-methylaniline (Aldrich) to give the title product. LC-MS (ES+) 772 [(M+H)+].

EXAMPLE 297

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-4-methyl-phenyl)-acetamide

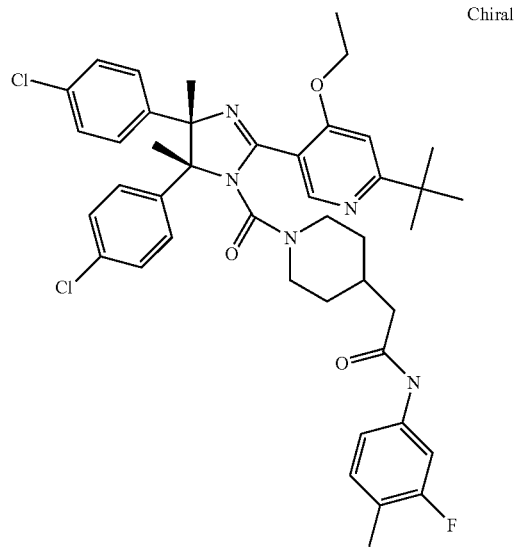 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)Nc2ccc(C)c(F)c2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 3-fluoro-4-methylaniline (Aldrich) to give the title product. LC-MS (ES+) 772 [(M+H)+].

EXAMPLE 298

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-chloro-2-methyl-phenyl)-acetamide

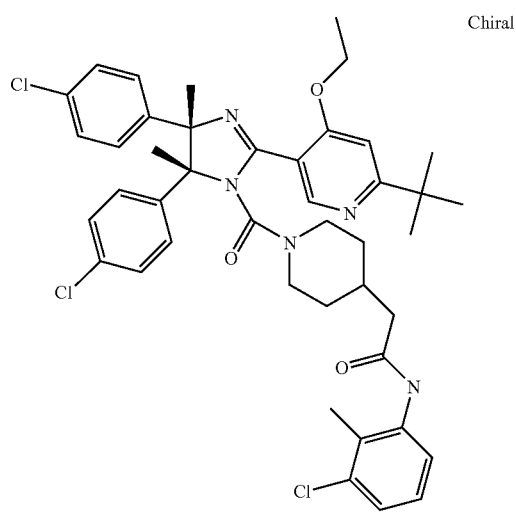 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)Nc2cccc(Cl)c2C)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with 3-chloro-2-methylaniline (Aldrich) to give the title product. LC-MS (ES+) 788 [(M+H)+].

EXAMPLE 299

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-fluoro-phenyl)-acetamide

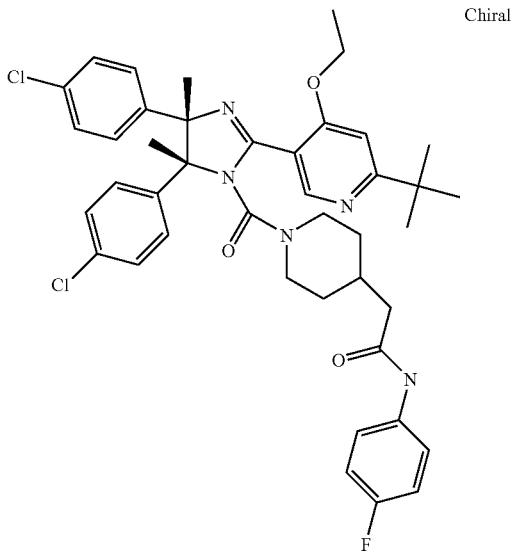 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)Nc2ccc(F)cc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 4-fluoroaniline (Aldrich) to give the title product. LC-MS (ES+) 758 [(M+H)+].

EXAMPLE 300

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-isopropyl-phenyl)-acetamide

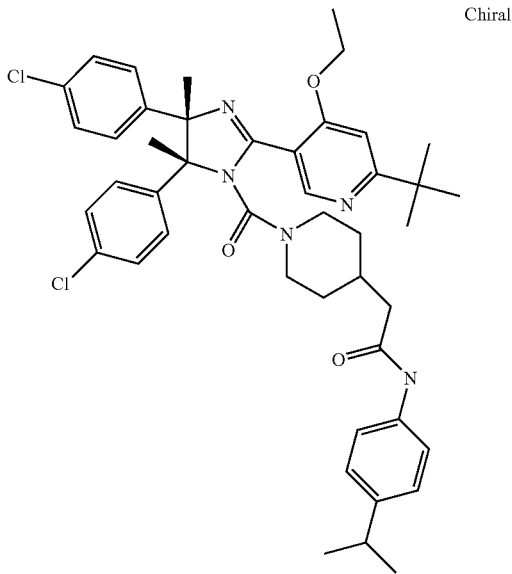 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)Nc2ccc(C(C)C)cc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 4-isopropylaniline (Aldrich) to give the title product. LC-MS (ES+) 782 [(M+H)+].

EXAMPLE 301

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-acetamide

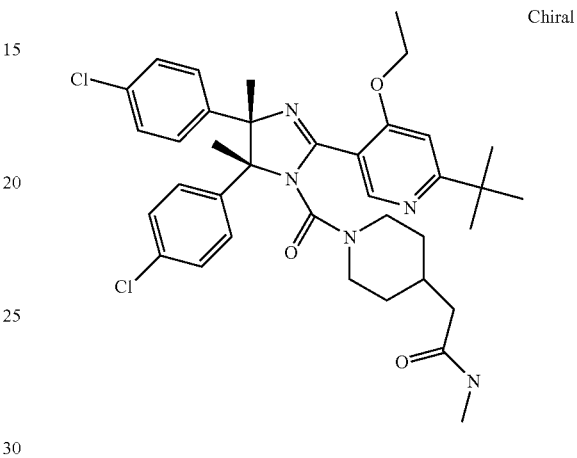

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with methylamine (Aldrich) to give the title product. LC-MS (ES+) 678 [(M+H)+].

EXAMPLE 302

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-chloro-benzyl)-acetamide

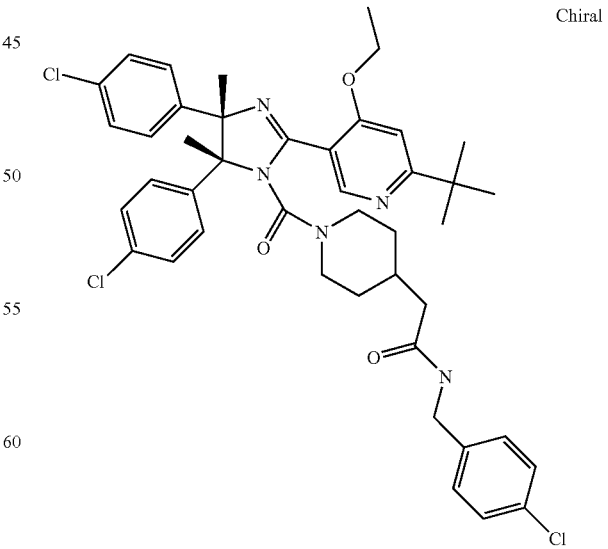

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with 4-chlorobenzylamine (Aldrich) to give the title product. LC-MS (ES⁺) 788 [(M+H)⁺].

EXAMPLE 303

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-methyl-butyl)-acetamide

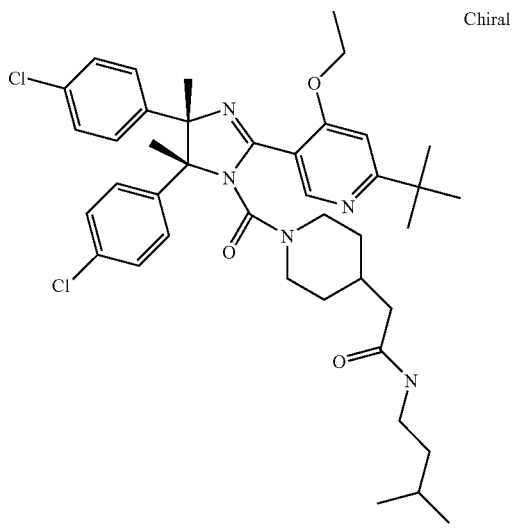 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCCC(C)C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with isoamylamine (Aldrich) to give the title product. LC-MS (ES⁺) 734 [(M+H)⁺].

EXAMPLE 304

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-pentyl-acetamide

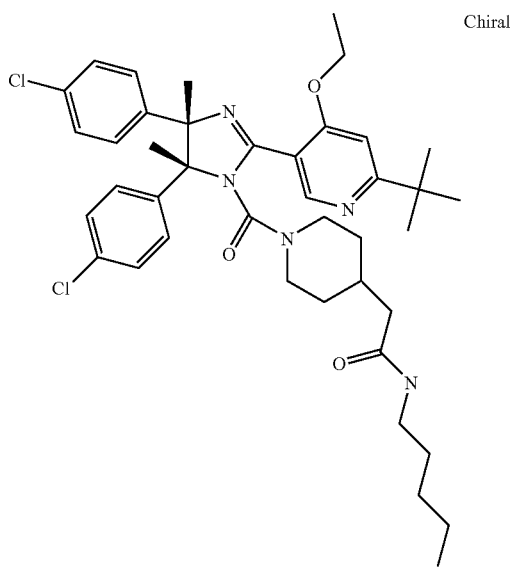 [SMILES: CCCCCNC(=O)CC1CCN(C(=O)N2C(c3cnc(C(C)(C)C)cc3OCC)=N[C@@](C)(c3ccc(Cl)cc3)[C@@]2(C)c2ccc(Cl)cc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with n-amylamine (Fluka) to give the title product. LC-MS (ES⁺) 734 [(M+H)⁺].

EXAMPLE 305

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-hexyl-acetamide

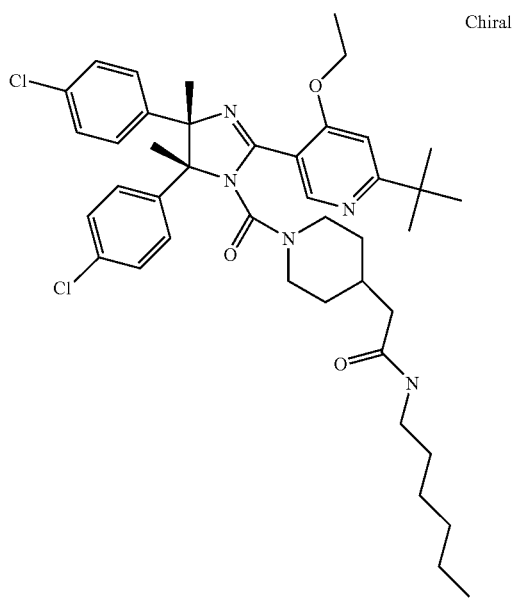 [SMILES: CCCCCCNC(=O)CC1CCN(C(=O)N2C(c3cnc(C(C)(C)C)cc3OCC)=N[C@@](C)(c3ccc(Cl)cc3)[C@@]2(C)c2ccc(Cl)cc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with hexylamine (MCB) to give the title product. LC-MS (ES⁺) 748 [(M+H)⁺].

EXAMPLE 306

N-Benzyl-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-acetamide

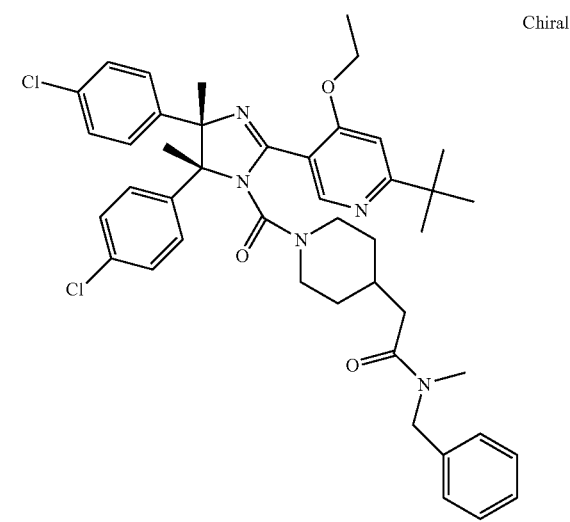 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)Cc2ccccc2)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with n-methylbenzylamine (MCB) to give the title product. LC-MS (ES$^+$) 768 [(M+H)$^+$].

EXAMPLE 307

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-phenethyl-acetamide

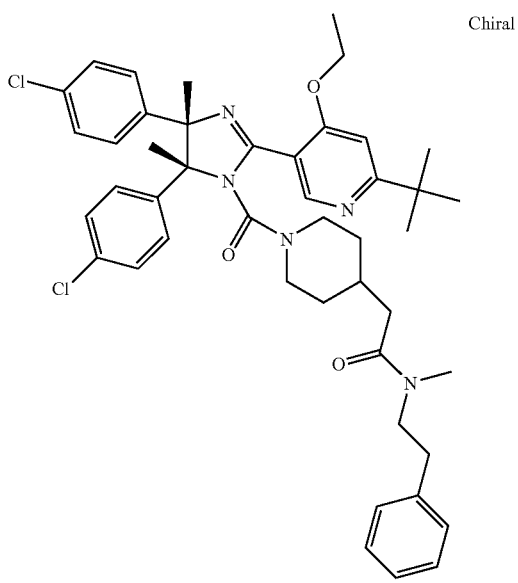 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)CCc2ccccc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with n-methylphenethylamine (Aldrich) to give the title product. LC-MS (ES$^+$) 782 [(M+H)$^+$].

EXAMPLE 308

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-propyl-acetamide

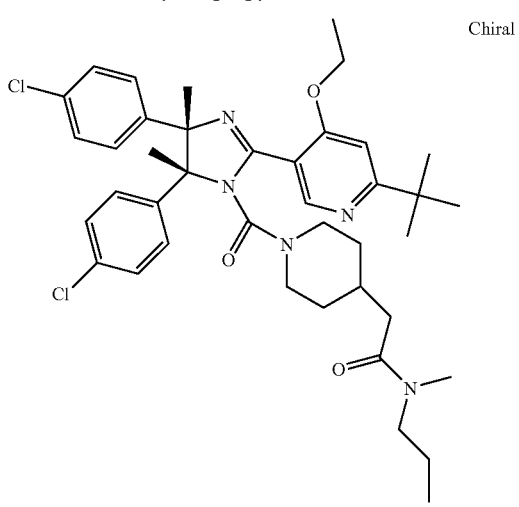

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with n-methyl-1-propylamine (Aldrich) to give the title product. LC-MS (ES$^+$) 720 [(M+H)$^+$].

EXAMPLE 309

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-dipropyl-acetamide In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with dipropylamine (Pennwalt) to give the title product. LC-MS (ES$^+$) 748 [(M+H)$^+$].

EXAMPLE 310

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-propyl-phenyl)-acetamide In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with 2-n-propylaniline (Aldrich) to give the title product. LC-MS (ES+) 782 [(M+H)+].

EXAMPLE 311

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2,4-difluoro-benzyl)-acetamide

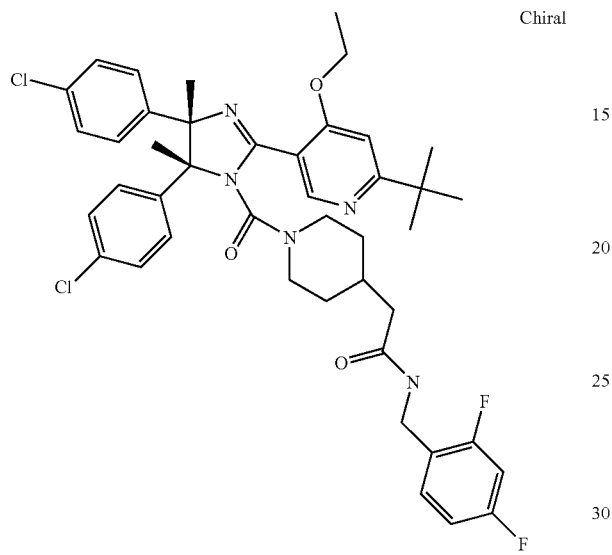

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 2,4-difluorobenzylamine (Aldrich) to give the title product. LC-MS (ES+) 790 [(M+H)+].

EXAMPLE 312

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2,5-difluoro-benzyl)-acetamide

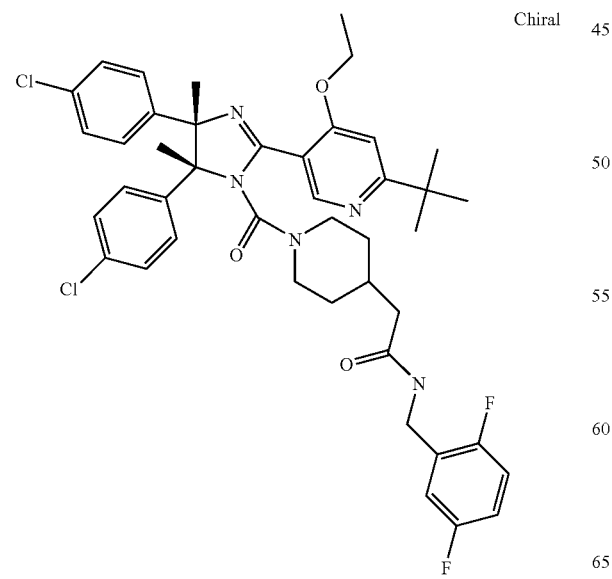

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 2,5-difluorobenzylamine (Aldrich) to give the title product. LC-MS (ES+) 790 [(M+H)+].

EXAMPLE 313

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(6-methyl-3,4-dihydro-2H-quinolin-1-yl)-ethanone

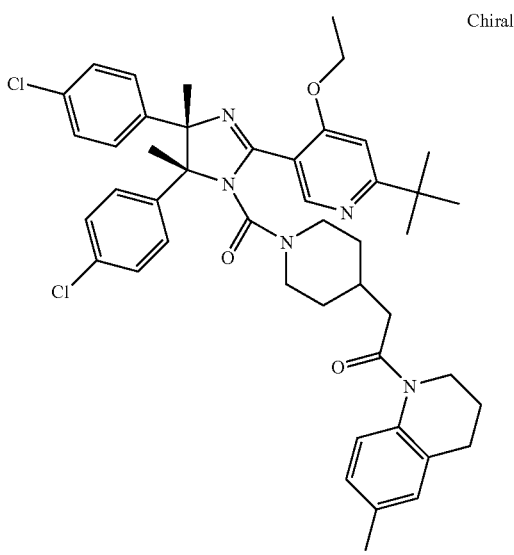 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCCc3cc(C)ccc32)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 6-methyl-1,2,3,4-tetrahydroquinoline (Alfa) to give the title product. LC-MS (ES+) 794 [(M+H)+].

EXAMPLE 314

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-isopropyl-N-phenyl-acetamide

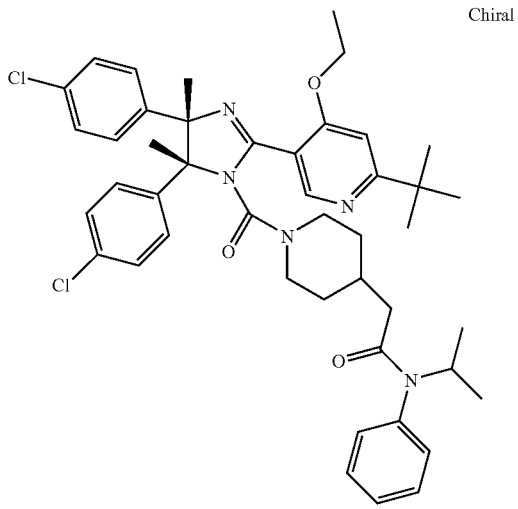 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(c2ccccc2)C(C)C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with n-isopropylaniline (Aldrich) to give the title product. LC-MS (ES$^+$) 782 [(M+H)$^+$].

EXAMPLE 315

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3,5-dimethyl-benzyl)-acetamide

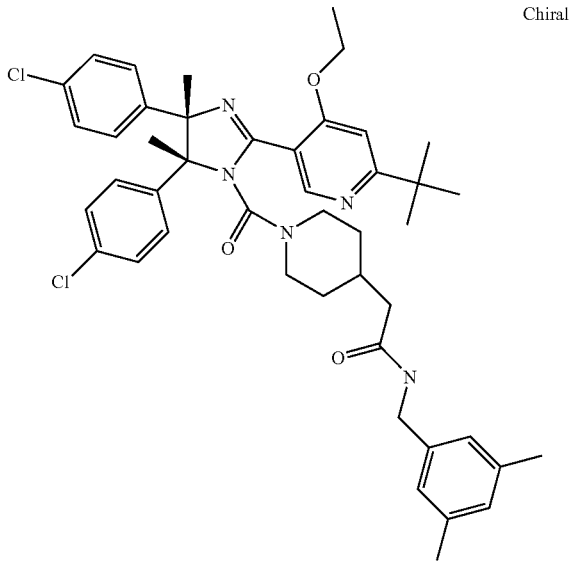 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCc2cc(C)cc(C)c2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 3,5-dimethylbenzylamine (Trans World chemicals) to give the title product. LC-MS (ES$^+$) 782 [(M+H)$^+$].

EXAMPLE 316

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-isopropyl-N-methyl-acetamide

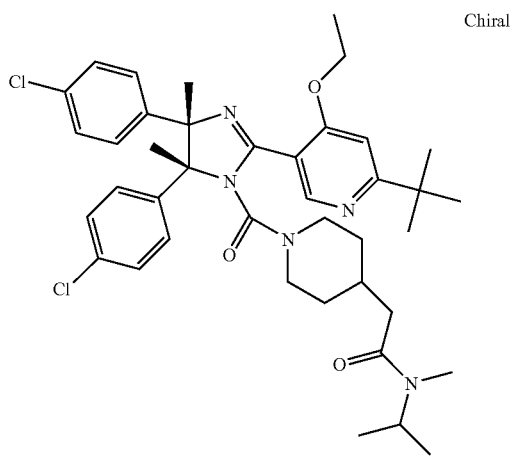 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)C(C)C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with n-methylisopropylamine (Aldrich) to give the title product. LC-MS (ES$^+$) 720 [(M+H)$^+$].

EXAMPLE 317

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-(3-methyl-butyl)-acetamide

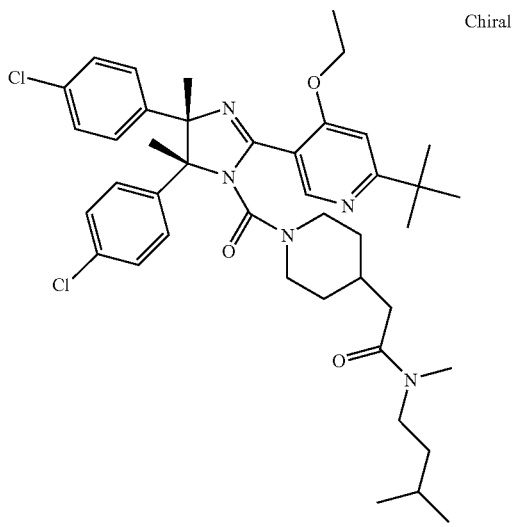 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)CCC(C)C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with n-methylisoamylamine (Matrix) to give the title product. LC-MS (ES+) 748 [(M+H)+].

EXAMPLE 318

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((R)-1-phenyl-ethyl)-acetamide

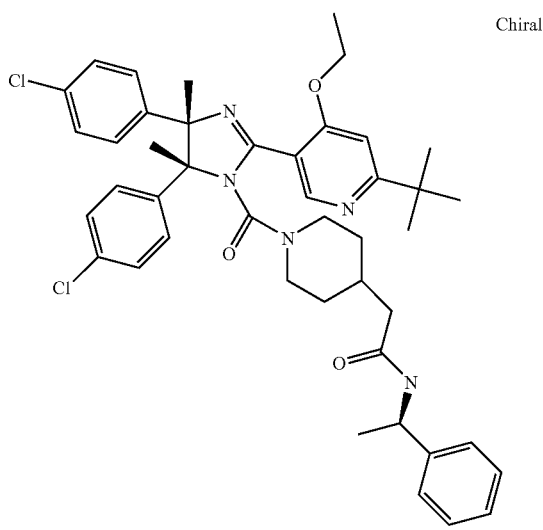 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N[C@H](C)c2ccccc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with (R)-(+)-1-phenylethylamine (Aldrich) to give the title product. LC-MS (ES+) 768 [(M+H)+].

EXAMPLE 319

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((S)-1-phenyl-ethyl)-acetamide

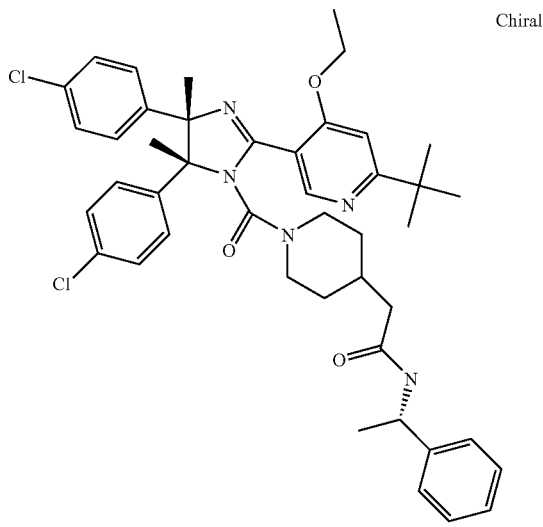 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N[C@@H](C)c2ccccc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with (S)-(−)-1-phenylethylamine (Aldrich) to give the title product. LC-MS (ES+) 768 [(M+H)+].

EXAMPLE 320

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[2-(3-fluoro-phenyl)-ethyl]-acetamide

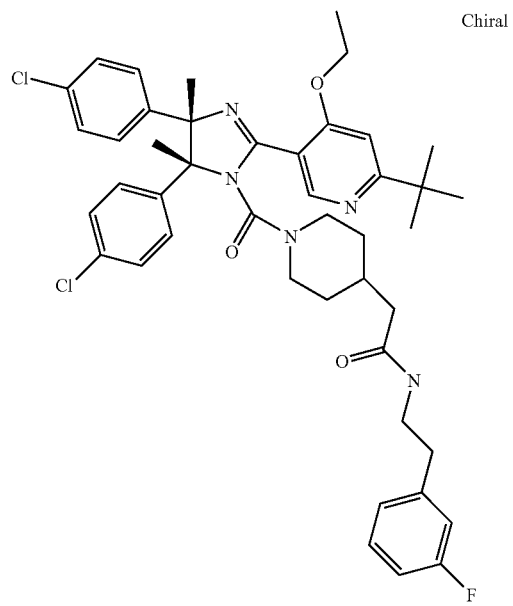 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCCc2cccc(F)c2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 3-fluorophenethyl-amine (Aldrich) to give the title product. LC-MS (ES+) 786 [(M+H)+].

EXAMPLE 321

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4aR,8aS)-octahydro-isoquinolin-2-yl-ethanone

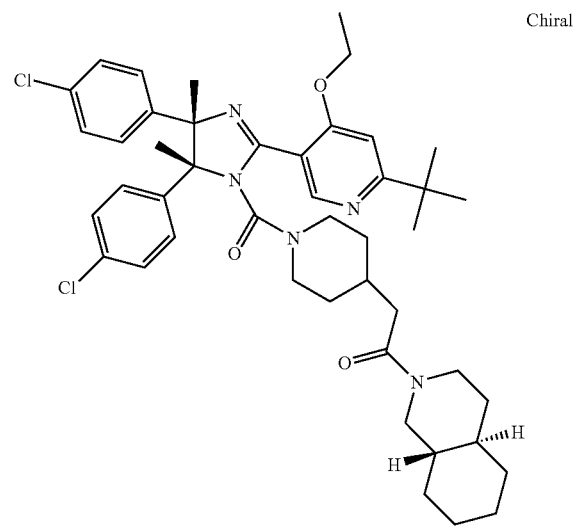 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CC[C@H]3CCCC[C@@H]3C2)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with trans-decahydroisoquinoline (TCI-US) to give the title product. LC-MS (ES⁺) 786 [(M+H)⁺].

EXAMPLE 322

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-isopropyl-phenyl)-acetamide

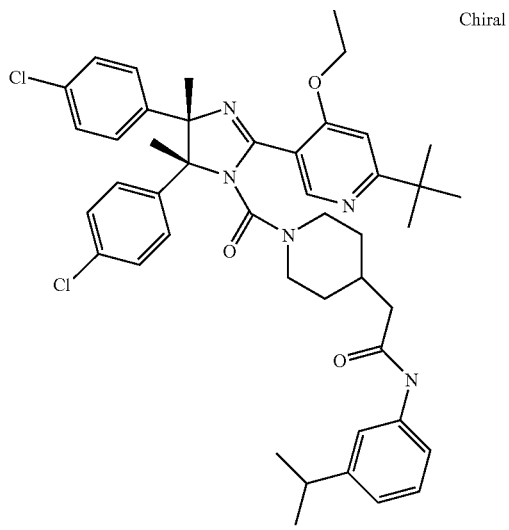 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)Nc2cccc(C(C)C)c2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 3-isopropylaniline (Aldrich) to give the title product. LC-MS (ES⁺) 782 [(M+H)⁺].

EXAMPLE 323

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-butyl-phenyl)-acetamide

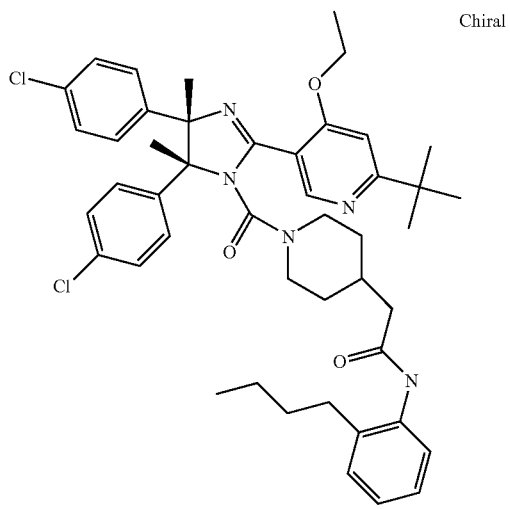 [SMILES: CCCCc1ccccc1NC(=O)CC1CCN(C(=O)N2C(c3cnc(C(C)(C)C)cc3OCC)=N[C@@](C)(c3ccc(Cl)cc3)[C@@]2(C)c2ccc(Cl)cc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 2-n-butylaniline (Aldrich) to give the title product. LC-MS (ES⁺) 796 [(M+H)⁺].

EXAMPLE 324

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(5,6,7,8-tetrahydro-naphthalen-2-yl)-acetamide

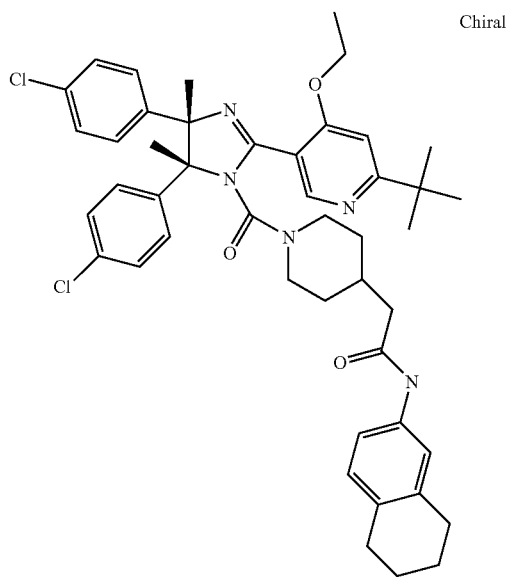 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)Nc2ccc3c(c2)CCCC3)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 5,6,7,8-tetrahydronaphthylene-2-amine (Aldrich) to give the title product. LC-MS (ES⁺) 794 [(M+H)⁺].

EXAMPLE 325

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((R)-1-p-tolyl-ethyl)-acetamide

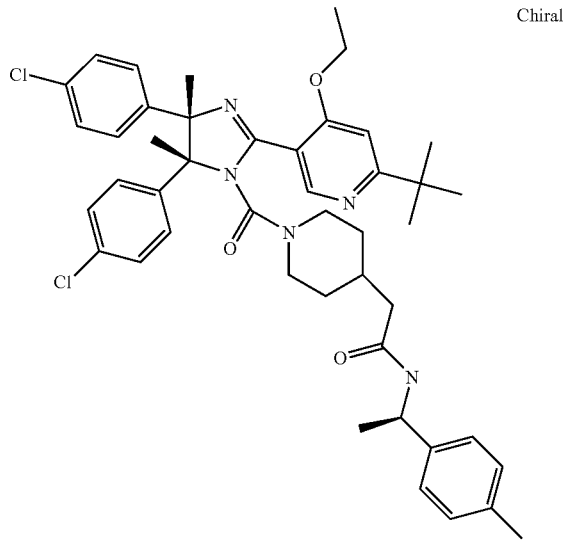 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N[C@H](C)c2ccc(C)cc2)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with (R)-(+)-1-(4-methylphenyl)ethylamine (Lancaster) to give the title product. LC-MS (ES⁺) 782 [(M+H)⁺].

EXAMPLE 326

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-isopropyl-piperazin-1-yl)-ethanone

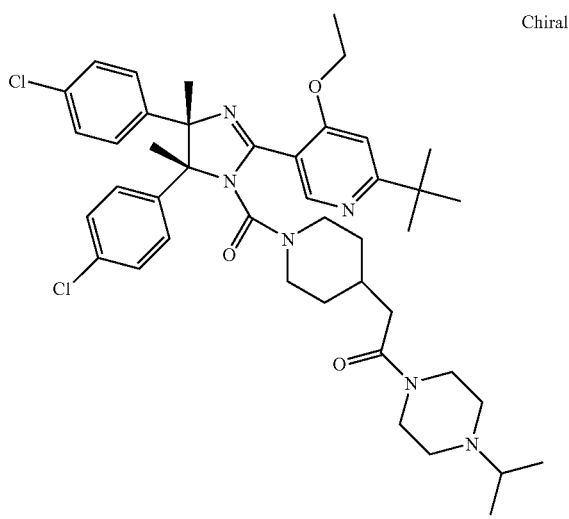 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCN(C(C)C)CC2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 1-isopropylpiperazine (Oakwood) to give the title product. LC-MS (ES⁺) 775 [(M+H)⁺].

EXAMPLE 327

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(hexahydro-cyclopenta[c]pyrrol-2-yl)-ethanone

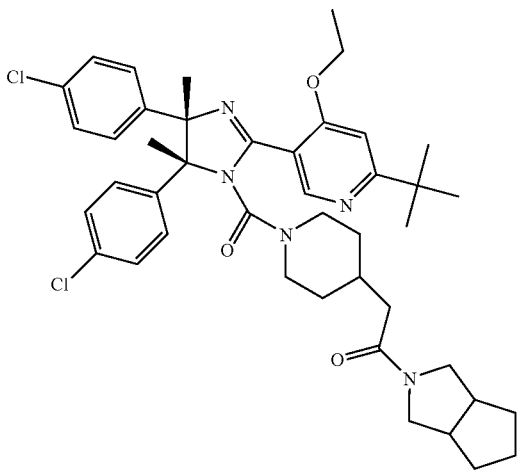 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CC3CCCC3C2)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with 3,4-(1,3-propanediyl)pyrrolidine (BetaPharm) to give the title product. LC-MS (ES⁺) 758 [(M+H)⁺].

EXAMPLE 328

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((R)-1,2-dimethyl-propyl)-acetamide

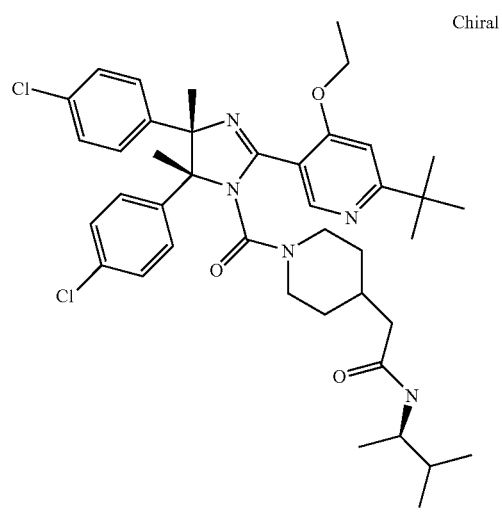 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N[C@H](C)C(C)C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with (R)-(−)-3-methyl-2-butylamine (Fluka) to give the title product. LC-MS (ES⁺) 734 [(M+H)⁺].

EXAMPLE 329

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-fluoro-3-methyl-benzyl)-acetamide

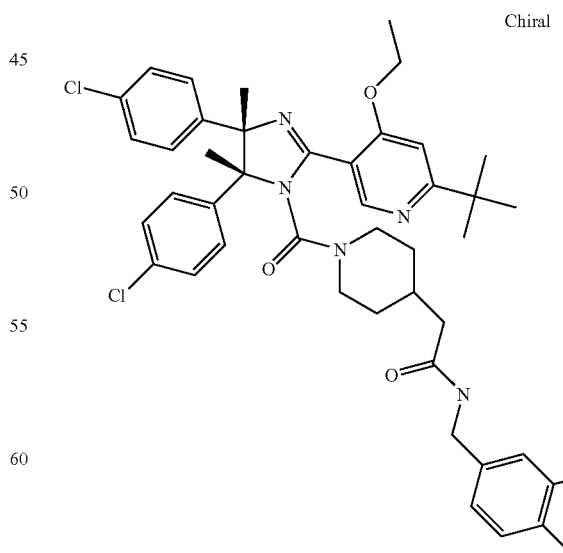

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with 4-fluoro-3-methylbenzylamine (Matrix) to give the title product. LC-MS (ES+) 786 [(M+H)+].

EXAMPLE 330

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-methoxy-phenyl)-N-methyl-acetamide

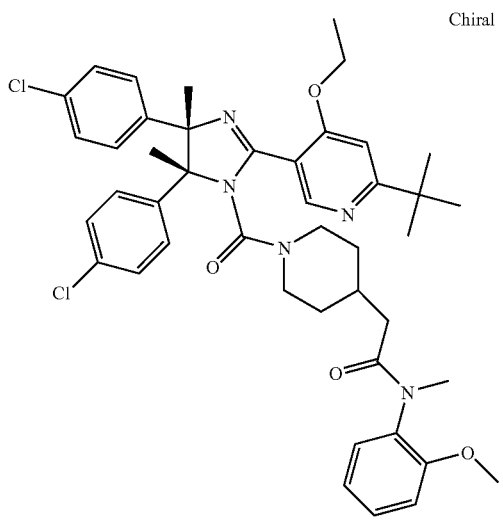 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)c2ccccc2OC)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 2-methoxy-n-methylaniline (Aldrich) to give the title product. LC-MS (ES+) 784 [(M+H)+].

EXAMPLE 331

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(3,3-dimethyl-piperidin-1-yl)-ethanone

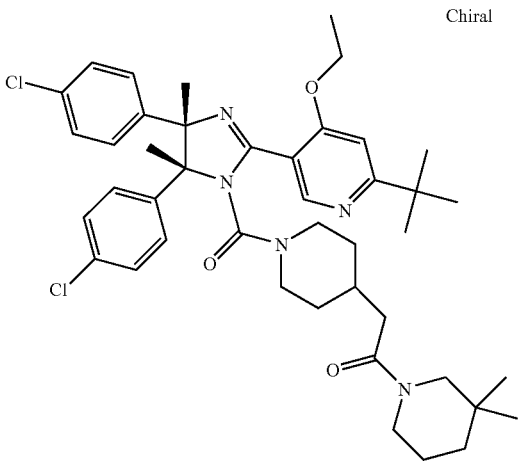 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCCC(C)(C)C2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 3,3-dimethylpiperidine (Chmsrv-As) to give the title product. LC-MS (ES+) 760 [(M+H)+].

EXAMPLE 332

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(1-ethyl-propyl)-acetamide

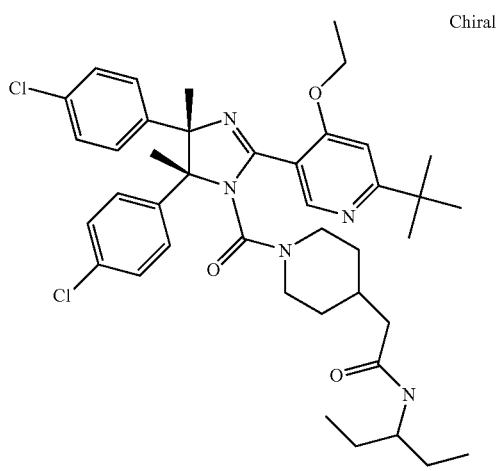 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NC(CC)CC)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 3-aminopentane (Alfa) to give the title product. LC-MS (ES+) 734 [(M+H)+].

EXAMPLE 333

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-di-isobutyl-acetamide

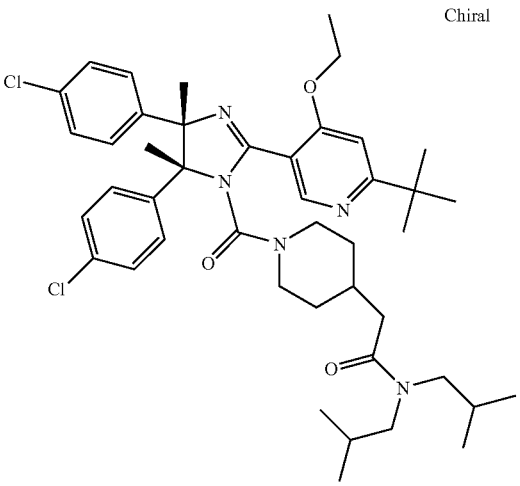 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(CC(C)C)CC(C)C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with diisobutylamine (Alfa) to give the title product. LC-MS (ES+) 776 [(M+H)+].

EXAMPLE 334

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-m-tolyl-acetamide

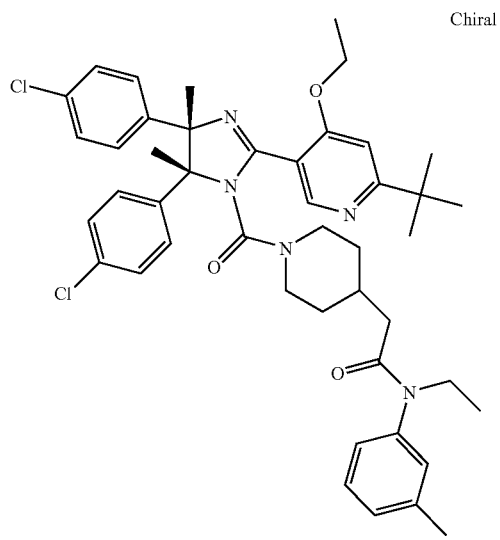 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(CC)c2cccc(C)c2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with n-ethyl-m-toluidine(VWR) to give the title product. LC-MS (ES+) 782 [(M+H)+].

EXAMPLE 335

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-isobutyl-N-methyl-acetamide

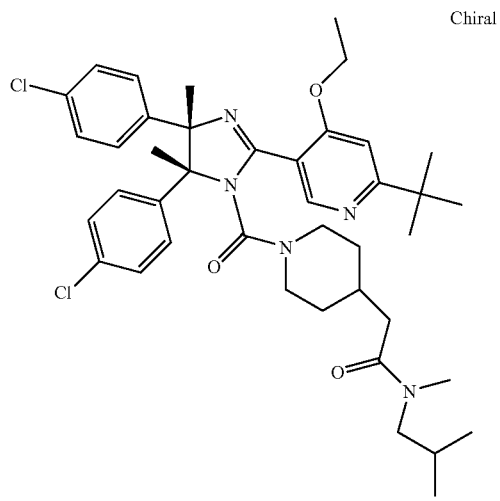 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)CC(C)C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with n-methyl-isobutylamine(VWR) to give the title product. LC-MS (ES+) 734 [(M+H)+].

EXAMPLE 336

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cyclopentyl-N-methyl-acetamide

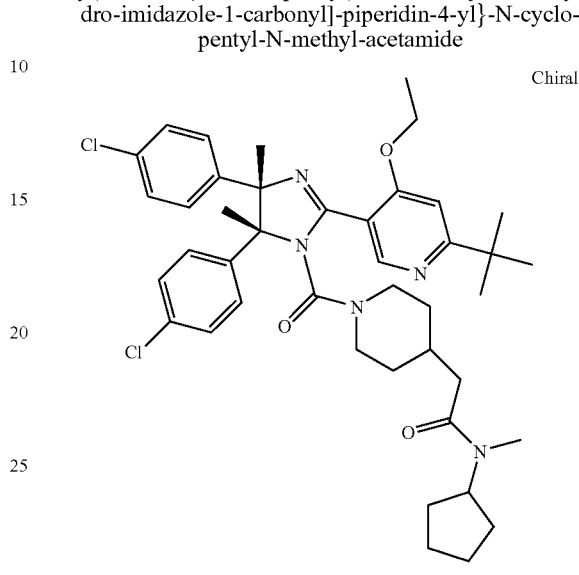

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with cyclopentyl-methyl-amine (Oakwood) to give the title product. LC-MS (ES+) 746 [(M+H)+].

EXAMPLE 337

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-p-tolyl-acetamide

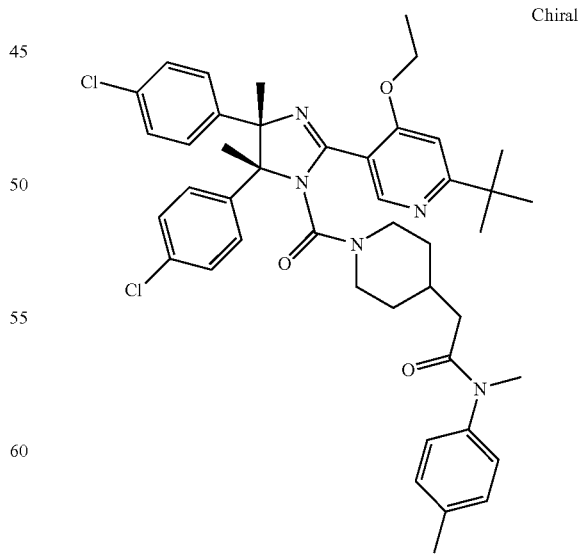

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with n-methyl-p-toluidine (Oakwood) to give the title product. LC-MS (ES$^+$) 768 [(M+H)$^+$].

EXAMPLE 338

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-p-tolyl-acetamide

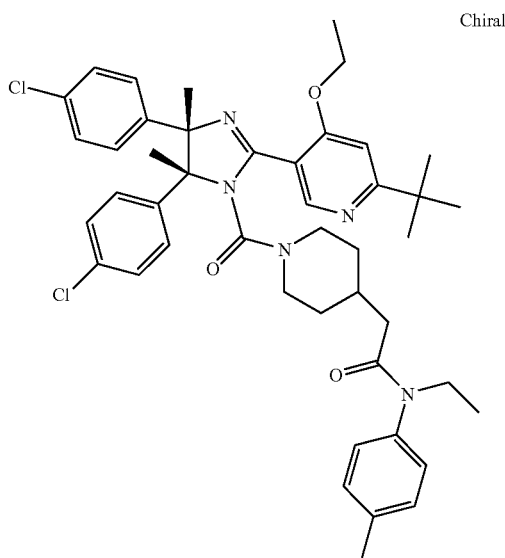 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(CC)c2ccc(C)cc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with n-ethyl-p-toluidine (VWR) to give the title product. LC-MS (ES$^+$) 782 [(M+H)$^+$].

EXAMPLE 339

N-((R)-sec-Butyl)-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide

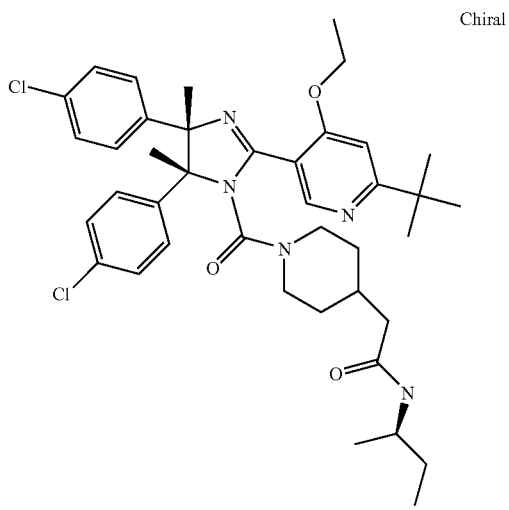 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N[C@H](C)CC)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with (R)-(-)-2-aminobutane (Alfa) to give the title product. LC-MS (ES$^+$) 720 [(M+H)$^+$].

EXAMPLE 340

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((S)-2-methyl-butyl)-acetamide

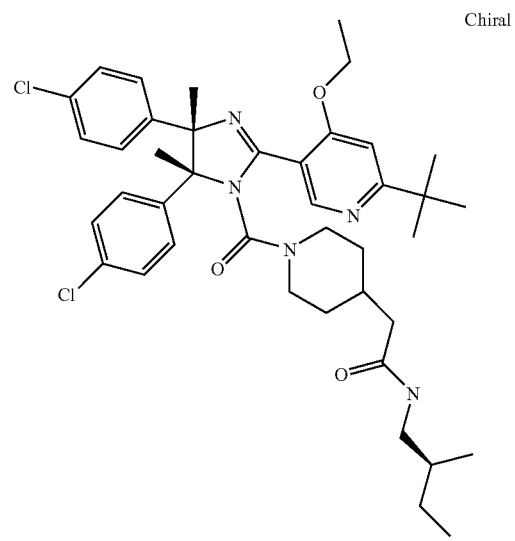 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NC[C@@H](C)CC)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with (S)-(–)-2-methylbutylamine (Alfa) to give the title product. LC-MS (ES$^+$) 734 [(M+H)$^+$].

EXAMPLE 341

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((R)-1-phenyl-propyl)-acetamide

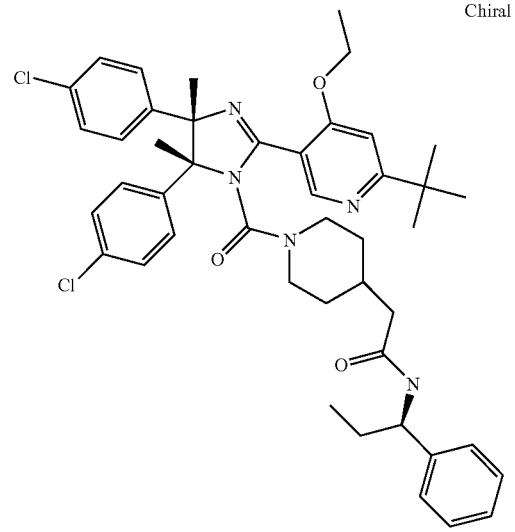 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N[C@H](CC)c2ccccc2)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with (R)-(+)-1-phenylpropylamine (Alfa) to give the title product. LC-MS (ES+) 782 [(M+H)+].

EXAMPLE 342

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((S)-1-methyl-pentyl)-acetamide

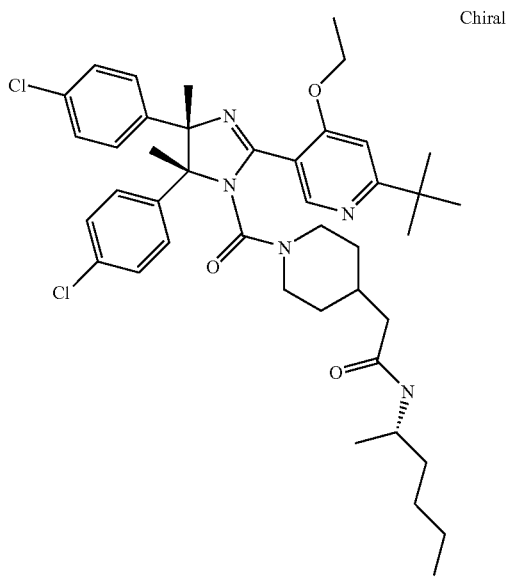 [SMILES: CCCC[C@H](C)NC(=O)CC1CCN(C(=O)N2C(c3cnc(C(C)(C)C)cc3OCC)=N[C@@](C)(c3ccc(Cl)cc3)[C@@]2(C)c2ccc(Cl)cc2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with (R)-(+)-2-aminohexane (Alfa) to give the title product. LC-MS (ES+) 748 [(M+H)+].

EXAMPLE 343

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((R)-1,2,2-trimethyl-propyl)-acetamide

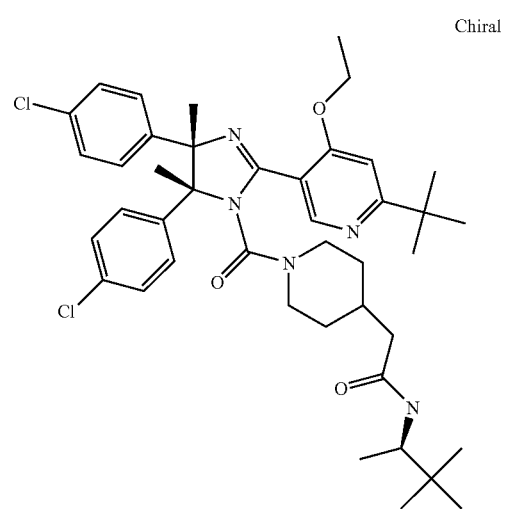 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N[C@H](C)C(C)(C)C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with (R)-(-)-3,3-dimethyl-2-butylamine (Aldrich) to give the title product. LC-MS (ES+) 748 [(M+H)+].

EXAMPLE 344

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-o-tolyl-ethyl)-acetamide

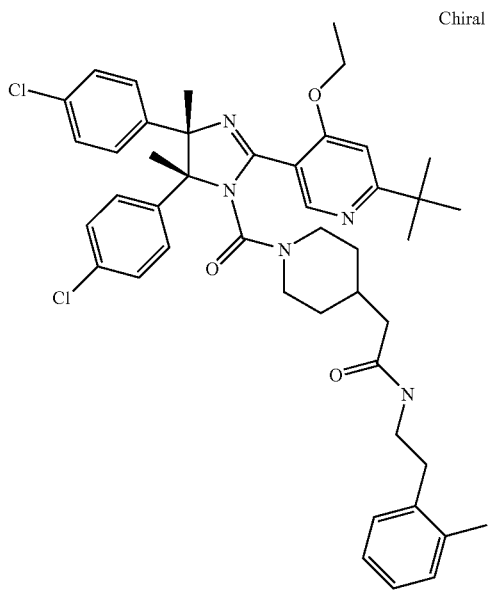 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCCc2ccccc2C)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 2-methyl-phenethylamine (Oakwood) to give the title product. LC-MS (ES+) 782 [(M+H)+].

EXAMPLE 345

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-((S)-2-methyl-piperidin-1-yl)-ethanone

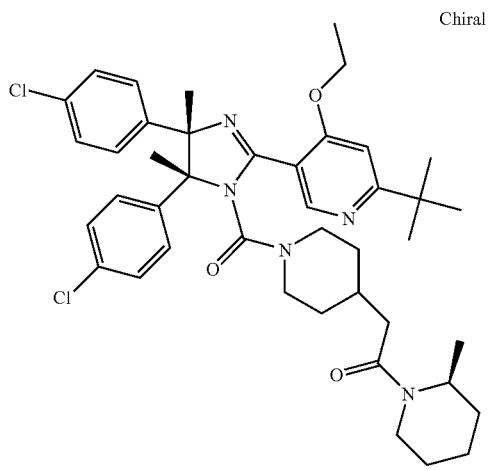 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N2CCCC[C@@H]2C)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with (S)-(+)-2-methylpiperidine (Aldrich) to give the title product. LC-MS (ES$^+$) 746 [(M+H)$^+$].

EXAMPLE 346

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[(R)-1-(4-fluoro-phenyl)-ethyl]-acetamide

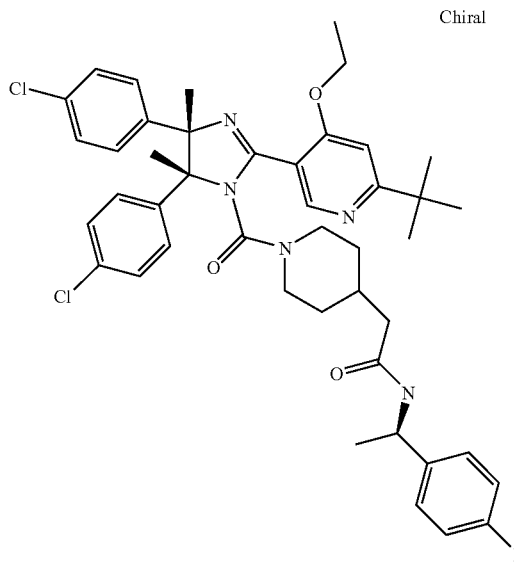

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with (R)-1-(4-fluorophenyl)ethylamine (Alfa) to give the title product. LC-MS (ES$^+$) 786 [(M+H)$^+$].

EXAMPLE 347

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-fluoro-benzyl)-N-methyl-acetamide

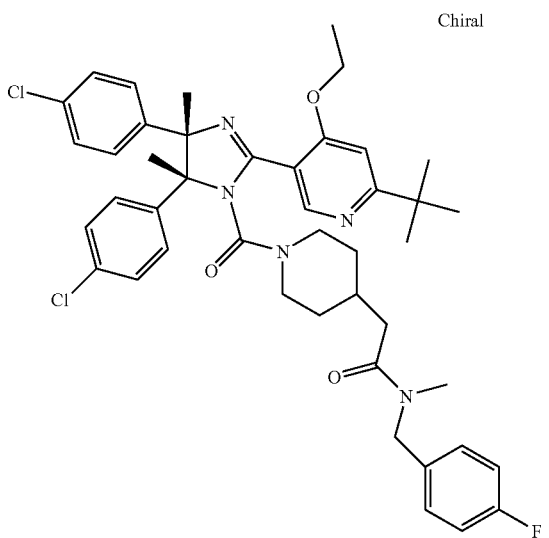 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)Cc2ccc(F)cc2)CC1]

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with 4-fluoro-n-methyl benzylamine (Aldrich) to give the title product. LC-MS (ES$^+$) 786 [(M+H)$^+$].

EXAMPLE 348

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-benzyl)-N-methyl-acetamide

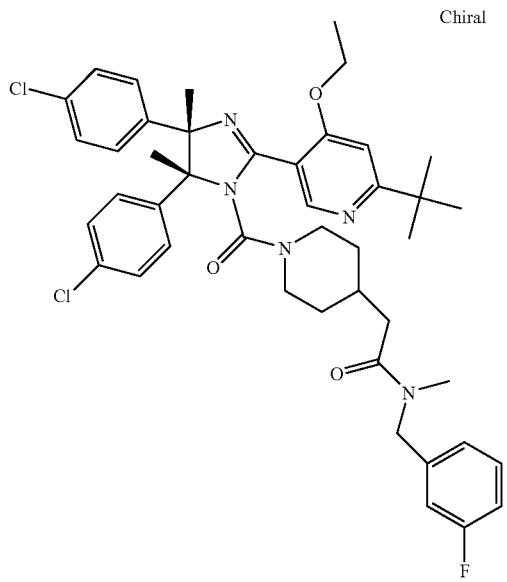 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)N(C)Cc2cccc(F)c2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with (3-fluorobenzyl)methylamine (Aldrich) to give the title product. LC-MS (ES$^+$) 786 [(M+H)$^+$].

EXAMPLE 349

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-(3-methyl-benzyl)-acetamide

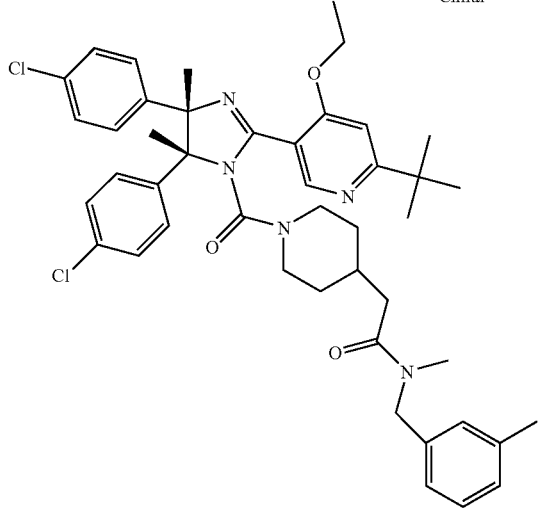

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with (3-methylbenzyl)-methylamine (Aldrich) to give the title product. LC-MS (ES⁺) 782 [(M+H)⁺].

EXAMPLE 350

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-fluoro-4-methyl-benzyl)-acetamide

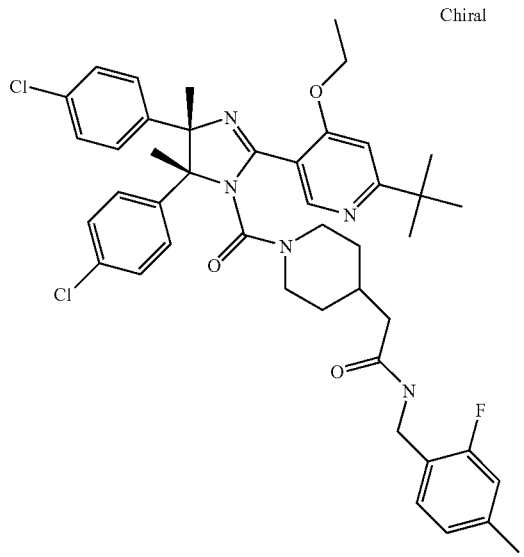 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCc2ccc(C)cc2F)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 2-fluoro-4-methylbenzylamine (Jrd-Fluoro) to give the title product. LC-MS (ES⁺) 786 [(M+H)⁺].

EXAMPLE 351

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-5-methyl-benzyl)-acetamide

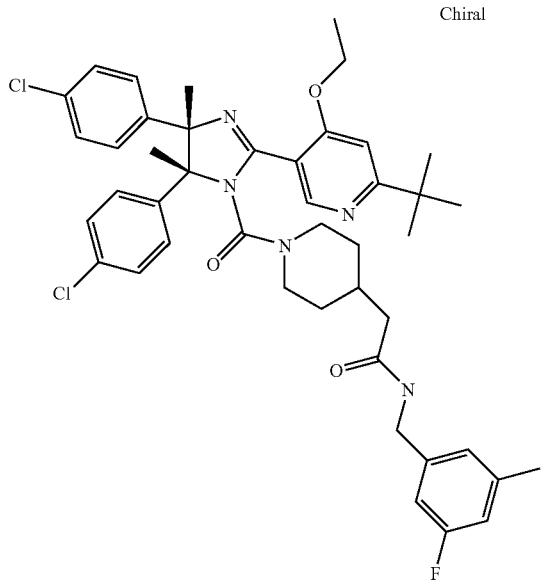 [SMILES: CCOc1cc(C(C)(C)C)ncc1C1=N[C@@](C)(c2ccc(Cl)cc2)[C@@](C)(c2ccc(Cl)cc2)N1C(=O)N1CCC(CC(=O)NCc2cc(C)cc(F)c2)CC1]

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 3-fluoro-5-methylbenzylamine (Jrd-Fluoro) to give the title product. LC-MS (ES⁺) 786 [(M+H)⁺].

EXAMPLE 352

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-ethoxymethyl-piperidin-1-yl)-ethanone

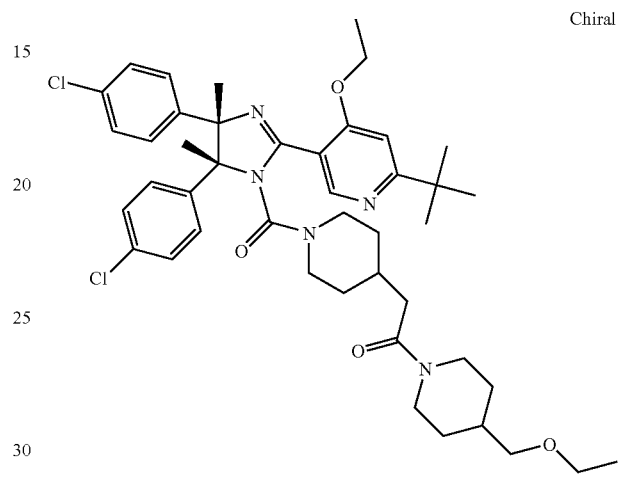

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 4-(ethoxymethyl)-piperidine (VWR) to give the title product. LC-MS (ES⁺) 790 [(M+H)⁺].

EXAMPLE 353

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-ethoxy-piperidin-1-yl)-ethanone

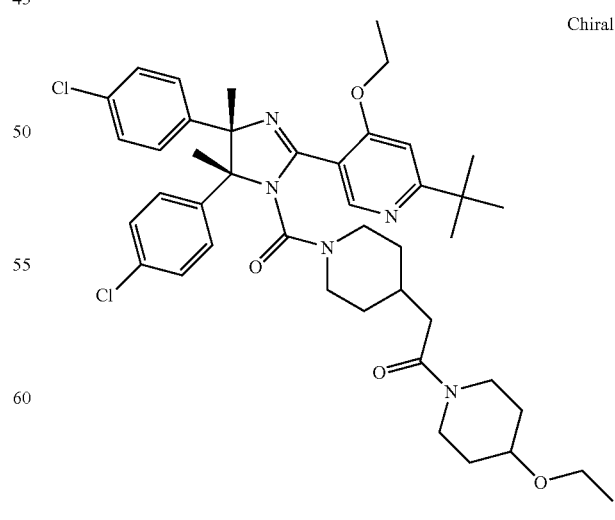

In a manner analogous to the method described in example 163, {1-[(4S,5R)-2-(6-tert-butyl-4-ethoxy-pyridin-3-yl)-4, 5-bis-(4-chloro-phenyl)-4,5-dimethyl-4,5-dihydro-imidazole-1-carbonyl]-piperidin-4-yl}-acetic acid was reacted with 4-ethoxypiperidine (VWR) to give the title product. LC-MS (ES⁺) 776 [(M+H)⁺].

EXAMPLE 354

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-methoxymethyl-piperidin-1-yl)-ethanone

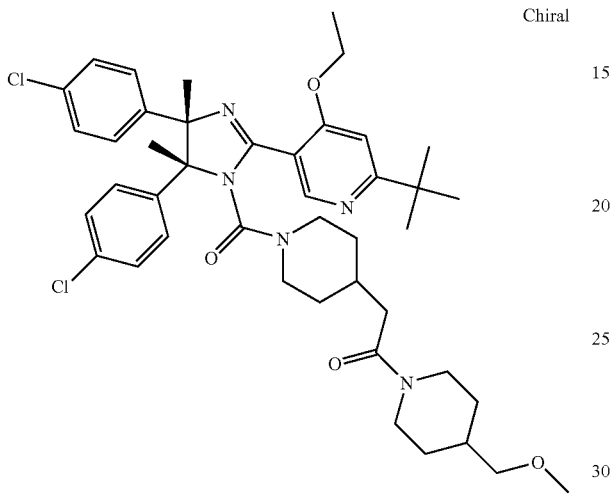

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 4-(methoxymethyl)piperidine (Alfa) to give the title product. LC-MS (ES⁺) 776 [(M+H)⁺].

EXAMPLE 355

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-(tetrahydro-pyran-4-yl)-acetamide

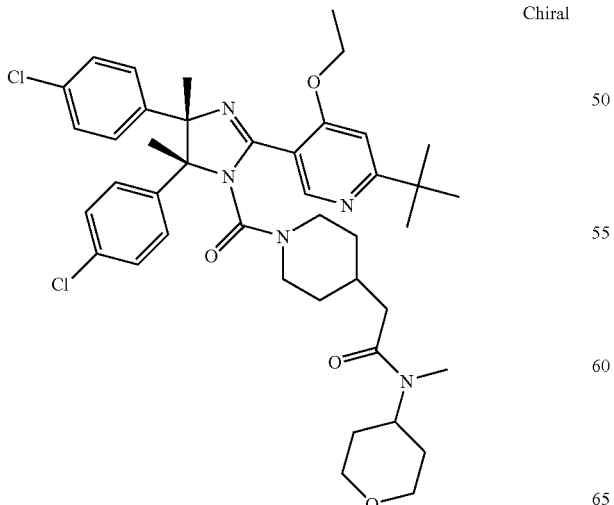

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with n-methyl-n-tetrahydro-2h-pyran-4-ylamine (Chem-Impex) to give the title product. LC-MS (ES⁺) 762 [(M+H)⁺].

EXAMPLE 356

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[(S)-1-(3-fluoro-phenyl)-ethyl]-acetamide

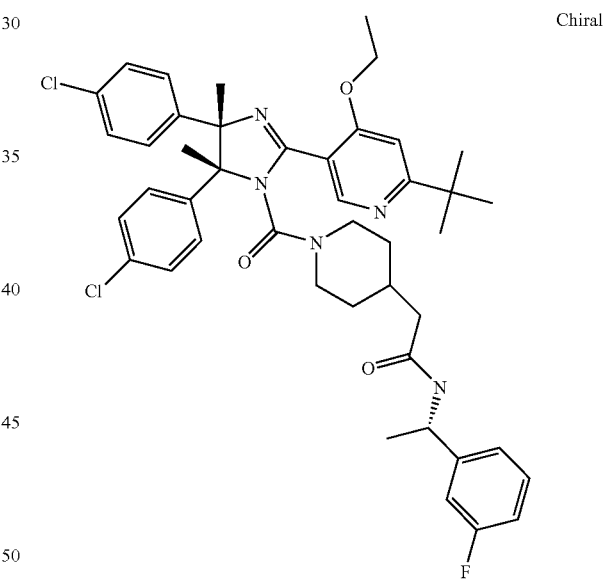

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with (S)-1-(3-fluorophenyl)ethylamine (Synquest) to give the title product. LC-MS (ES⁺) 786 [(M+H)⁺].

EXAMPLE 357

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(3-pyrrolidin-1-yl-azetidin-1-yl)-ethanone

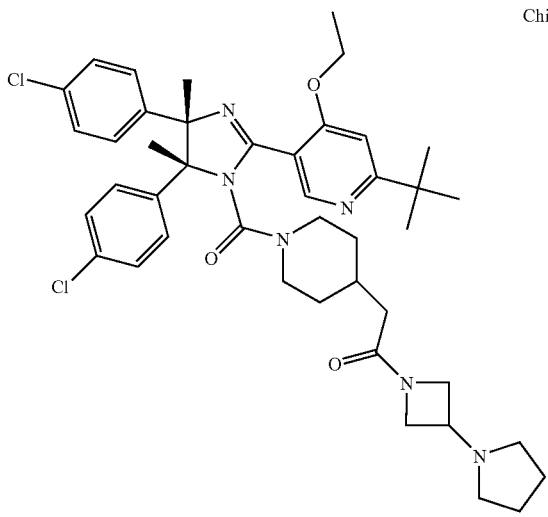

In a manner analogous to the method described in example 163, {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid was reacted with 1-azetidin-3-ylpyrrolidine (VWR) to give the title product. LC-MS (ES⁺) 773 [(M+H)⁺].

EXAMPLE 358

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

$IC_{50}$s showing biological activity that applies to compounds of the subject matter of this invention ranges from about 0.005 uM to about 2 uM. Specific data for some examples are as follows:

| Example No. | $IC_{50}$ 0.2% BSA μM |
|---|---|
| 4 | 0.046 |
| 9 | 0.178 |
| 22 | 0.031 |
| 29 | 0.252 |
| 40 | 0.077 |

What is claimed:
1. A compound of the formula

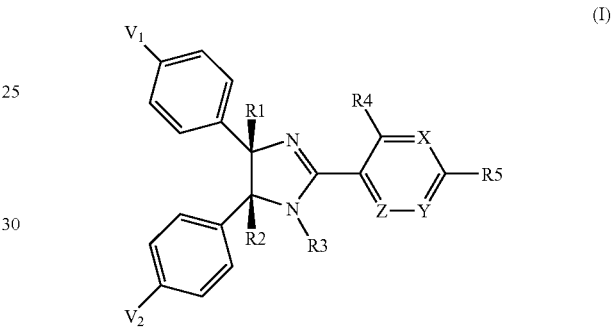

wherein X and Z are carbon;
Y is nitrogen;
$V_1$ and $V_2$ are selected from the group consisting of halogen, acetylene, cyano, trifluoromethyl and nitro;
$R^1$ and $R^2$ are H or $CH_3$,
with the proviso that $R^1$ and $R^2$ are not both H;
$R^3$ is H or —C(═O)—$R^6$;
$R^4$ is —$OCH_3$, —$OCH_2CH_3$, —$OCH_2CH_2F$, —$OCH_2CH_2OCH_3$, or —$OCH(CH_3)_2$;
$R^5$ is selected from the group consisting of:
i)—H
ii)-halogen,
iii)—$CH_3$,
iv)—$CF_3$,
v)—$OCH_3$ or —$COCH_2CH_3$,
vi)—$C(CH_3)_2$,
vii)-cyano,
viii)—$C(CH_3)_3$,
ix)—$C(CH_3)_2$ OR (where R is H, $CH_3$ or $CH_2CH_3$),
x)—$C(CH_3)_2$ CH—OR (where R is H, $CH_3$, $CH_2CH_2OH$ or $CH_2CH_2OCH_3$),
xi)—$C(CH_3)_2CN$,
xii)—$C(CH_3)_2COR$ (where R is $CH_3$),
xiii)—$C(CH_3)_2COOR$ (where R is H, $CH_3$, or $CH_2CH_3$),
xiv)—$C(CH_3)_2CONR^aR^b$ (where $R^a$ is H or $CH_3$ and $R^b$ is H or $CH_3$),
xv)—$SCH_3$ or —$SO_2CH_3$,
xvi)—$NR^aR^b$ (where $R^a$ is H or $CH_3$ and $R^b$ is H or $CH_3$), and
xvii)-4-morpholinyl;
and $R^6$ is selected from the group consisting of:
i)-lower alkyl, ii)-cyclopropyl or cyclobutyl,
iii)-phenyl or phenyl substituted by chloro, OCH₃ or cyano,
iv)-4-morpholinyl, 1-(3-oxopiperazinyl), 1-piperidinyl, 4-thiomorpholinyl, 4-thiomorpholinyl-1,1-dioxide or 1-(1,4-diazepinyl-5-oxo),
v)—NR$^c$₂ (wherein R$^c$ is hydrogen, —CH₃, —CH₂CH₃, —CH₂CH₂OH, —CH₂CH₂OCH₃ or —CH₂CH(OH)CH₂OH),
vi)-a substituted piperazine of the formula:

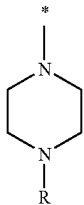

wherein R is selected from the group consisting of:
a) hydrogen,
b) lower alkyl,
c) —CH₂CH(OH)CH₂OH, —CH₂CH₂CH(OH)CH₂OH or 4-tetrahydro-2H-thiopyranyl-1,1-dioxide,
d) —CH₂CH₂R$^d$ (wherein R$^d$ is —OH, —OCH₃, —OCH₂CH₂OH, —OCH₂CH₂OCH₃, —CN, —CF₃, —SO₂CH₃, —SO₂NH₂, —SO₂N(CH₃)₂, —CONH₂, —CON(CH₃)₂, —NH₂, —NHCOCH₃, —NHSO₂CH₃, —N(CH₃)₂, 1-pyrrolidinyl, 1-piperidinyl or 4-morpholinyl),
e) —CH₂CH₂CH₂R$^e$ (wherein R$^e$ is —OH, —OCH₃, —SO₂CH₃, —SO₂CH₂CH₃, —SO₂N(CH₃)₂, —CN, —N(CH₃)₂, 1-pyrrolidinyl, 1-piperidinyl, 4-morpholinyl, —COOCH₃, —COOCH₂CH₃, —COOC(CH₃)₃, —CON(CH₃)₂, —CO—R$^f$ (wherein R$^f$ is CH₃, CH₂CH₃, cyclopropyl, phenyl, 2-thienyl, 3-thienyl, 2-furanyl or 3-furanyl), —COCH₂—R$^g$ (wherein R$^g$ is H, —NHCH₂CH₂OH, —NHCH₂CH₂OCH₃, —NHCH₂CH₂N(CH₃)₂, 1-piperidinyl, 1-(piperidinyl-4-methanol), 4-morpholinyl or —N(CH₃)-(3-(1-methylpyrrolidinyl))),
f) —CH₂—CO—R$^h$ (wherein R$^h$ is substituted or unsubstituted lower alkyl, —OH, —OCH₃, —OCH₂CH₃, —NH₂, —(CH₂)$_n$ substituted or unsubstituted heteroaryl where n is 0 or 1, —NH cycloalkyl, —N (lower alkyl)$_n$ where n is 1 or 2, —NHCH₂C(OH)CH₂OH,—NHCH₂CF₃, —NHCH₂CH₂CH₂OH, —N(CH₂CH₂OH)₂, —N(CH₂CH₂OCH₃)₂, —N(CH₃)CH₂CH₂OH, —NH(CH₂OH)(CH₃) CH₂CH₂OH, —NH(CH₂OH)(CH₃)CH₃,—CH₂CH₂CH₂SO₂NH₂, —N(CH₂CH₃)heteroaryl, —N(CH₃)CH₂CH₂OCH₃, —NHCH₂CH₂OCH₃, —NH(CH₂)$_n$ mono- or di- substituted heteroaryl where n is 0 or 1, —NHCH₂CH₂ substituted or unsubstituted heteroaryl, —NH mono- or di-substituted aryl, —NH(CH₂)$_n$ heterocycle where n is 0 or 1, —NH(CH₂)$_n$—OH where n is 2 or 3,
—(CH₂)$_n$substituted or unsubstituted heterocycle where n is 1 or 2 or —N(CH₂CH₃)mono- or di- substituted heteroaryl,
g) —SO₂R$^i$ (wherein R$^i$ is —CH₃, —CH₂CH₃, —CH(CH₃)₂, phenyl, 4-methylphenyl, 4-propylphenyl, CF₃, 2-thienyl, 3-thienyl, NH₂, NHCH₃, N(CH₃)₂, NHCH₂CH₂OCH₃, N(CH₂CH₂OCH₃)₂, 1-pyrrolidinyl, 1-piperidinyl, 4-morpholinyl, 1-piperazyl-4-ethanol, 1-(4-acetylpiperazinyl) or 1-(3-oxopiperazinyl)),
h) —COR$^j$ (wherein R$^j$ is lower alkyl, cycloalkyl, 2-tetrahydrofuranyl, 2-thienyl, 3-thienyl, NH₂, NHCH₃, N(CH₃)₂, 1-pyrrolidinyl, 1-piperidinyl, 4-morpholinyl, 1-piperazinyl-4-ethanol, 1-(4-acetylpiperazinyl) or 1-(3-oxopiperazinyl)), and
i) substituted or unsubstituted heteroaryl or heterocycle;
vii)-a substituted piperidine of the formula:

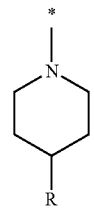

wherein R is hydrogen, lower alkyl, —CH₂CH(OH)CH₂OH, —CH₂CH₂CH(OH)CH₂OH or 4-tetrahydro-2H-thiopyranyl-1,1-dioxide,
—CH₂CH₂R$^d$ (wherein R$^d$ is —OH, —OCH₃, —OCH₂CH₂OH, —OCH₂CH₂OCH₃, —CN, —CF₃, —SO₂CH₃, —SO₂NH₂, —SO₂N(CH₃)₂, —CONH₂, —CON(CH₃)₂, —NH₂, —NHCOCH₃, —NHSO₂CH₃, —N(CH₃)₂, 1-pyrrolidinyl, 1-piperidinyl or 4-morpholinyl),
—CH₂CH₂CH₂R$^e$ (wherein R$^e$ is —OH, —OCH₃, —SO₂CH₃, —SO₂CH₂CH₃, —SO₂N(CH₃)₂, —CN, —N(CH₃)₂, 1-pyrrolidinyl, 1-piperidinyl, 4-morpholinyl, —COOCH₃, —COOCH₂CH₃, —COOC(CH₃)₃, —CON(CH₃)₂, —CO—R$^f$ (wherein R$^f$ is CH₃, CH₂CH₃, cyclopropyl, phenyl, 2-thienyl, 3-thienyl, 2-furanyl or 3-furanyl), —COCH₂—R$^g$ (wherein R$^g$ is H, —NHCH₂CH₂OH, —NHCH₂CH₂OCH₃, —NHCH₂CH₂N(CH₃)₂, 1-piperidinyl, 1-(piperidinyl-4-methanol), 4-morpholinyl or —N(CH₃)-(3-(1-methylpyrrolidinyl))),
—CH₂—CO—R$^h$ (wherein R$^h$ is substituted or unsubstituted lower alkyl, —OH, —OCH₃, —OCH₂CH₃, —NH₂, —(CH₂)$_n$ heteroaryl where n is 0 or 1 —NH lower alkyl, —NH cycloalkyl, —N (lower alkyl)$_n$ where n is 1 or 2, —NHCH₂C(OH)CH₂OH, —NHCH₂CF₃, —NHCH₂CH₂CH₂OH, —N(CH₂CH₂OH)₂, —N(CH₂CH₂OCH₃)₂, —N(CH₃)CH₂CH₂OH, —NH(CH₂OH)(CH₃) CH₂CH₂OH, —NH(CH₂OH)(CH₃)CH₃,—CH₂CH₂CH₂SO₂NH₂, —N(CH₂CH₃)heteroaryl, —N(CH₃)CH₂CH₂OCH₃, —NHCH₂CH₂OCH₃, —NH(CH₂)$_n$ mono- or di- substituted heteroaryl where n is 0 or 1, —NHCH₂CH₂ substituted or unsubstituted heteroaryl, —NH mono- or di- substituted aryl, —NH(CH₂)$_n$ heterocycle where n is 0 or 1, —NH(CH₂)$_n$—OH where n is 2 or 3, substituted or unsubstituted heterocycle or —N(CH₂CH₃) mono- or di- substituted heteroaryl,
—SO₂R$^i$ (wherein R$^i$ is —CH₃, —CH₂CH₃, —CH(CH₃)₂, phenyl, 4-methylphenyl, 4-propylphenyl, CF₃, 2-thienyl, 3-thienyl, NH₂, NHCH₃, N(CH₃)₂, NHCH₂CH₂OCH₃, N(CH₂CH₂OCH₃)₂, 1-pyrrolidinyl, 1-piperidinyl, 4-morpholinyl, 1-piperazyl-4-ethanol, 1-(4-acetylpiperazinyl) or 1-(3-oxopiperazinyl)),
—COR$^j$ (wherein R$^j$ is lower alkyl, cycloalkyl, 2-tetrahydrofuranyl, 2-thienyl, 3-thienyl, NH₂, NHCH₃, N(CH₃)

$_2$, 1-pyrrolidinyl, 1-piperidinyl, 4-morpholinyl, 1-piperazinyl-4-ethanol, 1-(4-acetylpiperazinyl) or 1-(3-oxopiperazinyl)), substituted or unsubstituted heteroaryl or heterocycle, NH$_2$, NHCOCH$_3$, NHCOCH$_2$NH$_2$, NHCOCH$_2$NHCH$_3$, NHCOCH$_2$N(CH$_3$)$_2$, NHCOCH$_2$N(CH$_2$CH$_2$OH)$_2$, NHCOCH$_2$N(CH$_2$CH$_2$OCH$_3$)$_2$, NHCOCH$_2$NHCH$_2$CH$_2$OH, NHCOCH$_2$-(1-(4-acetylpiperazinyl)), NHCOCH$_2$-(1-(3-oxopiperazinyl)), NHCOCH$_2$-NHCONHCH$_3$, NHCOO lower alkyl, NHCHCH$_3$, NHCO lower alkyl, NH(CH$_2$)n SO$_2$CH$_3$ where n is 0-2, NH(CH$_3$)SO$_2$CH$_3$,(1-piperidinecarboxamide), NHCOCH$_2$-(N,N-diethyl-1-piperidinylcarboxamide), NHCOCH$_2$-(1-(3-hydroxypiperidinyl)), NHCOCH$_2$-(1-(piperidinyl-4-methanol)), NHCON(CH$_3$)$_2$, NHCSNHCH$_3$, NHCSNHPh, NHCH$_2$CONH$_2$ or —NHCH$_2$CH$_2$SO$_2$CH$_3$ and viii)-a substituted piperidine of the formula:

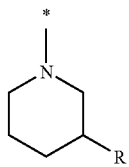

wherein R is —OH, CH$_2$OH, CH$_2$CH$_2$OH, or C(O)NH$_2$ and the pharmaceutically acceptable salts and esters thereof.

2. The compound of claim 1 wherein V$_1$ and V$_2$ are chloro.

3. The compound of claim of claim 2 wherein R$^3$ is —C(═O)—R$^6$ and R$^6$ is selected from the group consisting of i)-lower alkyl, ii)-cyclopropyl, cyclobutyl, iii)-phenyl or phenyl substituted by chloro, OCH$_3$ or cyano, iv)-4-morpholinyl, 1-(3-oxopiperazinyl), 1-piperidinyl, 4-thiomorpholinyl, or 4-thiomorpholinyl-1,1-dioxide, 1-(1,4-diazepinyl-5-oxo), v)—NR$^c_2$ (wherein R$^c$ is hydrogen, —CH$_3$, —CH$_2$CH$_3$, —CH$_2$CH$_2$OH, —CH$_2$CH$_2$OCH$_3$, or —CH$_2$CH(OH)CH$_2$OH), vi)-a substituted piperazine of the formula:

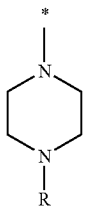

wherein R is selected from the group consisting of:

a) hydrogen, b) lower alkyl, c) —CH$_2$CH(OH)CH$_2$OH, —CH$_2$CH$_2$CH(OH)CH$_2$OH or 4-tetrahydro-2H-thiopyranyl-1,1-dioxide, d) —CH$_2$CH$_2$R$^d$ (wherein R$^d$ is —OH, —OCH$_3$, —OCH$_2$CH$_2$OH, —OCH$_2$CH$_2$OCH$_3$, —CN, —CF$_3$, —SO$_2$CH$_3$, —SO$_2$NH$_2$, —SO$_2$N(CH$_3$)$_2$, —CONH$_2$, —CON(CH$_3$)$_2$, —NH$_2$, —NHCOCH$_3$, —NHSO$_2$CH$_3$, —N(CH$_3$)$_2$, 1-pyrrolidinyl, 1-piperidinyl , or 4-morpholinyl), e)—CH$_2$CH$_2$CH$_2$R$^e$(wherein R$^e$ is —OH, —OCH$_3$, —SO$_2$CH$_3$, —SO$_2$CH$_2$CH$_3$, —SO$_2$N(CH$_3$)$_2$, —CN, —N(CH$_3$)$_2$, 1-pyrrolidinyl, 1-piperidinyl, 4-morpholinyl, —COOCH$_3$, —COOCH$_2$CH$_3$, —COOC(CH$_3$)$_3$, —CON(CH$_3$)$_2$, —CO—R$^f$ (wherein R$^f$ is CH$_3$, CH$_2$CH$_3$, cyclopropyl, phenyl, 2-thienyl, 3-thienyl, 2-furanyl, 3-furanyl), —COCH$_2$—R$^g$ (wherein R$^g$ is H, —NHCH$_2$CH$_2$OH, —NHCH$_2$CH$_2$OCH$_3$, —NHCH$_2$CH$_2$N(CH$_3$)$_2$, 1-piperidinyl, 1-(piperidinyl-4-methanol), 4-morpholinyl or —N(CH$_3$)-(3-(1-methylpyrrolidinyl)), f)—CH$_2$—CO—R$^h$ (wherein R$^h$ is —OCH$_3$, OCH$_2$CH$_3$, —NH$_2$, —NHCH$_2$CH(CH$_3$)$_2$, —NHCH$_2$CF$_3$, —NH-cyclopropyl, —NH-tert-butyl, —NHCH$_2$CH$_2$OH, —N(CH$_3$)$_2$, —N(CH$_2$CH$_3$)$_2$, —N(CH$_2$CH$_2$OH)$_2$, —N(CH$_2$CH$_2$OCH$_3$)$_2$, —N(CH$_3$)CH$_2$CH$_2$OH, —N(CH$_3$)CH$_2$CH$_2$OCH$_3$, —NHCH$_2$CH$_2$OCH$_3$, 1-pyrrolidinyl, 1-piperidinyl, 1-(piperidinyl-4-methanol), 1-(piperidinyl-3-carboxamide), 4-morpholinyl, 4-thiomorpholinyl, 4-thiomorpholinyl-1,1-dioxide, 1-piperazinyl, 1-(4-acetylpiperazinyl) or 1-(3-oxopiperazinyl), g)—SO$_2$R$^i$ (wherein R$^i$ is —CH$_3$, —CH$_2$CH$_3$, —CH(CH$_3$)$_2$, phenyl, 4-methylphenyl, 4-propylphenyl, CF$_3$, 2-thienyl, 3-thienyl, NH$_2$, NHCH$_3$, N(CH$_3$)$_2$, NHCH$_2$CH$_2$OCH$_3$, N(CH$_2$CH$_2$OCH$_3$)$_2$, 1-pyrrolidinyl, 1-piperidinyl, 4-morpholinyl, 1-piperazyl-4-ethanol, 1-(4-acetylpiperazinyl) or 1-(3-oxopiperazinyl)), h)—COR$^j$ (wherein R$^j$ is —CH$_3$, —CH$_2$CH$_3$, —CH(CH$_3$)$_2$, 2-tetrahydrofuranyl, 2-thienyl, 3-thienyl, NH$_2$, NHCH$_3$, N(CH$_3$)$_2$, 1-pyrrolidinyl, 1-piperidinyl, 4-morpholinyl, 1-piperazinyl-4-ethanol, 1-(4-acetylpiperazinyl) or 1-(3-oxopiperazinyl)), and i) 4-tetrahydro-2H-thiopyranyl-1,1-dioxide, 4-piperidinyl-1-acetyl, 4-piperidinyl-1-dimethylcarboxamide, or 3-tetrahydro-thiophenyl-1,1-dioxide;

vii)-a substituted piperidine of the formula:

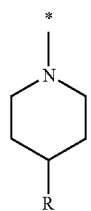

wherein R is H, COOCH$_3$, COOCH$_2$CH$_3$, CONH$_2$, —OH, CH$_2$OH, CH$_2$CH$_2$OH, CH$_2$—N(CH$_2$CH$_3$)$_2$, —CH$_2$-(1-piperazinyl), CH$_2$-(1-(3-oxopiperazinyl)), NH$_2$, NHCOCH$_3$, NHCOCH$_2$NH$_2$, NHCOCH$_2$NHCH$_3$, NHCOCH$_2$N(CH$_3$)$_2$, NHCOCH$_2$N(CH$_2$CH$_2$OH)$_2$, NHCOCH$_2$N(CH$_2$CH$_2$OCH$_3$)$_2$, NHCOCH$_2$NHCH$_2$CH$_2$OH, NHCOCH$_2$-(1-(4-acetylpiperazinyl)), NHCOCH$_2$-(1-(3-oxopiperazinyl)), NHCOCH$_2$-(1-piperidinecarboxamide), NHCOCH$_2$-(N,N-diethyl-1-piperidinylcarboxamide), NHCOCH$_2$-(1-(3-hydroxypiperidinyl)), NHCOCH$_2$-(1-(piperidinyl-4-methanol)), NHCON(CH$_3$)$_2$, NHCSNHCH$_3$, NHCSNHPh, NHCH$_2$CONH$_2$, 1-pyrrolidinyl, 1-piperidinyl, 1-(4-methylpiperazinyl), 4-morpholinyl, 1-(1,4-diazepinyl-5-oxo) or 4-hydroxypiperidine, and viii)-a substituted piperidine of the formula:

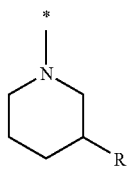

wherein R is —OH, CH₂OH, CH₂CH₂OH, or C(O)NH₂.

4. The compound of claim 3 wherein R⁴ is —OCH₃, —OCH₂CH₃, or —OCH(CH₃)₂ and R⁵ is —C(CH₃)₃, —C(CH₃)₂ or (where R is H or CH₃), —C(CH₃)₂ CH—OR (where R is H or CH₃), —C(CH₃)₂CN or —C(CH₃)₂COCH₃.

5. The compound of claim 4 wherein R⁶ is a substituted piperazine of the formula:

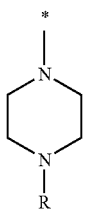

wherein R is —CH₂COR^h.

6. The compound of claim 5 wherein R^h is 4-morpholinyl, 1-pyrrolidinyl, 1-piperidinyl, NH₂ or N(CH₃)₂.

7. The compound of claim 4 wherein R⁶ is a substituted piperazine of the formula:

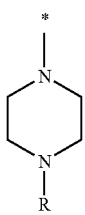

wherein R is —CH₂CH₂R^d.

8. The compound of claim 7 wherein R^d is —SO₂CH₃, —NHSO₂CH₃, —NHCOCH₃ or CF₃.

9. The compound of claim 4 wherein R⁶ is a substituted piperazine of the formula:

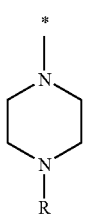

wherein R is —CH₂CH₂CH₂R^e.

10. The compound of claim 9 wherein R^e is —SO₂CH₃ or —SO₂CH₂CH₃.

11. The compound of claim 4 wherein R⁶ is a substituted piperidine of the formula

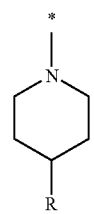

wherein R is 4-tetrahydro-2H-thiopyranyl-1,1-dioxide,1-(1,4-diazepinyl-5-oxo) or —CH₂COR^h where R^h is NH₂.

12. A compound of claim 1 selected from the group consisting of
[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3-methanesulfonyl-propyl)-piperazin-1-yl]-methanone,
2-{4-[(4S,5R)-2-(6-tert-Butyl-4-ethoxy-pyridin-3-yl)-4,5-bis-(4-chloro-phenyl)-4,5-dimethyl-4,5dihydro-imidazole-1-carbonyl]-peperazin-1-yl}-acetamide,
rac-[(4S*,5R*)-2-(6-tert-Butyl-4-ethoxy-pyridin-3yl)-4,5-bis-(4-chloro-phenyl)-4,5-dimethyl-4,5-dihydro-imidazol-1-yl]-[4-((S)-2,3-dihydroxy-propyl)-piperazin-1yl]-methanone,
[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3-methanesulfonyl-propyl)-piperidin-1-yl]-methanone, 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2-(4-methyl-tiazol-2-yl)-ethanone,
9[(4S,5R)-2-(6-tert-Butyl-4-ethoxy-pyridin-3-yl)-4,5-bis-(4-chloro-phenyl)-4,5dimethyl-4,5-dihydro-imidazole-1-carbonyl]-3,9-diaza-spiro[5,5]undecane-3-carboxylic acid tert-butyl ester,
[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3,9-diaza-spiro[5,5]undec-3yl)-methanone,
2-{9-[(4S,5R)-2-(6-tert-Butyl-4-ehtoxy-pyridin-3-yl)-4,5-bis-(4-chloro-phenyl)-4,5-dimethyl-4,5-dihydro-imidazole-1-carbonyl]-3,9-diaza-spiro[5,5]undec-3-yl}-acetamide,
[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(1,1-dioxo-tetrahydro-1λ6-thiophen-3-yl)-piperazin-1-yl]-methanone,
[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-ethanesulfonyl-piperazin-1-yl)-methanone,
[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-hydroxy-ethyl)-piperidin-1-yl]-methanone,
[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-pyrrolidin-1-yl-piperidin-1-yl)-methanone,
[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4isopropyl-piperazin-1-yl)-methanone and
[1,4']Bipiperidinyl-1'-yl-[(4S,5R)-2-(6-tert-butyl-4ethoxy-pyridin-3-yl)-4,5-bis-(4-chloro-phenyl)-4,5-dimethyl-4,5-dihydro-imidazol-1-yl]-methanone.

13. A compound of claim 1 selected from the group consisting of
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-methanesulfonylmethyl-piperidin-1-yl)-methanone,
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methanesulfonyl-ethyl)-piperidin-1-yl]-methanone,
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(1,1-dioxo-hexahydro-1$\lambda^6$-thiopyran-4-yl)-piperazin-1-yl]-methanone,
- 3-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-propane-1-sulfonic acid amide,
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methanesulfonyl-ethyl)-piperazin-1-yl]-methanone,
- 4-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-butyronitrile,
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3,3,3-trifluoro-propyl)-piperazin-1-yl]-methanone,
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3-ethanesulfonyl-propyl)-piperazin-1-yl]-methanone
- -(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}ethyl)-acetamide and
- 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2-(thiazol-2-ylamino)-ethanone.

14. A compound of claim 1 selected from the group consisting of
- 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2-methyl-propan-1-one,
- 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2,2-dimethyl-propan-1-one,
- 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-methoxy-ethyl)-acetamide,
- 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-cyclopropyl-acetamide,
- (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid dimethylamide,
- 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-2-tetrazol-1-yl-ethanone,
- 3-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-propionamide,
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl[-]4-(1-methyl-1H-pyrrole-2-carbonyl)-piperazin-1-yl]-methanone,
- 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-cyclopropyl-propionamide and
- 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(tetrahydro-furan-2-ylmethyl)-acetamide.

15. A compound of claim 1 selected from the group consisting of
- 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-ethanone,
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-dimethylamino-piperidin-1-yl)-methanone,
- {4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetic acid hydrochloride,
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(tetrahydro-furan-2-carbonyl)-piperazin-1-yl]-methanone,
- 4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazine-1-carboxylic acid dimethylamide,
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3-methoxy-propyl)-piperazin-1-yl]-methanone,
- 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-(1,1-dioxo-1$\lambda$6-thiomorpholin-4-yl)-ethanone,
- 4-(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetyl)-piperazin-2-one,
- 1-(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetyl)-[1,4]diazepan-5-one,
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-hydroxy-piperidin-1-yl)-methanone and
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3-hydroxy-piperidin-1-yl)-methanone.

16. A compound of claim 1 selected from the group consisting of
- [(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-hydroxymethyl-piperidin-1-yl)-methanone,
- 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-pyrrolidin-1-yl-ethanone, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-[1,4]diazepan-5-one,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-((R)-3-methyl-piperazin-1-yl)-methanone, -{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2,3-dihydroxy-propyl)-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-isopropyl-N-methyl-acetamide, N-tert-Butyl-2-{4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-acetamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-methanesulfonyl-piperazin-1-yl)-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-{4-[2-(2-hydroxy-ethoxy)-ethyl]-piperazin-1-yl}-methanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-(4-methyl-piperazin-1-yl)-ethanone and 4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(4-cyclopropanecarbonyl-piperazin-1-yl)-methanone.

17. A compound of claim 1 selected from the group consisting of

4-[4-(2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-acetyl)-piperazin-1-yl]-benzonitrile, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-hydroxy-1,1-dimethyl-ethyl)-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-hydroxy-1-hydroxymethyl-1-methyl-ethyl)-acetamide, 4-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-piperazin-2-one, 4-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-methyl-piperazin-2-one,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(3,4-dihydroxy-butyl)-piperazin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(1,1-dioxo-1λ6-thiomorpholin-4-yl)-methanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-piperidin-1-yl-ethanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(2-hydroxy-ethyl)-acetamide and 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-[1,4]dioxan-2-ylmethyl-acetamide.

18. A compound of claim 1 selected from the group consisting of

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3-hydroxy-pyrrolidin-1-yl)-methanone, {(S)-1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-pyrrolidin-3-yl}-carbamic acid tert-butyl ester, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-thiazol-5-yl-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-3-yl-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-phenyl-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-4-yl-acetamide, (3-Amino-pyrrolidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone, N-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-pyrrolidin-3-yl}-oxalamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(2,3,4,5-tetrahydro-benzo[b][1,4]diazepin-1-yl)-methanone 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-(3-hydroxy-azetidin-1-yl)-ethanone and 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-(tetrahydro-pyran-4-yl)-acetamide.

19. A compound of claim 1 selected from the group consisting of (1S,5R)-3-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-3-aza-bicyclo[3.1.0]hexane-6-carboxylic acid ethyl ester, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N,N-bis-(2-methoxy-ethyl)-acetamide, 1-Azetidin-1-yl-2-{4-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperazin-1-yl}-ethanone, 2-{4-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperazin-1-yl}-N,N-bis-(2-hy-
droxy-ethyl)-acetamide,
2-{4-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperazin-1-yl}-N-[2-(4-methoxy-
phenyl)-ethyl]-acetamide,
2-{4-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperazin-1-yl}-N-[2-(2-methoxy-
phenyl)-ethyl]-acetamide,
[(4S,5R)-2-(6-tert-Butyl-4-ethoxy-pyridin-3-yl)-4,5-bis-
(4-chloro-phenyl)-4,5-dimethyl-4,5-dihydro-imidazol-
1-yl]-(7,8-dimethoxy-1,2,3,5-tetrahydro-benzo[e][1,4]
diazepin-4-yl)-methanone,
[(4S,5R)-2-(6-tert-butyl-4-ethoxy-pyridin-3-yl)-4,5-bis-
(4-chloro-phenyl)-4,5-dimethyl-4,5-dihydro-imidazol-
1-yl]-(7,8-dimethoxy-2,3,4,5-tetrahydro-benzo[e][1,4]
diazepin-1-yl)-methanone,
[(4S,5R)-2-(6-tert-Butyl-4-ethoxy-pyridin-3-yl)-4,5-bis-
(4-chloro-phenyl)-4,5-dimethyl-4,5-dihydro-imidazol-
1-yl]-[(1S,5R)-6-(3-hydroxy-azetidine-1-carbonyl)-3-
aza-bicyclo[3.1.0]hex-3-yl]-methanone,
(1S,5R)-3-[(4S,5R)-2-(6-tert-Butyl-4-ethoxy-pyridin-3-
yl)-4,5-bis-(4-chloro-phenyl)-4,5-dimethyl-4,5-dihy-
dro-imidazole-1-carbonyl]-3-aza-bicyclo[3.1.0]hex-
ane-6-carboxylic acid (2-hydroxy-ethyl)-amide and
[(4S,5R)-2-(6-tert-Butyl-4-ethoxy-pyridin-3-yl)-4,5-bis-
(4-chloro-phenyl)-4,5-dimethyl-4,5-dihydro-imidazol-
1-yl]-[(1S,5R)-6-(3-hydroxy-pyrrolidine-1-carbonyl)-
3-aza-bicyclo[3.1.0]hex-3-yl]-methanone.

20. A compound of claim 1 selected from the group consisting of
[(4S,5R)-2-(6-tert-Butyl-4-ethoxy-pyridin-3-yl)-4,5-bis-
(4-chloro-phenyl)-4,5-dimethyl-4,5-dihydro-imidazol-
1-yl]-(4-methyl-[1,4]diazepan-1-yl)-methanone,
2-{4-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-[1,4]diazepan-1-yl}-acetamide,
4-(2-{4-[(4S,5R)-2-(6-tert-Butyl-4-ethoxy-pyridin-3-yl)-
4,5-bis-(4-chloro-phenyl)-4,5-dimethyl-4,5-dihydro-
imidazole-1-carbonyl]-[1,4]diazepan-1-yl}-acetyl)-
piperazin-2-one,
2-{4-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperazin-1-yl}-N-(6-methoxy-2-
methyl-pyridin-3-yl)-acetamide,
2-{4-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperazin-1-yl}-N-(2-methyl-pyri-
din-3-yl)-acetamide,
2-{4-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperazin-1-yl}-N-(2-methoxy-py-
ridin-3-yl)-acetamide,
2-{4-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperazin-1-yl}-N-ethyl-N-pyri-
din-3-yl-acetamide,
2-{4-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperazin-1-yl}-N-(2,6-dimethyl-
pyridin-3-yl)-acetamide,
(S)-4-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperazine-2-carboxylic acid tert-
butylamide,
[(4S,5R)-2-(6-tert-Butyl-4-ethoxy-pyridin-3-yl)-4,5-bis-
(4-chloro-phenyl)-4,5-dimethyl-4,5-dihydro-imidazol-
1-yl]-[4-(4-methyl-piperazin-1-yl)-piperidin-1-yl]-
methanone,
[(4S,5R)-2-(6-tert-Butyl-4-ethoxy-pyridin-3-yl)-4,5-bis-
(4-chloro-phenyl)-4,5-dimethyl-4,5-dihydro-imidazol-
1-yl]-(4-morpholin-4-yl-piperidin-1-yl)-methanone
and
N-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-acetamide.

21. A compound of claim 1 selected from the group consisting of
[(4S,5R)-2-(6-tert-Butyl-4-ethoxy-pyridin-3-yl)-4,5-bis-
(4-chloro-phenyl)-4,5-dimethyl-4,5-dihydro-imidazol-
1-yl]-(4-methyl-[1,4']bipiperidinyl-1'-yl)-methanone,
[(4S,5R)-2-(6-tert-Butyl-4-ethoxy-pyridin-3-yl)-4,5-bis-
(4-chloro-phenyl)-4,5-dimethyl-4,5-dihydro-imidazol-
1-yl]-[4-(4-ethyl-piperazin-1-yl)-piperidin-1-yl]-
methanone,
N-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-methyl-meth-
anesulfonamide,
N-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-methanesulfona-
mide,
[(4S,5R)-2-(6-tert-Butyl-4-ethoxy-pyridin-3-yl)-4,5-bis-
(4-chloro-phenyl)-4,5-dimethyl-4,5-dihydro-imidazol-
1-yl]-[4-(2-methanesulfonyl-ethylamino)-piperidin-1-
yl]-methanone,
{1-[(4S,5R)-2-(6-tert-Butyl-4-ethoxy-pyridin-3-yl)-4,5-
bis-(4-chloro-phenyl)-4,5-dimethyl-4,5-dihydro-imi-
dazole-1-carbonyl]-piperidin-4-yl}-acetic acid methyl
ester,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-1-pyrrolidin-1-yl-
ethanone,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N,N-dimethyl-ac-
etamide,
[(4S,5R)-2-(6-tert-Butyl-4-ethoxy-pyridin-3-yl)-4,5-bis-
(4-chloro-phenyl)-4,5-dimethyl-4,5-dihydro-imidazol-
1-yl]-(4-diethylamino-piperidin-1-yl)-methanone,
[(4S,5R)-2-(6-tert-Butyl-4-ethoxy-pyridin-3-yl)-4,5-bis-
(4-chloro-phenyl)-4,5-dimethyl-4,5-dihydro-imidazol-
1-yl]-{4-[(2-methanesulfonyl-ethyl)-methyl-amino]-
piperidin-1-yl}-methanone and
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(2-hydroxy-
ethyl)-acetamide.

22. A compound of claim 1 selected from the group consisting of
1-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-3-methyl-urea,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(pyrrolidine-1-carbonyl)-piperidin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(piperazine-1-carbonyl)-piperidin-1-yl]-methanone, 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-3-methylsulfanyl-propan-1-one, 1-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-3-methanesulfonyl-propan-1-one, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid (2-methanesulfonyl-ethyl)-amide, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid (2-methanesulfonyl-ethyl)-methyl-amide, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid (2-hydroxy-ethyl)-amide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(1,1-dioxo-1λ6-thiomorpholine-4-carbonyl)-piperidin-1-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[4-(2-methanesulfonyl-ethoxy)-piperidin-1-yl]-methanone and rac-4-[(4S*,5R*)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-2-one.

23. A compound of claim 1 selected from the group consisting of rac-[(4S*,5R*)-2-(6-tert-Butyl-4-ethoxy-pyridin-3-yl)-4,5-bis-(4-chloro-phenyl)-4,5-dimethyl-4,5-dihydro-imidazol-1-yl]-[4-(morpholine-4-carbonyl)-piperazin-1-yl]-methanone, 4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-2-one, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide, rac-1-{1-[(4S*,5R*)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-[1,4]diazepan-5-one, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-[1,4]diazepan-5-one, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-2-yl-acetamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-piperazin-1-yl-methanone, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid ((S)-3,4-dihydroxy-butyl)-amide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3,6-dihydro-2H-pyridin-1-yl)-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-(3,4-dihydroxy-piperidin-1-yl)-methanone, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid methyl-((2S,3R,4R,5R)-2,3,4,5,6-pentahydroxy-hexyl)-amide and 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-2-ylmethyl-acetamide.

24. A compound of claim 1 selected from the group consisting of

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-3-ylmethyl-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-pyridin-4-ylmethyl-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N-furan-2-ylmethyl-acetamide, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-acetic acid, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-pyridin-2-ylmethyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-pyridin-3-yl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-methyl-piperazin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-bis-(2-methoxy-ethyl)-acetamide, 4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazine-1-sulfonic acid dimethylamide, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid (2-hydroxy-ethyl)-amide and (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid (2-hydroxy-ethyl)-methyl-amide.

25. A compound of claim 1 selected from the group consisting of (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid bis-(2-methoxy-ethyl)-amide, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-carbamic acid tert-butyl ester, (4-Amino-piperidin-1-yl)-[(4S,5R)-2-(6-tert-butyl-4-ethoxy-pyridin-3-yl)-4,5-bis-(4-chloro-phenyl)-4,5-dimethyl-4,5-dihydro-imidazol-1-yl]-methanone, 4-{[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-amino}-piperidine-1-carboxylic acid tert-butyl ester, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid (1-methanesulfonyl-piperidin-4-yl)-amide, 4-{[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-amino}-piperidine-1-carboxylic acid ethylamide, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid (1-carbamoylmethyl-piperidin-4-yl)-amide, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-one, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid methyl ester, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid, 3-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yloxy}-propionamide, 3-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yloxy}-propionitrile, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-isopropyl-urea, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-pyridin-3-yl-urea and 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-acetamide.

26. A compound of claim 1 selected from the group consisting of

2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-((R)-3-methoxy-pyrrolidin-1-yl)-ethanone, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-1-((S)-3-methoxy-pyrrolidin-1-yl)-ethanone, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-ethyl-urea, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-phenyl-urea, (4-{[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-amino}-piperidin-1-yl)-acetic acid ethyl ester,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[(1S,5R)-6-((R)-3-methoxy-pyrrolidine-1-carbonyl)-3-aza-bicyclo[3.1.0]hex-3-yl]-methanone,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl]-[(1S,5R)-6-((S)-3-methoxy-pyrrolidine-1-carbonyl)-3-aza-bicyclo[3.1.0]hex-3-yl]-methanone, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid [1-(2-methanesulfonyl-ethyl)-piperidin-4-yl]-amide 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-cyclopentyl-urea, {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-acetic acid ethyl ester, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-pyridin-4-yl-urea, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-N-(2-hydroxy-ethyl)-acetamide and {1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-acetic acid.

27. A compound of claim 1 selected from the group consisting of

Pyrrolidine-1-carboxylic acid {1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-amide, 3-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1,1-dimethyl-urea, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-bis-(3-methoxy-propyl)-acetamide, 3-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-propionic acid, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-bis-(2-ethoxy-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-bis-(2-isopropoxy-ethyl)-acetamide, (4S,5R)-2-(6-tert-Butyl-4-ethoxy-pyridin-3-yl)-4,5-bis-(4-chloro-phenyl)-4,5-dimethyl-4,5-dihydro-imidazole-1-carboxylic acid [(2R,3R,4S)-3,4-dihydroxy-1-(2-hydroxy-ethyl)-pyrrolidin-2-ylmethyl]-amide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N,N-bis-(2-ethoxy-ethyl)-acetamide, 2-{4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazin-1-yl}-N,N-bis-(2-isopropoxy-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-diethyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-methyl-[1,4]diazepan-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(2-methyl-pyrrolidin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-((R)-1-phenyl-ethyl)-acetamide and 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N,N-diisopropyl-acetamide.

28. A compound of claim 1 selected from the group consisting of

N-Butyl-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cyclohexyl-N-isopropyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-chloro-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2,3-difluoro-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-fluoro-benzyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-propyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-piperidin-1-yl-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-isopropyl-N-(2-methoxy-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[2-(4-fluoro-phenyl)-ethyl]-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((S)-1-cyclohexyl-ethyl)-acetamide 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-m-tolyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-isobutyl-piperazin-1-yl)-ethanone, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(1,3-dihydro-isoindol-2-yl)-ethanone and 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[(S)-1-(2-fluoro-phenyl)-ethyl]-acetamide.

29. A compound of claim 1 selected from the group consisting of

2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-[2-(2,5-dimethyl-phenyl)-ethyl]-acetamide, N-Butyl-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-N-isopropyl-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-N-((S)-1-phenyl-ethyl)-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methoxy-acetamide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-fluoro-benzyl)-N-methyl-acetamide, 4-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperazine-1-carboxylic acid amide, 2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-ylamino}-N-(2,3-dihydroxy-propyl)-acetamide,

[(4S,5R)-2-(6-tert-Butyl-4-ethoxy-pyridin-3-yl)-4,5-bis-(4-chloro-phenyl)-4,5-dimethyl-4,5-dihydro-imidazol-1-yl[-]4-(4-methyl-piperazine-1-carbonyl)piperidin-1-yl]-methanone, 1-{1-[(4S, 5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-(1,1-dioxo-tetrahydro-1λ6-thiophen-3-yl)-urea, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid cyclopentylamide, 1-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-3-(1,1-dioxo-tetrahydro-1λ6-thiophen-3-yl)-urea, 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid cyclopentyl-methyl-amide and 1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid phenylamide.

30. A compound of claim 1 selected from the group consisting of
1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid cyclobutylamide,
1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid ([1,4]dioxan-2-ylmethyl)-amide,
1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidine-4-carboxylic acid methylamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-methoxy-phenyl)-N-methyl-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(2-trifluoromethyl-pyrrolidin-1-yl)-ethanone,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cycloheptylmethyl-acetamide,
N-But-3-enyl-2-{1-[(4S,5R)-2-(6-tert-butyl-4-ethoxy-pyridin-3-yl)-4,5-bis-(4-chloro-phenyl)-4,5-dimethyl-4,5-dihydro-imidazole-1-carbonyl]-piperidin-4-yl}-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-propyl-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-2-methyl-benzyl)-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-isopropyl-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-((S)-1-cyclopropyl-ethyl)-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-ethyl-N-methyl-acetamide and
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-propyl-N-(tetrahydro-pyran-4-yl)-acetamide.

31. A compound of claim 1 selected from the group consisting of
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-m-tolyl-ethyl)-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(4-dimethylamino-piperidin-1-yl)-ethanone,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-sec-butyl-phenyl)-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cyclohexyl-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cyclohexylmethyl-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-cycloheptyl-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-1-(3,4-dihydro-1H-isoquinolin-2-yl)-ethanone,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-fluoro-5-methyl-phenyl)-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2-chloro-5-methyl-phenyl)-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(2,5-dimethyl-phenyl)-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-phenyl)-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-2-methyl-phenyl)-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-fluoro-4-methyl-phenyl)-acetamide and
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(3-chloro-2-methyl-phenyl)-acetamide.

32. A compound of claim 1 selected from the group consisting of
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-fluoro-phenyl)-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-(4-isopropyl-phenyl)-acetamide,
2-{1-[(4S,5R)-2-(6-tert-Butyl-4-ethoxy-pyridin-3-yl)-4,5-bis-(4-chloro-phenyl)-4,5-dimethyl-4,5-dihydro-imidazole-1-carbonyl]-piperidin-4-yl}-N-methyl-acetamide, 2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(4-chloro-ben-
zyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(3-methyl-bu-
tyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-pentyl-aceta-
mide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-hexyl-aceta-
mide,
N-Benzyl-2-{1-[(4S,5R)-2-(6-tert-butyl-4-ethoxy-pyri-
din-3-yl)-4,5-bis-(4-chloro-phenyl)-4,5-dimethyl-4,5-
dihydro-imidazole-1-carbonyl]-piperidin-4-yl}-N-me-
thyl-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-methyl-N-phen-
ethyl-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-methyl-N-pro-
pyl-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N,N-dipropyl-ac-
etamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(2-propyl-phe-
nyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(2,4-difluoro-
benzyl)-acetamide and
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(2,5-difluoro-
benzyl)-acetamide.

33. A compound of claim 1 selected from the group consisting of
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-1-(6-methyl-3,4-
dihydro-2H-quinolin-1-yl)-ethanone,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-isopropyl-N-
phenyl-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(3,5-dimethyl-
benzyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-isopropyl-N-
methyl-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-methyl-N-(3-
methyl-butyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-((R)-1-phenyl-
ethyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-((S)-1-phenyl-
ethyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-[2-(3-fluoro-
phenyl)-ethyl]-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-1-(4aR,8aS)-oc-
tahydro-isoquinolin-2-yl-ethanone,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(3-isopropyl-
phenyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(2-butyl-phe-
nyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(5,6,7,8-tetrahy-
dro-naphthalen-2-yl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-((R)-1-p-tolyl-
ethyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-1-(4-isopropyl-pip-
erazin-1-yl)-ethanone and
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-1-(hexahydro-cy-
clopenta[c]pyrrol-2-yl)-ethanone.

34. A compound of claim 1 selected from the group consisting of
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-((R)-1,2-dim-
ethyl-propyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(4-fluoro-3-me-
thyl-benzyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(2-methoxy-
phenyl)-N-methyl-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-1-(3,3-dimethyl-
piperidin-1-yl)-ethanone,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(1-ethyl-pro-
pyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N,N-diisobutyl-ac-
etamide, 2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-ethyl-N-m-
tolyl-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-isobutyl-N-me-
thyl-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-cyclopentyl-N-
methyl-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-methyl-N-p-
tolyl-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-ethyl-N-p-tolyl-
acetamide,
N-((R)-sec-Butyl)-2-{1-[(4S,5R)-2-(6-tert-butyl-4-
ethoxy-pyridin-3-yl)-4,5-bis-(4-chloro-phenyl)-4,5-
dimethyl-4,5-dihydro-imidazole-1-carbonyl]-piperi-
din-4-yl}-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-((S)-2-methyl-
butyl)-acetamide and
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-((R)-1-phenyl-
propyl)-acetamide.

35. A compound of claim 1 selected from the group consisting of
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-((S)-1-methyl-
pentyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-((R)-1,2,2-trim-
ethyl-propyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(2-o-tolyl-
ethyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-1-((S)-2-methyl-
piperidin-1-yl)-ethanone,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-[(R)-1-(4-
fluoro-phenyl)-ethyl]-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(4-fluoro-ben-
zyl)-N-methyl-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(3-fluoro-ben-
zyl)-N-methyl-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-methyl-N-(3-
methyl-benzyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(2-fluoro-4-me-
thyl-benzyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-(3-fluoro-5-me-
thyl-benzyl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-1-(4-ethoxym-
ethyl-piperidin-1-yl)-ethanone,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-1-(4-ethoxy-pip-
eridin-1-yl)-ethanon,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-1-(4-methoxym-
ethyl-piperidin-1-yl)-ethanone,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-methyl-N-(tet-
rahydro-pyran-4-yl)-acetamide,
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-N-[(S)-1-(3-
fluoro-phenyl)-ethyl]-acetamide and
2-{1-[(4S,5R)-2-(6-tert-Butyl-4-ethoxy-pyridin-3-yl)-4,
5-bis-(4-chloro-phenyl)-4,5-dimethyl-4,5-dihydro-imi-
dazole-1-carbonyl]-piperidin-4-yl}-1-(3-pyrrolidin-1-
yl-azetidin-1-yl)-ethanone.

36. A pharmaceutical composition comprising a compound of the formula

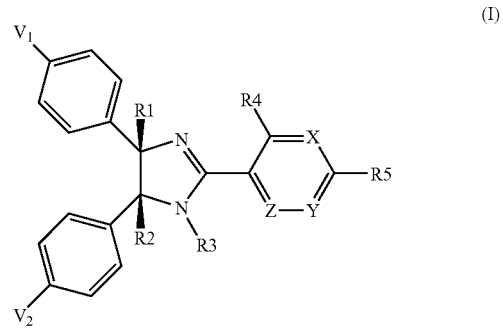

(I)

wherein X and Z are carbon;
Y is nitrogen;
$V_1$ and $V_2$ are selected from the group consisting of halogen, acetylene, cyano, trifluoromethyl and nitro;
$R^1$ and $R^2$ are H or $CH_3$,
with the proviso that $R^1$ and $R^2$ are not both H;
$R^3$ is H or —C(=O)—$R^6$;
$R^4$ is —$OCH_3$, —$OCH_2CH_3$, —$OCH_2CH_2F$, —$OCH_2CH_2OCH_3$, or —$OCH(CH_3)_2$;
$R^5$ is selected from the group consisting of:
i)—H
ii)-halogen,
iii)—$CH_3$,
iv)—$CF_3$,
v)—$OCH_3$ or —$COCH_2CH_3$,
vi)—$C(CH_3)_2$,
vii)-cyano, viii) —C(CH₃)₃,
ix) —C(CH₃)₂ OR (where R is H, CH₃ or CH₂CH₃),
x) —C(CH₃)₂ CH—OR (where R is H, CH₃, CH₂CH₂OH or CH₂CH₂OCH₃),
xi) —C(CH₃)₂CN,
xii) —C(CH₃)₂COR (where R is CH₃),
xiii) —C(CH₃)₂COOR (where R is H, CH₃, or CH₂CH₃),
xiv) —C(CH₃)₂CONR$^a$R$^b$ (where R$^a$ is H or CH₃ and R$^b$ is H or CH₃),
xv) —SCH₃ or —SO₂CH₃,
xvi) —NR$^a$R$^b$ (where R$^a$ is H or CH₃ and R$^b$ is H or CH₃), and
xvii)-4-morpholinyl;
and R⁶ is selected from the group consisting of:
i)-lower alkyl,
ii)-cyclopropyl or cyclobutyl,
iii)-phenyl or phenyl substituted by chloro, OCH₃ or cyano,
iv)-4-morpholinyl, 1-(3-oxopiperazinyl), 1-piperidinyl, 4-thiomorpholinyl, 4-thiomorpholinyl-1,1-dioxide or 1-(1,4-diazepinyl-5-oxo),
v) —NR$^c$₂ (wherein R$^c$ is hydrogen, —CH₃, —CH₂CH₃, —CH₂CH₂OH, —CH₂CH₂OCH₃ or —CH₂CH(OH)CH₂OH),
vi)-a substituted piperazine of the formula:

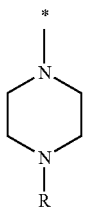

wherein R is selected from the group consisting of:
a) hydrogen,
b) lower alkyl,
c) —CH₂CH(OH)CH₂OH, —CH₂CH₂CH(OH)CH₂OH or 4-tetrahydro-2H-thiopyranyl-1,1-dioxide,
d) —CH₂CH₂R$^d$ (wherein R$^d$ is —OH, —OCH₃, —OCH₂CH₂OH, —OCH₂CH₂OCH₃, —CN, —CF₃, —SO₂CH₃, —SO₂NH₂, —SO₂N(CH₃)₂, —CONH₂, —CON(CH₃)₂, —NH₂, —NHCOCH₃, —NHSO₂CH₃, —N(CH₃)₂, 1-pyrrolidinyl, 1-piperidinyl or 4-morpholinyl),
e) —CH₂CH₂CH₂R$^e$ (wherein R$^e$ is —OH, —OCH₃, —SO₂CH₃, —SO₂CH₂CH₃, —SO₂N(CH₃)₂₃—CN, —N(CH₃)₂, 1-pyrrolidinyl, 1-piperidinyl, 4-morpholinyl, —COOCH₃, —COOCH₂CH₃, —COOC(CH₃)₃, —CON(CH₃)₂, —CO—R$^f$ (wherein R$^f$ is CH₃, CH₂CH₃, cyclopropyl, phenyl, 2-thienyl, 3-thienyl, 2-furanyl or 3-furanyl), —COCH₂—R$^g$ (wherein R$^g$ is H, —NHCH₂CH₂OH, —NHCH₂CH₂OCH₃, —NHCH₂CH₂N(CH₃)₂, 1-piperidinyl, 1-(piperidinyl-4-methanol), 4-morpholinyl or —N(CH₃)—(3-(1-methylpyrrolidinyl)),
f) —CH₂—CO—R$^h$ (wherein R$^h$ is substituted or unsubstituted lower alkyl, —OH, —OCH₃, —OCH₂CH₃, —NH₂, —(CH₂)$_n$ substituted or unsubstituted heteroaryl where n is 0 or 1, —NH cycloalkyl, —N (lower alkyl)$_n$ where n is 1 or 2, —NHCH₂C(OH)CH₂OH, —NHCH₂CF₃, —NHCH₂CH₂CH₂OH, —N(CH₂CH₂OH)₂, —N(CH₂CH₂OH)₂, —N(CH₂CH₂OCH₃)₂, —N(CH₃)CH₂CH₂OH, —NH(CH₂OH)(CH₃) CH₂CH₂OH, —NH(CH₂OH)(CH₃)CH₃, —CH₂CH₂CH₂SO₂NH₂, —N(CH₂CH₃)heteroaryl, —N(CH₃)CH₂CH₂OCH₃, —NHCH₂CH₂OCH₃, —NH(CH₂)$_n$ mono- or di- substituted heteroaryl where n is 0 or 1, —NHCH₂CH₂ substituted or unsubstituted heteroaryl, —NH mono- or di- substituted aryl, —NH(CH₂)$_n$ heterocycle where n is 0 or 1, —NH(CH₂)$_n$—OH where n is 2 or 3,
—(CH₂)$_n$ substituted or unsubstituted heterocycle where n is 1 or 2 or —N(CH₂CH₃)mono- or di- substituted heteroaryl,
g) —SO₂R$^i$ (wherein R$^i$ is —CH₃, —CH₂CH₃, —CH(CH₃)₂, phenyl, 4-methylphenyl, 4-propylphenyl, CF₃, 2-thienyl, 3-thienyl, NH₂, NHCH₃, N(CH₃)₂, NHCH₂CH₂OCH₃, N(CH₂CH₂OCH₃)₂, 1-pyrrolidinyl, 1-piperidinyl, 4-morpholinyl, 1-piperazyl-4-ethanol, 1-(4-acetylpiperazinyl) or 1-(3-oxopiperazinyl)),
h) —COR$^j$ (wherein R$^j$ is lower alkyl, cycloalkyl, 2-tetrahydrofuranyl, 2-thienyl, 3-thienyl, NH₂, NHCH₃, N(CH₃)₂, 1-pyrrolidinyl, 1-piperidinyl, 4-morpholinyl, 1-piperazinyl-4-ethanol, 1-(4-acetylpiperazinyl) or 1-(3-oxopiperazinyl)), and
i) substituted or unsubstituted heteroaryl or heterocycle;
vii)-a substituted piperidine of the formula:

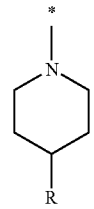

wherein R is hydrogen, lower alkyl, —CH₂CH(OH)CH₂OH, —CH₂CH₂CH(OH)CH₂OH or 4-tetrahydro-2H-thiopyranyl-1,1-dioxide,
—CH₂CH₂R$^d$ (wherein R$^d$ is —OH, —OCH₃, —OCH₂CH₂OH, —OCH₂CH₂OCH₃, —CN, —CF₃, —SO₂CH₃, —SO₂NH₂, —SO₂N(CH₃)₂, —CONH₂, —CON(CH₃)₂, —NH₂, —NHCOCH₃, —NHSO₂CH₃, —N(CH₃)₂, 1-pyrrolidinyl, 1-piperidinyl or 4-morpholinyl),
—CH₂CH₂CH₂R$^e$(wherein R$^e$ is —OH, —OCH₃, —SO₂CH₃, —SO₂CH₂CH₃, —SO₂N(CH₃)₂, —CN, —N(CH₃)₂, 1-pyrrolidinyl, 1-piperidinyl, 4-morpholinyl, —COOCH₃, —COOCH₂CH₃, —COOC(CH₃)₃, —CON(CH₃)₂, —CO—R$^f$ (wherein R$^f$ is CH₃, CH₂CH₃, cyclopropyl, phenyl, 2-thienyl, 3-thienyl, 2-furanyl or 3-furanyl), —COCH₂—R$^g$ (wherein R$^g$ is H, —NHCH₂CH₂OH, —NHCH₂CH₂OCH₃, —NHCH₂CH₂N(CH₃)₂, 1-piperidinyl, 1-(piperidinyl-4-methanol), 4-morpholinyl or —N(CH₃)—(3-(1-methylpyrrolidinyl)),
—CH₂—CO—R$^h$ (wherein R$^h$ is substituted or unsubstituted lower alkyl, —OH, —OCH₃, —OCH₂CH₃, —NH₂, —(CH₂)$_n$ heteroaryl where n is 0 or 1 —NH lower alkyl, —NH cycloalkyl, —N (lower alkyl)$_n$ where n is 1 or 2, —NHCH₂C(OH)CH₂OH, —NHCH₂CF₃, —NHCH₂CH₂CH₂OH, —N(CH₂CH₂OH)₂, —N(CH₂CH₂OCH₃)₂, —N(CH₃)CH₂CH₂OH, —NH(CH₂OH)(CH₃) CH₂CH₂OH, —NH(CH₂OH)(CH₃)CH₃, —CH₂CH₂CH₂SO₂NH₂, —N(CH₂CH₃)heteroaryl, —N(CH₃)CH₂CH₂OCH₃, —NHCH₂CH₂OCH₃, —NH(CH₂)$_n$ mono- or di- substituted heteroaryl where n is 0 or 1, —NHCH₂CH₂ substituted or unsubstituted heteroaryl, —NH mono- or disubstituted aryl, —NH(CH$_2$)$_n$ heterocycle where n is 0 or 1, —NH(CH$_2$)$_n$—OH where n is 2 or 3, substituted or unsubstituted heterocycle or—N(CH$_2$CH$_3$) mono- or di- substituted heteroaryl, —SO$_2$R$^i$ (wherein R$^i$ is —CH$_3$, —CH$_2$CH$_3$, —CH(CH$_3$)$_2$, phenyl, 4-methylphenyl, 4-propylphenyl, CF$_3$, 2-thienyl, 3-thienyl, NH$_2$, NHCH$_3$, N(CH$_3$)$_2$, NHCH$_2$CH$_2$OCH$_3$, N(CH$_2$CH$_2$OCH$_3$)$_2$, 1-pyrrolidinyl, 1-piperidinyl, 4-morpholinyl, 1-piperazyl-4-ethanol, 1-(4-acetylpiperazinyl) or 1-(3-oxopiperazinyl)), —COR$^j$ (wherein R$^j$ is lower alkyl, cycloalkyl, 2-tetrahydrofuranyl, 2-thienyl, 3-thienyl, NH$_2$, NHCH$_3$, N(CH$_3$)$_2$, 1-pyrrolidinyl, 1-piperidinyl, 4-morpholinyl, 1-piperazinyl-4-ethanol, 1-(4-acetylpiperazinyl) or 1-(3-oxopiperazinyl)), substituted or unsubstituted heteroaryl or heterocycle, NH$_2$, NHCOCH$_3$, NHCOCH$_2$NH$_2$, NHCOCH$_2$NHCH$_3$, NHCOCH$_2$N(CH$_3$)$_2$, NHCOCH$_2$N(CH$_2$CH$_2$OH)$_2$, NHCOCH$_2$N(CH$_2$CH$_2$OCH$_3$)$_2$, NHCOCH$_2$NHCH$_2$CH$_2$OH, NHCOCH$_2$-(1-(4-acetylpiperazinyl)), NHCOCH$_2$-(1-(3-oxopiperazinyl)), NHCOCH$_2$—NHCONHCH$_3$, NHCOO lower alkyl, NHCHCH$_3$, NHCO lower alkyl, NH(CH$_2$)n SO$_2$CH$_3$ where n is 0-2, NH(CH$_3$)SO$_2$CH$_3$,(1-piperidinecarboxamide), NHCOCH$_2$-(N,N-diethyl-1-piperidinylcarboxamide), NHCOCH$_2$-(1-(3-hydroxypiperidinyl)), NHCOCH$_2$-(1-(piperidinyl-4-methanol)), NHCON(CH$_3$)$_2$, NHCSNHCH$_3$, NHCSNHPh, NHCH$_2$CONH$_2$ or —NHCH$_2$CH$_2$SO$_2$CH$_3$ and viii)-a substituted piperidine of the formula:

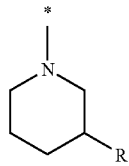

wherein R is —OH, CH$_2$OH, CH$_2$CH$_2$OH, or C(O)NH$_2$ and the pharmaceutically acceptable salts and esters thereof;

together with a pharmaceutically acceptable excipient.

* * * * *